US010612036B2

(12) United States Patent
Hey et al.

(10) Patent No.: US 10,612,036 B2
(45) Date of Patent: Apr. 7, 2020

(54) ENGINEERED CRY6A INSECTICIDAL PROTEINS

(71) Applicant: Dow AgroSciences LLC, Indianapolis, IN (US)

(72) Inventors: Timothy D. Hey, Zionsville, IN (US); Xu Xiaoping, Yinchuan (CN); Todd P. Glancy, Fairmount, IN (US); Diaa Alabed, Carmel, IN (US); Sarah E. Worden, Indianapolis, IN (US); Nick X. Wang, Westfield, IN (US); Carla Ausmus, Pasadena, MD (US); Shao-Ching Hung, Midland, MI (US)

(73) Assignee: DOW AGROSCIENCES LLC, Indianapolis, IN (US)

( * ) Notice: Subject to any disclaimer, the term of this patent is extended or adjusted under 35 U.S.C. 154(b) by 0 days.

(21) Appl. No.: 15/232,876

(22) Filed: Aug. 10, 2016

(65) Prior Publication Data

US 2017/0051304 A1 Feb. 23, 2017

Related U.S. Application Data

(60) Provisional application No. 62/205,797, filed on Aug. 17, 2015.

(51) Int. Cl.
*C12N 15/82* (2006.01)
*C07K 14/325* (2006.01)

(52) U.S. Cl.
CPC ........ *C12N 15/8286* (2013.01); *C07K 14/325* (2013.01); *Y02A 40/162* (2018.01)

(58) Field of Classification Search
None
See application file for complete search history.

(56) References Cited

U.S. PATENT DOCUMENTS

| | | | | |
|---|---|---|---|---|
| 5,874,288 | A | 2/1999 | Thompson et al. | |
| 6,303,364 | B1 | 10/2001 | Thompson et al. | |
| 6,642,030 | B1 * | 11/2003 | English ................ | C07K 14/325 435/320.1 |
| 6,831,062 | B2 | 12/2004 | Thompson et al. | |
| 7,122,516 | B2 * | 10/2006 | Altman ................ | C07K 14/195 514/2.3 |
| 2003/0115630 | A1 | 6/2003 | Romano | |
| 2011/0225681 | A1 * | 9/2011 | Hey ..................... | C07K 14/325 800/301 |
| 2011/0239334 | A1 | 9/2011 | Hey et al. | |
| 2014/0033361 | A1 * | 1/2014 | Altier ................... | C07K 14/195 800/279 |

FOREIGN PATENT DOCUMENTS

WO 2007/062064 A2 5/2007

OTHER PUBLICATIONS

Tounsi et al., J. Appl. Microbiol. 95:23-28 (2003).*
Angsuthanasombat et al., J Biochem Mol Biol 34:402-407 (2001).*
Dementiev et al., BMC Biol 14:71, 2 (2016).*
De Maagd et al., Trends Genet. 17:193-99 (2001).*
De Maagd et al., Appl. Environ Microbiol 65:4369-4374 (1999).*
Olsen et al., Trends Plant Sci 10(2):79-87 (2005).*
Guo et al., Proc Natl Acad Sci USA 101:9205-10 (2004).*
Wei et al., Proc Natl Acad Sci 100(5):2760-65, 2764 (2003).*
Brown, David P, et al., Characterisation of cysteine proteinases resonsible for digestive proteolysis in guts of larval western corn rootworm (*Diabrotica virgifera*) by expression in yeast Pichia pastoria, Insect Biochemistry and Molecular Biology, 2004, p. 305-320, V. 34, Elsevier—UK.
Bravo, Alejandra, et al., Mode of action of Bacillus thuringiensis Cry and Cyt toxins and their potential for insect control, Toxicon, 2007, p. 423-435, V. 49, Elsevier—MX.
Diaz-Mendoza, Mercedes, et al., Proteolytic processing of native Cry1Ab toxin by midgut extracts and purified trypsins from the Mediterranean corn borer *Sesamia nonagrioides*, Journal of Insect Physiology, 2007, p. 428-435, V 53, Elsevier—ES.
Gazit, Ehud, et al., The structure and organization within the membrane of the helices composing th spore-forming domain of Bacillus thuringiensis δ-endotoxin are consistent with and "umbrella-like" structure of the pore, Biophysics, 1998, p. 0027-8434, V. 9512289-6, PNAS—UK.
Goméz, Isabel et al., Cadherin-like receptor binding facilitates proteolytic cleavage of helix α-1 in domain I and oligomer pre-pore formation of Bacillus thuringiensis Cry1Ab toxin, FEBS Letters, 2002, p. 242-246, v. 513, FEBS 25809, (first published online) MX.
Nunez-Valdez, M. E. et al., Structural and functional studies of α-hexil 5 region from Bacillus thuringiensis Cry1Ab δ-endotoxin, Biochemica et Biophisica Acta, 2001, p. 122-131, V. 1546, Elsevier MX.
Pigott, Craig R., et al., Rose of Receptors in Bacillus thuringiensis Crystal Toxin Activity, Microbioloty and Molecular Biology Reviews, 2007, p. 255-281, V. 71, No. 2, American Society for Microbiology—UK.
Soberón, Marion, et al., Engineering Modified Bt Toxins to Counter Insect Resistance, Science 318, 1640, Published online Nov. 1, 2007; 10.1126/science.1146453, www.sciencemag.org.
Deist, Benjamin R.; et al.: "Bt Toxin Modification for Enhanced Efficacy", Toxins, Oct. 22, 2014 (Oct. 22, 2014), vol. 6, No. 10, pp. 3005-3027.
Lee, Dong Wook; et al.: "*Arabidopsis* Nuclear-Encoded Plastid Transit Peptides Contain Multiple Sequence Subgroups with Distinctive Chloroplast-Targeting Sequence Motifs", The Plant Cell, Jun. 2008, vol. 20, No. 6, pp. 1603-1622.
Pardo-Lopez, L.; et al.: "Strategies to improve the insecticidal activity of Cry toxins from Bacillus thuringiensis", Peptides, Mar. 1, 2009 (Mar. 1, 2009), vol. 30, No. 3, pp. 589-595.
Peng, Donghai; et al.: "Synergistic activity between Bacillus thuringiensis Cry6Aa and Cry55Aa toxins against Meloidogyne incognita", Microbial Biotechnology, 2011, vol. 4, No. 6, pp. 794-798.

(Continued)

*Primary Examiner* — Russell T Boggs

(57) ABSTRACT

Engineered and modified Cry6Aa insecticidal toxins, polynucleotides encoding such toxins, use of such toxins to control pests, and transgenic plants that produce such toxins are disclosed.

12 Claims, 6 Drawing Sheets

Specification includes a Sequence Listing.

(56) References Cited

OTHER PUBLICATIONS

Wei, J-Z; et al.: "Bacillus thuringiensis crystal proteins that target nematodes", Proceedings of the National Academy of Sciences of the United States of America (PNAS), Mar. 4, 2003 (Mar. 4, 2003), vol. 100, No. 5, pp. 2760-2765.

Supplementary European Search Report for Application No. EP16837514.5 (International Application No. PCT/US206/046231), dated Jan. 29, 2019.

Extended European Search Report for Application No. EP16837514.5 (International Application No. PCT/US206/046231), dated May 10, 2019.

International Search Report, International Preliminary Report on Patentability, and Written Opinion for International Application No. PCT/US2061/046231, dated Dec. 13, 2016.

* cited by examiner

Fig. 2

DIG-177
FL 0 5 10 30 50

DIG-1000
FL 0 5 10 30 50

1. Rainbow MWM
2. Fresh Negative B104
3.117261[1]-015.001AJ.084
4.126938[1]-016.AJ001.004
5.126937[1]-004.AJ001.031
6.126938[1]-010.AJ001.028
7.126939[1]-009.AJ001.021
8.117261[1]-027.001AJ.083
9.126938[1]-003.AJ001.019
10.126937[1]-003.AJ001.038
11.117261[1]-019.001AJ.046
12.126939[1]-005.AJ001.043
13.126938[1]-016.AJ001.039
14.117261[1]-015.001AJ.058
15. Standard DIG 1000 – 24 ng/lane
16. Standard DIG 1000 – 48 ng/lane
17. Standard DIG 1000– 96 ng/lane
18. Standard DIG 1000 – 192 ng/lane
19. Standard DIG 1000– 360 ng/lane
20. Standard DIG 1000– 770 ng/lane 150 kDa
76 kDa
52 kDa
31 kDa

ENGINEERED CRY6A INSECTICIDAL PROTEINS

CROSS-REFERENCE TO RELATED APPLICATIONS

This application claims priority from, and benefit of, U.S. Provisional Application 62/205,797 filed on Aug. 17, 2015. The entire contents of this application is hereby incorporated by reference into this application.

REFERENCE TO SEQUENCE LISTING SUBMITTED ELECTRONICALLY

The substitute sequence listing is submitted electronically via EFS-Web as an ASCII formatted sequence listing with a file named "77095_US_NP_ST25_20180723," created on Jul. 23, 2018, and having a size of 416 kilobytes. The sequence listing contained in this ASCII formatted document is part of the specification, and is incorporated herein by reference in its entirety.

TECHNICAL FIELD

The present invention relates generally to the field of molecular biology as applied to agricultural sciences. More particularly, certain embodiments concern methods for the use of DNA segments as diagnostic probes and templates for insecticidal protein expression. Methods of making and using the claimed nucleic acid segments in the development of plant incorporated protectants in transgenic plant cells and plants are disclosed.

BACKGROUND OF THE DISCLOSURE

Insects and other pests cost farmers billions of dollars annually in crop losses and in the expense of controlling insect pests. The losses caused by pests in agricultural production environments include decrease in crop yield, reduced crop quality, and increased harvesting costs.

Coleopterans are a significant group of agricultural pests that cause extensive damage to crops each year. Examples of coleopteran pests include but are not limited to: Colorado potato beetle (CPB), corn rootworm, alfalfa weevil, boll weevil, and Japanese beetle. The Colorado potato beetle is an economically important pest that feeds on the leaves of potato, eggplant, tomato, pepper, tobacco, and other plants in the nightshade family. The Colorado potato beetle is a problematic defoliator of potatoes, in part, because it has developed resistance to many classes of insecticides.

The western corn rootworm (WCR), *Diabrotica virgifera virgifera* LeConte, is one of the most devastating coleopterans in North America and is a particular concern in corn-growing areas of the Midwestern United States. Approximately 9.3 million acres of U.S. corn are infested with corn rootworm species complex each year. The northern corn rootworm (NCR), *Diabrotica barberi* Smith and Lawrence, is a closely-related species that co-inhabits much of the same range as WCR. There are several other related subspecies of *Diabrotica* that are significant pests in the Americas: the Mexican corn rootworm (MCR), *D. virgifera zeae* Krysan and Smith; the southern corn rootworm (SCR), *D. undecimpunctata howardi* Barber; *D. balteata* LeConte; *D. undecimpunctata tenella; D. speciosa* Germar; and *D. u. undecimpunctata* Mannerheim. The United States Department of Agriculture has estimated that corn rootworms cause $1 billion in lost revenue each year, including 800 million in yield loss and 200 million in treatment costs.

Both WCR and NCR eggs are deposited in the soil during the summer. The insects remain in the egg stage throughout the winter. The larvae hatch in late May or early June and begin to feed on corn roots. Corn rootworms go through three larval instars. After feeding for several weeks, the larvae molt into the pupal stage. They pupate in the soil, and then emerge from the soil as adults in July and August.

Most of the rootworm damage in corn is caused by larval feeding. Newly hatched rootworms initially feed on fine corn root hairs and burrow into root tips. As the larvae grow larger, they feed on and burrow into primary roots. When corn rootworms are abundant, larval feeding often results in the pruning of roots all the way to the base of the corn stalk. Severe root injury interferes with the roots ability to transport water and nutrients into the plant, reduces plant growth, and results in reduced grain production, thereby often drastically reducing overall yield. Severe root injury also often results in lodging of corn plants, which makes harvest more difficult and further decreases yield. Furthermore, feeding by adults on the corn reproductive tissues can result in pruning of silks at the ear tip. If this "silk clipping" is severe enough during pollen shed, pollination may be disrupted. In addition, members of the genus *Diabrotica* attack cucurbit crops (cucumbers, melons, squash, etc.) and many vegetable and field crops in commercial production as well as those being grown in home gardens.

Control of corn rootworms has been attempted by crop rotation, chemical insecticides, biopesticides such as the spore-forming gram-positive bacterium, *Bacillus thuringiensis* (B.t.), transgenic plants that express B.t. toxins, and a combination thereof. Crop rotation suffers from the disadvantage of placing unwanted restrictions upon the use of farmland. Moreover, oviposition of some rootworm species may occur in soybean fields, thereby compromising the effectiveness of crop rotation practiced with corn and soybean.

Chemical insecticides are the most heavily relied upon strategy for achieving corn rootworm control. Chemical insecticide use is an imperfect corn rootworm control strategy; high populations of larvae, heavy rains, and improper application of the insecticide(s) may all result in inadequate corn rootworm control. Furthermore, the continual use of insecticides may select for insecticide-resistant rootworm strains, as well as raise significant environmental concerns due to their toxicity to non-target species.

Damage to plants caused by nematodes is also a prevalent and serious economic problem. Nematodes cause widespread and serious damage in many plant species. Many genera of nematodes are known to cause such damage. Plant-parasitic nematodes include members of the Phylum Nematoda, Orders Tylenchida and Dorylaimide. In the Order Tylenchida, the plant-parasitic nematodes are found in two Super Families: Tylenchoidea and Criconematoidea. There are more than 100,000 described species of nematodes.

Chemical pesticides have provided an effective method of pest control; however, the public has become concerned about the amount of residual chemicals that might be found in food, ground water, and the environment. Stringent new restrictions on the use of chemical pesticides and the elimination of some effective pesticides from the marketplace could limit economical and effective options for controlling costly pests. Thus, there is an urgent need to identify new pest control agents and compositions.

Regular use of chemical pesticides for the control of unwanted insect pests can select for chemical resistant strains. Chemical resistance occurs in many species of economically important insects and has also occurred in nematodes of sheep, goats, and horses. For example, an accepted methodology for control of nematodes has centered around the drug benzimidazole and its congeners. The use of these drugs on a wide scale has led to many instances of resistance among nematode populations (Prichard, R. K. et al). The development of pesticide resistance necessitates a continuing search for new control agents having different modes of action.

At the present time there is a need to have more effective means to control the many coleopterans and nematodes that cause considerable damage to susceptible hosts and crops. Advantageously, such effective means would employ highly selective biological toxins. Several B.t. Cry proteins have been shown to be nematicidal, these include Cry5B, Cry6A, Cry14A and Cry21A (Wei et al., 2003; Aroian and Li (2010).

B.t. is a soil-borne bacterium that produces pesticidal crystal proteins known as delta endotoxins or Cry proteins. Cry proteins are oral intoxicants that function by acting on midgut cells of susceptible insects. Some Cry toxins have been shown to have activity against nematodes. An extensive list of delta endotoxins is maintained and regularly updated at the *Bacillus thuringiensis* Toxin Nomenclature web site maintained by Neil Crickmore. (See www.lifesci.sussex.ac.uk/home/Neil_Crickmore/Bt/toxins2.html and Crickmore et al. 1998, page 808). Cry toxins, including members of the Cry 1B, Cry 1I, Cry2A, Cry3, Cry7A, Cry8, Cry9D, Cry14, Cry18, Cry22, Cry23, Cry34, Cry35, Cry36, Cry37, Cry43, Cry55, Cyt1A, and Cyt2C (Frankenhuyzen, 2009) families have insecticidal activity against coleopteran insects.

Some B.t. toxins which are active against corn rootworm and other coleopterans are now known. Cry6Aa has reported activity against coleopteran and nematode pests (U.S. Pat. Nos. 5,186,934; 6,632,792 B2; U.S. Pat. No. 2011/0225681; U.S. Pat. No. 2011/0239334 A1; and Wei et al., 2003). For example, U.S. Pat. No. 4,849,217 discloses various isolates, including PS52A1 and PS86A1, as having activity against alfalfa weevils. U.S. Pat. No. 5,208,017 discloses PS86A1 as a having activity against Western corn rootworm. U.S. Pat. Nos. 5,427,786 and 5,186,934 each disclose B.t. isolates and toxins active against coleopterans. Specifically disclosed in these patents is the isolate known as PS86A1 and a coleopteran-active toxin obtainable therefrom known as 86A1. Toxin 86A1 is now also known as Cry6A (CryVIA). The wild-type Cry6Aa toxin is about 54.1 kDa. A Cry6B toxin is also known. This toxin can be obtained from the PS69D1 isolate. Cry6Aa is recognized as a new mode of action against western corn rootworm, complementing Cry3Aa and Cry34Ab1/Cry35Ab1 (Li et al, 2013) making it a pyramid partner in an integrated insect resistance management program (U.S. Pat. No. 2013/0167269 A1 and US 2013/0263331 A1).

The full length Cry6A and Cry6B toxins are known to have activity against nematodes. The PS69D1 isolate has been reported to have activity against nematodes (U.S. Pat. Nos. 4,948,734; 5,093,120; 5,262,399; and 5,439,881). A generic formula for the amino acid sequence of CryVI toxins has been disclosed in WO 92/19739, which also teaches that the full length toxin has activity against nematodes. The PS52A1 and PS69D1 isolates are disclosed therein. U.S. Pat. Nos. 5,262,159 and 5,468,636 also disclose a generic formula for toxins having activity against aphids.

Cry6A toxin is known to inhibit the growth of certain coleopterans and can be activated by enzymatically cleaving to yield an amino terminal core toxin that is lethal to coleopterans, such as the western corn rootworm (U.S. Pat. No. 6,831,062 B2). In addition, truncated Cry6A is active against nematodes. U.S. Pat. No. 6,831,062 describes Cry6A truncated holotoxins and fusion proteins and fusion genes. Thompson et al disclosed the insecticidally active peptide fragments identified as being residues 12-390 and 12-443 depending on the cleavage site. The large fragment, from approximately residues 12-390 or 12-443 resulting from trypsin, or other proteolytic digestion, are called the core fragments or toxins. The trypsin treatment of Cry6Aa, produced from recombinant B.t., increased activity against WCR (U.S. Pat. Nos. 5,874,288; 6,831,062 B2; and 6,303,364 B1).

Although production of the currently-deployed Cry proteins in transgenic plants can provide robust protection against the aforementioned pests, thereby protecting grain yield, adult pests have emerged in artificial infestation trials, indicating less than complete larval insect control. Additionally, development of resistant insect populations threatens the long-term durability of Cry proteins in insect pest control. Coleopteran insects have developed resistance in the field to Cry proteins (Gassman et al. PLoS ONE July 2011|Volume 6|Issue 7|e22629). Insect resistance to B.t. Cry proteins can develop through several mechanisms (Heckel et al., 2007; Pigott and Ellar, 2007). Multiple receptor protein classes for Cry proteins have been identified within insects, and multiple examples exist within each receptor class. Resistance to a particular Cry protein may develop, for example, by means of a mutation within the toxin-binding portion of a cadherin domain of a receptor protein. A further means of resistance may be mediated through a protoxin-processing protease.

While native Cry6Aa naturally expressed in B.t. strains has shown good efficacy against WCR and certain nematodes, its use as an effective plant incorporated protectant has not been demonstrated due to its susceptibility to proteolysis when expressed in plant cells. Therefore, engineering Cry6A toxins to be more resistant to proteolysis when expressed in plant cells would be highly desirable for use in recombinant plants, especially corn, as a plant-incorporated protectant.

BRIEF SUMMARY OF THE DISCLOSURE

The present invention includes engineered Cry6A based insecticidal protein toxins, including variants and analogs that in part, were designed to limit loss of an important carboxy terminal peptide (CTP). Other embodiments of the invention include nucleic acids encoding the claimed insecticidal toxins, methods of controlling pests using the toxins expressed from the claimed nucleic acid sequences, methods of producing the toxins in transgenic host cells, and transgenic plant seeds comprising such nucleic acids, and plants that express the toxins.

Modified Cry6Aa insecticidal proteins of the invention comprise modifications chosen from the group consisting of a modified proteolysis-susceptible region (residues 390-451 of SEQ ID NO:1), increased affinity of the CTP for the core protein, and addition of sub-cellular transit peptides. A preferred group of Cry6Aa variant insecticidal proteins is SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:132, SEQ ID NO:136, SEQ ID NO:138, and SEQ ID NO:140. A more preferred group of variants is SEQ ID NO:110, SEQ ID NO:112, SEQ ID NO:114, SEQ ID NO:116, SEQ ID NO:118, SEQ ID NO:120, SEQ ID NO:128, SEQ ID NO:132, and SEQ ID NO:144. A more highly preferred group of variants is SEQ ID NO:110, SEQ ID NO:116, SEQ ID NO:118, SEQ ID NO:120, SEQ ID NO:132. An even more preferred group of variants is SEQ ID NO:116, SEQ ID NO:118, SEQ ID NO:120. And the most preferred variant is SEQ ID NO:116.

A preferred group of nucleic acid sequences that encode Cry6Aa variant insecticidal proteins is SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:131, SEQ ID NO:135, SEQ ID NO:137, SEQ ID NO:139, SEQ ID NO:141, SEQ ID NO:142, and SEQ ID NO:143. A more preferred group of nucleic acids is SEQ ID NO:109, SEQ ID NO:111, SEQ ID NO:113, SEQ ID NO:115, SEQ ID NO:117, SEQ ID NO:119, SEQ ID NO:127, and SEQ ID NO:131. A more highly preferred group of nucleic acids is SEQ ID NO:109, SEQ ID NO:115, SEQ ID NO:117, SEQ ID NO:119, SEQ ID NO:131, and 139. An even more preferred group of nucleic acids is SEQ ID NO:115, SEQ ID NO:117, SEQ ID NO:119, and SEQ ID NO:139. And the most preferred nucleic acid is SEQ ID NO:115.

In another embodiment the invention provides a plant comprising an engineered Cry6Aa insecticidal polypeptide disclosed herein.

In another embodiment the invention provides a method for controlling plant pest populations and damage to plants by delivering an insecticidally effective amount of an insecticidal protein of the invention in a plant tissue such that an insect pest ingests the insecticidal protein.

In another embodiment the invention provides an isolated nucleic acid that encodes an engineered Cry6Aa insecticidal polypeptide disclosed herein.

In another embodiment the invention provides DNA constructs comprising a nucleotide sequence that encodes an engineered Cry6Aa insecticidal polypeptide operably linked to a promoter that is capable of driving expression in a plant and other regulatory sequences that stabilize messenger RNA. The promoter may be heterologous or native to B.t.

The invention also provides transgenic plants that comprise the DNA construct stably incorporated into its genome and a method for protecting a plant from a pest comprising introducing the construct into said plant.

BRIEF DESCRIPTION OF THE FIGURES

FIG. 2 is a ribbon 3D structure model of trypsin treated DIG-177 (Cry6Aa) (left) representing residues 12-125, 128-387 and 445-472 of SEQ ID NO:2. FIG. 2 (right), is a ribbon model of residues 12-472 of SEQ ID NO:2, residues missing from the trypsin treated structure (left) have been modeled. The carboxy terminal peptide in both structures is shown in black.

BRIEF DESCRIPTION OF THE SEQUENCES

Figure 1:
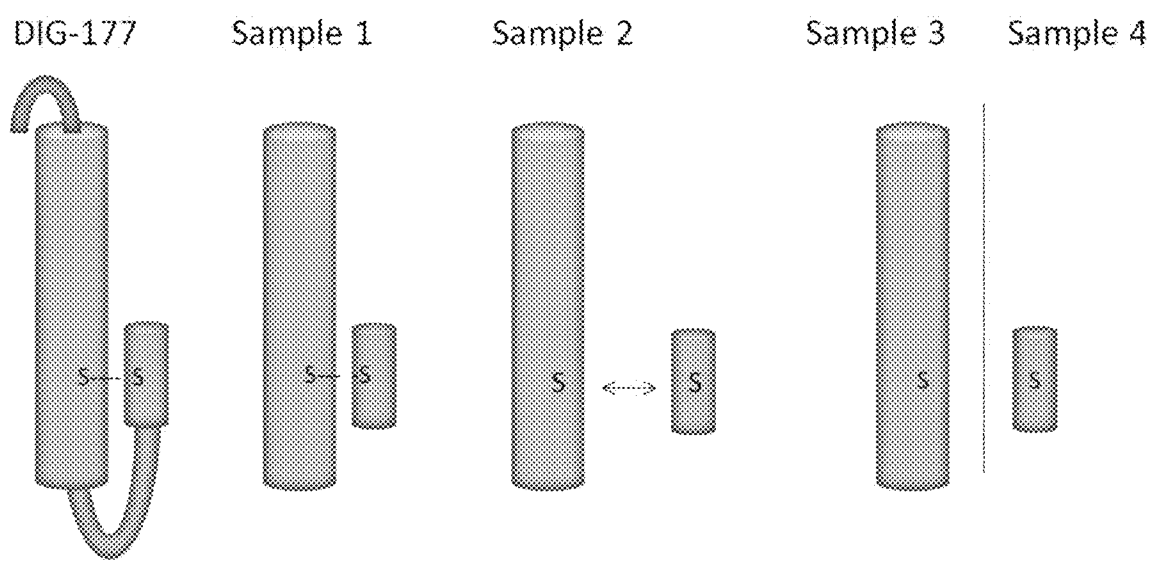
FIG. 1 is a schematic diagram of DIG-177 (Cry6Aa) samples 1-4 tested as described in Example 3. The diagram shows samples following trypsin digestion with and without disulfide bond reduction.

SEQ ID NO:1 is a DNA sequence comprising full length DIG-177 (Cry6Aa).

SEQ ID NO:2 is the deduced DIG-177 protein sequence.

SEQ ID NO:3 Maize codon optimized version of DIG-177, also known as IRDIG.522.28; encoding the protein identified as SEQ ID NO:2.

SEQ ID NO:4 Maize codon bias version of DIG-177 with an encoded mitochondrial transit peptide, also known as IRDIG.552.60.

SEQ ID NO:5 The polypeptide encoded by SEQ ID NO:4

SEQ ID NO:6 Maize codon optimized version of DIG-177 with an encoded mitochondrial transit peptide; also known as IRDIG.552.61

SEQ ID NO:7 The polypeptide encoded by SEQ ID NO:6

SEQ ID NO:8 Maize codon optimized version of DIG-177 with an encoded combination mitochondrial and chloroplast transit peptide; also known as IRDIG.552.62

SEQ ID NO:9 The polypeptide encoded by SEQ ID NO:8

SEQ ID NO:10 Maize codon optimized version of DIG-177 with an encoded peroxisome transit peptide; also known as IRDIG.552.63

SEQ ID NO:11 The polypeptide encoded by SEQ ID NO:10

SEQ ID NO:12 Maize codon optimized version of DIG-177 with an encoded peroxisome transit peptide; also known as IRDIG.552.64

SEQ ID NO:13 The polypeptide encoded by SEQ ID NO:12

SEQ ID NO:14 Maize codon optimized version of DIG-177 with an encoded peroxisome transit peptide; also known as IRDIG.552.65

SEQ ID NO:15 The polypeptide encoded by SEQ ID NO:14

SEQ ID NO:16 Maize codon optimized version of DIG-177 with an encoded vacuole transit peptide; also known as IRDIG.552.66

SEQ ID NO:17 The polypeptide encoded by SEQ ID NO:16

SEQ ID NO:18 Maize codon optimized version of DIG-177 with an encoded vacuole transit peptide; also known as IRDIG.552.67

SEQ ID NO:19 The polypeptide encoded by SEQ ID NO:18

SEQ ID NO:20 Maize codon optimized version of DIG-177 with an encoded vacuole transit peptide; also known as IRDIG.552.68

SEQ ID NO:21 The polypeptide encoded by SEQ ID NO:20

SEQ ID NO:22 Maize codon optimized version of DIG-177 with an encoded apoplast transit peptide; also known as IRDIG.552.69

SEQ ID NO:23 The polypeptide encoded by SEQ ID NO:22

SEQ ID NO:24 Maize codon optimized version of DIG-177 with an encoded endoplasmic reticulum transit peptides; also known as IRDIG.552.70

SEQ ID NO:25 The polypeptide encoded by SEQ ID NO:24

SEQ ID NO:26 Maize codon optimized version of DIG-177 with an encoded nuclear transit peptide; also known as IRDIG.552.71

SEQ ID NO:27 The polypeptide encoded by SEQ ID NO:26

SEQ ID NO:28 Maize codon optimized version of DIG-177 with an encoded nuclear transit peptide; also known as IRDIG.552.72

SEQ ID NO:29 The polypeptide encoded by SEQ ID NO:28

SEQ ID NO:30 Maize codon optimized version of DIG-177 with an encoded chloroplast transit peptide; also known as IRDIG.552.73

SEQ ID NO:31 The polypeptide encoded by SEQ ID NO:30

SEQ ID NO:32 Maize codon optimized version of DIG-177 with an encoded chloroplast transit peptide; also known as IRDIG.552.74

SEQ ID NO:33 The polypeptide encoded by SEQ ID NO:32

SEQ ID NO:34 DIG-177 coding sequence, encoding the mutation C88>A, also known as DIG-614

SEQ ID NO:35 The polypeptide encoded by SEQ ID NO:34

SEQ ID NO:36 DIG-177 coding sequence, encoding the mutation C88>S, also known as DIG-615

SEQ ID NO:37 The polypeptide encoded by SEQ ID NO:36

SEQ ID NO:38 DIG-177 coding sequence, encoding the mutation C162>A, also known as DIG-616

SEQ ID NO:39 The polypeptide encoded by SEQ ID NO:38

SEQ ID NO:40 DIG-177 coding sequence, encoding the mutation C162>S, also known as DIG-617

SEQ ID NO:41 The polypeptide encoded by SEQ ID NO:40

SEQ ID NO:42 DIG-177 coding sequence, encoding the mutation C451>A, also known as DIG-618

SEQ ID NO:43 The polypeptide encoded by SEQ ID NO:42

SEQ ID NO:44 DIG-177 coding sequence, encoding the mutation C451>S, also known as DIG-619

SEQ ID NO:45 The polypeptide encoded by SEQ ID NO:44

SEQ ID NO:46 DIG-177 coding sequence, encoding the mutations C88>S and C451>S, also known as DIG-983

SEQ ID NO:47 the polypeptide encoded by SEQ ID NO:46

SEQ ID NO:48 DIG-177 coding sequence, encoding the mutations C88>A and C451>A, also known as DIG-984

SEQ ID NO:49 The polypeptide encoded by SEQ ID NO:48

SEQ ID NO:50 LF (Large Fragment); amino acids 12-390 of SEQ ID NO:2

SEQ ID NO:51 CTP 1 (Carboxy terminal peptide 1), amino acids 444-475 of SEQ ID NO:2

SEQ ID NO:52 CTP 2 (Carboxy terminal peptide 2), amino acids or 451-475 of SEQ ID NO:2

SEQ ID NO:53 Encodes a protein of residues 1-443 SEQ ID NO 2, also known as DIG-137

SEQ ID NO:54 The polypeptide encoded by SEQ ID NO:53

SEQ ID NO:55 Encodes a protein of residues 1-432 of SEQ ID NO:2, also known as DIG-138.

SEQ ID NO:56 The polypeptide encoded by SEQ ID NO:55

SEQ ID NO:57 Encodes a protein of residues 1-423 of SEQ ID NO:2, also known as DIG-147

SEQ ID NO:58 The polypeptide encoded by SEQ ID NO:57

SEQ ID NO:59 Encodes a protein of residues 1-400 of SEQ ID NO:2, also known as DIG-148

SEQ ID NO:60 The polypeptide encoded by SEQ ID NO:59

SEQ ID NO:61 Encodes a protein of residues 1-390 of SEQ ID NO:2, also known as DIG-149

SEQ ID NO:62 The polypeptide encoded by SEQ ID NO:61

SEQ ID NO:63 Encodes a protein deleted for amino acid residues 391-395 of SEQ ID NO:2, known as DIG-921

SEQ ID NO:64 The polypeptide encoded by SEQ ID NO:63

SEQ ID NO:65 Encodes a protein deleted for amino acid residues 396-400 of SEQ ID NO:2, known as DIG-922

SEQ ID NO:66 The polypeptide encoded by SEQ ID NO:65

SEQ ID NO:67 Encodes a protein deleted for amino acid residues 401-405 of SEQ ID NO:2, known as DIG-923

SEQ ID NO:68 The polypeptide encoded by SEQ ID NO:67

SEQ ID NO:69 Encodes a protein deleted for amino acid residues 406-410 of SEQ ID NO:2, known as DIG-924

SEQ ID NO:70 The polypeptide encoded by SEQ ID NO:69

SEQ ID NO:71 Encodes a protein deleted for amino acid residues 406-410 of SEQ ID NO:2, known as DIG-925

SEQ ID NO:72 The polypeptide encoded by SEQ ID NO:71

SEQ ID NO:73 Encodes a protein deleted for amino acid residues 416-420 of SEQ ID NO:2, known as DIG-926

SEQ ID NO:74 The polypeptide encoded by SEQ ID NO: 73

SEQ ID NO:75 Encodes a protein deleted for amino acid residues 421-425 of SEQ ID NO:2, known as DIG-927

SEQ ID NO:76 The polypeptide encoded by SEQ ID NO: 75

SEQ ID NO:77 Encodes a protein deleted for amino acid residues 441-445 of SEQ ID NO:2, known as DIG-931

SEQ ID NO:78 The polypeptide encoded by SEQ ID NO: 77

SEQ ID NO:79 Encodes a protein deleted for amino acid residues 391-400 of SEQ ID NO:2, known as DIG-969

SEQ ID NO:80 The polypeptide encoded by SEQ ID NO: 79

SEQ ID NO:81 Encodes a protein deleted for amino acid residues 401-410 of SEQ ID NO:2, known as DIG-970

SEQ ID NO:82 The polypeptide encoded by SEQ ID NO: 81

SEQ ID NO:83 Encodes a protein deleted for amino acid residues 411-420 of SEQ ID NO:2, known as DIG-971

SEQ ID NO:84 The polypeptide encoded by SEQ ID NO: 83

SEQ ID NO:85 Encodes a protein deleted for amino acid residues 421-430 of SEQ ID NO:2, known as DIG-972

SEQ ID NO:86 The polypeptide encoded by SEQ ID NO: 85

SEQ ID NO:87 Encodes a protein deleted for amino acid residues 431-440 of SEQ ID NO:2, known as DIG-973

SEQ ID NO:88 The polypeptide encoded by SEQ ID NO: 87

SEQ ID NO:89 Encodes a protein deleted for amino acid residues 391-405 of SEQ ID NO:2, known as DIG-985

SEQ ID NO:90 The polypeptide encoded by SEQ ID NO: 89

SEQ ID NO:91 Encodes a protein deleted for amino acid residues 406-420 of SEQ ID NO:2, known as DIG-986

SEQ ID NO:92 The polypeptide encoded by SEQ ID NO: 91

SEQ ID NO:93 Encodes a protein deleted for amino acid residues 421-435 of SEQ ID NO:2, known as DIG-987

SEQ ID NO:94 The polypeptide encoded by SEQ ID NO:93

SEQ ID NO:95 Encodes a protein deleted for amino acid residues 429-443 of SEQ ID NO:2, known as DIG-988

SEQ ID NO:96 The polypeptide encoded by SEQ ID NO:95

SEQ ID NO:97 Encodes a protein deleted for amino acid residues 391-410 of SEQ ID NO:2, known as DIG-989

SEQ ID NO:98 The polypeptide encoded by SEQ ID NO:97

SEQ ID NO:99 Encodes a protein deleted for amino acid residues 411-430 of SEQ ID NO:2, known as DIG-990

SEQ ID NO:100 The polypeptide encoded by SEQ ID NO:99

SEQ ID NO:101 Encodes a protein deleted for amino acid residues 424-443 of SEQ ID NO:2, known as DIG-991

SEQ ID NO:102 The polypeptide encoded by SEQ ID NO:101

SEQ ID NO:103 Encodes a protein deleted for amino acid residues 391-415 of SEQ ID NO:2, known as DIG-992

SEQ ID NO:104 The polypeptide encoded by SEQ ID NO:103

SEQ ID NO:105 Encodes a protein deleted for amino acid residues 415-440 of SEQ ID NO:2, known as DIG-993

SEQ ID NO:106 The polypeptide encoded by SEQ ID NO:105

SEQ ID NO:107 Encodes a protein deleted for amino acid residues 419-443 of SEQ ID NO:2, known as DIG-994

SEQ ID NO:108 The polypeptide encoded by SEQ ID NO:107

SEQ ID NO:109 Encodes a protein deleted for amino acid residues 401-443 of SEQ ID NO:2, known as DIG-995

SEQ ID NO:110 The polypeptide encoded by SEQ ID NO:109

SEQ ID NO:111 Encodes a protein deleted for amino acid residues 391-433 of SEQ ID NO:2, known as DIG-996

SEQ ID NO:112 The polypeptide encoded by SEQ ID NO:111

SEQ ID NO:113 Encodes a protein deleted for amino acid residues 391-414 and 425-443 of SEQ ID NO:2, known as DIG-997

SEQ ID NO:114 The polypeptide encoded by SEQ ID NO:113

SEQ ID NO:115 Encodes a DIG-177 variant with a peptide linker replacement for a protease susceptible segment, also known as DIG-1000.

SEQ ID NO:116 The polypeptide encoded by SEQ ID NO:115

SEQ ID NO:117 Encodes a DIG-177 variant with a peptide linker replacement for a protease susceptible segment, also known as DIG-1049

SEQ ID NO:118 The polypeptide encoded by SEQ ID NO:117

SEQ ID NO:119 Encodes a DIG-177 variant with a peptide linker replacement for a protease susceptible segment, also known as DIG-1052

SEQ ID NO:120 The polypeptide encoded by SEQ ID NO:119

SEQ ID NO:121 Encodes a DIG-177 variant with a peptide linker replacement for a protease susceptible segment, also known as DIG-1038

SEQ ID NO:122 The polypeptide encoded by SEQ ID NO:121

SEQ ID NO:123 Encodes a DIG-177 variant with a peptide linker replacement for a protease susceptible segment, also known as DIG-1055

SEQ ID NO:124 The polypeptide encoded by SEQ ID NO:123

SEQ ID NO:125 Encodes a DIG-177 variant with a peptide linker replacement for a protease susceptible segment, also known as DIG-1039

SEQ ID NO:126 The polypeptide encoded by SEQ ID NO:125

SEQ ID NO:127 Encodes a DIG-177 variant with a peptide linker replacement for a protease susceptible segment, also known as DIG-1056

SEQ ID NO:128 The polypeptide encoded by SEQ ID NO:127

SEQ ID NO:129 Encodes a DIG-177 variant with a peptide linker replacement for a protease susceptible segment, also known as DIG-1040

SEQ ID NO:130 The polypeptide encoded by SEQ ID NO:129

SEQ ID NO:131 Encodes a DIG-177 variant with a peptide linker replacement for a protease susceptible segment, also known as DIG-1057

SEQ ID NO:132 The polypeptide encoded by SEQ ID NO:131

SEQ ID NO:133 Encodes a DIG-177 variant with a peptide linker replacement for a protease susceptible segment, also known as DIG-1041

SEQ ID NO:134 The polypeptide encoded by SEQ ID NO:133

SEQ ID NO:135 Encodes a DIG-177 variant with a peptide linker replacement for a protease susceptible segment, also known as DIG-1058

SEQ ID NO:136 The polypeptide encoded by SEQ ID NO:135

SEQ ID NO:137 Maize codon bias version of DIG-1000.

SEQ ID NO:138 The polypeptide encoded by SEQ ID NO:137

SEQ ID NO:139 Maize codon bias version of DIG-1000 with a chloroplast transit peptide SEQ ID NO:140 The polypeptide encoded by SEQ ID NO:139

SEQ ID NO:141 Maize codon bias version DIG-1036.

SEQ ID NO:142 Highest GC+ERLS maize highest GC version of DIG-1036 with ER Localization Sequence SEQ ID NO:143 Highest GC+VLS maize highest GC version of DIG-1036 with Vacuole Localization Sequence SEQ ID NO:144 The polypeptide encoded by DIG-1036 (DIG-1000 minus glycosylation sites: N69>Q; N144>Q; N403>Q; N409>Q)

DETAILED DESCRIPTION OF THE DISCLOSURE

The present invention is a result of protein engineering studies designed to discover the source and target sites of proteolytic damage to Cry6A toxins produced in plant cells. High-resolution analyses, including determination of the Cry6Aa trypsin-digested crystal structure, have been completed. This work disclosed several surprising molecular details related to how Cry6Aa insecticidal proteins function.

Of these discoveries, it was determined that Cry6Aa belongs to the alpha helical hemolysin family of proteins based on structural identity; other members of this group include HlyE and BLB-B (Eifler et al., 2006; Tzokov et al., 2006; Wallace, et al., 2000; Mueller, et al., 2009; Madegowda et al., 2008).

Two disulfide bonds, between cysteine residues 88 and 451, and between cysteines 402-404 were identified. Most surprisingly, these disulfide bonds were not required for insecticidal activity of full-length Cry6Aa in artificial diet-based WCR bioassays.

A third discovery is related to the insecticidal activity of the trypsin treated toxin. A carboxy terminal peptide (CTP), consisting of either residues 444-475 or 451-475, was found to be disulfide bonded to the core toxin fragment and was found to be required for activity. The small size of the CTP and the labile nature of the disulfide bond likely accounted for it not being identified previously (U.S. Pat. Nos. 5,874,288; 6,831,062; 6,303,364).

The utility of Cry6Aa as a robust transgenic trait in plants (plant incorporated protectant), especially for protection against WCR, is dependent on the intracellular accumulation of active insecticidal protein. Proteolytic cleavage between residues 390-451, in a reducing environment such as in a plant cell, is believed to cause dissociation of the carboxy terminal peptide leading to loss of insecticidal activity.

Several means of preventing the loss of insecticidal activity of plant-expressed Cry6Aa toxins form the basis of this invention. Such means are comprised of either reducing proteolysis in the susceptible region, e.g. the region between residues approximately 390-451, of the subject toxins or minimizing dissolution of the necessary CTP and may be used individually or in combination. They are as follows:

1. Redesign the primary amino acid structure of the susceptible region such that it is not recognized by proteases including shortening the susceptible region to make it less susceptible to proteases.
2. Redirect the expressed Cry6Aa toxin to a sub-cellular or extracellular compartment where it is not accessible to proteases.
3. Down regulate or inhibit proteases in the cellular environment where the subject toxins accumulate.
4. Maintain the association of the CTP to the core protein by redirecting the expressed Cry6Aa to the endoplasmic reticulum, to allow the core-CTP disulfide bond to remain intact. Under such circumstances, the Cry6Aa protein retains insecticidal activity following proteolysis.
5. Increase the affinity between the core protein and CTP, in the event proteolysis occurs, through protein engineering. Such methods are well known in the art of protein engineering and include engineering hydrogen bonds between the core and CTP polypeptides. Another way is to engineer in salt bridges between the non-covalently linked peptides. A third means is to engineer hydrophobic interactions between the CTP and core protein. A fourth method is to engineer new or the existing disulfide bonds such that they are less susceptible to reduction.

By “isolated” applicants mean that the nucleotide or polypeptide molecules have been removed from their native environment and have been placed in a different environment by the hand of man. Thus, isolated nucleotide and polypeptide molecules include DNA or protein molecules that have been purified, concentrated, or otherwise rendered substantially free of *Bacillus thuringiensis* cellular material. Embodiments of isolated engineered Cry6Aa insecticidal polypeptide or nucleotide molecules can have less than about 30%, less than about 20%, less than about 10%, less than about 9%, less than about 8%, less than about 7%, less than about 6%, less than about 5%, less than about 4%, less than about 3% or less than about 2%, or less than about 1% (by dry weight) of contaminating protein (e.g., from *Bacillus thuringiensis*). When the isolated engineered Cry6Aa insecticidal polypeptide or nucleotide embodiments is recombinantly produced, then the culture medium material, chemical precursors, and/or non-engineered Cry6Aa insecticidal polypeptide or nucleotide represent less than about 30%, less than about 20%, less than about 10%, less than about 5%, less than about 4%, less than about 3% or less than about 2%, or less than about 1% (by dry weight) of the isolated engineered Cry6Aa insecticidal polypeptide or nucleotide.

Cry6Aa and variants are potential pyramid partners for Cry34Ab1/Cry35Ab and other corn rootworm insecticidal agents due to its potency and unique sequence and structural identity. In addition, it does not compete for binding sites on WCR brush boarder membrane vesicles with Cry34Ab1/Cry35Ab1 or Cry3Aa (Li et al, 2013). Transgenic plants expressing Cry6Aa in the cytosol have not been efficacious; analysis shows that the protein is susceptible to proteolytic processing and possible inactivation as similar to that noted in Example 3. One strategy to limit proteolysis is to direct the recombinant protein to sub cellular compartments (reviewed by Benchabane, 2008) as describe in Example 1. Another strategy to limit proteolysis and possible inactivation is through protein engineering.

Engineered Cry6Aa Insecticidal Toxins.

The invention encompasses insecticidally active engineered Cry6Aa variants thereof. By the term “variant,” applicants intend to include fragments, certain deletion and insertion mutants, substitution and certain fusion or chimeric proteins.

The invention includes DIG-177 insecticidal protein variants having a toxin segment that is 90%, 91%, 92%, 93, 94%, 95%, 96%, 97%, 98%, or 99% identical to amino acids 1 to 475 of SEQ ID NO:2. Variants may be made by making random mutations or the variants may be designed. In the case of designed mutants, there is a high probability of generating variants with similar activity to the native toxin when amino acid identity is maintained in critical regions of the toxin which account for biological activity or are involved in the determination of three-dimensional configuration which ultimately is responsible for the biological activity. A high probability of retaining activity will also occur if substitutions are conservative. Amino acids may be placed in the following classes: non-polar, uncharged polar, basic, and acidic. Conservative substitutions whereby an amino acid of one class is replaced with another amino acid of the same type are least likely to materially alter the biological activity of the variant. Table 1 provides a listing of examples of amino acids belonging to each class.

TABLE 1

Biochemical classes of amino acids

| Class of Amino Acid | Examples of Amino Acids |
|---|---|
| Nonpolar Side Chains | Ala, Val, Leu, Ile, Pro, Met, Phe, Trp |
| Uncharged Polar Side Chains | Gly, Ser, Thr, Cys, Tyr, Asn, Gln |
| Acidic Side Chains | Asp, Glu |
| Basic Side Chains | Lys, Arg, His |
| Beta-branched Side Chains | Thr, Val, Ile |
| Aromatic Side Chains | Tyr, Phe, Trp, His |

In some instances, non-conservative substitutions can also be made. The critical factor is that these substitutions must not significantly detract from the biological activity of the toxin. Variants include polypeptides that differ in amino acid sequence due to mutagenesis. Variant proteins encompassed by the present invention are biologically active, that is they continue to possess the desired biological activity of the native protein, that is, retaining pesticidal activity.

Variant proteins can also be designed that differ at the sequence level but that retain the same or similar overall essential three-dimensional structure, surface charge distribution, and the like. See, for example, U.S. Pat. No. 7,058,515; Larson et al. (2002); Stemmer (1994a, 1994b, 1995) and Crameri et al. (1996a, 1996b, 1997). U.S. Pat. No. 8,513,492 B2.

Nucleic Acids.

Isolated nucleic acids and complements thereof encoding engineered Cry6Aa insecticidal toxins are one aspect of the present invention. The term "isolated" is defined herein above. Because of the redundancy of the genetic code, a variety of different DNA sequences can encode the amino acid sequences disclosed herein. It is well within the skill of a person trained in the art to create these alternative DNA sequences encoding the same, or essentially the same, insecticidal proteins.

Gene Synthesis.

Genes encoding the engineered Cry6Aa insecticidal proteins described herein can be made by a variety of methods well-known in the art. For example, synthetic gene segments and synthetic genes can be made by phosphite tri-ester and phosphoramidite chemistry (Caruthers et al., 1987), and commercial vendors are available to perform gene synthesis on demand. Full-length genes can be assembled in a variety of ways including, for example, by ligation of restriction fragments or polymerase chain reaction assembly of overlapping oligonucleotides (Stewart and Burgin, 2005). Further, terminal gene deletions and additions can be made by PCR amplification using site-specific terminal oligonucleotides.

Nucleic acids encoding engineered Cry6Aa insecticidal proteins can be made for example, by synthetic construction by methods currently practiced by any of several commercial suppliers. (e.g. U.S. Pat. No. 7,482,119). These genes, or portions or variants thereof, may also be constructed synthetically, for example, by use of a gene synthesizer and the design methods of, for example, U.S. Pat. No. 5,380,831. Alternatively, variations of synthetic or naturally occurring genes may be readily constructed using standard molecular biological techniques for making point mutations, additions, and/or deletions. Fragments of these genes can also be made using commercially available exonucleases or endonucleases according to standard procedures. For example, enzymes such as Bal31 or site-directed mutagenesis can be used to systematically cut off nucleotides from the ends of these genes. Also, gene fragments which encode active toxin fragments may be obtained using a variety of restriction enzymes.

Given the amino acid sequence for an engineered Cry6Aa insecticidal protein, a coding sequence can be designed by reverse translating the coding sequence using synonymous codons preferred by the intended host, and then refining the sequence using alternative synonymous codons to remove sequences that might cause problems in transcription, translation, or mRNA stability. Further, synonymous codons may be employed to introduce stop codons in the non-engineered Cry6Aa reading frames (i.e. reading frames 2, 3, 4, 5 and 6) to eliminate spurious long open reading frames.

Quantifying Polypeptide or Nucleic Acid Sequence Identity.

The percent identity of two amino acid sequences or of two nucleic acid sequences is determined by first aligning the sequences for optimal comparison purposes. The percent identity between the two sequences is a function of the number of identical positions shared by the sequences (i.e. percent identity=number of identical positions/total number of positions (e.g. overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of such an algorithm is that of Altschul et al. (1990), and Karlin and Altschul (1990), modified as in Karlin and Altschul (1993), and incorporated into the BLASTN and BLASTX programs. BLAST searches may be conveniently used to identify sequences homologous (similar) to a query sequence in nucleic or protein databases. BLASTN searches can be performed, (score=100, word length=12) to identify nucleotide sequences having homology to claimed nucleic acid molecules of the invention. BLASTX searches can be performed (score=50, word length=3) to identify amino acid sequences having homology to claimed insecticidal protein molecules of the invention.

Gapped BLAST (Altschul et al., 1997) can be utilized to obtain gapped alignments for comparison purposes. Alternatively, PSI-Blast can be used to perform an iterated search that detects distant relationships between molecules (Altschul et al., 1997). When utilizing BLAST, Gapped BLAST, and PSI-Blast programs, the default parameters of the respective programs can be used. See, www.ncbi.nlm.nih.gov.

A non-limiting example of a mathematical algorithm utilized for the comparison of sequences is the ClustalW algorithm (Thompson et al., 1994). ClustalW compares sequences and aligns the entirety of the amino acid or DNA sequence, and thus can provide data about the sequence conservation of the entire amino acid sequence or nucleotide sequence. The ClustalW algorithm is used in several commercially available DNA/amino acid analysis software packages, such as the ALIGNX module of the Vector NTI Program Suite (Invitrogen, Inc., Carlsbad, Calif.). When aligning amino acid sequences with ALIGNX, one may conveniently use the default settings with a Gap open penalty of 10, a Gap extend penalty of 0.1 and the blosum63mt2 comparison matrix to assess the percent amino acid similarity (consensus) or identity between the two sequences. When aligning DNA sequences with ALIGNX, one may conveniently use the default settings with a Gap open penalty of 15, a Gap extend penalty of 6.6 and the swgapdnamt comparison matrix to assess the percent identity between the two sequences.

Another non-limiting example of a mathematical algorithm utilized for the comparison of sequences is that of Myers and Miller (1988). Such an algorithm is incorporated into the wSTRETCHER program, which is part of the wEMBOSS sequence alignment software package (available at emboss.sourceforge.net/). wSTRETCHER calculates an optimal global alignment of two sequences using a modification of the classic dynamic programming algorithm which uses linear space. The substitution matrix, gap insertion penalty and gap extension penalties used to calculate the alignment may be specified. When utilizing the wSTRETCHER program for comparing nucleotide sequences, a Gap open penalty of 16 and a Gap extend penalty of 4 can be used with the scoring matrix file EDNAFULL. When used for comparing amino acid sequences, a Gap open penalty of 12 and a Gap extend penalty of 2 can be used with the EBLOSUM62 scoring matrix file.

A further non-limiting example of a mathematical algorithm utilized for the comparison of sequences is that of Needleman and Wunsch (1970), which is incorporated in the sequence alignment software packages GAP Version 10 and wNEEDLE (emboss.sourceforge.net/). GAP Version 10 may be used to determine sequence identity or similarity using the following parameters: for a nucleotide sequence, % identity and % similarity are found using GAP Weight of 50 and Length Weight of 3, and the nwsgapdna. cmp scoring matrix. For amino acid sequence comparison, % identity or % similarity are determined using GAP weight of 8 and length weight of 2, and the BLOSUM62 scoring program.

wNEEDLE reads two input sequences, finds the optimum alignment (including gaps) along their entire length, and writes their optimal global sequence alignment to file. The algorithm explores all possible alignments and chooses the best, using a scoring matrix that contains values for every possible residue or nucleotide match. wNEEDLE finds the alignment with the maximum possible score, where the score of an alignment is equal to the sum of the matches taken from the scoring matrix, minus penalties arising from opening and extending gaps in the aligned sequences. The substitution matrix and gap opening and extension penalties are user-specified. When amino acid sequences are compared, a default Gap open penalty of 10, a Gap extend penalty of 0.5, and the EBLOSUM62 comparison matrix are used. When DNA sequences are compared using wNEEDLE, a Gap open penalty of 10, a Gap extend penalty of 0.5, and the EDNAFULL comparison matrix are used.

Equivalent programs may also be used. By "equivalent program" is intended any sequence comparison program that, for any two sequences in question, generates an alignment having identical nucleotide or amino acid residue matches and an identical percent sequence identity when compared to the corresponding alignment generated by ALIGNX, wNEEDLE, or wSTRETCHER. The % identity is the percentage of identical matches between the two sequences over the reported aligned region (including any gaps in the length) and the % similarity is the percentage of matches between the two sequences over the reported aligned region (including any gaps in the length).

Alignment may also be performed manually by inspection.

Recombinant Hosts.

The insecticidal protein-encoding genes of the subject invention can be introduced into a wide variety of microbial, fungal, or plant hosts. Expression of the insecticidal protein gene results, directly or indirectly, in the intracellular production and maintenance of the pesticidal protein. With suitable microbial hosts, e.g. *Pseudomonas*, the microbes can be applied to the environment of the pest, where they will proliferate and be ingested. The result is control of the pest. Alternatively, the microbe hosting the pesticidal protein gene can be treated under conditions that prolong the activity of the protein and stabilize the recombinant host cell. The treated cell, which comprises a treated insecticidal polypeptide of the invention that retains the insecticidal activity, can be applied to the environment of the target pest to control for the pest.

Where the B.t. insecticidal protein gene is introduced via a suitable DNA construct, e.g., a vector, into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type indigenous microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms such as bacteria, e.g. genera *Pseudomonas, Erwinia, Serratia, Klebsiella, Xanthomonas, Streptomyces, Rhizobium, Sinorhizobium, Rhodopseudomonas, Methylophilius, Agrobacterium, Acetobacter, Lactobacillus, Arthrobacter, Azotobacter, Leuconostoc*, and *Alcaligenes*. Of particular interest are such phytosphere bacterial species as *Pseudomonas syringae, Pseudomonas fluorescens, Serratia marcescens, Acetobacter xylinum, Agrobacterium tumefaciens, Agrobacterium radiobacter, Rhodopseudomonas spheroides, Xanthomonas campestris, Sinorhizobium meliloti* (formerly *Rhizobium meliloti*), *Alcaligenes eutrophus*, and *Azotobacter vinelandii*. Of further interest are fungi, particularly yeast, e.g. genera *Saccharomyces, Cryptococcus, Kluyveromyces, Sporobolomyces, Rhodotorula*, and *Aureobasidium*, and of particular interest are phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Of particular interest are the pigmented microorganisms.

Isolated Toxin Polypeptides and Compositions of the Invention.

The engineered Cry6Aa insecticidal toxin polypeptides of the invention can be treated or prepared, for example, to make a formulated pesticide composition. Examples of formulated pesticide compositions include protein composition, sprayable protein composition, a bait matrix, or other delivery systems. In one example, B.t. cells or recombinant host cells expressing an engineered Cry6Aa insecticidal protein of the invention are cultured using standard art media and fermentation techniques. Upon completion of the fermentation cycle, the B.t. spores or other recombinant host cells and/or insecticidal protein crystals from the fermentation broth can be isolated by methods known in the art. B.t. spores or recombinant host cells also can be treated prior to being applied or formulated for application to plants. For example, isolated B.t. spores and/or toxin crystals can be chemically treated to prolong insecticidal activity and thereby include a treated polypeptide of the invention. Methods of growing B.t. pesticidal polypeptides in recombinant hosts and then treating the B.t. to prolong pesticidal activity are known and have been published. See, e.g., U.S. Pat. Nos. 4,695,462, and 4,695,455 and Gaertner et al., 1993.

The isolated or treated engineered Cry6Aa insecticidal protein of the invention can be formulated into compositions of finely-divided particulate solids granules, pellets, wettable powders, dusts, aqueous suspensions or dispersions, emulsions, spray, liquid concentrate, or other insecticide formulations. These insecticide formulations are made by combining an engineered Cry6Aa insecticide polypeptide herein with adjuvants, diluents, surfactants, dispersants, inert carriers and other components to facilitate handling and application to control one or more target pests. Such formulation ingredients are known in the art, as are methods of application and methods of determining levels of the B.t. spores and/or isolated engineered Cry6Aa polypeptide crystals that provide desired insecticidal activity.

Methods for Controlling Insect Pests.

When an insect ingests an effective amount of engineered Cry6Aa insecticidal protein disclosed herein, which is delivered via an insecticide composition (e.g., a formulated protein composition (s), sprayable protein composition(s), a bait matrix, transgenic plant expression, or another delivery system), the results are typically death of the insect, or the insects do not feed upon the source which makes the pesticidal protein available to the insects. The term "delivered" or "delivering" herein is meant to include any method of placing or providing on or in plant tissue an insecticidally effective amount of the protein toxin. This includes expressing an insecticidal protein in the cells of the plant, or applying an effective amount to any surface of the plant.

The subject protein insect toxins can be "applied" or provided to contact the target insects in a variety of ways. For example, the engineered Cry6Aa insecticidal protein of the invention can be applied after being formulated with adjuvants, diluents, carriers, etc. to provide compositions in the form of finely-divided particulate solids, granules, pellets, wettable powders, dusts, aqueous suspensions or dispersions, and emulsions. Alternatively, the engineered Cry6Aa insecticidal polypeptide can be delivered by transgenic plants (wherein the protein is produced by and present in the plant) and are well-known in the art. Expression of the toxin genes can also be achieved selectively in specific tissues of the plants, such as the roots, leaves, etc. This can be accomplished via the use of tissue-specific promoters, for example. Spray-on applications are another example and are also known in the art. The subject proteins can be appropriately formulated for the desired end use, and then sprayed (or otherwise applied) onto the plant and/or around the plant/to the vicinity of the plant to be protected—before an infestation is discovered, after target insects are discovered, both before and after, and the like. Bait granules, for example, can also be used and are known in the art.

Transgenic Plants.

The engineered Cry6Aa insecticidal proteins disclosed herein can be used to protect practically any type of plant from damage by an insect pest. Examples of such plants include potato, eggplant, tomato, pepper, tobacco, and other plants in the nightshade family. Other examples of such plants include maize, sunflower, soybean, cotton, canola, rice, sorghum, wheat, barley, vegetables, ornamentals, peppers (including hot peppers), sugar beets, fruit, and turf, to name but a few. Methods for transforming plants are well known in the art, and illustrative transformation methods are described in the Examples.

A preferred embodiment of the subject invention is genetically transformed plants with genes encoding engineered Cry6Aa insecticidal proteins and variants. The transformed plants are resistant to attack by an insect target pest by virtue of the presence of controlling amounts of the subject insecticidal proteins or variants in the cells of the transformed plant. By incorporating functional genetic material that encodes an insecticidal protein of the invention, the adult or larvae die after consuming the plant tissue containing the claimed toxins. Numerous members of the monocotyledonous and dicotyledonous classifications have been transformed. Transgenic agronomic crops as well as fruits and vegetables are of commercial interest. Such crops include but are not limited to maize, rice, soybeans, canola, sunflower, alfalfa, sorghum, wheat, cotton, peanuts, tomatoes, potatoes, and the like. A more preferred group of crops is maize, soybeans, and cotton. The most preferred crop is maize.

Several techniques exist for introducing foreign genetic material into plant cells, and for obtaining plants that stably maintain and express the introduced gene. Such techniques include acceleration of genetic material coated onto microparticles directly into cells (U.S. Pat. Nos. 4,945,050 and 5,141,131). Plants may be transformed using *Agrobacterium* technology, see U.S. Pat. No. 5,177,010, European Patent No. EP131624B1, European Patent No. EP159418B1, European Patent No. EP176112B1, U.S. Pat. No. 5,149,645, EP120516B1, U.S. Pat. Nos. 5,464,763, 4,693,976, European Patent No. EP116718B1, European Patent No. EP290799B1, European Patent No. EP320500B1, European Patent No. EP604662B1, U.S. Pat. Nos. 7,060,876, 6,037,526, 6,376,234, European Patent No. EP292435B1, U.S. Pat. Nos. 5,231,019, 5,463,174, 4,762,785, 5,608,142, and 5,159,135. Other transformation technology includes WHISKERS™ technology, see U.S. Pat. Nos. 5,302,523 and 5,464,765. Electroporation technology has also been used to transform plants, see WO1987006614, U.S. Pat. Nos. 5,472,869, 5,384,253, WO199209696, U.S. Pat. No. 6,074,877, WO1993021335, and U.S. Pat. No. 5,679,558. In addition to numerous technologies for transforming plants, the type of tissue which is contacted with the foreign genes may vary as well. Such tissue would include but would not be limited to embryogenic tissue, callus tissue type I and type II, hypocotyl, meristem, and the like. Almost all plant tissues may be transformed during dedifferentiation using appropriate techniques within the skill of an artisan.

Genes encoding engineered Cry6Aa insecticidal proteins can be inserted into plant cells using a variety of techniques which are well known in the art as disclosed above. For example, a large number of cloning vectors comprising a marker that permits selection of the transformed microbial cells and a replication system functional in *Escherichia coli* are available for preparation and modification of foreign genes for insertion into higher plants. Such manipulations may include, for example, the insertion of mutations, truncations, additions, or substitutions as desired for the intended use. The vectors comprise, for example, pBR322, pUC series, M13mp series, pACYC184, etc. Accordingly, the sequence encoding the protein toxins or variants of the invention can be inserted into the vector at a suitable restriction site. The resulting plasmid is used for transformation of *E. coli*, the cells of which are cultivated in a suitable nutrient medium, then harvested and lysed so that workable quantities of the plasmid are recovered. Sequence analysis, restriction fragment analysis, electrophoresis, and other biochemical-molecular biological methods are generally carried out as methods of analysis. After each manipulation, the DNA sequence used can be cleaved and joined to the next DNA sequence. Each manipulated DNA sequence can be cloned in the same or other plasmids.

The use of T-DNA-containing vectors for the transformation of plant cells has been intensively researched and sufficiently described in European Patent No. EP120516B1; Lee and Gelvin (2008), Fraley et al. (1986), and An et al. (1985), and is well established in the field.

Once the inserted DNA has been integrated into the plant genome, it is relatively stable throughout subsequent generations. The vector used to transform the plant cell normally contains a selectable marker gene encoding a protein that confers on the transformed plant cells tolerance to a herbicide or resistance to an antibiotic, such as phosphinothricin Bialaphos, Kanamycin, Neomycin, G418, Bleomycin, Hygromycin, or a gene which codes for tolerance to glyphosate, methotrexate, imidazolinones, sulfonylureas and triazolopyrimidine herbicides, such as chlorosulfuron, bromoxynil, dalapon and the like. Of further interest are genes conferring tolerance to herbicides such as haloxyfop, quizalofop, diclofop, and the like, as exemplified by AAD genes (US Patent Application No. 20090093366). The individually employed selectable marker gene should accordingly permit the selection of transformed cells while the growth of cells that do not contain the inserted DNA is suppressed by the selective compound.

A large number of techniques are available for inserting DNA into a host plant cell. Those techniques include transformation with T-DNA delivered by *Agrobacterium tumefaciens* or *Agrobacterium rhizogenes* as the transformation agent. Additionally, fusion of plant protoplasts with liposomes containing the DNA to be delivered, direct injection of the DNA, biolistics transformation (microparticle bombardment), or electroporation, as well as other possible methods, may be employed.

In a preferred embodiment of the subject invention, plants will be transformed with genes wherein the codon usage of the protein coding region has been optimized for plants. See, for example, U.S. Pat. No. 5,380,831. For example, an engineered Cry6Aa insecticidal toxin of the invention can be optimized for expression in a dicot such as potato, eggplant, tomato, pepper, tobacco, or other plants in the nightshade family. The engineered Cry6Aa insecticidal toxin of the invention can also be optimized for expression in other dicots such as soybean and cotton, or in monocots such as *Zea mays* (corn). Also, advantageously, plants encoding a truncated toxin may be used. The truncated toxin typically will encode about 55% to about 80% of the full length toxin. Methods for creating synthetic B.t. genes for use in plants are known in the art (Stewart 2007).

Regardless of transformation technique, the gene is preferably incorporated into a gene transfer vector adapted to express the B.t. insecticidal toxin genes and variants in the plant cell by including in the vector a plant promoter. In addition to plant promoters, promoters from a variety of sources can be used efficiently in plant cells to express foreign genes. For example, promoters of bacterial origin, such as the octopine synthase promoter, the nopaline synthase promoter, the mannopine synthase promoter; promoters of viral origin, such as the 35S and 19S promoters of cauliflower mosaic virus (CaMV), and the like may be used. Plant-derived promoters include, but are not limited to ribulose-1,6-bisphosphate (RUBP) carboxylase small subunit (ssu), beta-conglycinin promoter, phaseolin promoter, ADH (alcohol dehydrogenase) promoter, heat-shock promoters, ADF (actin depolymerization factor) promoter, and tissue specific promoters. Promoters may also contain certain enhancer sequence elements that may improve the transcription efficiency. Typical enhancers include but are not limited to ADH1-intron 1 and ADH1-intron 6. Constitutive promoters may be used. Constitutive promoters direct continuous gene expression in nearly all cells types and at nearly all times (e.g. actin, ubiquitin, CaMV 35S). Tissue specific promoters are responsible for gene expression in specific cell or tissue types, such as the leaves or seeds (e.g. zein, oleosin, napin, ACP (Acyl Carrier Protein)), and these promoters may also be used. Promoters may also be used that are active during a certain stage of the plants' development as well as active in specific plant tissues and organs. Examples of such promoters include but are not limited to promoters that are root specific, pollen-specific, embryo specific, corn silk specific, cotton fiber specific, seed endosperm specific, phloem specific, and the like.

Under certain circumstances it may be desirable to use an inducible promoter. An inducible promoter is responsible for expression of genes in response to a specific signal, such as: physical stimulus (e.g. heat shock genes); light (e.g. RUBP carboxylase); hormone (e.g. glucocorticoid); antibiotic (e.g. tetracycline); metabolites; and stress (e.g. drought). Other desirable transcription and translation elements that function in plants may be used, such as 5 untranslated leader sequences, RNA transcription termination sequences and poly-adenylate addition signal sequences. Numerous plant-specific gene transfer vectors are known to the art.

Target Pests.

The engineered Cry6Aa insecticidal proteins of the invention are particularly suitable for use in control of insect pests. Coleopterans are one important group of agricultural, horticultural, and household pests which cause a large amount of damage each year. This large insect order encompasses foliar- and root-feeding larvae and adults, including members of, for example, the insect families—Chrysomelidae, Coccinellidae, Curculionidae, Dermestidae, Elateridae, Scarabaeidae, Scolytidae, and Tenebrionidae. Included within these families are leaf beetles and leaf miners in the family Chrysomelidae, potato beetles (e.g. Colorado potato beetle (*Leptinotarsa decemlineata* Say), grape *colaspis* (*Colaspis brunnea* Fabricius), cereal leaf beetle (*Oulema melanopus* Linnaeus), sunflower beetle (*Zygogramma exclamationis* Fabricius), and beetles in the family Coccinellidae (e.g. Mexican bean beetle (*Epilachna varivestis* Mulsant)). Further examples are chafers and other beetles in the family Scarabaeidae (e.g. Japanese beetle (*Popillia japonica* Newman), northern masked chafer (white grub, *Cyclocephala borealis* Arrow), southern masked chafer (white grub, *Cyclocephala immaculata* Olivier), European chafer (*Rhizotrogus majalis* Razoumowsky), white grub (*Phyllophaga crinita* Burmeister), carrot beetle (*Ligyrus gibbosus* De Geer), and chafers of the genera *Holotrichia* spp and

*Melolontha* spp.). Further examples of coleopteran insects are weevils (e.g. boll weevil (*Anthonomus grandis* Boheman), rice water weevil (*Lissorhoptrus oryzophilus* Kuschel), granary weevil (*Sitophilus grananus* Linnaeus), rice weevil (*Sitophilus oryzae* Linnaeus), and clover leaf weevil (*Hypera punctata* Fabricius)). Also included are maize billbug (*Sphenophorus maidis* Chittenden), flea beetles (e.g. corn flea beetle (*Chaetocnema pulicara* Melsheimer), and crucifer flea beetle (*Phyllotreta cruciferae* Goeze)), spotted cucumber beetle (*Diabrotica undecimpunctata*), and rootworms, (e.g. western corn rootworm (*Diabrotica virgifera virgifera* LeConte), northern corn rootworm (*Diabrotica barben* Smith & Lawrence), southern corn rootworm (*Diabrotica undecimpunctata howardi* Barber), the Mexican corn rootworm (*D. virgifera zeae* Krysan and Smith), *D. balteata* LeConte, *D. undecimpunctata tenella, D. speciosa* Germar, and *D. u. undecimpunctata* Mannerheim). Further examples of coleopteran pests are beetles of the family Rutelinae (shining leaf chafers) such as the genus *Anomala* (including *A. marginata, A. lucicola, A. oblivia* and *A. orientalis*). Additional coleopteran insects are carpet beetles from the family Dermestidae, wireworms from the family Elateridae (e.g. *Melanotus* spp., *Conoderus* spp., *Limonius* spp., *Agriotes* spp., *Ctenicera* spp., *Aeolus* spp.)), bark beetles from the family Scolytidae, and beetles from the family Tenebrionidae (e.g. *Eleodes* spp). Any genus listed above (and others), generally, can also be targeted as a part of the subject invention by insecticidal compositions including engineered Cry6Aa insecticidal polypeptide alone or in combination with another insecticidal agent. Any additional insects in any of these genera (as targets) are also included within the scope of this invention.

Use of engineered Cry6Aa insecticidal proteins to control coleopteran pests of crop plants is contemplated. In some embodiments, Cry proteins may be economically deployed for control of insect pests that include but are not limited to, for example, rootworms such as western corn rootworm (*Diabrotica virgifera virgifera* LeConte), northern corn rootworm (*Diabrotica barberi* Smith & Lawrence), southern corn rootworm (*Diabrotica undecimpunctata howardi* Barber), the Mexican corn rootworm (*D. virgifera zeae* Krysan and Smith), *D. balteata* LeConte, *D. undecimpunctata tenella, D. speciosa* Germar, and *D. u. undecimpunctata* Mannerheim, and grubs such as the larvae of *Cyclocephala borealis* (northern masked chafer), *Cyclocephala immaculate* (southern masked chafer), and *Popillia japonica* (Japanese beetle).

Lepidopterans are another important group of agricultural, horticultural, and household pests which cause a very large amount of damage each year. The invention provides use of engineered Cry6Aa insecticidal proteins in combination with other insecticides to control insect pests within this order. This insect order encompasses foliar- and root-feeding larvae and adults, including members of, for example, the insect families Archidae, Gelechiidae, Geometridae, Lasiocampidae, Lymantriidae, Noctuidae, Pyralidae, Sesiidae, Sphingidae, Tineidae, and Tortricidae. Lepidopteran insect pests include, but are not limited to: *Achoroia grisella, Acleris gloverana, Acleris variana, Adoxophyes orana, Agrotis ipsilon* (black cutworm), *Alabama argillacea, Alsophila pometaria, Amyelois transitella, Anagasta kuehniella, Anarsia lineatella, Anisota senatoria, Antheraea pernyi, Anticarsia gemmatalis, Archips* sp., *Argyrotaenia* sp., *Athetis mindara, Bombyx mori, Bucculatrix thurberiella, Cadra cautella, Choristoneura* sp., *Cochylls hospes, Colias eurytheme, Corcyra cephalonica, Cydia latiferreanus, Cydia pomonella, Datana integerrima, Dendrolimus sibericus, Desmia feneralis, Diaphania hyalinata, Diaphania nitidalis, Diatraea grandiosella* (southwestern corn borer), *Diatraea saccharalis* (sugarcane borer), *Ennomos subsignaria, Eoreuma loftini, Esphestia elutella, Erannis tilaria, Estigmene acrea, Eulia salubricola, Eupocoellia ambiguella, Eupoecilia ambiguella, Euproctis chrysorrhoea, Euxoa messoria, Galleria mellonella, Grapholita molesta, Harrisina americana, Helicoverpa subflexa, Helicoverpa zea* (corn earworm), *Heliothis virescens* (tobacco budworm), *Hemileuca oliviae, Homoeosoma electellum, Hyphantia cunea, Keiferia lycopersicella, Lambdina fiscellaria fiscellaria, Lambdina fiscellaria lugubrosa, Leucoma salicis, Lobesia botrana, Loxagrotis albicosta* (western bean cutworm), *Loxostege sticticalis, Lymantria dispar, Macalla thyrisalis, Malacosoma* sp., *Mamestra brassicae, Mamestra configurata, Manduca quinquemaculata, Manduca sexta, Maruca testulalis, Melanchra picta, Operophtera brumata, Orgyia* sp., *Ostrinia nubilalis* (European corn borer), *Paleacrita vemata, Papiapema nebris* (common stalk borer), *Papilio cresphontes, Pectinophora gossypiella, Phryganidia californica, Phyllonorycter blancardella, Pieris napi, Pieris rapae, Plathypena scabra, Platynota flouendana, Platynota stultana, Platyptilia carduidactyla, Plodia interpunctella, Plutella xylostella* (diamondback moth), *Pontia protodice, Pseudaletia unipuncta* (armyworm), *Pseudoplasia includens, Sabulodes aegrotata, Schizura concinna, Sitotroga cerealella, Spilonta ocellana, Spodoptera frugiperda* (fall armyworm), *Spodoptera exigua* (beet armyworm), *Thaurnstopoea pityocampa, Ensola bisselliella, Trichoplusia ni*, (cabbage looper), *Udea rubigalis, Xylomyges curiails*, and *Yponomeuta padella*.

Use of the engineered Cry6Aa insecticidal proteins to control parasitic nematodes including, but not limited to, root knot nematode (*Meloidogyne incognita*) and soybean cyst nematode (*Heterodera glycines*) is also contemplated.

Anti-Toxin Antibodies.

Antibodies to the toxins disclosed herein, or to equivalent toxins, or fragments of these toxins, can readily be prepared using standard procedures in this art. Such antibodies are useful to purify or detect the presence of the engineered Cry6Aa toxins.

Once the B.t. insecticidal protein has been isolated, antibodies specific for the protein may be raised by conventional methods that are well known in the art. Repeated injections into a host of choice over a period of weeks or months will elicit an immune response and result in significant anti-B.t. toxin serum titers. Preferred hosts are mammalian species and more highly preferred species are rabbits, goats, sheep, and mice. Blood drawn from such immunized animals may be processed by established methods to obtain antiserum (polyclonal antibodies) reactive with the B.t. insecticidal toxin. The antiserum may then be affinity purified by adsorption to the toxin according to techniques known in the art. Affinity purified antiserum may be further purified by isolating the immunoglobulin fraction within the antiserum using procedures known in the art. The resulting material will be a heterogeneous population of immunoglobulins reactive with the B.t. insecticidal toxin.

Anti-B.t. toxin antibodies may also be generated by preparing a semi-synthetic immunogen consisting of a synthetic peptide fragment of the B.t. insecticidal toxin conjugated to an immunogenic carrier. Numerous schemes and instruments useful for making peptide fragments are well known in the art. Many suitable immunogenic carriers such as bovine serum albumin or keyhole limpet hemocyanin are also well known in the art, as are techniques for coupling the immunogen and carrier proteins. Once the semi-synthetic immunogen has been constructed, the procedure for making antibodies specific for the B.t. insecticidal toxin fragment is identical to those used for making antibodies reactive with natural B.t. toxin.

Anti-B.t. toxin monoclonal antibodies (MAbs) are readily prepared using purified B.t. insecticidal protein. Methods for producing MAbs have been practiced for over 20 years and are well known to those of ordinary skill in the art. Repeated intraperitoneal or subcutaneous injections of purified B.t. insecticidal protein in adjuvant will elicit an immune response in most animals Hyperimmunized B-lymphocytes are removed from the animal and fused with a suitable fusion partner cell line capable of being cultured indefinitely. Preferred animals whose B-lymphocytes may be hyperimmunized and used in the production of MAbs are mammals. More preferred animals are rats and mice and most preferred is the BALB/c mouse strain.

Numerous mammalian cell lines are suitable fusion partners for the production of hybridomas. Many such lines are available from the American Type Culture Collection (ATCC, Manassas, Va.) and commercial suppliers. Preferred fusion partner cell lines are derived from mouse myelomas and the HL-1 Friendly myeloma-653 cell line (Ventrex, Portland, Me.) is most preferred. Once fused, the resulting hybridomas are cultured in a selective growth medium for one to two weeks. Two well known selection systems are available for eliminating unfused myeloma cells, or fusions between myeloma cells, from the mixed hybridoma culture. The choice of selection system depends on the strain of mouse immunized and myeloma fusion partner used. The AAT selection system, described by Taggart and Samloff (1983), may be used; however, the HAT (hypoxanthine, aminopterin, thymidine) selection system, described by Littlefield (1964), is preferred because of its compatibility with the preferred mouse strain and fusion partner mentioned above. Spent growth medium is then screened for immunospecific MAb secretion. Enzyme linked immunosorbent assay (ELISA) procedures are best suited for this purpose; though, radioimmunoassays adapted for large volume screening are also acceptable. Multiple screens designed to consecutively pare down the considerable number of irrelevant or less desired cultures may be performed. Cultures that secrete MAbs reactive with the B.t. insecticidal toxin may be screened for cross-reactivity with known B.t. insecticidal toxins. MAbs that preferentially bind to the preferred B.t. insecticidal toxin may be isotyped using commercially available assays. Preferred MAbs are of the IgG class, and more highly preferred MAbs are of the $IgG_1$ and $IgG_{2a}$ subisotypes.

Hybridoma cultures that secrete the preferred MAbs may be sub-cloned several times to establish monoclonality and stability. Well known methods for sub-cloning eukaryotic, non-adherent cell cultures include limiting dilution, soft agarose and fluorescence activated cell sorting techniques. After each subcloning, the resultant cultures preferably are re-assayed for antibody secretion and isotype to ensure that a stable preferred MAb-secreting culture has been established.

The anti-B.t. toxin antibodies are useful in various methods of detecting the claimed B.t. insecticidal toxin of the instant invention, and variants or fragments thereof. It is well known that antibodies labeled with a reporting group can be used to identify the presence of antigens in a variety of milieus. Antibodies labeled with radioisotopes have been used for decades in radioimmunoassays to identify, with great precision and sensitivity, the presence of antigens in a variety of biological fluids. More recently, enzyme labeled antibodies have been used as a substitute for radiolabeled antibodies in the ELISA assay. Further, antibodies immunoreactive to the B.t. insecticidal toxin of the present invention can be bound to an immobilizing substance such as a polystyrene well or particle and used in immunoassays to determine whether the B.t. toxin is present in a test sample.

Detection Using Probes.

A further method for identifying the polypetides and genes of the subject invention is through the use of oligonucleotide probes. These probes are detectable nucleotide sequences. These sequences may be rendered detectable by virtue of an appropriate radioactive label or may be made inherently fluorescent as described in U.S. Pat. No. 6,268,132. As is well known in the art, if the probe molecule and nucleic acid sample hybridize by forming strong base-pairing bonds between the two molecules, it can be reasonably assumed that the probe and sample have substantial sequence homology. Preferably, hybridization is conducted under stringent conditions by techniques well-known in the art, as described, for example, in Keller and Manak (1993). Detection of the probe provides a means for determining in a known manner whether hybridization has occurred. Such a probe analysis provides a rapid method for identifying toxin-encoding genes of the subject invention. The nucleotide segments which are used as probes according to the invention can be synthesized using a DNA synthesizer and standard procedures. These nucleotide sequences can also be used as PCR primers to amplify genes of the subject invention.

Hybridization.

As is well known to those skilled in molecular biology, similarity of two nucleic acids can be characterized by their tendency to hybridize. As used herein the terms "stringent conditions" or "stringent hybridization conditions" are intended to refer to conditions under which a probe will hybridize (anneal) to its target sequence to a detectably greater degree than to other sequences (e.g. at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to pH 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide Exemplary low stringency conditions include hybridization with a buffer solution of 30% to 35% formamide, 1 M NaCl, 1% SDS (sodium dodecyl sulfate) at 37° C. and a wash in 1× to 2×SSC (20×SSC=3.0 M NaCl/0.3 M trisodium citrate) at 50° C. to 55° C. Exemplary moderate stringency conditions include hybridization in 40% to 45% formamide, 1.0 M NaCl, 1% SDS at 37° C. and a wash in 0.5× to 1×SSC at 55° C. to 60° C. Exemplary high stringency conditions include hybridization in 50% formamide, 1 M NaCl, 1% SDS at 37° C. and a wash in 0.1×SSC at 60° C. to 65° C. Optionally, wash buffers may comprise about 0.1% to about 1% SDS.

Duration of hybridization is generally less than about 24 hours, usually about 4 to about 12 hours.

Specificity is typically the function of post-hybridization washes, the critical factors being the ionic strength and temperature of the final wash solution. For DNA/DNA hybrids, the thermal melting point ($T_m$) is the temperature (under defined ionic strength and pH) at which 50% of a complementary target sequence hybridizes to a perfectly matched probe. $T_m$ is reduced by about 1° C. for each 1% of mismatching; thus, $T_m$, hybridization conditions, and/or wash conditions can be adjusted to facilitate annealing of sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, highly stringent conditions can utilize a hybridization and/or wash at 1° C., 2° C., 3° C., or 4° C. lower than the $T_m$; moderately stringent conditions can utilize a hybridization and/or wash at 6° C., 7° C., 8° C., 9° C., or 10° C. lower than the $T_m$, and low stringency conditions can utilize a hybridization and/or wash at 11° C., 12° C., 13° C., 14° C., 15° C., or 20° C. lower than the $T_m$.

$T_m$ (in ° C.) may be experimentally determined or may be approximated by calculation. For DNA-DNA hybrids, the $T_m$ can be approximated from the equation of Meinkoth and Wahl (1984):

$$T_m(°\text{ C.})=81.5°\text{ C.}+16.6(\log M)+0.41(\%\ GC)-0.61(\%\ \text{formamide})-500/L;$$

where M is the molarity of monovalent cations, % GC is the percentage of guanosine and cytosine nucleotides in the DNA, % formamide is the percentage of formamide in the hybridization solution (w/v), and L is the length of the hybrid in base pairs. Alternatively, the $T_m$ is described by the following formula (Beltz et al., 1983).

$$T_m(°\text{ C.})=81.5°\text{ C.}+16.6(\log\ [\text{Na+}])+0.41(\%\ \text{GC})-0.61(\%\ \text{formamide})-600/L$$

where [Na+] is the molarity of sodium ions, % GC is the percentage of guanosine and cytosine nucleotides in the DNA, % formamide is the percentage of formamide in the hybridization solution (w:v), and L is the length of the hybrid in base pairs Using the equations, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) and Ausubel et al. (1995). Also see Sambrook et al. (1989).

Hybridization of immobilized DNA on Southern blots with radioactively labeled gene-specific probes may be performed by standard methods (Sambrook et al., supra.). Radioactive isotopes used for labeling polynucleotide probes may include 32P, 33P, 14C, or 3H. Incorporation of radioactive isotopes into polynucleotide probe molecules may be done by any of several methods well known to those skilled in the field of molecular biology. (See, e.g. Sambrook et al., supra.) In general, hybridization and subsequent washes may be carried out under stringent conditions that allow for detection of target sequences with homology to the claimed insecticidal protein encoding genes. For double-stranded DNA gene probes, hybridization may be carried out overnight at 20° C. to 25° C. below the $T_m$ of the DNA hybrid in 6×SSPE, 5×Denhardt's Solution, 0.1% SDS, 0.1 mg/mL denatured DNA (20×SSPE is 3M NaCl, 0.2 M $NaHPO_4$, and 0.02M EDTA (ethylenediamine tetra-acetic acid sodium salt); 100×Denhardt's Solution is 20 gm/L Polyvinylpyrollidone, 20 gm/L Ficoll type 400 and 20 gm/L Bovine Serum Albumin (fraction V)).

Washes are typically carried out as follows:

Twice at room temperature for 15 minutes in 1×SSPE, 0.1% SDS (low stringency wash).

Once at $T_m$—20° C. for 15 minutes in 0.2×SSPE, 0.1% SDS (moderate stringency wash).

For oligonucleotide probes, hybridization may be carried out overnight at 10° C. to 20° C. below the $T_m$ of the hybrid in 6×SSPE, 5×Denhardt's solution, 0.1% SDS, 0.1 mg/mL denatured DNA. $T_m$ for oligonucleotide probes may be determined by the following formula (Suggs et al., 1981).

$$T_m(°\text{ C.})=2(\text{number of } T/A \text{ base pairs})+4(\text{number of } G/C \text{ base pairs})$$

Washes are typically carried out as follows:

Twice at room temperature for 15 minutes 1×SSPE, 0.1% SDS (low stringency wash).

Once at the hybridization temperature for 15 minutes in 1×SSPE, 0.1% SDS (moderate stringency wash).

Probe molecules for hybridization and hybrid molecules formed between probe and target molecules may be rendered detectable by means other than radioactive labeling. Such alternate methods are intended to be within the scope of this invention.

By the use of the term "genetic material" herein, it is meant to include all genes, nucleic acid, DNA and RNA. The term "dsRNA" refers to double-stranded RNA. For designations of nucleotide residues of polynucleotides, DNA, RNA, oligonucleotides, and primers, and for designations of amino acid residues of proteins, standard IUPAC abbreviations are employed throughout this document. Nucleic acid sequences are presented in the standard 5 to 3' direction, and protein sequences are presented in the standard amino (N) terminal to carboxy (C) terminal direction.

Unless specifically indicated or implied, the terms "a", "an", and "the" signify "at least one" as used herein.

All percentages are by weight and all solvent mixture proportions are by volume unless otherwise noted. All temperatures are in degrees Celsius.

All patents, patent applications, provisional applications, and publications referred to or cited herein are incorporated by reference in their entirety to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. These examples should not be construed as limiting.

EXAMPLE 1

Transformation of DIG-177 (Wild Type Cry6Aa) with Transit Peptides into Corn Design of a Plant-Optimized Version of the Coding Sequence for the DIG-177 B.t. Insecticidal Polypeptide.

One skilled in the art of plant molecular biology will understand that multiple DNA sequences may be designed to encode a single amino acid sequence. A common means of increasing the expression of a coding region for a protein of interest is to tailor the coding region in such a manner that its codon composition resembles the overall codon composition of the host in which the gene is destined to be expressed. Guidance regarding the design and production of synthetic genes can be found in, for example, WO1997013402, U.S. Pat. Nos. 6,166,302, and 5,380,831.

A DNA sequence having a maize codon bias was designed and synthesized to produce a DIG-177 insecticidal protein in transgenic monocot plants (SEQ ID NO:2). A codon usage table for maize (*Zea mays* L.) was calculated from hundreds of protein coding sequences obtained from sequences deposited in GenBank (www.ncbi.nlm.nih.gov). A rescaled maize codon set was calculated after omitting any synonymous codon used less than about 10% of total codon uses for that amino acid.

To derive a maize-codon-optimized DNA sequence encoding the DIG-177 protein, variants or chimeras of DIG-177 insecticidal proteins, or insecticidal fragments thereof, are the subject of codon substitutions to the experimentally determined (native) DIG-177 DNA sequence (SEQ ID NO:1) encoding the pesticidal protein were made such that the resulting DNA sequence had the overall codon composition of the maize-optimized codon bias table. Further refinements of the sequences were made to eliminate undesirable restriction enzyme recognition sites, potential plant intron splice sites, long runs of A/T or C/G residues, and other motifs that might interfere with mRNA stability, transcription, or translation of the coding region in plant cells. Other changes were made to introduce desired restriction enzyme recognition sites, and to eliminate long internal Open Reading Frames (frames other than +1). These changes were all made within the constraints of retaining the maize-biased rescaled codon composition. A maize-optimized DNA sequence encoding DIG-177 polypeptide is disclosed as SEQ ID NO:3.

Construct Design and Plasmid List.

All of the constructs were designed for standard nuclear transformation, nuclear transcription and cytoloslic translation. The maize ubiquitin promoter and maize perxoxidase 5 3' untranslated regions were used to regulate the DIG-177 coding regions. Herbicide selection was provided by the AAD-1 gene (Wright et al. 2010) under the control of the Sugarcane Bacilliform virus promoter with a maize streak virus leader and maize alcohol dehydrogenase intron; the 3' untranslated region was from the maize lipase gene. Seven different sub cellular compartments were tested for DIG-177 accumulation. A summary of the transit peptides used is shown in Table 2. Table 2

Summary of With the exception of the apoplast, multiple transit peptides were tested for each compartment. The native DIG-177 initiating methionine codon was removed for amino terminal transit peptides. The transit peptides were adjusted to reflect a similar codon bias as the DIG-177 coding region.

TABLE 2

Summary of plasmids, coding regions and transit peptides
(N denotes amino terminal location; C denotes carboxy terminal location)

| Plasmid | DIG-177 Coding Region | SEQ ID NO | Target Compartment | Transit Peptide Location | Transit Petide Reference |
|---|---|---|---|---|---|
| pDAB117247 | IRDIG.552.60 | 4 | Mitochondrion | N-terminal | Fallahi et al., 2005 |
| pDAB117248 | IRDIG.552.61 | 6 | Mitochondrion | N-terminal | White et al., 1989 |
| pDAB117249 | IRDIG.552.62 | 8 | Mitochondrion and Chloroplast | N-terminal | Rokov-Plavec et al., 2008 |
| pDAB117250 | IRDIG.552.63 | 10 | Peroxisome | C-terminal | Hahn, et al. 1999; Gnanasambandam, et al., 2012 |
| pDAB117251 | IRDIG.552.64 | 12 | Peroxisome | C-terminal | Mano, et al. 2002; Hyunjong, et al., 2006 |
| pDAB117252 | IRDIG.552.65 | 14 | Peroxisome | N-terminal | Mano, et al., 2002 |
| pDAB117253 | IRDIG.552.66 | 16 | Vacuole | N-terminal | Holwerda, et al., 1992 |
| pDAB117254 | IRDIG.552.67 | 18 | Vacuole | N-terminal C-terminal | Cervelli, et al., 2000; US20090193541 2012 |
| pDAB117255 | IRDIG.552.68 | 20 | Vacuole | N-terminal C-terminal | Miao, et al., 2006 |
| pDAB117256 | IRDIG.552.69 | 22 | Apoplast | N-terminal | Hood, et al., 2007 |
| pDAB117257 | IRDIG.552.70 | 24 | Endoplasmic Reticulum | N-terminal C-terminal | Hood, et al., 2007 |
| pDAB117258 | IRDIG.552.71 | 26 | Nucleus | N-terminal | Varagona, et al., 1994; Cao, et al., 2013 |
| pDAB117259 | IRDIG.552.72 | 28 | Nucleus | C-terminal | Varagona, et al., 1994; Cao, et al., 2013 |
| pDAB117260 | IRDIG.552.73 | 30 | Chloroplast | N-terminal | WO2013/116768 A1 |
| pDAB117261 | IRDIG.552.74 | 32 | Chloroplast | N-terminal | WO2013/116768 A1 |

$T_0$ and $T_1$ Experimental Design.

A goal of twenty five transgenic events per construction was set with fifteen being low copy. All events were analyzed for insert copy number and DIG-177 leaf accumulation by LC/MS/MS. The low copy events were set aside, the non-expressers discarded and the expressers carried forward for $T_1$ seed production. This ensured recovery of partially efficacious events which might be lost at the To bioassay. Multi copy expressing events were bioassayed at the To stage; those which passed were saved for $T_1$ seed production and further analysis. The $T_1$ seed were planted, the plants analyzed for protein (LC/MS/MS and Western blot) in both leaf and root tissues, five siblings were tested in bioassay.

*Agrobacterium* Culture Initiation.

The *Agrobacterium tumefaciens* strains containing the DIG-177 plant transformation constructions (Table 2) were obtained from the DAS Recombinant Culture Collection. The cultures were streaked from glycerol stocks onto *Agrobacterium* minimal medium and incubated at 20° C. in the dark for 3 days. *Agrobacterium* cultures were then streaked onto a plate of YEP medium and incubated at 20° C. in the dark for 1 day.

On the day of an experiment, a mixture of inoculation medium and acetosyringone was prepared in a volume appropriate to the number of constructs in the experiment. A 1 M stock solution of acetosyringone in 100% dimethyl sulfoxide was added to the flask containing inoculation medium in a volume appropriate to make a final acetosyringone concentration of 200 μM.

For each construct, 1-2 loops of *Agrobacterium* from the YEP plate were suspended in 15 ml of the inoculation medium/acetosyringone mixture inside a sterile, disposable, 50 ml centrifuge tube and the optical density of the solution at 600 nm ($O.D._{600}$) was measured in a spectrophotometer. The suspension was then diluted down to 0.25-0.35 $O.D._{600}$ using additional Inoculation medium/acetosyringone mixture. The tube of *Agrobacterium* suspension was then placed horizontally on a platform shaker set at 75 rpm at room temperature for between 1 and 4 hours before use.

Ear Sterilization and Embryo Isolation.

Ears from *Zea mays* cultivar B104 were produced in greenhouse facilities and harvested 10-12 days post pollination. Harvested ears were de-husked and surface-sterilized by immersion in a 20% solution of commercial bleach (Ultra Clorox® Germicidal Bleach, 6.15% sodium hypochlorite) and two drops of soap, for 20 minutes, followed by three rinses in sterile, deionized water inside a laminar flow hood. Immature zygotic embryos (1.8-2.2 mm long) were aseptically excised from each ear and distributed into one or more micro-centrifuge tubes containing 2.0 ml of *Agrobacterium* suspension into which 2 μl of 10% Break-Thru® S233 surfactant had been added.

*Agrobacterium* Co-Cultivation.

Upon completion of the embryo isolation activity the tube of embryos was closed and placed on a rocker platform for 5 minutes. The contents of the tube were then poured onto a plate of co-cultivation medium and the liquid *Agrobacterium* suspension was removed with a sterile, disposable, transfer pipette. The co-cultivation plate containing embryos was placed at the back of the laminar flow hood with the lid ajar for 30 minutes; after which time the embryos were oriented with the scutellum facing up using a microscope. The co-cultivation plate with embryos was then returned to the back of the laminar flow hood with the lid ajar for a further 15 minutes. The plate was then closed, sealed with 3M Micropore™ tape, and placed in an incubator at 25° C. with 24 hours/day light at approximately 60 μmol $m^{-2}$ $s^{-1}$ photosynthetically active radiation (PAR).

Callus Selection and Regeneration of Transgenic Events.

Following the co-cultivation period, embryos were transferred to Resting medium. No more than 36 embryos were moved to each plate. The plates were incubated at 27° C. with 24 hours/day light at approximately 50 μmol $m^{-2}$ $s^{-1}$ PAR for 7-10 days. Callused embryos were then transferred onto Selection I medium. The plates were incubated at 27° C. with 24 hours/day light at approximately 50 μmol $m^{-2}$ $s^{-1}$ PAR for 7 days. Callused embryos were then transferred to Selection II medium. The plates were incubated at 27° C. with 24 hours/day light at approximately 50 μmol $m^{-2}$ $s^{-1}$ PAR for 14 days.

At this stage resistant calli were moved to pre-regeneration medium. The plates were incubated at 27° C. with 24 hours/day light at approximately 50 μmol $m^{-2}$ $s^{-1}$ PAR for 7 days. Regenerating calli were then transferred to regeneration medium in Phytatrays™ and incubated at 28° C. with 16 hours light/8 hours dark per day at approximately 150 μmol $m^2$ $s^{-1}$ PAR for 7-14 days or until shoots develop. Small shoots with primary roots were then isolated and transferred to Robusting medium. Rooted plantlets about 6 cm or taller were transplanted into soil and moved to a growth chamber for hardening off.

Genomic DNA Isolation for PCR from Plant Tissues.

Tissue samples, leaf tear equivalent to 2 leaf punches, were collected in 96-well collection plates (Qiagen, Hilden, Germany). Tissue disruption was performed with a Klecko™ tissue pulverizer (Garcia Manufacturing, Visalia, Calif.) in the Biosprint96 AP1 lysis buffer with one stainless steel bead. Following tissue maceration, the genomic DNA was isolated in high throughput format. Genomic DNA was diluted 2:3 DNA/$H_2O$ prior to setting up the qPCR reaction to achieve appropriate Cp scores.

Hydrolysis Probe Assay.

Transgene detection by hydrolysis probe assay was performed by real-time PCR. Assays were designed at Dow AgroSciences for the genes of interest (GOI) Cry6Aa (IR-DIG522.28) using LightCycler® Probe Design Software 2.0. The RNA detection assays were run as single reactions using Maize TIP41-like as the reference. For amplification, LightCycler® 480 Probes Master mix (Roche Applied Science) was prepared at 1× final concentration in a 10 μL volume biplex reaction containing 0.4 μM of each primer and 0.2 μM of each probe. A two step amplification reaction was performed with an extension at 60° C. for 40 seconds with fluorescence acquisition. Cp scores, the point at which the florescence signal crosses the background threshold using the fit points algorithm (LightCycler® software release 1.5) and the Absolute Quant module (based on the ΔΔCt method), were used to perform the analysis of real time PCR data.

$T_0$ Greenhouse.

Plant bearing selected events were transplanted into 5 gallon pots. Shoot bags were placed over the shoots prior to silk emergence to prevent cross-contamination by stray pollen. The second shoot was then covered and used for pollinations. Silks were cut back the day prior to pollination to provide an even brush to accept pollen. Pollen from the inbred B104 was used for all pollinations. Reciprocal crosses were performed when possible. Ears were peeled back at 21 days after pollination to enhance dry down followed by complete harvest (ear removed from plant) at 42 days after pollinations. Ears were placed in the dryer for 1 week, followed by seed processing (shelling, counting, packaging).

Leaf Sampling for Western Blot and LC/MS/MS Analyses.

The plants were sampled at the V-3 to V-5 stage within a day of bioassay collection. Two 6 mm diameter leaf samples were stored in a 96 well cluster tube rack at −80° C. until the day of analysis. Two Daisy™ steel BB's and 300 μl of extraction buffer (PBS solution containing 0.05% of Tween 20 and 5 μl/ml of Sigma protease inhibitors) was added to each tube. The samples were milled in a Kelco bead mill for 3 minutes, on maximum setting. Samples were centrifuged at 3,000×g for 5 minutes; 100 μl of the supernatant was transferred to an empty sample tube. Another 100 μl of extraction buffer was added to the plant sample and bead milled 3 additional minutes, centrifuged and 100 μl of this extract was combined with the first 100 μl. The combined supernatants were mixed and analyzed the same day as the extraction.

Root Sampling for Western Blot and LC/MS/MS Analyses.

The complete root system was collected, washed with water, and stored at −80° C. for all of the $T_1$ plants at the V-3 to V-5 stage. Each plant remained a separate sample in individual plastic bags. Each root system was ground with dry ice in an industrial food processor, and the dry ice sublimed at −20° C. keeping the samples frozen. The ground, sublimed frozen samples were then lyophilized for 2 weeks. Portions of the lyophilized root systems were weighed and placed in individual cluster tubes, 96 well format. The samples were prepared as described above for the leaf sampling.

DIG-177 Quantitation by LC/MS/MS.

Leaf samples were extracted for each plant in 25 mM ammonium bicarbonate+0.05% Tween 20. The samples were extracted twice by bead mill and then pooled. For root samples, ground and lyophilized root tissue was weighed into a vial and extracted as described above. The samples were denatured with 6 mM DTT at 95° C. for 20 minutes. After the samples were cooled, 1 μg of trypsin was added to each sample and the samples were digested at 37° C. for 16 hours. Following digestion the samples were treated with 1% formic acid, incubated for 30 minutes at 4° C., and centrifuged at 4,000 rpm for 10 minutes. The digested samples were analyzed by LC/MS/MS. A standard curve of DIG-177 peptide standards was prepared in digested B104 matrix (prepared as described above). The standard curve was linear from 0.488-31.25 ng/mL. The samples were analyzed on Waters Acquity binary pump LC and a Sciex QTRAP 6500 using an Acquity UPLC BEH130 C18, 1.7 μm 2.1×50 mm column Each sample was injected at 20 μl and eluted using a quick gradient (95%-45% A over 1 min, 45-10% A over 1 min, hold 10% 1 min, 10-95% 1 min: Buffer A: Water+0.1% Formic Acid, Buffer B: Acetonitrile+0.1% Formic Acid). Two peptides were tracked (m/z 694.820 and m/z 586.778) for each sample. Quantitation was based off the most sensitive transition, m/z 694.820 to m/z 912.417.

Western Blot.

Conventional electrophoresis and blotting, (Gallagher, et al., 2008) methods were used with Invitrogen™ devices and basic reagents. A rabbit anti-Cry6a antibody was the primary antibody for the detection of Cry6a in leaf and root. All proteins were detected with a fluorescence detection system and an Avidin-Biotin, Alkaline phosphatase detection system.

$T_0$ and $T_1$ Maize Root Bioassay.

Non-diapausing *Diabrotica virgifera* (Western corn rootworm, WCR) eggs were received in soil from Crop Characteristics (Farmington, Minn.) and incubated at 28° C. and 60% RH for 10 days. On the $10^{th}$ day after start of incubation (approximately one day before expected hatch), the eggs were prepared for bioassay. The soil was rinsed from the eggs. The eggs were suspended in a 0.15% water agar solution at a concentration of approximately 100-200 eggs per 0.5 ml and placed into hatch plates. The number of viable eggs on the hatch plates were counted to determine the approximate concentration of eggs in the suspension and thus to calculate the volume of suspension needed to add to bioassay plants to achieve the desired infestation. The plates were maintained in a 28° C. incubator in a dark box.

Planting and Preparation for WCR Bioassay.

Transformed plants from the laboratory ($T_0$s) were moved to the conviron where they were maintained until they reached the V3-V4 growth stage. The V3-V4 healthy plants with good root systems were moved to the greenhouse. Plants that were weak, small, or had poor root development were left in the conviron until healthy enough for bioassay. After one to two days in the greenhouse, the plants were transplanted into root trainers filled with Metro-Mix soil.

Seeds for control plants were planted directly into Metro Mix soil in root trainer pots weekly beginning at least two weeks before the expected availability of the first To plants for bioassay. About 4 days after transplanting the T0 plants, along with five control plants of each type at the same growth stage were infested with WCR eggs.

Negative control plants were the following: the B104 inbred, the 7SH382 Herculex RW (HX-RW) inbred and 101556, a yellow fluorescent protein transgenic. The positive controls were corn line 7SH382RW Transgenic Herculex RW (HX-RW).

Plants were infested with approximately 200 eggs/plant. Hatch rate was assumed to be about 50%, therefore each plant was expected to have about 100 larvae hatch and feed on the roots. Watering was monitored carefully throughout the course of the bioassay to ensure that each pot stayed moist.

Two weeks after infestation, each plant was scored for root damage, beginning with the control plants. Each plant was carefully removed from the root trainer pot, keeping the root mass intact. The top one to two inches of soil were scraped from the root and the resulting exposed area of the roots were washed with water in order to clearly view feeding damage at the base of the plants (top of the nodal roots). Feeding damage was scored using the 0.0 to 1.0 root damage rating scale that is derived from a published field corn root damage rating scale 0.0 to 3.0 (J. D. Oleson et al 2005) for greenhouse corn seedling root damage rating need. The negative controls (RW inbred, B104 and 101556) were expected to have high damage (about 0.75 to 1.0 root rating), and the positive control (transgenic Herculex™ RW (HX-RW)), was expected to have low damage, (0.0 to 0.25 root rating). After evaluation of the control plants was completed, then the To plants were scored, employing a pass/fail method (0 to 1.00 scoring) and disturbing the root ball as little as possible. Passing plants were immediately transplanted to 5-gallon pots with promix-50-50 soil. After all plants were scored, passing plants were treated with a soil application of 1 tsp of FORCE (a.i. Tefluthrin) and cared for appropriately throughout development.

$T_1$ Greenhouse.

Selected plants were transplanted into 5 gallon pots. Shoot bags were placed over the shoots prior to silk emergence to prevent cross-contamination by stray pollen. The second shoot was then covered and used for pollinations. Silks were cut back the day prior to pollinations to provide an even brush to accept pollen. Pollen from the tassel of the plant was used to pollinate the ear on the same plant. Self pollinations were performed when possible. If a self pollination could not be performed then B104 pollen was taken to the transgenic ear. Ears were peeled back at 21 days after pollination to enhance dry down followed by complete harvest (ear removed from plant) at 42 days after pollinations. Ears were placed in the dryer for 1 week, followed by seed processing (shelling, counting, packaging in pre-printed envelopes).

Protein Accumulation Results from $T_0$ Events.

A range from 8 to 28 DIG-177 expressing low copy events were obtained with an overall transformation frequency of 9%. All of the regenerated events that passed the molecular analysis screen from each of the fifteen constructs were analyzed for DIG-177 leaf protein accumulation by LC/MS/MS. The average protein accumulation is shown in Table 3. Average To leaf protein accumulation level ranged from 0 ng/cm$^2$ to 98.9 ng/cm$^2$, with construct pDAB117255, targeted to the prevacuole, having the lowest average accumulation and construct pDAB117261, targeted to the chloroplast, having the highest average accumulation.

TABLE 3

Average DIG-177 protein leaf accumulation as determined by LC/MS/MS.

| Construction | Compartment | Accumulation $T_0$ ng/cm$^2$ | Accumulation $T_1$ ng/cm$^2$ |
|---|---|---|---|
| pDAB117247 | Mitochondrion | 3.5 | 18.9 |
| pDAB117248 | Mitochondrion | 21.0 | 88.7 |
| pDAB117249 | Mitochondrion Chloroplast | 0.3 | 20.1 |
| pDAB117250 | Peroxisome | 6.3 | 46.3 |
| pDAB117251 | Peroxisome | 13.1 | 64.6 |
| pDAB117252 | Peroxisome | 0.0 | 11.6 |
| pDAB117253 | Vacuole | 1.5 | 32.2 |
| pDAB117254 | Vacuole | 5.9 | 53.4 |
| pDAB117255 | Vacuole | 0.0 | 56.1 |
| pDAB117256 | Apoplast | 0.9 | 24.0 |
| pDAB117257 | Endoplasmic Reticulum | 27.9 | 93.8 |
| pDAB117258 | Nucleus | 8.4 | 47.4 |
| pDAB117259 | Nucleus | 8.8 | 114.1 |
| pDAB117260 | Chloroplast | 44.4 | 232.9 |
| pDAB117261 | Chloroplast | 98.9 | 731.5 |

Leaf tissue from select $T_0$ events for each of the fifteen constructs was analyzed by Western blot. The proteins were directed to the specific compartments by the use of transit peptides. The precursor proteins thereby had greater molecular weights than the full-length wild type DIG-177 protein at 54.2 kDa. Depending on the compartment, the transit peptides (TraP) may or may not be cleaved upon translocation, resulting in a mature form of the protein. The predicted molecular weights of the precursor and mature forms of the proteins are shown in Table 4.

TABLE 4

Key to plasmid, protein names, target compartment and molecular weights of the transit peptide modified DIG-177 proteins used in this study.

| Plasmid | Protein | Target Compartment | Precursor Protein Mwt kDa | Mature Protein Mwt kDa | Expected Transit Peptide (TraP) Processing |
|---|---|---|---|---|---|
| | DIG-177 | Cytosol | | 54.2 | |
| pDAB117247 | IRDIG.552.60 | Mitochondrion | 59.4 | 54.1 | N-term TraP cleaved |
| pDAB117248 | IRDIG.552.61 | Mitochondrion | 57.1 | 54.1 | N-term TraP cleaved |
| pDAB117249 | IRDIG.552.62 | Mito/Chloro. | 62.4 | 62.4 | N-term TraP cleaved |
| pDAB117250 | IRDIG.552.63 | Peroxisome | 54.8 | 54.8 | TraP not cleaved |
| pDAB117251 | IRDIG.552.64 | Peroxisome | 55.5 | 55.5 | TraP not cleaved |
| pDAB117252 | IRDIG.552.65 | Peroxisome | 59.2 | 59.2 | TraP not cleaved |
| pDAB117253 | IRDIG.552.66 | Vacuole | 58.3 | 54.1 | N-term TraP cleaved |
| pDAB117254 | IRDIG.552.67 | Vacuole | 57.4 | 54.9 | N-term TraP cleaved C-term TraP not cleaved |
| pDAB117255 | IRDIG.552.68 | Pre Vacuole | 64.3 | 61.2 | N-term TraP cleaved C-term TraP no cleaved |
| pDAB117256 | IRDIG.552.69 | Apoplast | 56.5 | 54.1 | N-term TraP cleaved |
| pDAB117257 | IRDIG.552.70 | ER | 57.2 | 54.7 | N-term TraP cleaved C-term TraP no cleaved |
| pDAB117258 | IRDIG.552.71 | Nucleus | 56.7 | 56.7 | TraP not cleaved |
| pDAB117259 | IRDIG.552.72 | Nucleus | 56.5 | 56.5 | TraP not cleaved |
| pDAB117260 | IRDIG.552.73 | Chloroplast | 61.7 | 54.1 | N-term TraP cleaved |
| pDAB117261 | IRDIG.552.74 | Chloroplast | 61.5 | 54.1 | N-term TraP cleaved |

Overall, the highest average protein accumulation levels were seen from the two constructs that targeted the DIG-177 protein to the chloroplast, pDAB117260 and pDAB11261 respectively. The protein accumulation for these two constructs was higher than what was seen in the previous cytosolic experiment which averaged 23.6 ng/cm$^2$. Conversely, constructs that targeted the vacuole, prevacuole and the apoplast resulted in the lowest leaf protein accumulation.

Non-transgenic negative control samples did not show any background bands which reacted with the DIG-177 antisera. In the transgenic samples, a distinct band of apparent mature protein (comigrating with DIG-177 standard) consistent with the transit peptide being removed, was detected in many samples. In some cases, bands larger than the mature protein were also detected, consistent with detection of the precursor proteins (transit peptides not removed). All constructions showed smears of DIG-177 material from the apparent mature band 54 kDa to approximately 40 kDa, consistent with partial degradation of the protein.

Bioassay Results of $T_0$ Events.

Root systems from events representing the 15 different backgrounds were challenged for two weeks with WCR larvae at the V3-V4 stage of development. The samples were then scored using a pass/fail rating system as described above for damage to the root system. A total of 228 events were assayed of which 15 events scored a 'pass' and were saved for $T_1$ bioassay.

Analysis of $T_1$ Events. The $T_1$ events were analyzed for transgenic protein production and accumulation in both leaf and root tissues. Average leaf protein accumulation increased for each of the fifteen backgrounds from the $T_0$ to $T_1$ generation and ranged from 11.6 to 731.5 ng/cm$^2$ (Table 3 above). $T_1$ root accumulation was significantly lower than $T_1$ leaf accumulation in all backgrounds (Table 5).

TABLE 5

Event average DIG-177 $T_1$ protein accumulation for leaf and root tissues as determined by LC/MS/MS

| Construction | Avg μg protein/g dry wt leaf | Avg μg protein/dry wt root |
|---|---|---|
| pDAB117247 | 43.4 | 1.3 |
| pDAB117248 | 126.2 | 2. |
| pDAB117249 | 29.6 | 0.9 |
| pDAB117250 | 44.4 | 1.7 |
| pDAB117251 | 55.9 | 2.6 |
| pDAB117252 | 20.3 | 0. |
| pDAB117253 | 36.9 | 4.1 |
| pDAB117254 | 57.7 | 5.2 |
| pDAB117255 | 99.6 | 3.0 |
| pDAB117256 | 29.6 | 2.2 |
| pDAB117257 | 126.7 | 12.3 |
| pDAB117258 | 72.8 | 3.1 |
| pDAB117259 | 131.8 | 13.3 |
| pDAB117260 | 364.2 | 12.4 |
| pDAB117261 | 1099.9 | 42.2 |

Both leaf and root tissue from each of the $T_1$ events were analyzed for protein stability by Western blot. The results were similar to those seen at $T_0$; distinct bands of apparent mature protein (comigrating with DIG-177 standard) consistent with the transit peptide being removed. In addition, bands larger than the mature protein were also detected, consistent with precursor proteins. Finally all constructions resulted in smear of DIG-177 material from approximately 54 kDa to approximately 40 kDa, consistent with partial degradation of the protein.

Bioassay Results of $T_1$ Events.

Five plants from events representing the 15 different backgrounds were challenged for two weeks with WCR larvae at the V3-V4 stage of development. The samples were graded as before for damage to the root system; plants with a Root Rating≤0.5 were considered passing. None of the tested events passed this bioassay; none of the events were significantly different than the negative control with regard to root protection. Therefore localization to various subcellular compartments alone, using transit peptides, did not sufficiently protect DIG-177 from protease degradation.

Western Blot Analysis.

Figure 6:
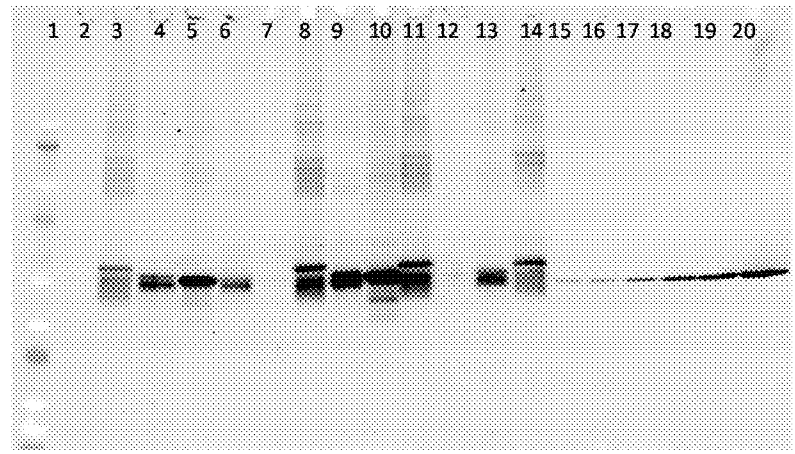
FIG. 6 shows the results of the $T_1$ maize leaf expression Western blot experiments.

The results of the $T_1$ maize leaf expression experiments are shown in FIG. 6. Western analysis showed no expression of Cry6Aa proteins in the negative controls; B104 (lane 2) and pDAB115782 (lane 3) or in the transformation controls containing YFP and PAT (lane 12). The six far right lanes are protein standards of DIG-1000 (47.3 kDa).

The pDAB117261 (DIG-177) lanes 3, 8, 11, and 14 contain $T_1$ samples as control to compare processing with DIG 1000. The results were similar to those seen at To; distinct bands of apparent mature protein (comigrating with DIG-177 standard) consistent with the transit peptide being removed. In addition, bands larger than the mature protein were also detected, consistent with precursor proteins. This control construct produced a smear of DIG-177 material from approximately 54 kDa to approximately 40 kDa, consistent with partial degradation of the protein.

The results for pDAB126937 (DIG-1000) targeted to the peroxisome are located in lanes 5 and 10 of FIG. 6. There is one major band produced at the correct size corresponding to the DIG 1000 standard. Lane 10 contains one distinct smaller band slightly lower than 40 kDa smear produced with DIG 177, indicating one specific processing site.

The DIG-1000 targeted to the mitochondria pDAB126938 are located in lanes 4, 6, 9 and 13 of FIG. 6. This construct produced two bands one of the correct size and one slightly higher, likely representing the precursor protein. These data are consistent with the DIG-1000 coding sequence expressing a plant cell stable, insecticidal protein useful for western corn rootworm control.

EXAMPLE 2

Identification of DIG-177 Disulfide Bonds

Recombinant Protein Expression Plasmids. DIG-177 and DIG-177 variant coding sequences were cloned into individual *Pseudomonas* expression vector, pDOW1169. The expression vectors were then transformed into *Pseudomonas fluorescens* and the resulting transformed colonies were characterized and stored.

Recombinant Protein Expression. One milliliter glycerol stocks were inoculated into 500 mL Ultra™ of production medium in a 2.5 L Ultra Yield flask (Thomson Instrument Company, Oceanside, Calif.) and incubated for 24 hrs at 30° C., shaking at 225 rpm with a 1 inch throw. Expression was induced with 150 μL of 1M IPTG. Cells were incubated at 25° C. for 24 hrs, at which time a 0.5 mL sample was taken and flasks were removed from the shaker. Cultures were harvested by centrifugation at either 19,000 rpm for 10 minutes in a JA-20 rotor (Beckman Coulter, Brea, Calif.) or 11,409 rpm for 15 mM in a FIBERLite™ F12-6×500 LEX rotor (Thermo Scientific); cell pastes were stored at −80° C.

Recombinant Protein Enrichment.

DIG-177 and the variant proteins, described below, accumulated in *P. fluorescens* as inclusion bodies (IBs). The cell paste was thawed at 4° C. The cells were suspended to 10% w/v in lysis buffer (50 mM Tris, pH 7.5, 200 mM NaCl, 10% Glycerol, 20 mM EDTA, 0.5% Triton X-100, 5 mM benzamidine, and 1 mM DTT—added just prior to use) and mixed through with a homogenizer. The slurry was passed two times through a Microfluidics Microfluidizer (Westwood, Mass. USA) at 12000+ psi. The lysate was centrifuged at 14,000×g at 4° C. for 40 mM The supernatant was retained. The inclusion body pellet was re-suspended to 10% w/v in lysis buffer and lysozyme (L-7651; Sigma-Aldrich, St. Louis, Mo.) was added to a final concentration of 400 μg/mL. The suspension was incubated at room temperature (~20° C.) for 60 mM, and centrifuged. The inclusion body pellet was washed with lysis buffer one time and with lysis buffer minus Triton™ X-100 a second time. Finally, the inclusion body pellet was re-suspended to 30% w/v in 10 mM EDTA solution and stored at −80° C. in 2 mL aliquots. The sample purity was analyzed by SDS-PAGE (NuPAGE Bis-Tris gels, Protocol Pub. No. MAN0007894 Rev. A.0, Invitrogen Life technologies, Waltham, Mass.).

Inclusion Body Solubilization.

The IB paste stored at −80° C., was thawed at 4° C. overnight and then centrifuged at 23,000×g for 25 min at 4° C., and the supernatant was removed. The IB pellet was suspended to 20% (w/v) in 100 mM CAPS, pH 11, and solubilized at room temperature for 2 hours. The sample was centrifuged as above and the supernatant collected. The buffer was exchanged into 10 mM CAPS, pH 10, by PD-10 desalting column. The protein was quantified by Bradford protein assay following the "Quick Start™ Bradford Protein Assay—Bio-Rad" (Bio-Rad, Hercules, Calif.) protocol. The standard was BSA (bovine-serum-albumin, Albumin Standard from Pierce, Grand Island, N.Y.).

SDS-PAGE.

SDS-PAGE was run following the protocol NuPAGE Bis-Tris gels from Invitrogen Life technologies (Protocol Pub. No. MAN0007894 Rev. A.0, Ref. 2). Briefly, samples were mixed with denaturing sample buffer (Invitrogen) plus 5 mM DTT (for reducing PAGE) or minus DTT (for non reducing PAGE) and heated at 95° C. for 5 minutes. The samples were loaded onto Invitrogen Bis/Tris gel. The gel was run with MOPS or MES running buffer under 200 V for ~43 minutes. The gel was stained with Coomassie blue staining solution (Bio-Rad) for 30 minutes and de-stained with de-staining solution (7% Acetic acid and 5% Methanol in water) until the background cleared.

Intact Molecular Weight Analysis/Charged State Distribution.

Intact mass analysis was performed on an Agilent 1200 HPLC/MSD TOF 1969A system using a Michrom desalting trap heated to 50° C. Each sample was diluted to a concentration of 0.2 μg/μL in 10 mM CAPS, pH 11, buffer. Samples were also analyzed after being reduced with 50 mM TCEP ((2-carboxyethyl) phosphine hydrochloride) for 10 minutes. Approximately 1 μg protein was injected on column. The sample was eluted using a gradient (10% buffer D for 1 minute, 10-60% buffer D over 2 minutes, 60-98% buffer D over 2 minutes, 10% buffer D for 1 min), where buffer A is 0.1% Formic Acid in water and buffer D is 70% Isopropanol, 20% Acetonitrile, 10% water+0.1% Formic Acid. The mass was calculated using the Mass Hunter Qualitative Analysis software and the maximum entropy de-convolution algorithm.

Mass spectrometric analysis of DIG-177 under both reducing and not reducing conditions verified two disulfide bonds present in the protein. DIG-177 has five cysteine residues located at positions 88, 162, 402, 404, and 451. To identify the residues contributing to the disulfide bonds, mutations were made at selected cysteins and the recombinant proteins were expressed. The intact molecule weights of the variant proteins were analyzed in the presence or absence of a reducing agent. Under these conditions, each disulfide bond present in the protein is expected to account for an m/z increase of 2 when reduced with TCEP. Upon reduction of the wild type protein (DIG-177), an m/z increase of 3.8 was observed indicating that two disulfide bonds are present in the protein. DIG-614 (SEQ ID NO:35), 615 (SEQ ID NO:37), 618 (SEQ ID NO:43), 619 (SEQ ID NO:45), 983 (SEQ ID NO:47), and 984 (SEQ ID NO:49) each showed a mass change of approximately +2 upon reduction, representing a single disulfide bond. Each of these variants was expected to result in elimination of the disulfide bond between cysteine residues 88 and 451. Based on these data, an additional disulfide bond was present involving two of the cysteine residues 162, 402, or 404. Mutants DIG-616 (SEQ ID NO:39) and 617 (SEQ ID NO:41), which were expected to disrupt a disulfide bond involving Cys162, showed a change of approximately +4 upon reduction, again as with DIG-177, indicating the presence of two disulfide bonds. Since one of these disulfide bonds was found between cysteines 88 and 451, the second disulfide bond was shown by inference to be between cysteine residues 402 and 404.

TABLE 6

Intact MW of cysteine mutants plus and minus reduction with TCEP.

| Protein | Mutant | Expected Avg. Mass | Observed Avg. Mass w/o TCEP | Mass difference | PPM Error | Disulfide bonds | Observed Avg. Mass w/TCEP | Mass difference | PPM Error |
|---|---|---|---|---|---|---|---|---|---|
| DIG-177 | WT | 54075.9333 | 54072.1020 | 3.8313 | 70.85 | 2 | 54075.7579 | 0.1754 | 3.24 |
| DIG-614 | C88 > A | 54043.8672 | 54041.8036 | 2.0636 | 38.18 | 1 | 54043.8125 | 0.0547 | 1.01 |
| DIG-615 | C88 > S | 54059.8665 | 54057.6129 | 2.2536 | 41.69 | 1 | 54059.7123 | 0.1542 | 2.85 |
| DIG-616 | C162 > A | 54043.8672 | 54040.2870 | 3.5802 | 66.25 | 2 | 54043.8329 | 0.0343 | 0.63 |
| DIG-617 | C162 > S | 54059.8666 | 54055.9330 | 3.9336 | 72.76 | 2 | 54059.6086 | 0.2580 | 4.77 |
| DIG-618 | C451 > A | 54043.8672 | 54042.1269 | 1.7403 | 32.20 | 1 | 54044.0511 | −0.1839 | −3.40 |
| DIG-619 | C451 > S | 54059.8666 | 54058.3141 | 1.5525 | 28.72 | 1 | 54060.0444 | −0.1778 | −3.29 |
| DIG-983 | C88 > S; C451 > S | 54043.7999 | 54041.5638 | 2.2361 | 41.38 | 1 | 54044.7883 | −0.9884 | −18.29 |
| DIG-984 | C88 > A; C451 > A | 54011.8011 | 54010.2630 | 1.5381 | 28.48 | 1 | 54012.0540 | −0.2529 | −4.68 |

EXAMPLE 3

Characterization of Trypsin Treated DIG-177

In summary, trypsin treated DIG-177 (trypsin core, TC) consisted of a large fragment (LF; amino acids 12-390 of SEQ ID NO:50) and either of two small fragments (amino acids 444-475 (SEQ ID NO:51 or 451-475 SEQ ID NO:52) called carboxy terminal peptides (CTP). The LF and the CTP were found to be joined through a disulfide bond between cys88 and cys451. Under non-reducing conditions, the trypsin treated sample had insecticidal activity; and under reducing conditions, the fragments dissociated (LF and CTP) and activity decreased. Neither the LF nor the CTP showed insecticidal activity at the levels tested. These observations indicate that the CTP, attached to the LF, are necessary for maintaining activity of the toxin following trypsin proteolysis.

Overview of Trypsin Treated Samples Prepared, Characterized and Tested.

Four different samples were prepared, characterized, and bioassayed to determine which combination of peptides had WCR insecticidal activity (see FIG. 1).

Sample 1: Trypsin treated DIG-177, CTP present and disulfide bond linked to the LF.

Sample 2: Trypsin treated DIG-177, CTP present, the sample was treated with reducing agent after digestion; the reducing agent was then removed by dialysis.

Sample 3: Trypsin treated DIG-177, isolated LF

Sample 4: Trypsin treated DIG-177, isolated CTP

Trypsin Digestion.

The DIG-177 protein was produced in *Pseudomonas fluorescens* and purified as described in Example 2. The recombinant protein was treated with trypsin in a digestion buffer (100 mM CAPS buffer, pH 10.5, 5 mM $CaCl_2$, 5 mM $MgCl_2$) containing trypsin (TPCK treated Sigma-Aldrich, St. Louis, Mo.) to a final ratio of 15 parts protein to 1 part trypsin (W/W). The reaction was agitated with gentle rocking at room temperature. An aliquot was removed at each time point (5 min, 2 and 17 hours) for analysis, the digestion was stopped by addition of lithium dodecyl sulfate (LDS) sample buffer with 5 mM DTT and heating at 95° C. for 5 min The trypsin treated proteins were purified by ion exchange chromatography (IEC) using an AKTA protein purifier (Amersham Pharmacia Biotech, Piscataway, N.J.). The sample was diluted with 10 mM CAPS, pH 10, at 1:1 and filtered by a vacuum driven filter with a 0.22 μM membrane. The sample was injected over a pre-equilibrated HiTrap™ Q column (GE, Pittsburgh, Pa.) at 3 mL/min flow rate, the column was washed with ~25 mL of buffer A (50 mM CAPS, pH 10) and the protein was eluted with 20% buffer B (buffer A+1M NaCl), and then followed by 30%, 40%, and 50% buffer B. Each elution was ~25 mL. Fractions were collected from each elution based on UV absorbance, respectively. These fractions were analyzed by SDS-PAGE (see protocol NuPAGE Bis-Tris gels from Invitrogen Life technologies, Protocol Pub. No. MAN0007894 Rev. A.0).

The fractions that contained the target protein were pooled and concentrated to ~3 mL using a centrifugal filter device with 10 kDa molecular weight cut off (MWCO) membrane (Millipore, Billerica, Mass.). The sample buffer was exchanged into 10 mM CAPS, pH 10, by dialysis. The concentrated samples were transferred into a Slide-A-Lyzer™ dialysis cassette (Thermo Scientific). The cassettes were replaced in 4 L of 10 mM CAPS, pH 10, and dialyzed at 4° C. for overnight (~18 hours). The samples, assessed at greater than 95% purity by SDS-PAGE (as described in Example 2), were collected for WCR bioassay and/or characterization, respectively.

The protein concentration was measured by Bradford protein assay following the manufacturer's protocol "Quick Start™ Bradford Protein Assay—Bio-Rad" (Bio-Rad). The BSA (bovine-serum-albumin) was used as standard.

Sample 1: Preparation and Characterization of Trypsin Treated DIG-177 (LF Plus CTP).

Wild type DIG-177; SEQ ID NO:2) was digested with trypsin for 16 hours and run on an ion exchange column to remove the trypsin. The samples were analyzed by SDS-PAGE (as described in Example 2) under reducing-denaturing conditions. Undigested full-length material migrated at ~54 kDa, a small amount of dimer appeared at approximately ~108 kDa. DIG-177 can form detectable amounts of high molecular weight aggregates. The trypsin treated sample, before fractionation ran as a single band of approximately 43 kDa representing the LF, predicted to be residues 12-390, based on trypsin cleavage sites.

N-Terminal Sequencing.

The amino terminus of the LF was confirmed by Edman degradation N-terminal sequencing performed on a Shimadzu Protein Sequencer (Model PPSQ-33A) using basic Edman degradation chemistry. The protein sample was separated with SDS-PAGE under reducing condition, and then the proteins were blotted onto PVDF membrane by liquid transfer). The target protein bands were excised and loaded into a glass reaction chamber. Then chamber was inserted into the Sequencer and subjected to Edman degradation. A standard mix of 20 PTH-amino acids (Shimadzu, Kyoto, Japan) was run each time. The amino acid residues from each Edman degradation cycle were determined based on their retention times from the C-18 column compared to standards. This process was repeated sequentially to obtain the amino terminal sequence of the protein. Edman degradation determined the N-terminus of the LF to begin at residue 12 of SEQ ID NO:2.

Protein intact molecular weight analysis (as described in Example 2) was performed, without reduction, resulted in a dominant species with a mass of 46,844.19 Da and a minor species with a mass of 45,995.25 Da (Table 7). The de-convoluted intact MW avg. value of 46,844.19 Da matches the theoretical value (46,843.43 Da) expected for a protein containing polypeptide chains of 12-390 disulfide bonded to chain 444-475 (CTP1). The minor species with MW avg. of 45,995.25 Da matches the theoretical value of 45,996.51 for a protein containing polypeptide chains of 12-390 disulfide bonded to chain 451-475 (CTP2).

TABLE 7

Intact molecular weight anlaysis of Sample 1 under non-reducing conditions

| Sample | Observed Not Reduced | PPM error | Consistent Residues | Predicted |
|---|---|---|---|---|
| DIG-177 Trypsin Treated | 46,844.19 Da Major | −16.2 ppm | 12-390 disulfide bonded to chain 444-475 (CTP1) | 46,843.43 Da |
| | 45,995.25 Da Minor | −5.4 ppm | 12-390 disulfide bonded to chain 451-475 (CTP2) | 45,995.0 Da |

The intact molecular weight of the sample was determined following TCEP treatment (reducing conditions); two components were observed (Table 8). A major component at 42,729.71 Da, matches the theoretical mass of 42,729.4 for the trypsin treated DIG-177 LF (residues 12-390, no CTP). A minor component was also observed, with a mass of 46,844.14 Da, matching the mass of the LF with CTP1 still attached (incomplete reduction). The results indicate the CTP1 and 2 were largely removed by reduction with TCEP.

TABLE 8

Intact molecular weight anlaysis of Sample 1 under reducing conditions.

| Sample | Observed Reduced | PPM error | Consistent Residues | Predicted |
|---|---|---|---|---|
| DIG-177 Trypsin Treated | 42,729.71 Da Major | −7.2 ppm | 12-390 | 42,729.4 Da |
| | 46,844.14 Da Minor | −15.1 ppm | 12-390 disulfide bonded to chain 444-475 (CTP1) | 46,843.43 Da |

Sample 2: Preparation and Characterization of Trypsin Treated DIG-177 (LF with CTP Following Reduction).

Trypsin treated DIG-177 was purified under non-reducing conditions as described for Sample 1. DTT was added to the sample at a final concentration of 5 mM and incubated at room temperature for 10 minutes. The sample was then dialyzed overnight against 10 mM CAPS, pH 10, to remove the DTT to create Sample 2. Samples 1 and 2 were analyzed by SDS-PAGE using a 4-12% Bis/Tris gel and MOPS running buffer to obtain better resolution around 40 kDa. Under reducing conditions Sample 1 and Sample 2 (DTT treated), showed one band at the expected molecular weight of ~43 kDa, consistent with the LF (12-390), a second band at the bottom of the gel are the CTP (CTP1 and CTP2 are not resolved under these conditions) having been released by disulfide reduction. Under non-reducing conditions, Sample 1 ran at expected molecular weight of ~46 kDa consistent with the LF (residues 12-390) and the CTP being linked. Sample 2 (DTT treated, removed) showed two higher molecular weight bands, one at ~43 kDa, consistent with the LF (residues 12-390); the second ~46 kDa band, consistent with the LF plus CTP. A third band is present at the bottom of the gel which corresponds to the CTP. These results demonstrate that in Sample 2, most of the CTP is not linked to the large fragment; a fraction of the sample appears to be re-associated.

The spectrum without TCEP treatment showed three dominant peaks with measured MW avg. of 42,729.46, 45,994.89 and 46,844.14 Da (Table 9). The 42,729.46 peak matched the theoretical mass (42,729.0 Da) of the LF, residues 12-390. The 45,994.89 component matched the theoretical mass (45,995.0 Da) of the LF plus CTP2 (residues 12-390+451-475). The 46,844.14 component matched the theoretical MW avg. (46,843.72 Da) of the LF plus CTP1 (residues 12-390+444-475).

TABLE 9

Intact molecular weight anlaysis of Sample 2 under non-reducing conditions

| Sample | Observed Not Reduced | PPM error | Consistent Residues | Predicted |
|---|---|---|---|---|
| DIG-177 Trypsin Treated | 42,729.46 Da Major | −1.4 ppm | 12-390 | 42,729.4 Da |
| | 45,994.89 Da Minor | +2.4 ppm | 12-390 disulfide bonded to chain 451-475 (CTP2) | 45,995.0 Da |
| | 46,844.14 Da Minor | −15.1 ppm | 12-390 disulfide bonded to chain 444-475 (CTP1) | 46,843.43 Da |

The spectrum with 50 mM TCEP treatment showed only one component with MW avg. of 42,729.27 (Table 10); the CTP were not captured in this spectrum window. These results confirmed the DTT treatment released the CTP, and after removing the DTT, a fraction of the CTPs re-associated with the LF.

TABLE 10

Intact molecular weight anlaysis of Sample 2 under reducing conditions.

| Sample | Observed Not Reduced | PPM error | Consistent Residues | Predicted |
|---|---|---|---|---|
| DIG-177 Trypsin Treated | 42,729.27 Da | +3.0 ppm | 12-390 | 42,729.4 Da |

Sample 3: Preparation and Characterization of the LF.

To separate the DIG-177 trypsin generated LF and the CTPs, IEC purification following trypsin digestion was performed under reducing conditions (5 mM DTT). The samples were analyzed by non-reducing SDS-PAGE. The trypsin treated, non reduced sample, migrated at the expected molecular weight of ~46 kDa, consistent with the both the LF (12-390) linked to the CTP. The starting material sample (treated with DTT during preparation) migrated substantially faster and was consistent with the loss of the CTP. The LF minus the CTP was obtained in Fraction 3.

To verify the composition of Fraction 3, the sample was subjected to intact molecular weight analysis (Table 11). The spectrum without TCEP treatment showed a dominant species with a MW avg. of 42,729.76 Da and a minor component with 45,995.19 Da. The dominant component at 42,729.76 Da matched the theoretical MW avg. (42,729.0 Da) of the trypsin LF (residues 12-390), confirming the CTP were removed. The minor component at 45,995.19 Da matched the theoretical MW avg. of 45,995.0 Da of a second species composed of the LF (residues 12-390) and CTP2 (residues 451-475), indicating the reduction was not complete during purification. These results confirm the majority of the sample represents the LF without the CTP.

TABLE 11

Intact molecular weight anlaysis of Sample 3 under reducing conditions.

| Sample | Observed Not Reduced | PPM error | Interpretation Consistent Residues | Predicted |
|---|---|---|---|---|
| LF | 42,729.76 Da Major | −8.4 ppm | 12-390 | 42,729.4 Da |
| | 45,995.19 Da Minor | −4.1 ppm | 12-390 disulfide bonded to chain 451-475 (CTP2) | 45,995.0 Da |

Sample 4: Isolation and Characterization of the C-Terminal Peptides (CTP).

The trypsin digested DIG-177, purified under non-reducing conditions (see above), was treated with 5 mM DTT to release the C-terminal peptide. The treated sample was passed through a centrifugal filter device with 10 kDa MWCO (Millipore). The C-terminal peptide was present in the flow through while the large fragment was retained in the filtration unit. The flow through and retained sample were collected and the buffers were exchanged in 10 mM CAPS, pH 10, by dialysis.

The C-terminal peptide sample (Sample 4) was analyzed by MALDI-TOF/TOF MS to determine the peptide masses and subsequently fragmented in the LIFT mode to confirm the sequence of the peptide. The MALDI-TOF MS and MS/MS were conducted with Bruker UltraFlextreme™ mass spectrometer. The C-terminal peptide sample was diluted with 0.2% TFA (Trifluoroacetic acid) at 1:1 (v/v) and desalted using a C-18 Ziptip (Millipore). The peptides were eluted with 60% acetonitrile (ACN) in 0.1% TFA and mixed with 2,5-dihydroxybenzoic acid (DHB) matrix (15 mg/ml in ACN:$H_2O$ (50:50)). After spotting 1 μL of the mix on a MALDI sample plate, the peptide mass was analyzed using reflection-positive mode and the peptide was fragmented using the LIFT mode. The instrument was calibrated with CM 2 (calibration mixture 2, Peptide mass standards kit, Applied Biosystems Sciex, Foster City, Calif.). The mass spectrum was collected and analyzed using flex analysis software. The sequence was verified using BioTools software (Bruker) and MASCOT search engine (Matrix Science, Boston, Mass.). MALDI MS showed three major peaks with masses of 4,114.894, 3,266.38, and 2,154.933 Da, and several minor peaks (Table 12). The peak at 4,114.89 m/z matched the theoretical mass 4,113.66 representing residues 444-475 (CTP1); the peak at 3,266.38 m/z matched the theoretical mass 3,265.26 representing residues 451-475 (CTP2). The peak at 2,154.933 m/z did not match any peptides from C-terminus and its origin has yet to be determined.

TABLE 12

Intact molecular weight analysis of Sample 2 under reducing conditions

| Sample | Observed Not Reduced | PPM error | Consistent Residues | Predicted theoretical mass + H+ in Daltons |
|---|---|---|---|---|
| CTP | 4,114.89 m/z Major | +55.9 ppm | 444-475 | 4,113.66 + 1 |
| | 3,266.38 m/z Minor | +36.7 ppm | 451-475 | 3,265.26 + 1 |
| | 2,154.933 m/z Minor | | | |

The two peptides, m/z 4,114.894 and 3,266.38 Da, were sequenced by MALDI MS/MS. The results confirmed the 4,114.894 peak had the sequence NSNLEYKCPENNFMIYWYNNSDWYNNSDWYNN (underlined residues were identified and assigned) which matched the CTP1 sequence of residues 444-475 of SEQ ID NO: 51.

The 3,266.38 peak had the sequence CPENNFMIYWYNNSDWYNNSDWYNN which matched the CTP2 sequence from residues #451-475 of SEQ ID NO:52.

Insecticidal Activity of Samples 1-4.

Non-diapausing WCR eggs (Crop Characteristics Inc., Farmington, Minn.) were incubated at 28° C. in soil for 10 days. These eggs were washed from soil with water, surface sterilized with 10% formaldehyde and triple rinsed with sterile water. These eggs were allowed to hatch and fed with a proprietary WCR diet. Overlay diet bioassays were conducted in 24-well titer plates with each well containing 1.5 mL of the artificial WCR diet. The test samples were applied onto diet surface at 100 μg/cm² dose (80 μL) (unless otherwise stated), and dried under room temperature in laminar flow. Treated diet surface of each well was infested with five *D. virgifera* neonates (24-48 hr old) and test insects were enclosed in the bioassay plate with Breathe Easy® gas permeable covers, the plate was sealed and held under controlled environmental conditions (28° C., 24 hr scotophase, 60-80% relative humidity). Twenty insects were tested per replicate. The number of live insects, dead insects, and pooled live weight of insects per treatment were recorded after five days incubation. The number of dead insects and the weight of surviving insects were recorded.

Percent mortality and percent growth inhibition were calculated for each treatment. Growth inhibition (GI) is calculated as follows:

$$GI=[1-(TWIT/TNIT)/(TWIBC/TNIBC)]$$

where TWIT is the Total Weight of Insects in the Treatment, TNIT is the Total Number of Insects in the Treatment, TWIBC is the Total Weight of Insects in the Background Check (Buffer control), and TNIBC is the Total Number of Insects in the Background Check (Buffer control). Negative controls were 20 mM sodium citrate buffer, pH 3.5, 10 mM CAPS buffer, pH 10, and 350 μg/cm² Cry1Fa. Positive controls were 100 μg/cm² Cry34/35Ab1 in sodium citrate buffer and/or 100 μg/cm² DIG-177 in CAPS buffer. Samples 1-4 from the trypsin treated DIG-177 were bioassayed at 100 μg/cm² ($LC_{50}$ DIG-177 ~40 μg/cm²). The bioassay results are summarized in Table 13, Cry1Fa and two buffer samples were used as negative controls. Full length DIG-177 was used as the positive control.

Sample 1, the large fragment+CTP showed insecticidal activity nearly equivalent to the full-length positive control. Sample 2, the large fragment with the CTP released, but present in the sample, had low but measurable activity demonstrating that treatment with DTT, followed by dialysis, substantially reduced insecticidal activity. The analytical mass spectrometry data show some of the CTP was associated with the large fragment to create an active toxin complex in these samples. Samples 3 and 4, the large fragment and the CTP were tested separately; in all cases, these samples did not show activity significantly different than the negative control at this single dose, indicating that both fragments are required.

TABLE 13

Insecticidal activity of trypsin treated DIG-177 samples 1-4 against western corn rootworm

| Sample | % Growth Inhibition | % Mortality |
|---|---|---|
| DIG-177 (non treated Cry6Aa); Rep 1 | 99 | 94.7 |
| DIG-177 (non treated Cry6Aa); Rep 2 | 99 | 90 |
| Sample 1 (LF + CTP); Rep 1 | 95 | 56.2 |
| Sample 1 (LF + CTP); Rep 2 | 97 | 70 |
| Sample 2 (LF + CTP reduced); Rep 1 | 57 | 20 |
| Sample 2 (LF + CTP reduced); Rep 2 | 72 | 30 |
| Sample 3 (LF); Rep 1 | 0 | 0 |
| Sample 3 (LF); Rep 2 | 22 | 5 |
| Sample 4 (CTP); Rep 1 | 0 | 5 |
| Sample 4 (CTP); Rep 2 | 11 | 0 |
| Buffer Rep 2 | 0 | 0 |
| Buffer Rep 2 | 0 | 0 |
| Cry1F Rep 1 | 0.24 | 0 |
| Cry1F Rep 2 | 0.6 | 0 |

TABLE 13-continued

| Insecticidal activity of trypsin treated DIG-177 samples 1-4 against western corn rootworm | | |
|---|---|---|
| Sample | % Growth Inhibition | % Mortality |
| Cry34/35 Rep 1 | 93 | 63 |
| Cry34/35 Rep 2 | 98 | 80 |

* Mean percent larval mortality and Mean percent growth inhibition of first instar western corn rootworm after exposure to 100 μg/cm². Negative controls were 350 μg/cm² Cry1Fa, 10 mM CAPS (pH 10) and 20 mM sodium citrate (pH 3.5) buffers while positive control was 100 μg/cm² Cry34/35Ab1.

TABLE 14

| Dose response of TcdA, Cry34/35Ab1, and DIG-1000 | | | | | | | | |
|---|---|---|---|---|---|---|---|---|
| Dose Response | TcdA | | Cry34/35Ab1 | | DIG-177 | | DIG-1000 | |
| # Exper. Dates | 2 | | 2 | | 6 | | 8 | |
| # test larvae | 479 | | 413 | | 1034 | | 1314 | |
| | Estimate | CI or SE | Estimate | CI or SE | Estimate | CI or SE | Estimate | CI or SE |
| Mortality + Moribund | | | | | | | | |
| LC50 | 4.5 | 3.6-5.7 | 69.3 | 42.8-112.2 | 15.5 | 13.9-17.2 | 61 | 55.9-66.6 |
| LC90 | 16.1 | 11.1-23.3 | out of range* | | 40.4 | 35.2-46.5 | 146.7* | 126.1-170.6* |
| Slope [c] | 1.01 | 0.14 | 0.49 | 0.07 | 1.35 | 0.09 | 1.46 | 0.12 |
| Normalized live weight, pooled (GI) | | | | | | | | |
| EC50 | 1.7 | 0.7-4.3 | 1.8 | 1.2-2.6 | 5.6 | 3.9-8.0 | 15.7 | 11.2-21.19 |
| EC90 | 16.7 | 3.5-79.1 | 14.2 | 6.9-29.4 | 26.4 | 17.0-40.8 | 124.9* | 74.4-209.8* |
| Slope | 0.97 | 0.44 | 1.06 | 0.19 | 1.42 | 0.26 | 1.06 | 0.16 |

*Values have been extrapolated beyond the tested rate range

EXAMPLE 4

Genetic Deletion of the Carboxy Terminus of DIG-177

A series of five coding regions, DIG-137 (SEQ ID NO:53), DIG-138 (SEQ ID NO:55), DIG-147 (SEQ ID NO:57), DIG-148 (SEQ ID NO:59), and DIG-149 (SEQ ID NO:61), resulting in sequential deletions from the carboxy terminus of DIG-177 were constructed and expressed as described in Example 2. The recombinant proteins accumulated in the soluble fraction of the *Pseudomonas* host cells and were purified as follows: The recombinant protein containing cell paste from −80° C. freezer was transferred to −20° C. overnight, it was re-suspended in extract buffer (50 mM Tris, 5 mM EDTA, pH 8.0). It was mixed thoroughly with a homogenizer and sonicated in 5 cycles of 3 mM using a 250 (Branson) Sonifier with a flat tip (probe) at a 30% duty cycle, followed by a 5 min break after each cycle on ice. After cell lysis, the mix was centrifuged at 22,000×g for 25 minutes at 4° C. The supernatant was filtered through 0.45 μm filters. The purification was a two-step chromatography protocol using ion exchange and hydrophobic interaction resins. First, the supernatant was injected into a Q column (5 mL HiTrap Q HP column from GE Healthcare, Piscataway, N.J.) pre-equilibrated in 50 mM Tris, 5 mM EDTA, pH 8.0, and proteins were eluted by 0-0.6 M NaCl salt gradient. Fractions were collected based on UV absorbance and checked by SDS-PAGE. Fractions containing the recombinant protein were pooled and diluted with buffer A plus 2 M ammonia sulfate at a 1:1 ratio, the final ammonia sulfate concentration reached 1 M. The sample was applied onto a Phenyl HIC column (5 mL HiTrap Phenyl FF high sub column from GE Healthcare), the proteins were eluted by 1-0 M $(NH_4)_2SO_4$ gradient. Fractions which contained the target protein were pooled and concentrated with 10 kDa MWCO centrifugal filter and dialyzed against 10 mM COPS, pH 10. The protein concentration was determined by Bradford and Densitometry.

The compositions of the protein samples were confirmed by mass spectrometry as described in Example 3. The materials were tested for insecticidal activity against western corn rootworm as described in Example 3. The results show the deletion of the region from residues 444-475 (DIG-137) had activity similar to DIG-177 at the concentration tested. When treated with trypsin, DIG-137 showed decreased activity whereas DIG-177 retained activity when not reduced as shown in Example 3.

This observation demonstrated that the CTP was not specifically required for activity in the absence of trypsin treatment. Larger deletions (DIG-138, DIG-147, DIG-148, and DIG-149) showed less insecticidal activity than the DIG-177 control. Trypsin treatment of these samples reduced insecticidal activity beyond the non trypsin treated samples against WCR. These results were consistent with those of Wei et al, which showed carboxy terminal deletions of Cry6Aa, up to residue 382 maintained some activity against nematodes in the absence of proteolysis. These results confirmed the importance of stabilizing the DIG-177 polypeptide in the region between residues 390-475 to maintain potent insecticidal activity.

TABLE 14

Insecticidal activity of carboxy terminal deletions against WCR

| Sample | % Mortality | % Growth Inhibition |
|---|---|---|
| DIG-177 | 100 | 100 |
| DIG-137 | 100 | 100 |
| DIG-137 + Trypsin | 10 | 0 |
| DIG-138 | 9 | 2 |
| DIG-138 + Trypsin | 0 | 0 |
| DIG-147 | 3 | 27 |
| DIG-147 + Trypsin | 6 | 16 |
| DIG-148 | 3 | 16 |
| DIG-148 + Trypsin | 7 | 9 |
| DIG-149 | 6 | 43 |
| DIG-149 + Trypsin | 3 | 7 |
| Cry1Fa (Negative Control) | 3 | −11 |
| 20 mM NaCitrate pH 3.5 (Negative Control) | 6 | 0 |
| 10 mM CAPS pH 10 (Negative Control) | 0 | 0 |
| Cry 34/35 (Positive Control) | 94 | 100 |

* Mean percent larval mortality and mean percent growth inhibition of first instar western corn rootworm after exposure to 100 μg/cm² of various samples, the average of two data sets. Negative controls were 350 μg/cm² Cry1Fa, 10 mM CAPS (pH 10) and 20 mM sodium citrate (pH 3.5) buffers while positive control was 100 μg/cm² Cry34/35Ab1.

EXAMPLE 5

Study of the C88-C451 Disulfide Bond

To investigate the importance of the cys88-cys451 disulfide bond to insecticidal activity mutants DIG-616 (C163>A; (SEQ ID NO:39)) and DIG-984 (C88>A; 451>A; (SEQ ID NO:49)) were characterized as described in Examples 2 and 3. The DIG-616 and DIG-984 proteins were shown to have the expected molecular weight and number of disulfide bonds by mass spectrometry.

TABLE 15

Intact molecular weight analysis of DIG-177 mutants under non-reducing and reducing conditions.

| Sample | Expected Avg. Mass | Observed Avg. Mass w/o TCEP | Mass difference | PPM Error | Observed Avg. Mass w/TCEP | Mass difference | PPM Error | Interpretation Residues |
|---|---|---|---|---|---|---|---|---|
| DIG-177 | 54,075.9333 | 54,072.102 | 3.8313 | 70.85 | 54075.7579 | 0.1754 | 3.24 | 1-475 2 disulfides |
| DIG-616 C162 > A | 54,043.8672 | 54,040.287 | 3.5802 | 66.25 | 54043.8329 | 0.0343 | 0.63 | 1-475 2 disulfides |
| DIG-984 C88 > A; 451 > A | 54,011.8011 | 54,010.263 | 1.5381 | 28.48 | 54012.054 | −0.2529 | −4.68 | 1-475 1 disulfide |

Both DIG-616 and DIG-984 had insecticidal activity against WCR at 100 μg/cm² equivalent to DIG-177 in diet bioassays (Table 17). When treated with trypsin, DIG-616 maintained insecticidal activity whereas DIG-984 less insecticidal activity than either DIG-616 or DIG-177 when treated with trypsin. Mass spectrometric analysis showed trypsin treated DIG-616 retained the CTP and DIG-984 lost the CTP confirming the requirement of the peptide for western corn rootworm activity (Table 16) following proteolysis and the limited affinity of the LF and CTP in the absence of the disulfide bond.

TABLE 16

Intact molecular weight anlaysis of DIG-177 mutants following digestion with trypsin under non-reducing and reducing conditions

| Sample | Mass in Daltons Not Reduced | Consistent Residues Non-Reducing | PPM error | Mass in Daltons Reduced | Consistent Residues Reducing | PPM error |
|---|---|---|---|---|---|---|
| DIG-616 C162 > A | 46,811.34 | 12-390 + 444-475 | −9.92 | 42,696.84 | 12-390 | −10.87 |
| | 45,962.33 | 12-390 + 451-475 | | | | |
| | 43,372.88 | 16-400 | | | | |
| DIG-984 C88 > A; 451 > A | 42,697.00 | 12-390 | | 42,697.00 | 12-390 | −9.92 |

TABLE 17

| Insecticidal activity of DIG-177 and mutants with and without trypsin treatment against WCR | | | |
|---|---|---|---|
| Sample | Replications | % Mortality | % Growth Inhibition |
| DIG-177 | 6 | 100.0 | 100 |
| DIG-177 | | 100.0 | 100 |
| DIG-177 | | 95.0 | 99 |
| DIG-177 | | 100.0 | 100 |
| DIG-177 | | 80.0 | 94 |
| DIG-177 | | 90.0 | 99 |
| DIG-177 Trypsin Treated | 2 | 95.0 | 99 |
| DIG-177 Trypsin Treated | | 85.0 | 88 |
| DIG-616 | | 87.5 | 97 |
| DIG-616 | | 100.0 | 100 |
| DIG-616 Trypsin Treated | | 95.0 | 99 |
| DIG-616 Trypsin Treated | | 95.0 | 100 |
| DIG-984 | | 85.0 | 84 |
| DIG-984 | | 78.3 | 98 |
| DIG-984 | | 80.0 | 97 |
| DIG-984 | | 90.0 | 100 |
| DIG-984 Trypsin Treated | | 0.0 | 22 |
| DIG-984 Trypsin Treated | | 0.0 | 43 |
| DIG-984 Trypsin Treated | | 21.1 | 16 |
| DIG-984 Trypsin Treated | | 15.0 | 34 |
| Buffer Avg of 8 reps | | 7 | 0.000 |
| Cry1F Avg of 6 reps | | 9.5 | 0.11 |

* Mean percent larval mortality and mean percent growth inhibition of first instar western corn rootworm after exposure to 100 μg/cm² of various samples. Negative controls were 350 μg/cm² Cry1Fa, 10 mM CAPS (pH 10) and 20 mM sodium citrate (pH 3.5) buffers while positive control was 100 μg/cm² DIG-177.

EXAMPLE 6

Proteinase K Digestion of DIG-177

The proteolytic susceptibility of the DIG-177 protein was determined using proteinase K. (Proteinase K has been shown to have broader specificity than trypsin, cleaving on the carboxyl side of aliphatic and aromatic residues, whereas trypsin cleaved at lysine and arginine residues.) The DIG-177 sample protein was prepared as described in Example 2. It was digested in 50 mM Tris, pH 7.5, 2 mM $CaCl_2$ at a concentration 1 mg/mL at a 40:1 mass ration to proteinase K (SIGMA-ALDRICH, St. Louis, Mo.) with gentle rocking at 20° C. Time point samples were taken at 0, 5, 10, 30, 50, and 90 minutes with the digestions terminated by adding PMSF to a final concentration of 5 mM. The 0 time point was taken immediately after proteinase K was added to the sample. Samples were analyzed by SDS-PAGE, mass spectrometry, and insect bioassay as described in Examples 2 and 3.

Digestion of full length DIG-177 to 50 minutes, under these conditions, resulted in a large fragment of approximately 43 kDa. Due to the broad specificity of proteinase K, the peptides endpoints were heterogeneous ranging, at the amino terminus, of residues 5-73 and the carboxyl terminus, of residues 386-456. Depending on the peptide endpoints, in some cases the CTP fragments were linked to the large fragment by the C88-C451 disulfide bond. The proteinase K regions of susceptibility were found to be consistent with the trypsin results presented in Example 3.

EXAMPLE 7

Characterization of DIG-177 Internal Deletions for Insecticidal Activity and Proteinase K Stability Three series of sequential deletions were made across the proteolytically processed region of DIG-177, residues~390-443 of SEQ ID NO: 2. The first deletion set was 5 amino acids resulting in proteins (DIG-921 to 927 (SEQ ID NOs: 64, 66, 68, 70, 72, 74, 76) and DIG-931 (SEQ ID NO:78), the second 10 (DIG-969 to 973 (SEQ ID NOs:80, 82, 84, 86, 88)), the third (DIG-985 to 997 (SEQ ID NOs:90, 92, 94, 96, 98, 100, 102, 104, 106, 108, 110, 112 114)) was 15, 20, 25, and 43 residues. Each series was expressed in *Pseudomonas*, purified, and tested for insecticidal activity against western corn rootworm as described in Examples 2 and 3. The stability of the proteins was determined by digestion with proteinase K digestion as described above. In all cases, the mutant proteins had insecticidal activity. The proteins were approximately as susceptible to proteinase K as DIG-177; a notable exception is DIG-995 (SEQ ID NO:110), a 43 amino acid deletion which showed less digestion.

TABLE 18

| Description of DIG-177 deletions | | |
|---|---|---|
| SEQ ID NO: | Protein Name | Residues Deleted from DIG-177 |
| 2 | DIG-177 | None |
| 64 | DIG-921 | 391-395 |
| 66 | DIG-922 | 396-400 |
| 68 | DIG-923 | 401-405 |
| 70 | DIG-924 | 406-410 |
| 72 | DIG-925 | 411-415 |
| 74 | DIG-926 | 416-420 |
| 76 | DIG-927 | 421-425 |
| 78 | DIG-931 | 441-445 |
| 80 | DIG-969 | 391-400 |
| 82 | DIG-970 | 401-410 |
| 84 | DIG-971 | 411-420 |
| 86 | DIG-972 | 421-430 |
| 88 | DIG-973 | 431-440 |
| 90 | DIG-985 | 391-405 |
| 92 | DIG-986 | 406-420 |
| 94 | DIG-987 | 421-435 |
| 96 | DIG-988 | 429-443 |
| 98 | DIG-989 | 391-410 |
| 100 | DIG-990 | 411-430 |
| 102 | DIG-991 | 424-443 |
| 104 | DIG-992 | 391-415 |
| 106 | DIG-993 | 415-440 |
| 108 | DIG-994 | 419-443 |
| 110 | DIG-995 | 401-443 |
| 112 | DIG-996 | 391-433 |
| 114 | DIG-997 | 391-414; 425-443 |

EXAMPLE 8

Crystal Structure Determination of Trypsin Treated DIG-177

Inclusion body (IB) preparation. *Pseudomonas fluorescens* derived cell paste expressing full length, DIG-177 (SEQ ID NO:2) was transferred from −80° C. storage to 4° C. and resuspended at 20% w/v in cold lysis buffer (50 mM Tris, 200 mM NaCl, 10% glycerol, 0.5% Triton X-100, 20 mM EDTA, 1 mM TCEP, pH 7.5) and mixed thoroughly with a hand held homogenizer. The suspension was then passed through a Microfluidizer (M-110EH) twice at 16,000 psi then centrifuged (SLC-6000 rotor/14,000 g/40 minutes/4° C.). The supernatant was discarded. The inclusion body pellet was resuspended in 10% w/v room temperature lysis buffer with 0.4 g/L Lysozyme (L-6876; Sigma-Aldrich) and fully resuspended by homogenization. The suspension was incubated at 30° C. for 30 minutes, with brief homogenizations every 10 minutes. The inclusion bodies were then centrifuged (SLC-6000 rotor/14,000 g/40 minutes/4° C.)

and the supernatant discarded. The pellet was resuspended for a final time in 10% w/v cold lysis buffer using the homogenizer and centrifuged (SLC-6000 rotor/14,000 g/40 minutes/4° C.) and the supernatant discarded. The inclusion body pellet was suspended in 10% w/v in cold lysis buffer without Triton X-100 (50 mM Tris, 200 mM NaCl, 10% glycerol, 20 mM EDTA, 1 mM TECP, pH 7.5) using the homogenizer and centrifuged (SLC-6000 rotor/14,000 g/40 minutes/4° C.) and the supernatant discarded; this step was repeated. The inclusion bodies were either resuspended to 30% (w/v) in 10 mM EDTA, pH 8.0, or aliquoted into 1.5 mL aliquots and frozen at −80° C. until needed.

Preparation of the DIG-177 Trypsin Core.

Eight, 2 ml tubes of IB suspension of full length, DIG-177 were thawed and extracted in 80 ml final volume (1:5 dilution) of 10 mM CAPS, pH 11.0. The pH was measured at 9.1 and then adjusted to 11.0 with NaOH. To the extract, 50 mg of freshly prepared trypsin (25 mg/ml Trypsin solution (Sigma, T1426-1G TLCK treated) in (1 mM HCl, 5 mM $CaCl_2$). The pH was maintained at 11.0 and stirred overnight at 4° C.

The solution was applied to a Source 15Q 16/10 column pre-equilibrated in buffer A (25 mM CAPS, pH 11.0) at a flow rate of 10 mL/minute and eluted with a gradient of Buffer A+1 M NaCl over 75 minutes. Truncated DIG-177 eluted as a single, large peak, which was concentrated from 100 mL to 10 mL using four, 15 ml Amicon 10,000 MWCO spin concentrators in a JA-12 rotor at 4° C. and 5000×g. The concentrated ion exchange sample was applied to a Superdex 75 26/90 gel filtration column pre-equilibrated in 25 mM CAPS, pH 11.0, and 50 mM NaCl. The sample was eluted using a 2.5 mL/minute flow rate. The fractions contained in the large DIG-177 core peak were pooled (80 mL at 2.05 mg/mL).

Preparation of Full Length DIG-177.

About 500 mg of IB was thawed at 4° C., and centrifuged at 23,000×g for 25 mM at 4° C. The supernatant was removed and the IB pellet was solubilized in 30 mL, 100 mM CAPS, pH 11.0, and the suspension was gently rocked for two hours at room temperature to solubilize the DIG-177 protein. After solubilization, the mix was centrifuged at 23,000×g for 25 mM at 4° C. The supernatant was dialyzed against 25 mM CAPS, pH 10.0, overnight.

The buffer exchanged DIG-177 sample was then filtered through a 0.22 micron syringe filter and applied to a Source 15Q 16/6 ion exchange column at 5 mL/min flow rate. The column pre-equilibrated with buffer A (25 mM CAPS, pH 10). Protein was eluted with a step gradient of 20%, 30%, 40%, and 50% buffer B (buffer A+1M NaCl). Each elution was ~50 mL. Fractions were collected from each elution based on UV absorbance and analyzed by SDS-PAGE.

Full length DIG-177 was in the 20% B fractions which were pooled and concentrated to ~30 mL using a centrifugal filter devices with 10 kDa molecular weight cut off membrane (Millipore).

The concentrated sample was further purified by size exclusion chromatography. For each run, 4.0 mL of the sample was applied over a Superdex 75 26/90 gel filtration column pre-equilibrated in 25 mM CAPS, pH 10, 50 mM NaCl buffer, at a flow rate of 2.5 mL/min. Two peaks were observed; the first peak, eluted at the void volume and contained DIG-177 dimers. The fractions from peak 2 contained predominantly monomer. The fractions from peak 2 were pooled separately and submitted for crystallization experiments.

Protein Concentration Determination.

BCA assay (Pierce Life Technologies, Grand Island, N.Y.) was performed according to the manufacturer's instructions except a 1000 μL working reagent was added to a 50 μl sample. Bradford Protein Assay (Bio-Rad, Hercules, Calif., USA) was performed according to the manufacturer's instructions except a 1000 μL working reagent was added to a 20 μL sample.

Crystallization, Data Collection and Structure Determination of the DIG-177 Trypsin Core.

The DIG-177 trypsin core was concentrated to 100 mg/mL. Initial crystals were obtained using Rigaku Reagents, Inc. Wizard Classic I (Bainbridge Island, Wash.). After screening multiple conditions, suitable crystals were obtained from 20% (w/v) PEG 1000, 0.1 M Na Phosphate/citric acid, pH 4.2; 0.2 M Lithium sulfate. Data were collected at 100 K from a single crystal on a Mar CCD-300 detector at LS-CAT (Advanced Proton Sources, Argonne National Laboratory). The cell constants were a=112.07, b=112.07, c=76.6, a=90.0, β=90.0, γ=120.0. The initial data collections at the home source suggested space group $P6_5$ or $P6_1$; therefore, the data was initially processed in $P6_5$. However, subsequent analysis led to the realization that the space group was $P6_3$.

The structure of the truncated form of DIG-177 toxin was solved by molecular replacement method using PHASER (1) (CCP4 package (Winn, M. D. et al., 2011) followed by manual rebuilding and model refinement. The poly-alanine chain of the crystal structure of Hemolysin B from *Bacillus cereus* (Protein Data Bank entry 2NRJ) consisting of residues 19-334 was used as a search model. The final model was obtained by carrying out several cycles of refinement consisting of manual model building using COOT (Emsley et. al., 2010), followed by restrained refinement with REFMAC (Murshudov et. al., 1997).

TABLE 19

Crytallagraphic data collection and refinement statistics for the DIG-177 trypsin treated (PDB:).

| | |
|---|---|
| Wavelength (Å) | 1.1276 |
| Resolution range (Å) | 33.3-1.764 (1.827-1.764) |
| Space group | P 65 |
| Unit cell (a, b, c) | 112.965, 112.965, 76.628 |
| Total reflections | 41,916 |
| Unique reflections | 41,898 (352) |
| Multiplicity | 3.4 (1.2) |
| Completeness (%) | 76.59 (6.48) |
| <I>/sigma(I) | 20.12 (2.59) |
| Wilson B-factor | 25.73 |
| R-merge (%) | 5.4 (36.3) |
| R-work[a] (%) | 15.8 (22.9) |
| R-cryst[b] (%) | 22.0 (34.9) |
| Number of non-hydrogen atoms | 3,556 |
| Macromolecules | 3,165 |
| Ligands | 0 |
| Water | 391 |
| Protein residues | 402 |
| RMS(bonds) | 0.006 |
| RMS(angles) | 0.89 |
| Ramachandran favored (%) | 97 |
| Ramachandran outliers (%) | 0 |
| Clashscore | 3.03 |
| Average B-factor | 37.60 |
| Macromolecules | 36.80 |
| Ligands | 0 |
| Solvent | 44.70 |

[a]$R_{merge} = 100\Sigma(h)\Sigma(i)|I(i) - \langle I\rangle|/\Sigma(h)\Sigma(i)I(i)$ where I(i) is the ith intensity measurement of reflection h, and <I> is the average intensity from multiple observations.

[b]$R_{cryst} = \Sigma||F_{obs}| - |F_{calc}||/\Sigma|F_{obs}|$. Where $F_{obs}$ and $F_{calc}$ are the structure factor amplitudes from the data and the model, respectively. $R_{free}$ is $R_{cryst}$ with 10% of the structure factors.

Crystallization, Data Collection, and Structure Determination of the Full Length DIG-177.

Full-length DIG-177 protein was concentrated to 15 mg/ml using Amicon centrifugal filter with a 10 kDa molecular weight cut-off (Millipore) in 10 mM HEPES buffer, pH 7.5, and 25 mM NaCl. Initial crystallization screens were performed using commercially available Classics, Classics Lite, Classics II, PEG's, PEG's II, PhClear and PACT screens (Hampton Research, Aliso Viejo, Calif.) by the sitting drop method in 96-round bottom well crystallization plates (Greiner Bio-One, GmbH, Germany) using a Mosquito Robotic System (TTP LabTech, Hertfordshire, U.K.). Diffraction quality DIG-177 protein crystals were grown at 291 K from sitting drops containing 3 μL of the protein sample and 1.5 μL of reservoir solution (0.1 M citric acid, pH 4.6, 4% PEG 6,000). SDS-PAGE analysis of protein samples obtained by dissolving the crystals in SDS-buffer did not reveal any degradation products and confirmed the presence of only full-length DIG-177 protein in the 3 s used for the data collection.

For data collection, crystals were harvested with 20% (v/v) glycerol in the reservoir solution. Diffraction data were collected at 100 K from a single crystal on a Mar CCD-300 detector at LS-CAT (Advanced Proton Sources, Argonne National Laboratory). Data were indexed and processed with HKL-2000 (Z. Otwinowski and W. Minor, 1997). The crystals belonged to orthorhombic space group $P2_12_12$ and contained one molecule of full-length DIG-177 per asymmetric unit.

The structure of full-length DIG-177 was solved by molecular replacement using PHASER (McCoy, A. J. J. Appl. Cryst. (2007)) with the structure of the truncated form of DIG-177 as a search model. The final model of full-length DIG-177 toxin was obtained by carrying out several cycles consisting of manual model building using COOT (Winn, M. D. et al., 2011), followed by structure refinement with REFMAC (Murshudov et, al., 1997).

TABLE 20

Data collection and refinement statistics for full length DIG-177 (PDB: Ronda to check submission)

| | |
|---|---|
| Wavelength (Å) | 0.9876 |
| Resolution range (Å) | 50-2.7 (2.8-2.7) |
| Space group | P 21 21 2 |
| Unit cell (α, β, γ, a, b, c) | 50.4, 71.7, 143, 90, 90, 90 |
| Total reflections | 97894 |
| Unique reflections | 14755 |
| Multiplicity | 6.6 (7.1) |
| Completeness (%) | 99.50 (100.00) |
| I/sigma(I) | 10.98 (2.88) |
| Wilson B-factor | 55.48 |
| R-sym | 0.16 (0.907) |
| R-work[a] (%) | 28.35 |
| R-cryst[b] (%) | 34.40 |

TABLE 20-continued

Data collection and refinement statistics for full length DIG-177 (PDB: Ronda to check submission)

| | |
|---|---|
| Number of atoms | 3,038 |
| Protein residues | 393 |
| Water molecules | 43 |
| RMS(bonds) | 0.014 |
| RMS(angles) | 1.62 |
| Ramachandran favored (%) | 97 |
| Ramachandran outliers (%) | 0 |
| Average B-factor | 82.30 |

[a]$R_{merge} = 100\Sigma(h)\Sigma(i)|I(i) - \langle I\rangle|/\Sigma(h)\Sigma(i)I(i)$ where I(i) is the ith intensity measurement of reflection h, and $\langle I\rangle$ is the average intensity from multiple observations.
[b]$R_{cryst} = \Sigma||F_{obs}| - F_{calc}||/\Sigma|F_{obs}|$. Where $F_{obs}$ and $F_{calc}$ are the structure factor amplitudes from the data and the model, respectively. $R_{free}$ is $R_{cryst}$ with 10% of the structure factors.

The Molecular Structure of Trypsin Treated DIG-177 and Full-Length DIG-177.

Figure 2:
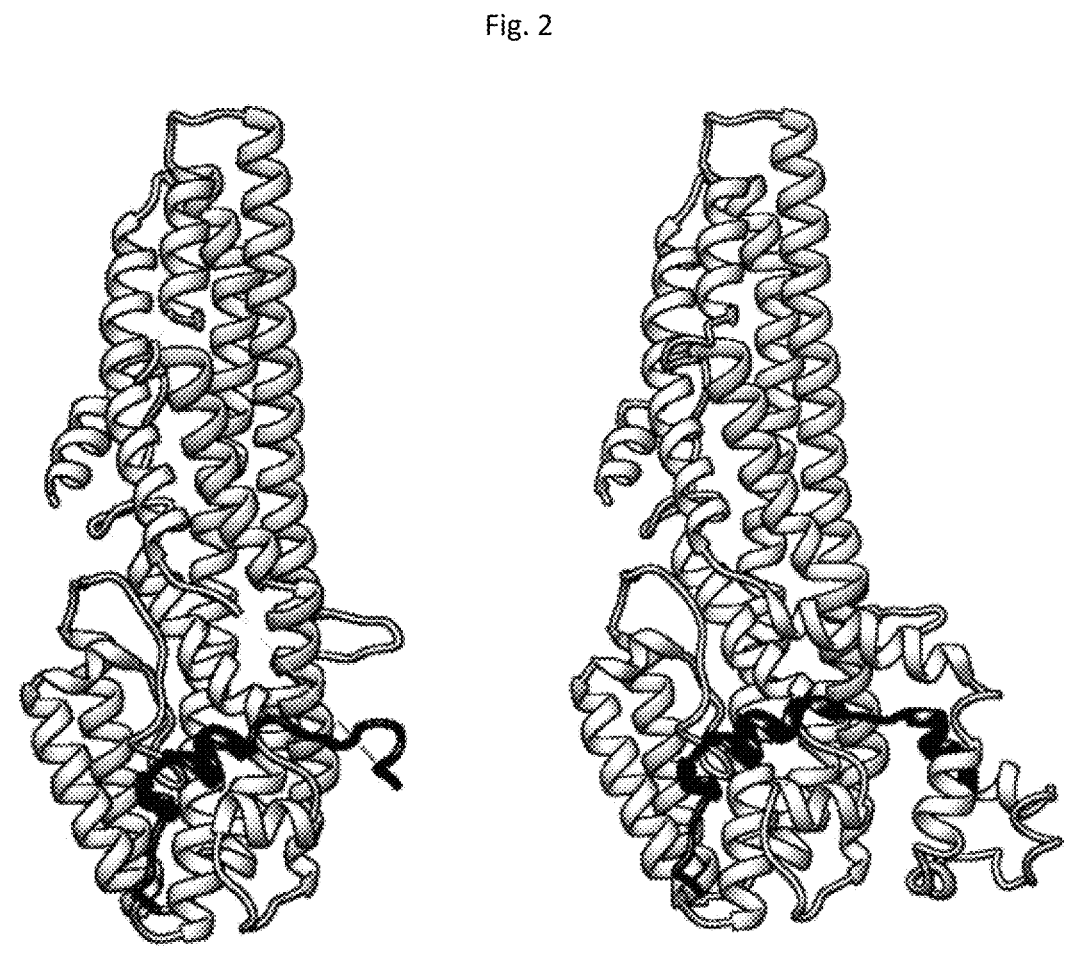

The ribbon diagram of the molecular structure of trypsin treated Cry6Aa (DIG-177) shown in FIG. 2 consists of an alpha helical bundle core with an alpha helical hairpin structure folded up onto the bundle. Structurally DIG-177 was recognized as an alpha helical hemolysin and shares structural similarity to *Escherichia coli* hemolysin E (1QOY; Wallace 2000) and the B component of hemolysin BL from *Bacillus cereus* (2NRJ; Madegowda et al 2008).

The molecular structure of full-length DIG-177 was nearly superimposable with the trypsin treated structure; the residues between 125-128 and 387-451 were not resolved; the residues between 387-452 were modeled. The structures are shown in FIG. 2.

EXAMPLE 9

Construction of Proteolytic Ally Stable DIG-177 Variants

Cry6Aa (DIG-177) has been shown to be a crystal protein from *Bacillus thuringiensis* which has insecticidal activity against western corn rootworm (*Diabrotica virgifera virgifera*) in diet bioassays. Proteolysis in the region approximately between residues 390-451, leads to a reduction of insecticidal activity. To limit proteolytic susceptibility of DIG-177, the 3D molecular structure was used to design replacement linkers for this region. The segment replaced with the linkers used several endpoints between residues 381 and 457. Some of the linkers were modeled using the loop modeler function of the MOE (Molecular Operating Environment) software from the Chemical Computing Group (Montreal, Quebec, Canada).

The new designs were expressed in *Pseudomonas*, purified, and tested for insecticidal activity and relative proteinase K resistance as described in Examples 4, and 6. This work demonstrated that several variants had both insecticidal activity and increased resistance to proteinase K than the parent protein DIG-177.

TABLE 21

DIG-177 variants tested to provide increased protease resistance

| SEQ ID NO | Protein | Linker Sequence | Insecticidal Activity % Mortality | Relative Proteinase K Resistance |
|---|---|---|---|---|
| 2 | DIG-177 | TLN/AYSTNSRQNLPINVISDS CNCSTTNMTSNQYSNPTTNM TSNQYMISHEYTSLPNNFMLS RNSNLEYKCPENNF/MIY | 100 100 | 0 |

TABLE 21-continued

DIG-177 variants tested to provide increased protease resistance

| SEQ ID NO | Protein | Linker Sequence | Insecticidal Activity % Mortality | | Relative Proteinase K Resistance |
|---|---|---|---|---|---|
| 116 | DIG-1000 | TLNAYS/VATITSG/--ENNFMIY | 85 | 95 | + |
| 118 | DIG-1049 | TLNAYS/VATITSGE/----FMIY | 100 | 100 | + |
| 120 | DIG-1052 | TLNAY-/ATITSG/---ENNFMIY | 100 | 100 | + |
| 122 | DIG-1038 | TLN---/WVIYNEFV/-----MIY | 16 | 20 | ND |
| 124 | DIG-1055 | TLNAYS/WVIYNEFV/NNFMIY | 35 | 15 | + |
| 126 | DIG-1039 | TLN---/GWVIYNEFVG/---MIY | 10 | 15 | + |
| 128 | DIG-1056 | TLNAY-/GWVIYNEFVG/-NFMIY | 70 | 60 | ND |
| 130 | DIG-1040 | TLN---/GDSSIKKDG/---FMIY | 35 | 20 | ND |
| 132 | DIG-1057 | TLNAY-/GDSSIKKDG/-NNFMIY | 86 | 90 | ND |
| 134 | DIG-1041 | TLN---/GDPSIKKDG/---FMIY | 0 | 20 | ND |
| 136 | DIG-1058 | TLNAY-/GDPSIKKDG/-NNFMIY | 35 | 30 | + |

The linker sequence is shown between the slash marks. Insecticidal activity against western corn rootworm is shown as % mortality and relative protease K resistance were determined using the proteinase K assay described in Example 6 (0 = similar proteinase K susceptibility to DIG-177; + = increased proteinase K resistance over DIG-177). -- are deletions within the DIG-177 protein.

EXAMPLE 10

Characterization of DIG-1000

Figure 3:
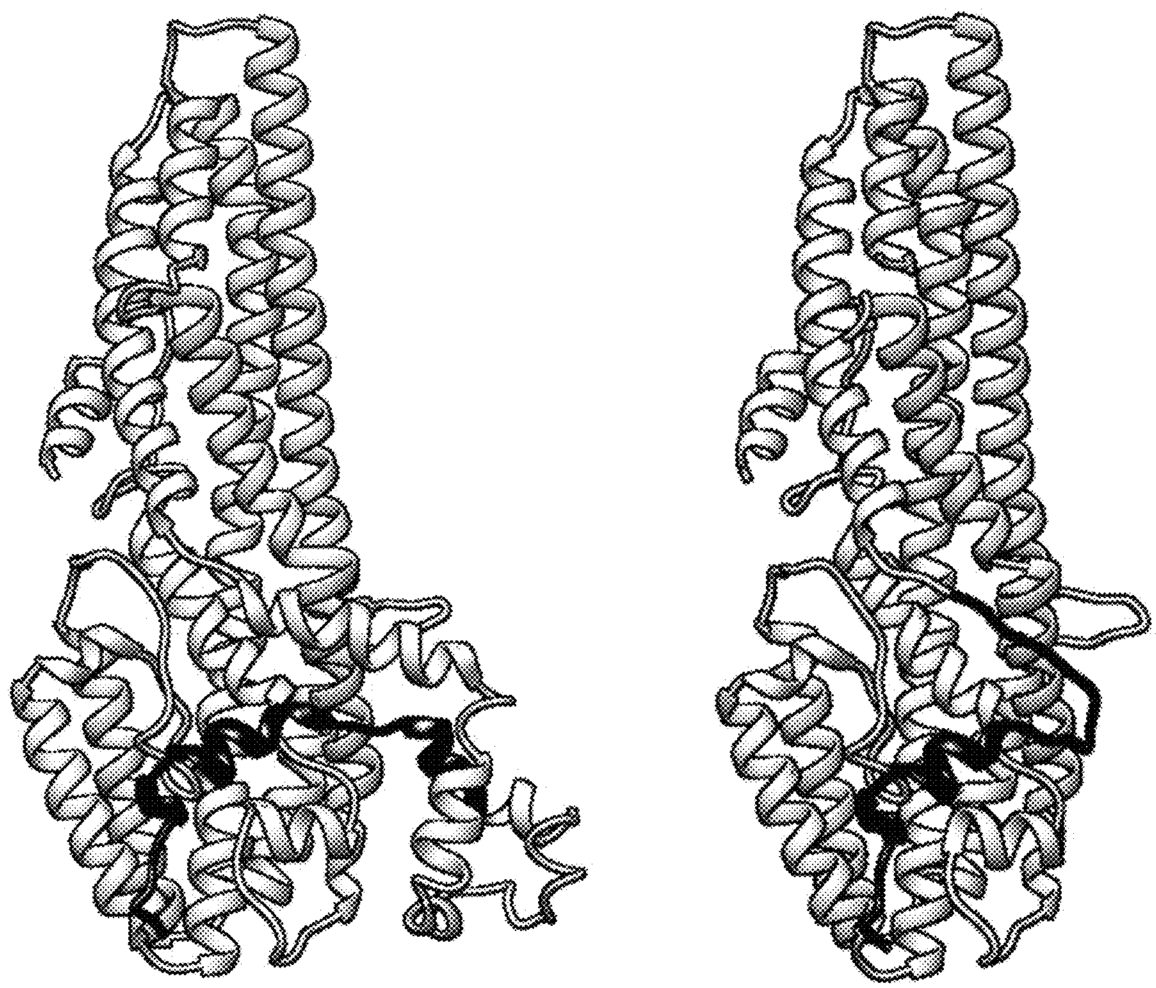
FIG. 3 is a depiction of the structural model comparison of residues 12-472 (left; as from FIG. 2) and the variant DIG-1000 (right). The carboxy terminal peptide (CTP) is shown in black on the left; the CTP and engineered linker are shown in black in DIG-1000 (right).

DIG-1000 (SEQ ID NO:116), a new variant of Cry6Aa that has replaced residues threonine 387 to proline 452 with the 7 residue linker: VATITSG, was prepared. The linker region was selected using the 3D crystal structure for the DIG-177 trypsin core and the loop modeler function of the MOE (Molecular Operating Environment) software from the Chemical Computing Group (Montreal, Quebec, Canada). The linker was designed to limit proteolysis by replacing the larger susceptible loop with a shorter less susceptible segment (see FIG. 3).

DIG-1000 was expressed in *Pseudomonas*, purified, and bioassayed as described in Example 3. DIG-1000 was shown to have insecticidal activity against western corn rootworm.

TABLE 22

Insecticidal activity of DIG-177 and DIG-1000 against western corn rootworm

| Sample | Dose Micrograms/cm2 | % Mortality Average of 4 Replicates |
|---|---|---|
| DIG-177 | 100 | 99 |
| DIG-177 | 33 | 88 |
| DIG-177 | 11 | 18 |
| DIG-1000 | 100 | 85 |
| DIG-1000 | 33 | 28 |
| DIG-1000 | 11 | 6 |
| Buffer | 0 | 8 |
| Cry1F | 350 | 6 |

Proteinase K Resistance.

Figure 4:
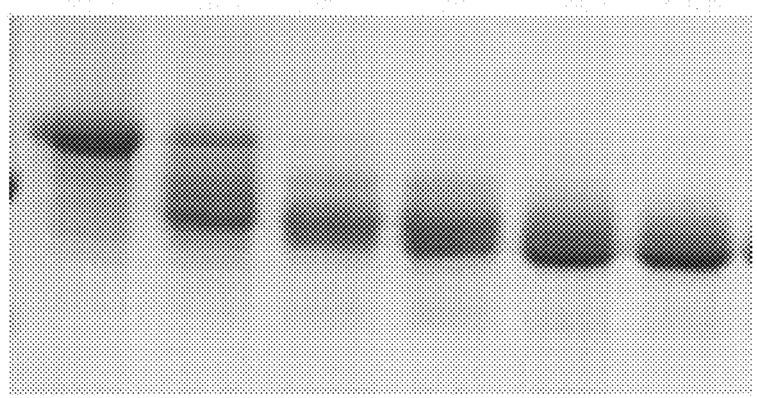
FIG. 4 shows the SDS-PAGE analysis of DIG-177 and DIG-1000 treated with proteinase K under the conditions described in Example 10. FL refers to untreated, undigested full-length protein; 0-50 are incubation times in minutes.
Figure 4:
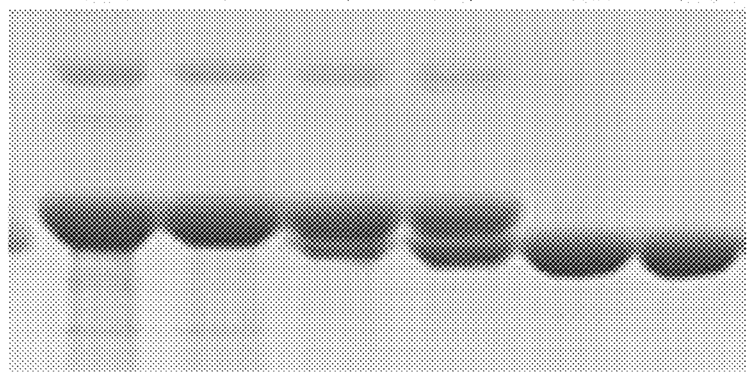

DIG-177 and DIG-1000 were expressed and purified as described in Example 3. The proteins were tested for susceptibility to proteinase K resistance (FIG. 4) as in Example 6. DIG-177 (54.2 kDa) showed substantial partial degradation at the T=0 time point (proteinase added, sample immediately withdrawn). The degradation continued until a proteolytically stable core was observed at 90 minutes. In contrast, DIG-1000 (47.3 kDa) did not show degradation at T=0, some partial degradation was observed at T=5 minutes, approximately 50 percent of the full length protein was converted at 10 minutes. Conversion to a proteolytically stable core was complete at 50 minutes. These data confirmed that DIG-1000 is substantially more resistant to proteinase K in vitro.

EXAMPLE 11

Transient Maize Expression of DIG-1000

The transient expression of DIG-177 and DIG-1000 was tested using particle bombardment of immature maize (B104) embryos harvested 10-12 days post pollination (WO 2014/028295 A; US 2012/0060238 A1). The coding regions of DIG-177 (SEQ ID NO:1) and DIG-1000 (SEQ ID NO:115) were rebuilt, as described in Example 1, to reflect a maize codon bias for transient testing in maize cells resulting in SEQ ID NO:3 and SEQ ID NO:137 respectively. A transit peptide (TraP), to direct the expressed proteins to the chloroplast compartment, was also tested on DIG-177 and DIG-1000. The modified coding regions are shown in SEQ ID NO:32 and SEQ ID NO:139 resulting in polypeptides SEQ ID NO:33 and SEQ ID NO:140 respectively.

Expression was directed from a pUC-based plasmid containing the maize ubiquitin promoter, the coding region of interest, and the maize peroxidase 5 3' untranslated region as shown in Table 23. Yellow fluorescent protein and PAT (phosphinothricin acetyl transferase) expressing plasmids were used as expression controls.

TABLE 23

Plasmids used for maize embryo transient expression

| Plasmid | Description (promoter/CDS/3' Untranslated Region) | Details |
|---|---|---|
| pDAB112771 | ZmUbi1/DIG-177 Zm/ZmPer5 | DIG-177 |
| DASDNA522 | ZmUbi1 v2/DIG-952/ZmPer5 | DIG-177 + TraP8 |
| pDAB122665 | ZmUbi1 promoter/DIG-1000/ZmPer5 | DIG-1000 |
| pDAB122666 | ZmUbi1 promoter/TraP8 DIG-1000/ZmPer5 | DIG-1000 + TraP8 |
| pDAB8393 | ZmUbi/YFP::OsAct/PAT | Yellow Fluorescent Protein |
| pDAB112364 | OsUbi3 promoter v3/PAT v6/ZmLip | phosphinothricin acetyl transferase |
| pDAB126939 | ZmUbi1 promoter/DIG-1036 + ERLS/ ZmUbi1::ZCZ018::SCBV(MAM)/AAD-1 v3/ZmLip | DIG-1036 + ERLS |
| pDAB126940 | ZmUbi1/DIG-1036 + VLS/ZmUbi1::ZCZ018::SCBV(MAM)/AAD-1 v3/ZmLip | DIG-1036 + VLS |

A gold particle stock was prepared by weighing 50 mg of 0.6 μm or 1 μm gold macrocarriers (Bio-Rad, Hercules, Calif.) in a sterile 2.0 ml microfuge tube. The particles were washed three times with ethanol followed by three washes with sterile water, at each wash the material was collected by spinning in a microcentrifuge at 1500 g for 2 minutes. The particles were suspended in 500 μl sterile 50% glycerol and stored at −20° C.

Surface sterilized B104 immature ears were used for the isolation of embryos. Immature embryos (10-12 days post pollination; 1.8-2.4 mm) from 3-4 ears were isolated into 2 ml microfuge tubes containing 1.75 ml of liquid either 2.2-4.3 g/L MS salts (Murshige and Skoog, 1962) and 1 ml/l modified MS vitamin solution (1000×) or 4.3 LS media (Linsmaier and Skoog, 1965) and 1 ml/l Chu N6 vitamin solution (1000×), 68.4 g/l sucrose, 36 g/l glucose, 100-700 mg/l L. proline, and with or without 1.5 mg/l 2, 4 D (2,4-dichlorophenoxyacetic acid).

After embryo isolation, the liquid medium was removed and discarded. Embryos were then cultured onto petri plates containing a semi-solid media for osmotic treatment. This media consisted of 4.3 g/l MS salts, 1 ml/l modified MS vitamin solution (1000×), 500 mg/l MES, 100 mg/l myo-inositol, 100 mg/l casein enzymatic hydrolysate, either 120 g/l sucrose or 45 g/l of each sorbitol and mannitol, either with or without 3.3 mg/l dicamba, 15 mg/l silver nitrate, and 2.5 g/l gelzan (gelrite). The embryos were arranged in 5×8 square grids within the target area for particle bombardment. All plates were incubated for 24 hours prior to particle bombardment in a 24 hour, under 50 μM low light chamber at 27° C.

Prior to coating the gold particles, each of the DNA were mixed from constructs of interest with a control construct containing the standard gene PAT in a 1:1 ratio. In addition, DNA from a construct containing a YFP gene was used for transformation as a visual control. Each of the tubes containing 50 μl of gold particles stock from above was suspended into a sterile 2.0 ml tube. The following were added to each of the gold particles tubes: Test construct DNA (5 μg)/Control construct DNA (5 μg) of pDAB112364, 50 μl of 2.5 M $CaCl_2$ and 20 μl of 0.1 M Spermidine. The tubes were then vortexed at high speed for 10-15 minutes at room temperature. Followed by three washes with 200 μl of 100% ethanol and finally the coated gold particles were resuspended in 30 μl of 100% ethanol and all tubes were placed on ice.

Two macrocarriers for each of the constructs tested were labeled and 5 μl of the DNA/Gold mixture was spread evenly over the center of a macrocarrier and allowed to dry for 10 minutes. Rupture disks ranging between 650-1100 psi (Bio-Rad, Hercules, Calif.) were sterilized with 70% propanol and allowed to partially dry before bombardment. Two plates containing 40 embryos for each of the constructs were bombarded. Bombarded embryos were kept on the same media and incubated for 24 hours, under 50 μM low light conditions at 27° C. overnight.

After 24 hours of bombardment, transformed embryos with control construct pDAB100286 were observed for YFP expression. This control was used to monitor DNA/gold coating process as well as the particle bombardment process. After confirming YFP expression in control embryos, two plates from each of the constructs tested were sampled for protein analysis. Each sample contained 20 embryos allowing multiple technical replicates for protein analysis as well as for the transformation process. A total of four samples for each of the constructs were submitted for protein analysis.

After bombardment and incubations the samples were stored in a 96 well cluster tube rack at −80° C. until the day of analysis. Two Daisy™ steel BB's and 300 μl of extraction buffer (PBS solution containing 0.05% of Tween 20 and 5 μl/ml of Sigma protease inhibitors, catalog number 9599)

was added to each tube. The samples were milled in a Kelco bead mill for 3 minutes, on maximum setting. Samples were centrifuged at 3,000× g for 5 minutes; 100 μl of the supernatant was transferred to an empty sample tube.

Conventional electrophoresis and blotting (Gallagher, S. et. al., 2008) methods were used with Invitrogen™ devices and basic reagents. A rabbit anti-Cry6a antibody was the primary antibody for the detection of Cry6a. All proteins were detected with a Cy3 fluorescence detection system and scanned using a GE Typhoon™ imaging system (GE Healthcare, Pittsburgh, Pa.).

Figure 5:
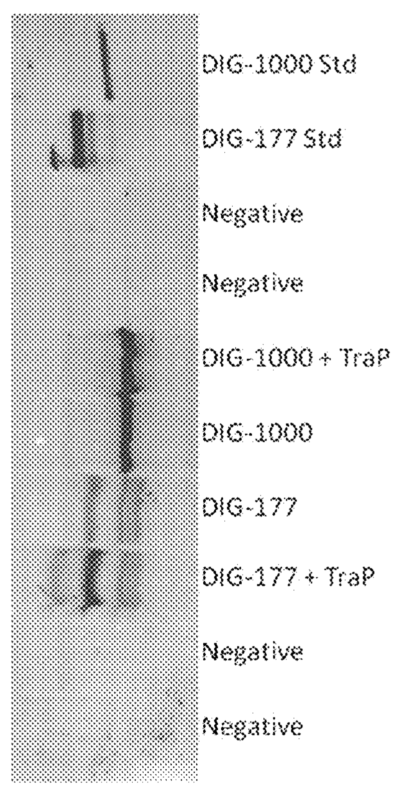
FIG. 5 is a Western blot maize transient expression analysis of Cry6Aa proteins. Antisera used was specific for DIG-177, Cry6Aa. The protein encoded by the bombarded plasmid DNA is noted: Lane 1, Fluorescent Rainbow Marker (GE Healthcare, Pittsburgh, Pa.); Lane 2, non bombarded embryo control; Lane 3, DIG-177 with TraP8; Lane 4, DIG-177; Lane 5 DIG-1000; Lane 6, DIG-1000 with TraP8; Lane 7, PAT (negative control); Lane 8, YFP (negative control) Lane 9, DIG-177 standard at 0.5 ng/lane; Lane 10, DIG-1000 standard at 1 ng/lane.

The results of the expression experiments are shown in FIG. 5. Western analysis shows no expression of Cry6Aa proteins in the negative controls, which included non-bombarded maize embryos, and those bombarded with YFP and PAT plasmids. The two far right lanes are protein standards of DIG-177, full length Cry6Aa (54.1 kDa) and DIG-1000 (47.3 kDa). The DIG-177+TraP lane contains a faint band above the standard, likely representing the precursor protein. Three other bands are present, one close to the DIG-177 standard in size while the others are substantially smaller, likely indicating partial degradation; the DIG-177 lane shows a similar pattern, however without the putative precursor protein. The DIG-1000 and DIG-1000+TraP look identical with single bands that appear to migrate with the DIG-1000 standard (accounting for some distortion of the end lanes of the gel). These data are consistent with the DIG-1000 coding sequence expressing a plant cell stable, insecticidal protein useful for western corn rootworm control.

EXAMPLE 12

Stable Dicot Expression of DIG-1000 Insecticidal Toxin

*Arabidopsis* Transformation.

*Arabidopsis thaliana* Col-01 is transformed using the floral dip method (Weigel and Glazebrook, 2002). The selected *Agrobacterium* colony is used to inoculate 1 mL to 15 mL cultures of YEP broth containing appropriate antibiotics for selection. The culture is incubated overnight at 28° C. with constant agitation at 220 rpm. Each culture is used to inoculate two 500 mL cultures of YEP broth containing appropriate antibiotics for selection and the new cultures are incubated overnight at 28° C. with constant agitation. The cells are pelleted at approximately 8700×g for 10 minutes at room temperature, and the resulting supernatant is discarded. The cell pellet is gently resuspended in 500 mL of infiltration media containing: 1/2× Murashige and Skoog salts (Sigma-Aldrich)/Gamborg's B5 vitamins (Gold BioTechnology, St. Louis, Mo.), 10% (w/v) sucrose, 0.044 μM benzylaminopurine (10 μL/liter of 1 mg/mL stock in DMSO) and 300 μL/liter Silwet L-77. Plants approximately 1 month old are dipped into the media for 15 seconds, with care taken to assure submergence of the newest inflorescence. The plants are then laid on their sides and covered (transparent or opaque) for 24 hours, washed with water, and placed upright. The plants are grown at 22° C., with a 16-hour light/8-hour dark photoperiod. Approximately 4 weeks after dipping, the seeds are harvested.

*Arabidopsis* Growth and Selection.

Freshly harvested T1 seed is allowed to dry for at least 7 days at room temperature in the presence of desiccant. Seed is suspended in a 0.1% agar/water (Sigma-Aldrich) solution and then stratified at 4° C. for 2 days. To prepare for planting, Sunshine Mix LP5 (Sun Gro Horticulture Inc., Bellevue, Wash.) in 10.5 inch×21 inch germination trays (T.O. Plastics Inc., Clearwater, Minn.) is covered with fine vermiculite, sub-irrigated with Hoagland's solution (Hoagland and Arnon, 1950) until wet, then allowed to drain for 24 hours. Stratified seed is sown onto the vermiculite and covered with humidity domes (KORD Products, Bramalea, Ontario, Canada) for 7 days. Seeds are germinated and plants are grown in a Conviron™ growth chamber (Models CMP4030 or CMP3244; Controlled Environments Limited, Winnipeg, Manitoba, Canada) under long day conditions (16 hours light/8 hours dark) at a light intensity of 120-150 μmol/m$^2$ sec under constant temperature (22° C.) and humidity (40-50%). Plants are initially watered with Hoagland's solution and subsequently with deionized water to keep the soil moist but not wet.

The domes are removed 5-6 days post sowing and plants are sprayed with a chemical selection agent to kill plants germinated from nontransformed seeds. For example, if the plant expressible selectable marker gene provided by the binary plant transformation vector is a pat or bar gene (Wehrmann et al., 1996), transformed plants may be selected by spraying with a 1000× solution of Finale (5.78% glufosinate ammonium, Farnam Companies Inc., Phoenix, Ariz.). Two subsequent sprays are performed at 5-7 day intervals. Survivors (plants actively growing) are identified 7-10 days after the final spraying and transplanted into pots prepared with Sunshine Mix LP5. Transplanted plants are covered with a humidity dome for 3-4 days and placed in a Conviron™ growth chamber under the above-mentioned growth conditions.

Those skilled in the art of dicot plant transformation will understand that other methods of selection of transformed plants are available when other plant expressible selectable marker genes (e.g. herbicide tolerance genes) are used.

Insect Bioassays of Transgenic *Arabidopsis*.

Transgenic *Arabidopsis* lines expressing DIG-1000 insecticidal toxin proteins are demonstrated to be active against sensitive insect species in artificial diet overlay assays. Protein extracted from transgenic and non-transgenic *Arabidopsis* lines is quantified by appropriate methods and sample volumes are adjusted to normalize protein concentration. Bioassays are conducted on artificial diet as described above. Non-transgenic *Arabidopsis* and/or buffer and water are included in assays as background check treatments.

EXAMPLE 13

Stable Maize Expression of DIG-1000 Insecticidal Toxin

*Agrobacterium*-Mediated Transformation of Maize. Seeds from a High II F1 cross (Armstrong et al., 1991) are planted into 5-gallon-pots containing a mixture of 95% Metro-Mix 360 soilless growing medium (Sun Gro Horticulture, Bellevue, Wash.) and 5% clay/loam soil. The plants are grown in a greenhouse using a combination of high pressure sodium and metal halide lamps with a 16:8 hour Light:Dark photoperiod. For obtaining immature $F_2$ embryos for transformation, controlled sib-pollinations are performed. Immature embryos are isolated at 8-10 days post-pollination when embryos are approximately 1.0 to 2.0 mm in size.

Infection and Co-Cultivation.

Maize ears are surface sterilized by scrubbing with liquid soap, immersing in 70% ethanol for 2 minutes, and then immersing in 20% commercial bleach (0.1% sodium hypochlorite) for 30 minutes before being rinsed with sterile water. A suspension *Agrobacterium* cells containing a superbinary vector is prepared by transferring 1-2 loops of bacteria grown on YEP solid medium containing 100 mg/L spectinomycin, 10 mg/L tetracycline, and 250 mg/L streptomycin at 28° C. for 2-3 days into 5 mL of liquid infection medium (LS Basal Medium (Linsmaier and Skoog, 1965), N6 vitamins (Chu et al., 1975), 1.5 mg/L 2,4-Dichlorophenoxyacetic acid (2,4-D), 68.5 gm/L sucrose, 36.0 gm/L glucose, 6 mM L-proline, pH 5.2) containing 100 μM acetosyringone. The solution is vortexed until a uniform suspension is achieved, and the concentration is adjusted to a final density of 200 Klett units, using a Klett-Summerson colorimeter with a purple filter, or an equivalent optical density measured at 600 nm ($OD_{600}$). Immature embryos are isolated directly into a micro centrifuge tube containing 2 mL of the infection medium. The medium is removed and replaced with 1 mL of the *Agrobacterium* solution with a density of 200 Klett units or equivalent OD600, and the *Agrobacterium* and embryo solution is incubated for 5 minutes at room temperature and then transferred to co-cultivation medium (LS Basal Medium, N6 vitamins, 1.5 mg/L 2,4-D, 30.0 gm/L sucrose, 6 mM L-proline, 0.85 mg/L $AgNO_3$, 100 μM acetosyringone, 3.0 gm/L Gellan gum (PhytoTechnology Laboratories., Lenexa, Kans.), pH 5.8) for 5 days at 25° C. under dark conditions.

After co-cultivation, the embryos are transferred to selective medium after which transformed isolates are obtained over the course of approximately 8 weeks. For selection of maize tissues transformed with a superbinary plasmid containing a plant expressible pat or bar selectable marker gene, an LS based medium (LS Basal medium, N6 vitamins, 1.5 mg/L 2,4-D, 0.5 gm/L MES (2-(N-morpholino)ethanesulfonic acid monohydrate; PhytoTechnologies Labr.), 30.0 gm/L sucrose, 6 mM L-proline, 1.0 mg/L $AgNO_3$, 250 mg/L cefotaxime, 2.5 gm/L Gellan gum, pH 5.7) is used with Bialaphos (Gold BioTechnology). The embryos are transferred to selection media containing 3 mg/L Bialaphos until embryogenic isolates are obtained. Recovered isolates are bulked up by transferring to fresh selection medium at 2-week intervals for regeneration and further analysis.

Those skilled in the art of maize transformation will understand that other methods of selection of transformed plants are available when other plant expressible selectable marker genes (e.g. herbicide tolerance genes) are used.

Regeneration and Seed Production.

For regeneration, the cultures are transferred to "28" induction medium (MS salts and vitamins, 30 gm/L sucrose, 5 mg/L Benzylaminopurine, 0.25 mg/L 2, 4-D, 3 mg/L Bialaphos, 250 mg/L cefotaxime, 2.5 gm/L Gellan gum, pH 5.7) for 1 week under low-light conditions (14 $\mu Em^{-2}s^{-1}$) then 1 week under high-light conditions (approximately 89 $\mu Em^{-2}s^{-1}$). Tissues are subsequently transferred to "36" regeneration medium (same as induction medium except lacking plant growth regulators). When plantlets grow to 3-5 cm in length, they are transferred to glass culture tubes containing SHGA medium (Schenk and Hildebrandt (1972) salts and vitamins); PhytoTechnologies Labr.), 1.0 gm/L myo-inositol, 10 gm/L sucrose and 2.0 gm/L Gellan gum, pH 5.8) to allow for further growth and development of the shoot and roots. Plants are transplanted to the same soil mixture as described earlier herein and grown to flowering in the greenhouse. Controlled pollinations for seed production are conducted.

EXAMPLE 14

Bioassay of Transgenic Maize

Bioactivity of the stably transformed plants expressing insecticidal toxins of the invention produced in plant cells is demonstrated by conventional bioassay methods (see, for example Huang et al., 2006). One is able to demonstrate efficacy, for example, by feeding various plant tissues or tissue pieces derived from a plant producing an engineered Cry6Aa insecticidal toxin to target insects in a controlled feeding environment. Alternatively, protein extracts may be prepared from various plant tissues derived from a plant producing the engineered Cry6Aa insecticidal toxin and the extracted proteins incorporated into artificial diet bioassays as previously described herein. It is to be understood that the results of such feeding assays are to be compared to similarly conducted bioassays that employ appropriate control tissues from host plants that do not produce an engineered Cry6Aa insecticidal toxin, or to other control samples.

REFERENCES

Alistair J. Wallace, Timothy J. Stillman, Angela Atkins, Stuart J. Jamieson, Per A. Bullough, Jeffrey Green, and Peter J. Artymiuk (2000). "*E. coli* Hemolysin E (HlyE, ClyA, SheA): X-Ray Crystal Structure of the Toxin and Observation of Membrane Pores by Electron Microscopy". Cell, Vol. 100: 265-276, January Altschul, S. F., Gish, W., Miller, W., Myers, E. W., Lipman, D. J. (1990) Basic local alignment search tool. J. Mol. Biol. 215:403-410.

Altschul, S. F., Madden, T. L., Schäffer, A. A., Zhang, J., Zhang, Z., Miller, W., Lipman, D. J. (1997) Gapped BLAST and PSI-BLAST: a new generation of protein database search programs. Nucl. Acids Res. 25:3389-3402.

An, G., Watson, B. D., Stachel, S., Gordon, M. P., Nester, E. W. (1985) New cloning vehicles for transformation of higher plants. EMBO J. 4:277-284.

Armstrong, C. L., Green, C. E., Phillips, R. L. (1991) Development and availability of germplasm with high TypeII culture formation response. Maize Genet. Coop. Newslett. 65:92-93.

Aronson, A. I., Han, E.-S., McGaughey, W., Johnson, D. (1991) The solubility of inclusion proteins from *Bacillus thuringiensis* is dependent upon protoxin composition and is a factor in toxicity to insects. Appl. Environ. Microbiol. 57:981-986.

Aronson, A. I., Geng, C., Wu. L. (1999) Aggregation of *Bacillus thuringiensis* Cry1A toxins upon binding to target insect larval midgut vesicles. Appl. Environ. Microbiol. 65:2503-2507.

Arvidson, H., Dunn, P. E., Strand, S., Aronson, A. I. (1989) Specificity of *Bacillus thuringiensis* for lepidopteran larvae: factors involved in vivo and in the structure of a purified toxin. Molec. Microbiol. 3:1533-1543.

Ausubel et al., eds. (1995) *Current Protocols in Molecular Biology*, Chapter 2 (Greene Publishing and Wiley-Interscience, New York).

Bailey, J. M., Shenov, N. R., Ronk, M., and Shively, J. E., (1992) Automated carboxy-terminal sequence analysis of peptides. Protein Sci. 1:68-80.

Baum J A, Bogaert T, Clinton W, Heck G R, Feldmann P, Ilagan O, Johnson S, Plaetinck G, Munyikwa T, Pleau M, Vaughn T, Roberts J., (2007) Control of coleopteran insect pests through RNA interference. Nat Biotechnol. November; 25(11):1322-6. Epub 2007 Nov. 4.

Beltz, G. A., Jacobs, K. A., Eickbush, T. H., Cherbas, P. T., Kafatos, F. C. (1983) Isolation of multigene families and determination of homologies by filter hybridization methods. In Wu, R., Grossman, L., Moldave, K. (eds.) Methods of Enzymology, Vol. 100 Academic Press, New York pp. 266-285.

Benchabane, M., Goulet, C., Rivard, D., Faye, L., Gomord, V., Michaud, D., (2008). "Preventing Unitended Proteolysis in Plant Protein Biofactories". Plant Biotechnology Journal 6: 633-648.

Bown, D. P., Wilkinson, H. S., Jongsma, M. A., Gatehouse, J. A. (2004) Characterization of cysteine proteinases responsible for digestive proteolysis in guts of larval western corn rootworm (*Diabrotica virgifera*) by expression in the yeast *Pichia pastoris*. Insect Biochem. Molec. Biol. 34:305-320.

Bravo, A., Gill, S. S., Soberon, M. (2007) Mode of action of *Bacillus thuringiensis* Cry and Cyt toxins and their potential for insect control. Toxicon 49:423-435.

Caruthers, M. H., Kierzek, R., Tang, J. Y. (1987) Synthesis of oligonucleotides using the phosphoramidite method. Bioactive Molecules (Biophosphates Their Analogues) 3:3-21.

Cervelli, M., Tavladoraki, P., Agostino, S., Angelini, R., Rodolfo, F., and Mariottini, P. (2000). "Isolation and characterization of three polyamine oxidase genes from *Zea mays*". Plant Physiol. Biochem. 38:667-677.

Christeller, J. T., Laing, W. A., Markwick, N. P., Burgess, E. P. J. (1992) Midgut protease activities in 12 phytophagous lepidopteran larvae: dietary and protease inhibitor interactions. Insect Biochem. Molec. Biol. 22:735-746.

Chu, C. C., Wand, C. C., Sun, C. S., Hsu, C., Yin, K. C., Chu, C. Y., Bi, F. Y. (1975) Establishment of an efficient medium for anther culture of rice through comparative experiments on the nitrogen sources. Scientia *Sinica* 18:659-668.

Crameri, A., Cwirla, S., Stemmer, W. P. C. (1996a) Construction and evolution of antibody-phage libraries by DNA shuffling. Nat. Med. 2:100-103.

Crameri, A., Whitehom, E. A., Tate, E., Stemmer, W. P. C. (1996b) Improved green fluorescent protein by molecular evolution using DNA shuffling. Nat. Biotech. 14:315-319.

Crameri, A., Dawes, G., Rodriguez, E., Silver, S., Stemmer, W. P. C. (1997) Molecular evolution of an arsenate detoxification pathway by DNA shuffling. Nat. Biotech. 15:436-438.

Crickmore N., Zeigler, D. R., Feitelson J., Schnepf, E., Van Rie J., Lereclus D., Baum J., and Dean D. H. (1998) Revision of the Nomenclature for the *Bacillus thuringiensis* Pesticidal Crystal Proteins Microbiol. Mol. Biol. Reviews 62:807-813.

de Maagd, R. A., Kwa, M. S., van der Klei, H., Yamamoto, T., Schipper, B., Vlak, J. M., Stiekema, W. J., Bosch, D. (1996) Domain III substitution in *Bacillus thuringiensis* delta-endotoxin CryIA(b) results in superior toxicity for *Spodoptera exigua* and altered membrane protein recognition. Appl. Environ. Microbiol. 62:1537-1543.

de Maagd, R. A., Bravo, A., Berry, C., Crickmore, N., Schnepf, E. (2003) Structure, diversity, and evolution of protein toxins from spore-forming entomopathogenic bacteria. Annu. Rev. Genet. 37:409-433.

Diaz-Mendoza, M., Farinos, G. P., Castanera, P., Hernandez-Crespo, P., Ortego, F. (2007) Proteolytic processing of native Cry1Ab toxin by midgut extracts and purified trypsins from the Mediterranean corn borer *Sesamia nonagrioide*. J. Insect Physiol. 53:428-435.

Ellis, R. T., Stockhoff, B. A., Stamp, L., Schnepf, H. E., Schwab, G. E., Knuth, M., Russell, J., Cardineau, G. A., Narva, K. E. (2002) Novel *Bacillus thuringiensis* binary insecticidal crystal proteins active on western corn rootworm, *Diabrotica virgifera virgifera* LeConte. Appl. Environ. Microbiol. 68:1137-1145.

Emsley, P., Bernhard Lohkamp, William G. Scott, and Kevin Cowtan. (2010). "Features and Development of Coot." Acta Cryst D66: 486-501.

Englemann, F., Geraerts, W. P. M., (1980) The proteases and the protease inhibitor in the midgut of *Leucophaea maderae*. J. Insect Physiol. 261:703-710.

Fallahi, M., Crosthwait, J., Calixte, S., and Bonen, L., (2005). "Fate of Mitochondrially Located S19 Ribosomal Protein Genes after Transfer of a Functional Copy to the Nucleus in Cereals" Mol Gen Genomics 273: 76-83.

Fraley, R. T., Rogers, S. G., Horsch, R. B. (1986) Genetic transformation in higher plants. Crit. Rev. Plant Sci. 4:1-46.

Frankenhuyzen, K., (2009) Insecticidal activity of *Bacillus thuringiensis* crystal proteins. Journal of Invertebrate Pathology, Vol: 101 (1): 1-16.

Gallagher, S., Winston, S., Fuller, S., Hurrell, J. (2008) Immunoblotting and Immunodetection. Current Protocols in immunology 8.10.1-8.10.28.

Gazit, E., La Rocca, P., Sansom, M. S. P., Shai, Y. (1998) The structure and organization within the membrane of the helices composing the pore-forming domain of *Bacillus thuringiensis* delta-endotoxin are consistent with an "umbrella-like" structure of the pore. Proc. Nat. Acad. Sci. USA 95:12289-12294.

Ge, A., Rivers, D., Milne, R., Dean, D. H. (1991) Functional domains of *Bacillus thuringiensis* insecticidal crystal proteins. Refinement of *Heliothis virescens* and *Trichoplusia ni* specificity domains on CryIA(c). J. Biol. Chem. 266: 17954-17958.

Gillikin, J. W., Bevilacqua, S., Graham, J. S. (1992) Partial characterization of digestive tract proteinases from western corn rootworm larvae, *Diabrotica virgifera*. Arch. Insect Biochem. Physiol. 19:285-298.

Gnanasambandam, A., Anderson, D. J., Mills, E., and Brumbley, S. M. (2012). "Heterologous C-terminal Signals Effectively Target Fluorescent Fusion Proteins to Leaf Peroxisomes in Diverse Plant Species" Journal of Plant Physiology 169: 830-833.

Gomez, I., Sanchez, J., Miranda, R., Bravo, A., Soberon, M. (2002) Cadherin-like receptor binding facilitates proteolytic cleavage of helix alpha-1 in domain I and oligomer pre-pore formation of *Bacillus thuringiensis* Cry1Ab toxin. FEBS Lett. 513:242-246.

Hahn, J. J., Eschenlauer, A. C., Sleyter, U. B., Somers, D. A. and Srienc, F., (1999) "Peroxisomes as Sites for Synthesis of Polyhydroxyalkanoates in Transgenic Plants" *Biotechnol. Prog./*5:1053-1057.

Haider, M. Z., Knowles, B. H., Ellar, D. J. (1986) Specificity of *Bacillus thuringiensis* var. *colmeri* insecticidal δ-endotoxin is determined by differential proteolytic processing of the protoxin by larval gut proteases. Eur. J. Biochem. 156:531-540.

Heckel, D. G., Gahan, L. J., Baxter, S. W., Zhao, J-Z., Shelton, A. M., Gould, F., Tabashnik, B. E. (2007) The diversity of Bt resistance genes in species of Lepidoptera. J. Invert. Pathol. 95:192-197.

Hepburn, A. G., White, J., Pearson, L., Maunders, M. J., Clarke, L. E., Prescott, A. G. Blundy, K. S. (1985) The use of pNJ5000 as an intermediate vector for the genetic manipulation of *Agrobacterium* Ti-plasmids. J. Gen. Microbiol. 131:2961-2969.

Hoagland, D. R., Arnon, D. I. (1950) The water-culture method of growing plants without soil. Calif. Agr. Expt. Sta. Circ. 347.

Hofte, H., de Greve, H., Seurinck, J., Jansens, S., Mahillon, J., Ampe, C., Vandekerckhove, J., Vanderbruggen, H., van Montagu, M., Zabeau, M., Vaeck, M. (1986) Structural and functional analysis of a cloned delta endotoxin of *Bacillus thuringiensis* berliner 1715. Eur. J. Biochem. 161:273-280.

Holwerda, B., Padgett, H. and Rogers, J. (1992). "Proaleurain Vacuolar Targeting Is Mediated by Short Contiguous Peptide interactions". The Plant Cell 4: 307-318.

Honée, G., Convents, D., Van Rie, J., Jansens, S., Peferoen, M., Visser, B. (1991) The C-terminal domain of the toxic fragment of a *Bacillus thuringiensis* crystal protein determines receptor binding. Mol. Microbiol. 5:2799-2806

Hood, E. E., Love, R., Lane, J., Bray, J., Clough, R., Pappu, K., Drees, C., Hood, K. R., Yoon, S., Ahmad, A., and Howard, J. A. (2007). "Subcellular Targeting is a Key Condition for High-Level Accumulation of Cellulase Protein in Transgenic Maize Seed". Plant Biotechnolgy Journal 5:709-719.

Horton, R. M., Hunt, H. D., Ho, S. N., Pullen, J. K., Pease, L. R. (1989) Engineering hybrid genes without the use of restriction enzymes: gene splicing by overlap extension. Gene 77:61-68.

Huang, F., Rogers, L. B., Rhett, G. H. (2006) Comparative susceptibility of European corn borer, southwestern corn borer, and sugarcane borer (Lepidoptera: Crambidae) to Cry1Ab protein in a commercial *Bacillus thuringiensis* corn hybrid. J. Econ. Entomol. 99:194-202.

Huang, K-X., Badger, M., Haney, K., Evans, S. L. (2007) Large scale production of *Bacillus thuringiensis* PS149B1 insecticidal proteins Cry34Ab1 and Cry35Ab1 from *Pseudomonas fluorescens*. Prot. Express. Purific. 53:325-330.

Hyunjong, B., Lee, D-S. and Hwang, I. (2006). "Dual Targeting of Xylanase to Chloroplasts and Peroxisomes as a Means to Increase Protein Accumulation in Plant Cells" J. Exp. Bot. 57: 161-169.

Janmaat, A. F., Myers, A. H. (2003) Rapid evolution and the cost of resistance to *Bacillus thuringiensis* in greenhouse populations of cabbage loopers, *Trichoplusia ni*. Proc. Royal Soc. London. Ser. B, Biolog. Sci. 270:2263-2270.

Janmaat, A. F., Myers, A. H. (2005) The cost of resistance to *Bacillus thuringiensis* varies with the host plant of *Trichoplusia ni*. Proc. Royal Soc. London. Ser. B, Biolog. Sci. 272:1031-1038.

Karlin, S., Altschul, S. F. (1990) Methods for assessing the statistical significance of molecular sequence features by using general scoring schemes. Proc. Natl. Acad. Sci. USA 87:2264-2268.

Karlin, S., Altschul, S. F. (1993) Applications and statistics for multiple high-scoring segments in molecular sequences. Proc. Natl. Acad. Sci. USA 90:5873-5877.

Keller, G. H., Manak, M. M. (1993) DNA Probes, Background, Applications, Procedures. Stockton Press, New York, N.Y.

Knight, J. S., Broadwell, A. H., Grant, W. N., Shoemaker, C. B. (2004) A Strategy for Shuffling Numerous *Bacillus thuringiensis* Crystal Protein Domains. J. Econ. Entomol. 97:1805-1813.

Koiwa, H., Shade, R. E., Zhu-Salzman, K., D'Urzo, M. P., Murdock, L. L., Bressan, R. A., Hasegawa, P. M. (2000) A plant defensive cystatin (soyacystatin) targets cathepsin L-like digestive cysteine proteinases (DvCALs) in the larval midgut of western corn rootworm *Diabrotica virgifera virgifera*. FEBS Letters 471:67-70.

Larson, S. M., England, J. L., Desjarlais, J. R., Pande, V. S. (2002) Thoroughly sampling sequence space: Large-scale protein design of structural ensembles. Protein Sci. 11:2804-2813.

Lee, L.-Y., Gelvin, S. B. (2008) T-DNA binary vectors and systems. Plant Physiol. 146: 325-332.

Li, H., Olson, M., Lin, G., Hey, T., Tan, S. Y. and Narva, K. (2013). "*Bacillus thuringiensis* Cry34Ab1/Cry35Ab1 Interactions with Western Corn Rootworm Midgut Membrane Binding Sites". PLoS One 8: e53079.

Linsmaier, E. M., Skoog, F. (1965) Organic growth factor requirements of tobacco tissue. Physiologia Plant 18:100-127.

Littlefield, J. W. (1964) Selection of hybrids from matings of fibroblasts in vitro and their presumed recombinants. Science 145:709-710.

Mahendra Madegowda, Subramaniam Eswaramoorthy, Stephen K. Burley, and Subramanyam Swaminathan (2008). "X-ray crystal structure of the B component of Hemolysin BL from *Bacillus cereus*" Proteins. 2008 May 1; 71(2): 534-540.

Mano, S., Nakamori, C., Hayashi, M., Kato, A., Kondo, M., Nishimura, M. (2002). "Distribution and Characterization of Peroxisomes in *Arabdopsis* by Visualization with GFP: Dynamic Morphology and Actin-Dependent Movement". Plant Cell Physiol. 43: 331-341.

McCoy, A. J., Grosse-Kunstleve, R. W., Adams, P. D., Winn, M. D., Storoni, L. C., & Read, R. J. (2007). "Phaser crystallographic software." J. Appl. Cryst. 40: 658-674.

Meinkoth, J., Wahl, G. (1984) Hybridization of nucleic acids immobilized on solid supports. Anal. Biochem. 138:267-284.

Metcalf, R. L. (1986) The ecology of insecticides and the chemical control of insects. pp. 251-297. In (Marcos Kogan (ed.)) Ecological theory and integrated pest management practice. John Wiley & Sons, N.Y. 362 pp.

Miao, Y., Yan P. K., Kim, H., Hwang, I., and Jiang, L. (2006). "Localization of Green Fluorescent Protein Fusions with the Seven *Arabidopsis* Vacuolar Sorting Receptors to Pre-vacuolar Compartments in Tobacco BY-2 Cells". Plant Physiol. 142:945-962.

Moellenbeck, D. J., Peters, M. L., Bing, J. W., Rouse, J. R., Higgins, L. S., Sims, L., Nevshemal, T., Marshall, L., Ellis, R. T., Bystrak, P. G., Lang, B. A., Stewart, J. L., Kouba, K., Sondag, V., Gustafson, V., Nour, K., Xu, D., Swenson, J., Zhang, J., Czapla, T., Schwab, G., Jayne, S., Stockhoff, B. A., Narva, K., Schnepf, H. E., Stelman, S. J., Poutre, C., Koziel, M., Duck, N. (2001) Insecticidal proteins from *Bacillus thuringiensis* protect corn from corn rootworms. Nat. Biotech. 19:668-672.

Mueller, Marcus, Ulla Grauschopf, Timm Maier, Rudi Glockshuber and Nenad Ban (2009). "The structure of a cytolytic a-helical toxin pore reveals its assembly mechanism". Nature Vol 459: 4 Jun. 2009: 726.

Murashige, T. and Skoog, F. (1962). A revised medium for rapid growth and bioassays with tobacco tissue cultures. Physiol. Plant 15: 473-497.

Murshudov, G. N., A. A. Vagin and E. J. Dodson, (1997). "Refinement of Macromolecular Structures by the Maximum-Likelihood method." Acta Cryst. D53: 240-255.

Myers, E., Miller, W. (1988) Optimal alignments in linear space. CABIOS 4:11-17.

Naimov, S., Weemen-Hendriks, M., Dukiandjiev, S., de Maagd, R. A. (2001) *Bacillus thuringiensis* delta-endotoxin Cry1 hybrid proteins with increased activity against the Colorado potato beetle. Appl. Environ. Microbiol. 11:5328-5330.

Needleman, S. B., Wunsch, C. D. (1970) A general method applicable to the search for similarities in the amino acid sequence of two proteins. J. Mol. Biol. 48:443-453.

Nora Eifler, Michael Vetsch, Marco Gregorini, Philippe Ringler, MohamedChami, Ansgar Philippsen, Andrea Fritz, Shirley A Muller, Rudi Glockshuber, Andreas Engel, and Ulla Grauschopf (2006). "Cytotoxin ClyA from *Escherichia coli* assembles to a 13-meric pore independent of its redox-state" The EMBO Journal 25: 2652-2661

Nunez-Valdez, M.-E., Sanchez, J., Lina, L., Guereca, L., Bravo, A. (2001) Structural and functional studies of alpha-helix 5 region from *Bacillus thuringiensis* Cry1Ab delta-endotoxin. Biochim Biophys. Acta, Prot. Struc. Molec. Enzymol. 1546:122-131.

Ochoa-Campuzano, C., Real, M. D., Martinez-Ramirez, A. C., Bravo, A., Rausell, C. (2007) An ADAM metalloprotease is a Cry3Aa *Bacillus thuringiensis* toxin receptor. Biochem. Biophys. Res. Commun. 362:437-442.

Oleson J D[1], Park Y L, Nowatzki T M, Tollefson J J. (2005). "Node-injury scale to evaluate root injury by corn rootworms (Coleoptera: Chrysomelidae)" J Econ Entomol. 2005 February; 98(1):1-8.

Otwinowski, Z. and W. Minor, "Processing of X-ray Diffraction Data Collected in Oscillation Mode", Methods in Enzymology, Volume 276: Macromolecular Crystallography, part A, p. 30'7-326, 1997, C. W. Carter, Jr. & R. M. Sweet, Eds., Academic Press (New York).

Pigott, C. R., Ellar, D. J. (2007) Role of receptors in *Bacillus thuringiensis* crystal toxin activity. Microbiol. Molec. Biol. Rev. 71:255-281.

Prichard, R. K. et al. [1980] "The problem of anthelmintic resistance in nematodes," *Austr. Vet. J.* 56:239-251; Coles, G. C. [1986] "Anthelmintic resistance in sheep," In *Veterinary Clinics of North America: Food Animal Practice*, Vol 2:423-432 [Herd, R. P., eds.] W. B. Saunders, New York Rang, C., Vachon, V., de Maagd, R. A., Villalon, M., Schwartz, J.-L., Bosch, D., Frutos, R., Laprade R. (1999) Interaction between functional domains of *Bacillus thuringiensis* insecticidal crystal proteins. Appl. Environ. Microbiol. 65:2918-2925.

Rokov-Plavec, Dulic, M., Duchene, A-M., Weygand-Durasevic, I. (2008). "Dual Targeting of Organellar Seryl-tRNA Synthetase to Maize Mitochondria and Chloroplasts" Plant Cell Rep 27: 1157-1168.

Sambrook, J., Fritsch, E. F., Maniatis, T. (1989) *Molecular Cloning: A Laboratory Manual* (2nd ed., Cold Spring Harbor Laboratory Press, Plainview, N.Y.)

Schenk, R. U., Hildebrandt, A. C. (1972) Medium and techniques for induction and growth of monocotyledonous and dicotyledonous plant cell cultures. Can. J. Bot. 50:199-204

Schnepf, H. E., Tomczak, K., Ortega, J. P., Whiteley, H. R. (1990) Specificity-determining regions of a Lepidopteran-specific insecticidal protein produced by *Bacillus thuringiensis*. J. Biol. Chem. 265:20923-20930.

Soberon, M., Pardo-Lopez, L., Lopez, I., Gomez, I., Tabashnik, B. E., Bravo, A. (2007) Engineering modified Bt toxins to counter insect resistance. Science 318:1640-1642.

Squires, C. H., Retallack, D. M., Chew, L C, Ramseier, T. M., Schneider, J. C., Talbot, H. W. (2004) Heterologous protein production in *P. fluorescens*. Bioprocess Intern. 2:54-59.

Stemmer, W. P. C. (1994a) DNA shuffling by random fragmentation and reassembly: in vitro recombination for molecular evolution. Proc. Natl. Acad. Sci. USA 91:10747-10751

Stemmer, W. P. C. (1994b) Rapid evolution of a protein in vitro by DNA shuffling. Nature 370: 389-391.

Stemmer, W. P. C. (1995) Searching sequence space. Bio/Technology 13:549-553.

Stewart, L. (2007) Gene synthesis for protein production. Encyclopedia of Life Sciences. John Wiley and Sons, Ltd.

Stewart, L., Burgin, A. B., (2005) Whole gene synthesis: a gene-o-matic future. Frontiers in Drug Design and Discovery 1:297-341.

Suggs, S. V., Miyake, T., Kawashime, E. H., Johnson, M. J., Itakura, K., R. B. Wallace, R. B. (1981) ICN-UCLA Symposium. Dev. Biol. Using Purified Genes, D. D. Brown (ed.), Academic Press, New York, 23:683-69

Tabashnik, B. E., Finson, N., Groeters, F. R., Moar, W. J., Johnson, M. W., Luo, K., Adang, M. J. (1994) Reversal of resistance to *Bacillus thuringiensis* in *Plutella xylostella*. Proc. Nat. Acad. Sci. USA 91:4120-4124.

Tabashnik, B. E., Gassmann, A. J., Crowder, D. W., Carriere, T. (2008) Insect resistance to Bt crops: evidence versus theory. Nat. Biotech. 26:199-202.

Taggart, R. T., Samloff, I. M. (1983) Stable antibody-producing murine hybridomas. Science 219:1228-1230.

Terry R. Wright, Guomin Shana, Terence A. Walsh, Justin M. Lira, Cory Cui, Ping Song, Meibao Zhuang, Nicole L. Arnold, Gaofeng Lin, Kerrm Yau, Sean M. Russell, Robert M. Cicchillo, Mark A. Peterson, David M. Simpson, Ning Zhou, Jayakumar Ponsamuel, and Zhanyuan Zhang. (2010) "*Robust crop resistance to broadleaf and grass herbicides provided by aryloxyalkanoate dioxygenase transgenes*". 20240-20245|PNAS|Nov. 23, 2010|vol. 107|no. 47.

Thie, N. M. R., Houseman J G. (1990) Identification of cathepsin B, D and H in the larval midgut of Colorado potato beetle, *Leptinotarsa decemlineata* say (Coleoptera: Chrysomelidae) Insect Biochem. 20:313-318.

Thompson, J. D., Higgins, D. G., Gibson, T. J. (1994) CLUSTAL W: improving the sensitivity of progressive multiple sequence alignment through sequence weighting, position-specific gap penalties and weight matrix choice. Nucl. Acids Res. 22:4673-4680.

Tijssen, P. (1993) Laboratory Techniques in Biochemistry and Molecular Biology Hybridization with Nucleic Acid Probes, Part I, Chapter 2. P. C. van der Vliet (ed.), (Elsevier, N.Y.)

Tzokov, S. B., Wyborn, N. R., Stillman, T. J., Jamieson, S., Czudnochowski, N., Artymuik, P. J., Green, J., Bullough, P. A. (2006). "Structure of the Hemolysin E (HlyE, ClyA and SheA) Channel in Its Membrane-bound Form". *J. Biol. Chem.* 2006, 281:23042-23049.

Varagona, M., and Raikhel, N. (1994). "The Basic Domain in the bZIP Regulatory Protein Opaque2 Serves Two Independent Functions: DNA Binding and Nuclear Localization". The Plant Journal 5:207-214.

Varshaysky, A. (1997) The N-end rule pathway of protein degradation. Genes to Cells 2:13-28.

Vaughn, T., Cavato, T., Brar, G., Coombe, T., DeGooyer, T., Ford, S., Groth, M., Howe, A., Johnson, S., Kolacz, K., Pilcher, C., Prucell, J., Romano, C., English, L., Pershing, J. (2005) A method of controlling corn rootworm feeding using a *Bacillus thuringiensis* protein expressed in transgenic maize. Crop. Sci. 45:931-938.

Walters, F. S., Slatin, S. L., Kulesza, C. A., English, L. H. (1993) Ion channel activity of N-terminal fragments from CryIA(c) delta-endotoxin. Biochem. Biophys. Res. Commun. 196:921-926.

Walters, F. S., Stacy, C. M., Lee, M. K., Palekar, N., Chen, J. S. (2008) An engineered chymotrypsin/cathepsin G site in domain I renders *Bacillus thuringiensis* Cry3A active against western corn rootworm larvae. Appl. Environ. Microbiol. 74:367-374.

Wehrmann, A., Van Vliet, A., Opsomer, C., Botterman, J., Schulz, A. (1996) The similarities of bar and pat gene products make them equally applicable for plant engineers. Nat. Biotechnol. 14:1274-1278.

Weigel, D., Glazebrook, J. (eds.) (2002) *Arabidopsis*: A Laboratory Manual. Cold Spring Harbor Press, Cold Spring Harbor, N.Y., 354 pages.

Wei, J-Z., Hale, K., Carta, L., Platzer, E., Wong, C., Fang, S-C., Aroian, R. (2003). "*Bacillus thuringiensis* crystal proteins that target nematodes". PNAS 100: 2760-2765.

White, J. A., and Scandalios, J. G. (1989). "Deletion Analysis of the Maize Mitochondrial Superoxide Dismutase Transit Peptide" PNAS 86:3534-3538.

Winn, M. D. et al. (2011). "Overview of the CCP4 suite and current developments." Acta. Cryst. D67: 235-242.

Witkowski, J. F., Wedberg, J. L., Steffey, K. L., Sloderbeck, P. E., Siegfried, B. D., Rice, M. E., Pilcher, C. D., Onstad, D. W., Mason, C. E., Lewis, L. C., Landis, D. A., Keaster, A. J., Huang, F., Higgins, R. A., Haas, M. J., Gray, M. E., Giles, K. L., Foster, J. E., Davis, P. M., Calvin, D. D., Buschman, L. L., Bolin, P. C., Barry, B. D., Andow, D. A., Alstad, D. N. (2002) Bt corn and European Corn Borer (Ostlie, K. R., Hutchison, W. D., Hellmich, R. L. (eds)). University of Minnesota Extension Service. Publ. WW-07055.

Wolfson, J. L., Murdock, L. L. (1990) Diversity in digestive proteinase activity among insects. J. Chem. Ecol. 16:1089-1102.

Worley, C. K., Ling, R., Callis, J. (1998) Engineering in vivo instability of firefly luciferase and *Escherichia coli* β-glucuronidase in higher plants using recognition elements from the ubiquitin pathway. Plant Molec. Biol. 37:337-347.

We claim:

1. A modified Cry6Aa insecticidal protein comprising SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:132, SEQ ID NO:136, SEQ ID NO:138, SEQ ID NO:140, or SEQ IDNO:144.

2. The modified Cry6Aa insecticidal protein of claim 1, wherein the protein comprises SEQ ID NO:110, SEQ ID NO:112, SEQ ID NO:114, SEQ ID NO:116, SEQ ID NO:118, SEQ ID NO:120, SEQ ID NO:132, SEQ ID NO:140, or SEQ ID NO:144.

3. The modified Cry6Aa insecticidal protein of claim 1, wherein the protein comprises SEQ ID NO:116, SEQ ID NO:118, SEQ ID NO:120, SEQ ID NO:140, or SEQ ID NO:144.

4. The modified Cry6Aa insecticidal protein of claim 1, wherein the protein comprises SEQ ID NO:116.

5. A nucleic acid sequence encoding the modified Cry6Aa insecticidal protein of claim 1.

6. A nucleic acid sequence encoding the modified Cry6Aa insecticidal protein of claim 2.

7. A nucleic acid sequence encoding the modified Cry6Aa insecticidal protein of claim 3.

8. A nucleic acid sequence encoding the modified Cry6Aa insecticidal protein of claim 4.

9. A transgenic plant or plant part that comprises the nucleic acid sequence of claim 6.

10. A method of controlling insect pest damage to plants which comprises preparing the transgenic plant of claim 9 and presenting said plant to an insect pest population.

11. The method of claim 10 wherein the insect pest damage is caused by insects of the order Coleoptera.

12. The method of claim 10 wherein the insect pest damage is caused by western corn rootworms.

* * * * *

SEQUENCE LISTING

```
<160> NUMBER OF SEQ ID NOS: 144

<210> SEQ ID NO 1
<211> LENGTH: 1428
<212> TYPE: DNA
<213> ORGANISM: Bacillus thuringiensis

<400> SEQUENCE: 1

atgattattg attctaaaac aacattacca agacattctt taattcatac tataaaatta      60

aattctaata agaaatatgg tcctggtgat atgactaatg gaaatcaatt tattatttca     120

aaacaagaat gggctactat tggagcatat attcagactg gattaggttt accagtaaat     180

gaacaacaat taagaacaca tgttaattta agtcaggata tatcaatacc tagtgatttt     240

tctcaattat atgatgttta ttgttctgat aaaacttcag cagaatggtg gaataaaaat     300

ttatatcctt taattattaa atctgctaat gatattgctt catatggttt taaagttgct     360

ggtgatcctt ctattaagaa agatggatat tttaaaaaat tgcaagatga attagataat     420

attgttgata ataattccga tgatgatgca atagctaaag ctattaaaga ttttaaagcg     480

cgatgtggta ttttaattaa agaagctaaa caatatgaag aagctgcaaa aaatattgta     540

acatctttag atcaattttt acatggtgat cagaaaaaat tagaaggtgt tatcaatatt     600

caaaaacgtt taaaagaagt tcaaacagct cttaatcaag cccatgggga aagtagtcca     660

gctcataaag agttattaga aaaagtaaaa aatttaaaaa caacattaga aaggactatt     720

aaagctgaac aagatttaga gaaaaaagta gaatatagtt ttctattagg accattgtta     780

ggatttgttg tttatgaaat tcttgaaaat actgctgttc agcatataaa aaatcaaatt     840

gatgagataa agaaacaatt agattctgct cagcatgatt tggatagaga tgttaaaatt     900

ataggaatgt taaatagtat taatacagat attgataatt tatatagtca aggacaagaa     960

gcaattaaag ttttccaaaa gttacaaggt atttgggcta ctattggagc tcaaatagaa    1020

aatcttagaa caacgtcgtt acaagaagtt caagattctg atgatgctga tgagatacaa    1080

attgaacttg aggacgcttc tgatgcttgg ttagttgtgg ctcaagaagc tcgtgatttt    1140
```

```
acactaaatg cttattcaac taatagtaga caaaatttac cgattaatgt tatatcagat   1200

tcatgtaatt gttcaacaac aaatatgaca tcaaatcaat acagtaatcc aacaacaaat   1260

atgacatcaa atcaatatat gatttcacat gaatatacaa gtttaccaaa taattttatg   1320

ttatcaagaa atagtaattt agaatataaa tgtcctgaaa ataattttat gatatattgg   1380

tataataatt cggattggta taataattcg gattggtata ataattaa               1428


<210> SEQ ID NO 2
<211> LENGTH: 475
<212> TYPE: PRT
<213> ORGANISM: Bacillus thuringiensis

<400> SEQUENCE: 2

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
```

```
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser Asn Gln Tyr Ser Asn
                405                 410                 415

Pro Thr Thr Asn Met Thr Ser Asn Gln Tyr Met Ile Ser His Glu Tyr
            420                 425                 430

Thr Ser Leu Pro Asn Asn Phe Met Leu Ser Arg Asn Ser Asn Leu Glu
        435                 440                 445

Tyr Lys Cys Pro Glu Asn Asn Phe Met Ile Tyr Trp Tyr Asn Asn Ser
    450                 455                 460

Asp Trp Tyr Asn Asn Ser Asp Trp Tyr Asn Asn
465                 470                 475


<210> SEQ ID NO 3
<211> LENGTH: 1428
<212> TYPE: DNA
<213> ORGANISM: Artificial Sequence
<220> FEATURE:
<223> OTHER INFORMATION: synthesized maize optimized coding region

<400> SEQUENCE: 3

atgatcattg actccaagac caccctgccg cgtcacagcc tgatccacac catcaagctg     60

aactccaaca agaagtacgg acctggcgac atgaccaacg gcaaccagtt catcatctcc    120

aagcaagagt gggccaccat cggagcgtac atccagaccg gcctgggcct gccggtgaac    180

gagcagcagc tgaggactca cgtgaacctg tcccaagaca tcagcatccc gtccgacttc    240

tcccagctgt acgacgtgta ttgcagcgac aagacctccg ccgagtggtg gaacaagaac    300

ctgtacccgc tgatcatcaa gagcgccaac gacatcgcct cctacggctt caaggtggcg    360

ggcgacccga gcatcaagaa ggacggctac ttcaagaagc tccaagacga gctggacaac    420

atcgtggaca acaactccga cgacgacgcc atcgccaagg cgatcaagga cttcaaggcg    480

aggtgcggca tcctgatcaa ggaggcgaag cagtacgagg aggcggcgaa gaacatcgtg    540

acctccctgg accagttcct gcacggcgac cagaagaagc tggagggcgt gatcaacatc    600

cagaagaggc tgaaggaggt gcagaccgcc ctgaatcaag cccacggcga gagcagcccg    660

gcgcacaagg agctgctgga gaaggtgaag aacctcaaga ccaccctgga gaggaccatc    720

aaggccgagc aagacctgga gaagaaggtg gagtactcct tcctgctggg tccgctgctg    780

ggcttcgtgg tgtacgagat cctggagaac accgccgtgc agcacatcaa gaatcagatc    840

gacgagatca agaagcagct ggactccgcc cagcacgacc tggaccgcga cgtgaagatc    900

atcgggatgc tgaacagcat caacaccgac atcgacaacc tgtacagcca aggccaagag    960

gccatcaagg tgttccagaa gctccaaggc atctgggcga ccatcggcgc gcagatcgag   1020

aacctgagga ccaccagcct ccaagaggtc caagacagcg acgacgccga cgagatccag   1080

atcgagctgg aggacgccag cgacgcgtgg ctggtggtgg cccaagaggc gagggacttc   1140

accctgaacg cgtacagcac caactcccgt cagaacctgc cgatcaacgt gatcagcgac   1200
```

```
agctgcaact gctccaccac caacatgacc agcaaccagt actccaaccc gaccaccaac   1260

atgaccagca accagtacat gatctcccac gagtacacca gcctgccgaa caacttcatg   1320

ctgtcccgca actctaacct ggagtacaag tgcccggaga acaacttcat gatctactgg   1380

tacaacaact ccgactggta caacaactca gactggtaca acaactga                1428


<210> SEQ ID NO 4

<400> SEQUENCE: 4

000


<210> SEQ ID NO 5
<211> LENGTH: 529
<212> TYPE: PRT
<213> ORGANISM: Artificial Sequence
<220> FEATURE:
<223> OTHER INFORMATION: translated from synthesized maize optimized
      coding region

<400> SEQUENCE: 5

Met Ala Ile Gly Ser Leu Ile Ala Ser Thr Phe Ala Arg Ser Ser His
1               5                   10                  15

Ala Leu Pro Ala Ala Ala Ala Ser Ala Ile Ser Gln Ala Pro Arg Ser
            20                  25                  30

Gln His Thr Ala Ser Pro Leu Leu Ser Gly Leu Gly Ala Ala Ala Arg
        35                  40                  45

Ala Phe Ser Ser Arg Ala Leu Ile Ile Asp Ser Lys Thr Thr Leu Pro
    50                  55                  60

Arg His Ser Leu Ile His Thr Ile Lys Leu Asn Ser Asn Lys Lys Tyr
65                  70                  75                  80

Gly Pro Gly Asp Met Thr Asn Gly Asn Gln Phe Ile Ile Ser Lys Gln
                85                  90                  95

Glu Trp Ala Thr Ile Gly Ala Tyr Ile Gln Thr Gly Leu Gly Leu Pro
            100                 105                 110

Val Asn Glu Gln Gln Leu Arg Thr His Val Asn Leu Ser Gln Asp Ile
        115                 120                 125

Ser Ile Pro Ser Asp Phe Ser Gln Leu Tyr Asp Val Tyr Cys Ser Asp
    130                 135                 140

Lys Thr Ser Ala Glu Trp Trp Asn Lys Asn Leu Tyr Pro Leu Ile Ile
145                 150                 155                 160

Lys Ser Ala Asn Asp Ile Ala Ser Tyr Gly Phe Lys Val Ala Gly Asp
                165                 170                 175

Pro Ser Ile Lys Lys Asp Gly Tyr Phe Lys Lys Leu Gln Asp Glu Leu
            180                 185                 190

Asp Asn Ile Val Asp Asn Asn Ser Asp Asp Asp Ala Ile Ala Lys Ala
        195                 200                 205

Ile Lys Asp Phe Lys Ala Arg Cys Gly Ile Leu Ile Lys Glu Ala Lys
    210                 215                 220

Gln Tyr Glu Glu Ala Ala Lys Asn Ile Val Thr Ser Leu Asp Gln Phe
225                 230                 235                 240

Leu His Gly Asp Gln Lys Lys Leu Glu Gly Val Ile Asn Ile Gln Lys
                245                 250                 255

Arg Leu Lys Glu Val Gln Thr Ala Leu Asn Gln Ala His Gly Glu Ser
            260                 265                 270

Ser Pro Ala His Lys Glu Leu Leu Glu Lys Val Lys Asn Leu Lys Thr
        275                 280                 285
```

```
Thr Leu Glu Arg Thr Ile Lys Ala Glu Gln Asp Leu Glu Lys Lys Val
    290                 295                 300

Glu Tyr Ser Phe Leu Leu Gly Pro Leu Leu Gly Phe Val Val Tyr Glu
305                 310                 315                 320

Ile Leu Glu Asn Thr Ala Val Gln His Ile Lys Asn Gln Ile Asp Glu
                325                 330                 335

Ile Lys Lys Gln Leu Asp Ser Ala Gln His Asp Leu Asp Arg Asp Val
            340                 345                 350

Lys Ile Ile Gly Met Leu Asn Ser Ile Asn Thr Asp Ile Asp Asn Leu
        355                 360                 365

Tyr Ser Gln Gly Gln Glu Ala Ile Lys Val Phe Gln Lys Leu Gln Gly
    370                 375                 380

Ile Trp Ala Thr Ile Gly Ala Gln Ile Glu Asn Leu Arg Thr Thr Ser
385                 390                 395                 400

Leu Gln Glu Val Gln Asp Ser Asp Asp Ala Asp Glu Ile Gln Ile Glu
                405                 410                 415

Leu Glu Asp Ala Ser Asp Ala Trp Leu Val Val Ala Gln Glu Ala Arg
            420                 425                 430

Asp Phe Thr Leu Asn Ala Tyr Ser Thr Asn Ser Arg Gln Asn Leu Pro
        435                 440                 445

Ile Asn Val Ile Ser Asp Ser Cys Asn Cys Ser Thr Thr Asn Met Thr
    450                 455                 460

Ser Asn Gln Tyr Ser Asn Pro Thr Thr Asn Met Thr Ser Asn Gln Tyr
465                 470                 475                 480

Met Ile Ser His Glu Tyr Thr Ser Leu Pro Asn Asn Phe Met Leu Ser
                485                 490                 495

Arg Asn Ser Asn Leu Glu Tyr Lys Cys Pro Glu Asn Asn Phe Met Ile
            500                 505                 510

Tyr Trp Tyr Asn Asn Ser Asp Trp Tyr Asn Asn Ser Asp Trp Tyr Asn
        515                 520                 525

Asn
```

<210> SEQ ID NO 6
<211> LENGTH: 1518
<212> TYPE: DNA
<213> ORGANISM: Artificial Sequence
<220> FEATURE:
<223> OTHER INFORMATION: synthesized maize optimized coding region

<400> SEQUENCE: 6

```
atggccctta ggaccttagc gagcaagaag gtgctgagct tcccgttcgg cggagcgggc     60

agaccgttag cagcagcggc ctcagctagg ggcatcattg actccaagac caccctgccg    120

cgtcacagcc tgatccacac catcaagctg aactccaaca agaagtacgg acctggcgac    180

atgaccaacg gcaaccagtt catcatctcc aagcaagagt gggccaccat cggagcgtac    240

atccagaccg gcctgggcct gccggtgaac gagcagcagc tgaggactca cgtgaacctg    300

tcccaagaca tcagcatccc gtccgacttc tcccagctgt acgacgtgta ttgcagcgac    360

aagacctccg ccgagtggtg gaacaagaac ctgtacccgc tgatcatcaa gagcgccaac    420

gacatcgcct cctacggctt caaggtggcg ggcgacccga gcatcaagaa ggacggctac    480

ttcaagaagc tccaagacga gctggacaac atcgtggaca acaactccga cgacgacgcc    540

atcgccaagg cgatcaagga cttcaaggcg aggtgcggca tcctgatcaa ggaggcgaag    600

cagtacgagg aggcggcgaa gaacatcgtg acctccctgg accagttcct gcacggcgac    660
```

```
cagaagaagc tggagggcgt gatcaacatc cagaagaggc tgaaggaggt gcagaccgcc    720

ctgaatcaag cccacggcga gagcagcccg gcgcacaagg agctgctgga gaaggtgaag    780

aacctcaaga ccaccctgga gaggaccatc aaggccgagc aagacctgga gaagaaggtg    840

gagtactcct tcctgctggg tccgctgctg ggcttcgtgg tgtacgagat cctggagaac    900

accgccgtgc agcacatcaa gaatcagatc gacgagatca agaagcagct ggactccgcc    960

cagcacgacc tggaccgcga cgtgaagatc atcgggatgc tgaacagcat caacaccgac   1020

atcgacaacc tgtacagcca aggccaagag gccatcaagg tgttccagaa gctccaaggc   1080

atctgggcga ccatcggcgc gcagatcgag aacctgagga ccaccagcct ccaagaggtc   1140

caagacagcg acgacgccga cgagatccag atcgagctgg aggacgccag cgacgcgtgg   1200

ctggtggtgg cccaagaggc gagggacttc accctgaacg cgtacagcac caactcccgt   1260

cagaacctgc cgatcaacgt gatcagcgac agctgcaact gctccaccac caacatgacc   1320

agcaaccagt actccaaccc gaccaccaac atgaccagca accagtacat gatctcccac   1380

gagtacacca gcctgccgaa caacttcatg ctgtcccgca actctaacct ggagtacaag   1440

tgcccggaga acaacttcat gatctactgg tacaacaact ccgactggta caacaactca   1500

gactggtaca acaactga                                                 1518
```

```
<210> SEQ ID NO 7
<211> LENGTH: 505
<212> TYPE: PRT
<213> ORGANISM: Artificial Sequence
<220> FEATURE:
<223> OTHER INFORMATION: translated from synthesized maize optimized
      coding region

<400> SEQUENCE: 7

Met Ala Leu Arg Thr Leu Ala Ser Lys Lys Val Leu Ser Phe Pro Phe
1               5                   10                  15

Gly Gly Ala Gly Arg Pro Leu Ala Ala Ala Ala Ser Ala Arg Gly Ile
            20                  25                  30

Ile Asp Ser Lys Thr Thr Leu Pro Arg His Ser Leu Ile His Thr Ile
        35                  40                  45

Lys Leu Asn Ser Asn Lys Lys Tyr Gly Pro Gly Asp Met Thr Asn Gly
    50                  55                  60

Asn Gln Phe Ile Ile Ser Lys Gln Glu Trp Ala Thr Ile Gly Ala Tyr
65                  70                  75                  80

Ile Gln Thr Gly Leu Gly Leu Pro Val Asn Glu Gln Gln Leu Arg Thr
                85                  90                  95

His Val Asn Leu Ser Gln Asp Ile Ser Ile Pro Ser Asp Phe Ser Gln
            100                 105                 110

Leu Tyr Asp Val Tyr Cys Ser Asp Lys Thr Ser Ala Glu Trp Trp Asn
        115                 120                 125

Lys Asn Leu Tyr Pro Leu Ile Ile Lys Ser Ala Asn Asp Ile Ala Ser
    130                 135                 140

Tyr Gly Phe Lys Val Ala Gly Asp Pro Ser Ile Lys Lys Asp Gly Tyr
145                 150                 155                 160

Phe Lys Lys Leu Gln Asp Glu Leu Asp Asn Ile Val Asp Asn Asn Ser
                165                 170                 175

Asp Asp Asp Ala Ile Ala Lys Ala Ile Lys Asp Phe Lys Ala Arg Cys
            180                 185                 190

Gly Ile Leu Ile Lys Glu Ala Lys Gln Tyr Glu Glu Ala Ala Lys Asn
```

```
        195                 200                 205

Ile Val Thr Ser Leu Asp Gln Phe Leu His Gly Asp Gln Lys Lys Leu
    210                 215                 220

Glu Gly Val Ile Asn Ile Gln Lys Arg Leu Lys Glu Val Gln Thr Ala
225                 230                 235                 240

Leu Asn Gln Ala His Gly Glu Ser Ser Pro Ala His Lys Glu Leu Leu
                245                 250                 255

Glu Lys Val Lys Asn Leu Lys Thr Thr Leu Glu Arg Thr Ile Lys Ala
            260                 265                 270

Glu Gln Asp Leu Glu Lys Lys Val Glu Tyr Ser Phe Leu Leu Gly Pro
        275                 280                 285

Leu Leu Gly Phe Val Val Tyr Glu Ile Leu Glu Asn Thr Ala Val Gln
    290                 295                 300

His Ile Lys Asn Gln Ile Asp Glu Ile Lys Lys Gln Leu Asp Ser Ala
305                 310                 315                 320

Gln His Asp Leu Asp Arg Asp Val Lys Ile Ile Gly Met Leu Asn Ser
                325                 330                 335

Ile Asn Thr Asp Ile Asp Asn Leu Tyr Ser Gln Gly Gln Glu Ala Ile
            340                 345                 350

Lys Val Phe Gln Lys Leu Gln Gly Ile Trp Ala Thr Ile Gly Ala Gln
        355                 360                 365

Ile Glu Asn Leu Arg Thr Thr Ser Leu Gln Glu Val Gln Asp Ser Asp
    370                 375                 380

Asp Ala Asp Glu Ile Gln Ile Glu Leu Glu Asp Ala Ser Asp Ala Trp
385                 390                 395                 400

Leu Val Val Ala Gln Glu Ala Arg Asp Phe Thr Leu Asn Ala Tyr Ser
                405                 410                 415

Thr Asn Ser Arg Gln Asn Leu Pro Ile Asn Val Ile Ser Asp Ser Cys
            420                 425                 430

Asn Cys Ser Thr Thr Asn Met Thr Ser Asn Gln Tyr Ser Asn Pro Thr
        435                 440                 445

Thr Asn Met Thr Ser Asn Gln Tyr Met Ile Ser His Glu Tyr Thr Ser
    450                 455                 460

Leu Pro Asn Asn Phe Met Leu Ser Arg Asn Ser Asn Leu Glu Tyr Lys
465                 470                 475                 480

Cys Pro Glu Asn Asn Phe Met Ile Tyr Trp Tyr Asn Asn Ser Asp Trp
                485                 490                 495

Tyr Asn Asn Ser Asp Trp Tyr Asn Asn
            500                 505
```

<210> SEQ ID NO 8
<211> LENGTH: 1665
<212> TYPE: DNA
<213> ORGANISM: Artificial Sequence
<220> FEATURE:
<223> OTHER INFORMATION: synthesized maize optimized coding region

<400> SEQUENCE: 8

```
atgctgacct gcggaaggtt catcagctcc agcgcggcca ccagcaccgc ctccttcttc     60

ccgtttagga ccctgacaag gagcctggtg aggagaccgg ccccgcacct gctcagctcc    120

gcgtcagctg ccgccgccac agcggtggag ctggacacca acggagacgg ctcagcgggc    180

ggcggagccg gcgtggtgag gcctcagtgg aaggcggcaa tcgacttcaa gtggatcagg    240

atcattgact ccaagaccac cctgccgcgt cacagcctga tccacaccat caagctgaac    300
```

```
tccaacaaga agtacggacc tggcgacatg accaacggca accagttcat catctccaag    360

caagagtggg ccaccatcgg agcgtacatc cagaccggcc tgggcctgcc ggtgaacgag    420

cagcagctga ggactcacgt gaacctgtcc caagacatca gcatcccgtc cgacttctcc    480

cagctgtacg acgtgtattg cagcgacaag acctccgccg agtggtggaa caagaacctg    540

tacccgctga tcatcaagag cgccaacgac atcgcctcct acggcttcaa ggtggcgggc    600

gacccgagca tcaagaagga cggctacttc aagaagctcc aagacgagct ggacaacatc    660

gtggacaaca actccgacga cgacgccatc gccaaggcga tcaaggactt caaggcgagg    720

tgcggcatcc tgatcaagga ggcgaagcag tacgaggagg cggcgaagaa catcgtgacc    780

tccctggacc agttcctgca cggcgaccag aagaagctgg agggcgtgat caacatccag    840

aagaggctga aggaggtgca gaccgccctg aatcaagccc acggcgagag cagcccggcg    900

cacaaggagc tgctggagaa ggtgaagaac ctcaagacca ccctggagag gaccatcaag    960

gccgagcaag acctggagaa gaaggtggag tactccttcc tgctgggtcc gctgctgggc   1020

ttcgtggtgt acgagatcct ggagaacacc gccgtgcagc acatcaagaa tcagatcgac   1080

gagatcaaga agcagctgga ctccgcccag cacgacctgg accgcgacgt gaagatcatc   1140

gggatgctga acagcatcaa caccgacatc gacaacctgt acagccaagg ccaagaggcc   1200

atcaaggtgt tccagaagct ccaaggcatc tgggcgacca tcggcgcgca gatcgagaac   1260

ctgaggacca ccagcctcca agaggtccaa gacagcgacg acgccgacga gatccagatc   1320

gagctggagg acgccagcga cgcgtggctg gtggtggccc aagaggcgag ggacttcacc   1380

ctgaacgcgt acagcaccaa ctcccgtcag aacctgccga tcaacgtgat cagcgacagc   1440

tgcaactgct ccaccaccaa catgaccagc aaccagtact ccaacccgac caccaacatg   1500

accagcaacc agtacatgat ctcccacgag tacaccagcc tgccgaacaa cttcatgctg   1560

tcccgcaact ctaacctgga gtacaagtgc ccggagaaca acttcatgat ctactggtac   1620

aacaactccg actggtacaa caactcagac tggtacaaca actga                   1665
```

<210> SEQ ID NO 9
<211> LENGTH: 554
<212> TYPE: PRT
<213> ORGANISM: Artificial Sequence
<220> FEATURE:
<223> OTHER INFORMATION: translated from synthesized maize optimized coding region

<400> SEQUENCE: 9

```
Met Leu Thr Cys Gly Arg Phe Ile Ser Ser Ser Ala Ala Thr Ser Thr
1               5                   10                  15

Ala Ser Phe Phe Pro Phe Arg Thr Leu Thr Arg Ser Leu Val Arg Arg
            20                  25                  30

Pro Ala Pro His Leu Leu Ser Ser Ala Ser Ala Ala Ala Ala Thr Ala
        35                  40                  45

Val Glu Leu Asp Thr Asn Gly Asp Gly Ser Ala Gly Gly Gly Ala Gly
    50                  55                  60

Val Val Arg Pro Gln Trp Lys Ala Ala Ile Asp Phe Lys Trp Ile Arg
65                  70                  75                  80

Ile Ile Asp Ser Lys Thr Thr Leu Pro Arg His Ser Leu Ile His Thr
                85                  90                  95

Ile Lys Leu Asn Ser Asn Lys Lys Tyr Gly Pro Gly Asp Met Thr Asn
            100                 105                 110

Gly Asn Gln Phe Ile Ile Ser Lys Gln Glu Trp Ala Thr Ile Gly Ala
```

-continued

```
        115                 120                 125

Tyr Ile Gln Thr Gly Leu Gly Leu Pro Val Asn Glu Gln Gln Leu Arg
    130                 135                 140

Thr His Val Asn Leu Ser Gln Asp Ile Ser Ile Pro Ser Asp Phe Ser
145                 150                 155                 160

Gln Leu Tyr Asp Val Tyr Cys Ser Asp Lys Thr Ser Ala Glu Trp Trp
                165                 170                 175

Asn Lys Asn Leu Tyr Pro Leu Ile Ile Lys Ser Ala Asn Asp Ile Ala
            180                 185                 190

Ser Tyr Gly Phe Lys Val Ala Gly Asp Pro Ser Ile Lys Lys Asp Gly
        195                 200                 205

Tyr Phe Lys Lys Leu Gln Asp Glu Leu Asp Asn Ile Val Asp Asn Asn
    210                 215                 220

Ser Asp Asp Asp Ala Ile Ala Lys Ala Ile Lys Asp Phe Lys Ala Arg
225                 230                 235                 240

Cys Gly Ile Leu Ile Lys Glu Ala Lys Gln Tyr Glu Glu Ala Ala Lys
                245                 250                 255

Asn Ile Val Thr Ser Leu Asp Gln Phe Leu His Gly Asp Gln Lys Lys
            260                 265                 270

Leu Glu Gly Val Ile Asn Ile Gln Lys Arg Leu Lys Glu Val Gln Thr
        275                 280                 285

Ala Leu Asn Gln Ala His Gly Glu Ser Ser Pro Ala His Lys Glu Leu
    290                 295                 300

Leu Glu Lys Val Lys Asn Leu Lys Thr Thr Leu Glu Arg Thr Ile Lys
305                 310                 315                 320

Ala Glu Gln Asp Leu Glu Lys Lys Val Glu Tyr Ser Phe Leu Leu Gly
                325                 330                 335

Pro Leu Leu Gly Phe Val Val Tyr Glu Ile Leu Glu Asn Thr Ala Val
            340                 345                 350

Gln His Ile Lys Asn Gln Ile Asp Glu Ile Lys Lys Gln Leu Asp Ser
        355                 360                 365

Ala Gln His Asp Leu Asp Arg Asp Val Lys Ile Ile Gly Met Leu Asn
    370                 375                 380

Ser Ile Asn Thr Asp Ile Asp Asn Leu Tyr Ser Gln Gly Gln Glu Ala
385                 390                 395                 400

Ile Lys Val Phe Gln Lys Leu Gln Gly Ile Trp Ala Thr Ile Gly Ala
                405                 410                 415

Gln Ile Glu Asn Leu Arg Thr Thr Ser Leu Gln Glu Val Gln Asp Ser
            420                 425                 430

Asp Asp Ala Asp Glu Ile Gln Ile Glu Leu Glu Asp Ala Ser Asp Ala
        435                 440                 445

Trp Leu Val Val Ala Gln Glu Ala Arg Asp Phe Thr Leu Asn Ala Tyr
    450                 455                 460

Ser Thr Asn Ser Arg Gln Asn Leu Pro Ile Asn Val Ile Ser Asp Ser
465                 470                 475                 480

Cys Asn Cys Ser Thr Thr Asn Met Thr Ser Asn Gln Tyr Ser Asn Pro
                485                 490                 495

Thr Thr Asn Met Thr Ser Asn Gln Tyr Met Ile Ser His Glu Tyr Thr
            500                 505                 510

Ser Leu Pro Asn Asn Phe Met Leu Ser Arg Asn Ser Asn Leu Glu Tyr
        515                 520                 525

Lys Cys Pro Glu Asn Asn Phe Met Ile Tyr Trp Tyr Asn Asn Ser Asp
    530                 535                 540
```

Trp Tyr Asn Asn Ser Asp Trp Tyr Asn Asn
545 550

<210> SEQ ID NO 10
<211> LENGTH: 1446
<212> TYPE: DNA
<213> ORGANISM: Artificial Sequence
<220> FEATURE:
<223> OTHER INFORMATION: synthesized maize optimized coding region

<400> SEQUENCE: 10
atgatcattg actccaagac caccctgccg cgtcacagcc tgatccacac catcaagctg 60
aactccaaca agaagtacgg acctggcgac atgaccaacg gcaaccagtt catcatctcc 120
aagcaagagt gggccaccat cggagcgtac atccagaccg gcctgggcct gccggtgaac 180
gagcagcagc tgaggactca cgtgaacctg tcccaagaca tcagcatccc gtccgacttc 240
tcccagctgt acgacgtgta ttgcagcgac aagacctccg ccgagtggtg gaacaagaac 300
ctgtacccgc tgatcatcaa gagcgccaac gacatcgcct cctacggctt caaggtggcg 360
ggcgacccga gcatcaagaa ggacggctac ttcaagaagc tccaagacga gctggacaac 420
atcgtggaca acaactccga cgacgacgcc atcgccaagg cgatcaagga cttcaaggcg 480
aggtgcggca tcctgatcaa ggaggcgaag cagtacgagg aggcggcgaa gaacatcgtg 540
acctccctgg accagttcct gcacggcgac cagaagaagc tggagggcgt gatcaacatc 600
cagaagaggc tgaaggaggt gcagaccgcc ctgaatcaag cccacggcga gagcagcccg 660
gcgcacaagg agctgctgga gaaggtgaag aacctcaaga ccaccctgga gaggaccatc 720
aaggccgagc aagacctgga gaagaaggtg gagtactcct tcctgctggg tccgctgctg 780
ggcttcgtgg tgtacgagat cctggagaac accgccgtgc agcacatcaa gaatcagatc 840
gacgagatca agaagcagct ggactccgcc cagcacgacc tggaccgcga cgtgaagatc 900
atcgggatgc tgaacagcat caacaccgac atcgacaacc tgtacagcca aggccaagag 960
gccatcaagg tgttccagaa gctccaaggc atctgggcga ccatcggcgc gcagatcgag 1020
aacctgagga ccaccagcct ccaagaggtc caagacagcg acgacgccga cgagatccag 1080
atcgagctgg aggacgccag cgacgcgtgg ctggtggtgg cccaagaggc gagggacttc 1140
accctgaacg cgtacagcac caactcccgt cagaacctgc cgatcaacgt gatcagcgac 1200
agctgcaact gctccaccac caacatgacc agcaaccagt actccaaccc gaccaccaac 1260
atgaccagca accagtacat gatctcccac gagtacacca gcctgccgaa caacttcatg 1320
ctgtcccgca actctaacct ggagtacaag tgcccggaga acaacttcat gatctactgg 1380
tacaacaact ccgactggta caacaactca gactggtaca acaacagggc agtggcgagg 1440
ctgtga 1446

<210> SEQ ID NO 11
<211> LENGTH: 481
<212> TYPE: PRT
<213> ORGANISM: Artificial Sequence
<220> FEATURE:
<223> OTHER INFORMATION: translated from synthesized maize optimized coding region

<400> SEQUENCE: 11

Met Ile Ile Asp Ser Lys Thr Thr Leu Pro Arg His Ser Leu Ile His
1 5 10 15

Thr Ile Lys Leu Asn Ser Asn Lys Lys Tyr Gly Pro Gly Asp Met Thr

```
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser Asn Gln Tyr Ser Asn
                405                 410                 415

Pro Thr Thr Asn Met Thr Ser Asn Gln Tyr Met Ile Ser His Glu Tyr
            420                 425                 430

Thr Ser Leu Pro Asn Asn Phe Met Leu Ser Arg Asn Ser Asn Leu Glu
        435                 440                 445
```

```
Tyr Lys Cys Pro Glu Asn Asn Phe Met Ile Tyr Trp Tyr Asn Asn Ser
    450                 455                 460

Asp Trp Tyr Asn Asn Ser Asp Trp Tyr Asn Asn Arg Ala Val Ala Arg
465                 470                 475                 480

Leu
```

<210> SEQ ID NO 12
<211> LENGTH: 1464
<212> TYPE: DNA
<213> ORGANISM: Artificial Sequence
<220> FEATURE:
<223> OTHER INFORMATION: synthesized maize optimized coding region

<400> SEQUENCE: 12

```
atgatcattg actccaagac caccctgccg cgtcacagcc tgatccacac catcaagctg     60

aactccaaca agaagtacgg acctggcgac atgaccaacg gcaaccagtt catcatctcc    120

aagcaagagt gggccaccat cggagcgtac atccagaccg gcctgggcct gccggtgaac    180

gagcagcagc tgaggactca cgtgaacctg tcccaagaca tcagcatccc gtccgacttc    240

tcccagctgt acgacgtgta ttgcagcgac aagacctccg ccgagtggtg gaacaagaac    300

ctgtacccgc tgatcatcaa gagcgccaac gacatcgcct cctacggctt caaggtggcg    360

ggcgacccga gcatcaagaa ggacggctac ttcaagaagc tccaagacga gctggacaac    420

atcgtggaca acaactccga cgacgacgcc atcgccaagg cgatcaagga cttcaaggcg    480

aggtgcggca tcctgatcaa ggaggcgaag cagtacgagg aggcggcgaa gaacatcgtg    540

acctccctgg accagttcct gcacggcgac cagaagaagc tggagggcgt gatcaacatc    600

cagaagaggc tgaaggaggt gcagaccgcc ctgaatcaag cccacggcga gagcagcccg    660

gcgcacaagg agctgctgga gaaggtgaag aacctcaaga ccaccctgga gaggaccatc    720

aaggccgagc aagacctgga gaagaaggtg gagtactcct tcctgctggg tccgctgctg    780

ggcttcgtgg tgtacgagat cctggagaac accgccgtgc agcacatcaa gaatcagatc    840

gacgagatca agaagcagct ggactccgcc cagcacgacc tggaccgcga cgtgaagatc    900

atcgggatgc tgaacagcat caacaccgac atcgacaacc tgtacagcca aggccaagag    960

gccatcaagg tgttccagaa gctccaaggc atctgggcga ccatcggcgc gcagatcgag   1020

aacctgagga ccaccagcct ccaagaggtc caagacagcg acgacgccga cgagatccag   1080

atcgagctgg aggacgccag cgacgcgtgg ctggtggtgg cccaagaggc gagggacttc   1140

accctgaacg cgtacagcac caactcccgt cagaacctgc cgatcaacgt gatcagcgac   1200

agctgcaact gctccaccac caacatgacc agcaaccagt actccaaccc gaccaccaac   1260

atgaccagca accagtacat gatctcccac gagtacacca gcctgccgaa caacttcatg   1320

ctgtcccgca actctaacct ggagtacaag tgcccggaga acaacttcat gatctactgg   1380

tacaacaact ccgactggta caacaactca gactggtaca acaacgacct gaaggctctg   1440

gagctgccag tgagcaagct gtga                                           1464
```

<210> SEQ ID NO 13
<211> LENGTH: 487
<212> TYPE: PRT
<213> ORGANISM: Artificial Sequence
<220> FEATURE:
<223> OTHER INFORMATION: translated from synthesized maize optimized coding region

<400> SEQUENCE: 13

```
Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser Asn Gln Tyr Ser Asn
                405                 410                 415
```

```
Pro Thr Thr Asn Met Thr Ser Asn Gln Tyr Met Ile Ser His Glu Tyr
            420                 425                 430

Thr Ser Leu Pro Asn Asn Phe Met Leu Ser Arg Asn Ser Asn Leu Glu
        435                 440                 445

Tyr Lys Cys Pro Glu Asn Asn Phe Met Ile Tyr Trp Tyr Asn Asn Ser
    450                 455                 460

Asp Trp Tyr Asn Asn Ser Asp Trp Tyr Asn Asn Asp Leu Lys Ala Leu
465                 470                 475                 480

Glu Leu Pro Val Ser Lys Leu
                485


<210> SEQ ID NO 14
<211> LENGTH: 1575
<212> TYPE: DNA
<213> ORGANISM: Artificial Sequence
<220> FEATURE:
<223> OTHER INFORMATION: synthesized maize optimized coding region

<400> SEQUENCE: 14

atgccgaccg acatggagct gtccccgtcc aacgtggcga ggcacagact ggcagttctg     60

gcggcgcacc tgtcagccgc gagcctggag cctccggtga tggcgagcag cctggaggcc    120

cactgcgtta gcgctcagac aatgggcggc atcattgact ccaagaccac cctgccgcgt    180

cacagcctga tccacaccat caagctgaac tccaacaaga agtacggacc tggcgacatg    240

accaacggca accagttcat catctccaag caagagtggg ccaccatcgg agcgtacatc    300

cagaccggcc tgggcctgcc ggtgaacgag cagcagctga ggactcacgt gaacctgtcc    360

caagacatca gcatcccgtc cgacttctcc cagctgtacg acgtgtattg cagcgacaag    420

acctccgccg agtggtggaa caagaacctg tacccgctga tcatcaagag cgccaacgac    480

atcgcctcct acggcttcaa ggtggcgggc gacccgagca tcaagaagga cggctacttc    540

aagaagctcc aagacgagct ggacaacatc gtggacaaca actccgacga cgacgccatc    600

gccaaggcga tcaaggactt caaggcgagg tgcggcatcc tgatcaagga ggcgaagcag    660

tacgaggagg cggcgaagaa catcgtgacc tccctggacc agttcctgca cggcgaccag    720

aagaagctgg agggcgtgat caacatccag aagaggctga aggaggtgca gaccgccctg    780

aatcaagccc acggcgagag cagcccggcg cacaaggagc tgctggagaa ggtgaagaac    840

ctcaagacca ccctggagag gaccatcaag gccgagcaag acctggagaa gaaggtggag    900

tactccttcc tgctgggtcc gctgctgggc ttcgtggtgt acgagatcct ggagaacacc    960

gccgtgcagc acatcaagaa tcagatcgac gagatcaaga agcagctgga ctccgcccag   1020

cacgacctgg accgcgacgt gaagatcatc gggatgctga acagcatcaa caccgacatc   1080

gacaacctgt acagccaagg ccaagaggcc atcaaggtgt tccagaagct ccaaggcatc   1140

tgggcgacca tcggcgcgca gatcgagaac ctgaggacca ccagcctcca agaggtccaa   1200

gacagcgacg acgccgacga gatccagatc gagctggagg acgccagcga cgcgtggctg   1260

gtggtggccc aagaggcgag ggacttcacc ctgaacgcgt acagcaccaa ctcccgtcag   1320

aacctgccga tcaacgtgat cagcgacagc tgcaactgct ccaccaccaa catgaccagc   1380

aaccagtact ccaacccgac caccaacatg accagcaacc agtacatgat ctcccacgag   1440

tacaccagcc tgccgaacaa cttcatgctg tcccgcaact ctaacctgga gtacaagtgc   1500

ccggagaaca acttcatgat ctactggtac aacaactccg actggtacaa caactcagac   1560

tggtacaaca actga                                                    1575
```

<210> SEQ ID NO 15
<211> LENGTH: 524
<212> TYPE: PRT
<213> ORGANISM: Artificial Sequence
<220> FEATURE:
<223> OTHER INFORMATION: translated from synthesized maize optimized coding region

<400> SEQUENCE: 15

```
Met Pro Thr Asp Met Glu Leu Ser Pro Ser Asn Val Ala Arg His Arg
1               5                   10                  15

Leu Ala Val Leu Ala Ala His Leu Ser Ala Ala Ser Leu Glu Pro Pro
            20                  25                  30

Val Met Ala Ser Ser Leu Glu Ala His Cys Val Ser Ala Gln Thr Met
        35                  40                  45

Gly Gly Ile Ile Asp Ser Lys Thr Thr Leu Pro Arg His Ser Leu Ile
    50                  55                  60

His Thr Ile Lys Leu Asn Ser Asn Lys Lys Tyr Gly Pro Gly Asp Met
65                  70                  75                  80

Thr Asn Gly Asn Gln Phe Ile Ile Ser Lys Gln Glu Trp Ala Thr Ile
                85                  90                  95

Gly Ala Tyr Ile Gln Thr Gly Leu Gly Leu Pro Val Asn Glu Gln Gln
            100                 105                 110

Leu Arg Thr His Val Asn Leu Ser Gln Asp Ile Ser Ile Pro Ser Asp
        115                 120                 125

Phe Ser Gln Leu Tyr Asp Val Tyr Cys Ser Asp Lys Thr Ser Ala Glu
    130                 135                 140

Trp Trp Asn Lys Asn Leu Tyr Pro Leu Ile Ile Lys Ser Ala Asn Asp
145                 150                 155                 160

Ile Ala Ser Tyr Gly Phe Lys Val Ala Gly Asp Pro Ser Ile Lys Lys
                165                 170                 175

Asp Gly Tyr Phe Lys Lys Leu Gln Asp Glu Leu Asp Asn Ile Val Asp
            180                 185                 190

Asn Asn Ser Asp Asp Asp Ala Ile Ala Lys Ala Ile Lys Asp Phe Lys
        195                 200                 205

Ala Arg Cys Gly Ile Leu Ile Lys Glu Ala Lys Gln Tyr Glu Glu Ala
    210                 215                 220

Ala Lys Asn Ile Val Thr Ser Leu Asp Gln Phe Leu His Gly Asp Gln
225                 230                 235                 240

Lys Lys Leu Glu Gly Val Ile Asn Ile Gln Lys Arg Leu Lys Glu Val
                245                 250                 255

Gln Thr Ala Leu Asn Gln Ala His Gly Glu Ser Ser Pro Ala His Lys
            260                 265                 270

Glu Leu Leu Glu Lys Val Lys Asn Leu Lys Thr Thr Leu Glu Arg Thr
        275                 280                 285

Ile Lys Ala Glu Gln Asp Leu Glu Lys Lys Val Glu Tyr Ser Phe Leu
    290                 295                 300

Leu Gly Pro Leu Leu Gly Phe Val Val Tyr Glu Ile Leu Glu Asn Thr
305                 310                 315                 320

Ala Val Gln His Ile Lys Asn Gln Ile Asp Glu Ile Lys Lys Gln Leu
                325                 330                 335

Asp Ser Ala Gln His Asp Leu Asp Arg Asp Val Lys Ile Ile Gly Met
            340                 345                 350

Leu Asn Ser Ile Asn Thr Asp Ile Asp Asn Leu Tyr Ser Gln Gly Gln
        355                 360                 365
```

```
Glu Ala Ile Lys Val Phe Gln Lys Leu Gln Gly Ile Trp Ala Thr Ile
    370                 375                 380

Gly Ala Gln Ile Glu Asn Leu Arg Thr Thr Ser Leu Gln Glu Val Gln
385                 390                 395                 400

Asp Ser Asp Asp Ala Asp Glu Ile Gln Ile Glu Leu Glu Asp Ala Ser
                405                 410                 415

Asp Ala Trp Leu Val Val Ala Gln Glu Ala Arg Asp Phe Thr Leu Asn
            420                 425                 430

Ala Tyr Ser Thr Asn Ser Arg Gln Asn Leu Pro Ile Asn Val Ile Ser
        435                 440                 445

Asp Ser Cys Asn Cys Ser Thr Thr Asn Met Thr Ser Asn Gln Tyr Ser
    450                 455                 460

Asn Pro Thr Thr Asn Met Thr Ser Asn Gln Tyr Met Ile Ser His Glu
465                 470                 475                 480

Tyr Thr Ser Leu Pro Asn Asn Phe Met Leu Ser Arg Asn Ser Asn Leu
                485                 490                 495

Glu Tyr Lys Cys Pro Glu Asn Asn Phe Met Ile Tyr Trp Tyr Asn Asn
            500                 505                 510

Ser Asp Trp Tyr Asn Asn Ser Asp Trp Tyr Asn Asn
        515                 520
```

```
<210> SEQ ID NO 16
<211> LENGTH: 1554
<212> TYPE: DNA
<213> ORGANISM: Artificial Sequence
<220> FEATURE:
<223> OTHER INFORMATION: synthesized maize optimized coding region

<400> SEQUENCE: 16

atggctcacg ctagggtgct gttgcttgcg ctggcggtgc tggcaacagc agccgtggcg     60

gtggcgtcaa gctccagctt cgcggacagc aacccgatta ggcctgtgac cgacagggcc    120

gcctcaacca tcattgactc caagaccacc ctgccgcgtc acagcctgat ccacaccatc    180

aagctgaact ccaacaagaa gtacggacct ggcgacatga ccaacggcaa ccagttcatc    240

atctccaagc aagagtgggc caccatcgga gcgtacatcc agaccggcct gggcctgccg    300

gtgaacgagc agcagctgag gactcacgtg aacctgtccc aagacatcag catcccgtcc    360

gacttctccc agctgtacga cgtgtattgc agcgacaaga cctccgccga gtggtggaac    420

aagaacctgt acccgctgat catcaagagc gccaacgaca tcgcctccta cggcttcaag    480

gtggcgggcg acccgagcat caagaaggac ggctacttca agaagctcca agacgagctg    540

gacaacatcg tggacaacaa ctccgacgac gacgccatcg ccaaggcgat caaggacttc    600

aaggcgaggt gcggcatcct gatcaaggag gcgaagcagt acgaggaggc ggcgaagaac    660

atcgtgacct ccctggacca gttcctgcac ggcgaccaga agaagctgga gggcgtgatc    720

aacatccaga agaggctgaa ggaggtgcag accgccctga atcaagccca cggcgagagc    780

agcccggcgc acaaggagct gctggagaag gtgaagaacc tcaagaccac cctggagagg    840

accatcaagg ccgagcaaga cctggagaag aaggtggagt actccttcct gctgggtccg    900

ctgctgggct tcgtggtgta cgagatcctg gagaacaccg ccgtgcagca catcaagaat    960

cagatcgacg agatcaagaa gcagctggac tccgcccagc acgacctgga ccgcgacgtg   1020

aagatcatcg ggatgctgaa cagcatcaac accgacatcg acaacctgta cagccaaggc   1080

caagaggcca tcaaggtgtt ccagaagctc caaggcatct gggcgaccat cggcgcgcag   1140
```

```
atcgagaacc tgaggaccac cagcctccaa gaggtccaag acagcgacga cgccgacgag   1200

atccagatcg agctggagga cgccagcgac gcgtggctgg tggtggccca agaggcgagg   1260

gacttcaccc tgaacgcgta cagcaccaac tcccgtcaga acctgccgat caacgtgatc   1320

agcgacagct gcaactgctc caccaccaac atgaccagca accagtactc caacccgacc   1380

accaacatga ccagcaacca gtacatgatc tcccacgagt acaccagcct gccgaacaac   1440

ttcatgctgt cccgcaactc taacctggag tacaagtgcc cggagaacaa cttcatgatc   1500

tactggtaca acaactccga ctggtacaac aactcagact ggtacaacaa ctga         1554
```

<210> SEQ ID NO 17
<211> LENGTH: 517
<212> TYPE: PRT
<213> ORGANISM: Artificial Sequence
<220> FEATURE:
<223> OTHER INFORMATION: translated from synthesized maize optimized coding region

<400> SEQUENCE: 17

```
Met Ala His Ala Arg Val Leu Leu Leu Ala Leu Ala Val Leu Ala Thr
1               5                   10                  15

Ala Ala Val Ala Val Ala Ser Ser Ser Ser Phe Ala Asp Ser Asn Pro
            20                  25                  30

Ile Arg Pro Val Thr Asp Arg Ala Ala Ser Thr Ile Ile Asp Ser Lys
        35                  40                  45

Thr Thr Leu Pro Arg His Ser Leu Ile His Thr Ile Lys Leu Asn Ser
    50                  55                  60

Asn Lys Lys Tyr Gly Pro Gly Asp Met Thr Asn Gly Asn Gln Phe Ile
65                  70                  75                  80

Ile Ser Lys Gln Glu Trp Ala Thr Ile Gly Ala Tyr Ile Gln Thr Gly
                85                  90                  95

Leu Gly Leu Pro Val Asn Glu Gln Gln Leu Arg Thr His Val Asn Leu
            100                 105                 110

Ser Gln Asp Ile Ser Ile Pro Ser Asp Phe Ser Gln Leu Tyr Asp Val
        115                 120                 125

Tyr Cys Ser Asp Lys Thr Ser Ala Glu Trp Trp Asn Lys Asn Leu Tyr
    130                 135                 140

Pro Leu Ile Ile Lys Ser Ala Asn Asp Ile Ala Ser Tyr Gly Phe Lys
145                 150                 155                 160

Val Ala Gly Asp Pro Ser Ile Lys Lys Asp Gly Tyr Phe Lys Lys Leu
                165                 170                 175

Gln Asp Glu Leu Asp Asn Ile Val Asp Asn Asn Ser Asp Asp Asp Ala
            180                 185                 190

Ile Ala Lys Ala Ile Lys Asp Phe Lys Ala Arg Cys Gly Ile Leu Ile
        195                 200                 205

Lys Glu Ala Lys Gln Tyr Glu Glu Ala Ala Lys Asn Ile Val Thr Ser
    210                 215                 220

Leu Asp Gln Phe Leu His Gly Asp Gln Lys Lys Leu Glu Gly Val Ile
225                 230                 235                 240

Asn Ile Gln Lys Arg Leu Lys Glu Val Gln Thr Ala Leu Asn Gln Ala
                245                 250                 255

His Gly Glu Ser Ser Pro Ala His Lys Glu Leu Leu Glu Lys Val Lys
            260                 265                 270

Asn Leu Lys Thr Thr Leu Glu Arg Thr Ile Lys Ala Glu Gln Asp Leu
        275                 280                 285
```

```
Glu Lys Lys Val Glu Tyr Ser Phe Leu Leu Gly Pro Leu Leu Gly Phe
    290                 295                 300

Val Val Tyr Glu Ile Leu Glu Asn Thr Ala Val Gln His Ile Lys Asn
305                 310                 315                 320

Gln Ile Asp Glu Ile Lys Lys Gln Leu Asp Ser Ala Gln His Asp Leu
                325                 330                 335

Asp Arg Asp Val Lys Ile Ile Gly Met Leu Asn Ser Ile Asn Thr Asp
            340                 345                 350

Ile Asp Asn Leu Tyr Ser Gln Gly Gln Glu Ala Ile Lys Val Phe Gln
        355                 360                 365

Lys Leu Gln Gly Ile Trp Ala Thr Ile Gly Ala Gln Ile Glu Asn Leu
    370                 375                 380

Arg Thr Thr Ser Leu Gln Glu Val Gln Asp Ser Asp Asp Ala Asp Glu
385                 390                 395                 400

Ile Gln Ile Glu Leu Glu Asp Ala Ser Asp Ala Trp Leu Val Val Ala
                405                 410                 415

Gln Glu Ala Arg Asp Phe Thr Leu Asn Ala Tyr Ser Thr Asn Ser Arg
            420                 425                 430

Gln Asn Leu Pro Ile Asn Val Ile Ser Asp Ser Cys Asn Cys Ser Thr
        435                 440                 445

Thr Asn Met Thr Ser Asn Gln Tyr Ser Asn Pro Thr Thr Asn Met Thr
    450                 455                 460

Ser Asn Gln Tyr Met Ile Ser His Glu Tyr Thr Ser Leu Pro Asn Asn
465                 470                 475                 480

Phe Met Leu Ser Arg Asn Ser Asn Leu Glu Tyr Lys Cys Pro Glu Asn
                485                 490                 495

Asn Phe Met Ile Tyr Trp Tyr Asn Asn Ser Asp Trp Tyr Asn Asn Ser
            500                 505                 510

Asp Trp Tyr Asn Asn
        515
```

```
<210> SEQ ID NO 18
<211> LENGTH: 1524
<212> TYPE: DNA
<213> ORGANISM: Artificial Sequence
<220> FEATURE:
<223> OTHER INFORMATION: synthesized maize optimized coding region

<400> SEQUENCE: 18

atgagtagct caccgtcctt tggcctgctg gcggttgcgg ccctgcttct ggcgcttagc     60

ctggcgcaac acggcatcat tgactccaag accaccctgc cgcgtcacag cctgatccac    120

accatcaagc tgaactccaa caagaagtac ggacctggcg acatgaccaa cggcaaccag    180

ttcatcatct ccaagcaaga gtgggccacc atcggagcgt acatccagac cggcctgggc    240

ctgccggtga acgagcagca gctgaggact cacgtgaacc tgtcccaaga catcagcatc    300

ccgtccgact tctcccagct gtacgacgtg tattgcagcg acaagacctc cgccgagtgg    360

tggaacaaga acctgtaccc gctgatcatc aagagcgcca acgacatcgc ctcctacggc    420

ttcaaggtgg cgggcgaccc gagcatcaag aaggacggct acttcaagaa gctccaagac    480

gagctggaca acatcgtgga caacaactcc gacgacgacg ccatcgccaa ggcgatcaag    540

gacttcaagg cgaggtgcgg catcctgatc aaggaggcga agcagtacga ggaggcggcg    600

aagaacatcg tgacctccct ggaccagttc ctgcacggcg accagaagaa gctggagggc    660

gtgatcaaca tccagaagag gctgaaggag gtgcagaccg ccctgaatca agcccacggc    720
```

```
gagagcagcc cggcgcacaa ggagctgctg gagaaggtga agaacctcaa gaccaccctg    780

gagaggacca tcaaggccga gcaagacctg gagaagaagg tggagtactc cttcctgctg    840

ggtccgctgc tgggcttcgt ggtgtacgag atcctggaga acaccgccgt gcagcacatc    900

aagaatcaga tcgacgagat caagaagcag ctggactccg cccagcacga cctggaccgc    960

gacgtgaaga tcatcgggat gctgaacagc atcaacaccg acatcgacaa cctgtacagc   1020

caaggccaag aggccatcaa ggtgttccag aagctccaag gcatctgggc gaccatcggc   1080

gcgcagatcg agaacctgag gaccaccagc ctccaagagg tccaagacag cgacgacgcc   1140

gacgagatcc agatcgagct ggaggacgcc agcgacgcgt ggctggtggt ggcccaagag   1200

gcgagggact tcaccctgaa cgcgtacagc accaactccc gtcagaacct gccgatcaac   1260

gtgatcagcg acagctgcaa ctgctccacc accaacatga ccagcaacca gtactccaac   1320

ccgaccacca acatgaccag caaccagtac atgatctccc acgagtacac cagcctgccg   1380

aacaacttca tgctgtcccg caactctaac ctggagtaca agtgcccgga gaacaacttc   1440

atgatctact ggtacaacaa ctccgactgg tacaacaact cagactggta caacaacgac   1500

gagctgaagg ctgaggccaa gtga                                          1524
```

<210> SEQ ID NO 19
<211> LENGTH: 507
<212> TYPE: PRT
<213> ORGANISM: Artificial Sequence
<220> FEATURE:
<223> OTHER INFORMATION: translated from synthesized maize optimized coding region

<400> SEQUENCE: 19

```
Met Ser Ser Ser Pro Ser Phe Gly Leu Leu Ala Val Ala Ala Leu Leu
1               5                   10                  15

Leu Ala Leu Ser Leu Ala Gln His Gly Ile Ile Asp Ser Lys Thr Thr
            20                  25                  30

Leu Pro Arg His Ser Leu Ile His Thr Ile Lys Leu Asn Ser Asn Lys
        35                  40                  45

Lys Tyr Gly Pro Gly Asp Met Thr Asn Gly Asn Gln Phe Ile Ile Ser
    50                  55                  60

Lys Gln Glu Trp Ala Thr Ile Gly Ala Tyr Ile Gln Thr Gly Leu Gly
65                  70                  75                  80

Leu Pro Val Asn Glu Gln Gln Leu Arg Thr His Val Asn Leu Ser Gln
                85                  90                  95

Asp Ile Ser Ile Pro Ser Asp Phe Ser Gln Leu Tyr Asp Val Tyr Cys
            100                 105                 110

Ser Asp Lys Thr Ser Ala Glu Trp Trp Asn Lys Asn Leu Tyr Pro Leu
        115                 120                 125

Ile Ile Lys Ser Ala Asn Asp Ile Ala Ser Tyr Gly Phe Lys Val Ala
    130                 135                 140

Gly Asp Pro Ser Ile Lys Lys Asp Gly Tyr Phe Lys Lys Leu Gln Asp
145                 150                 155                 160

Glu Leu Asp Asn Ile Val Asp Asn Asn Ser Asp Asp Asp Ala Ile Ala
                165                 170                 175

Lys Ala Ile Lys Asp Phe Lys Ala Arg Cys Gly Ile Leu Ile Lys Glu
            180                 185                 190

Ala Lys Gln Tyr Glu Glu Ala Ala Lys Asn Ile Val Thr Ser Leu Asp
        195                 200                 205

Gln Phe Leu His Gly Asp Gln Lys Lys Leu Glu Gly Val Ile Asn Ile
```

```
    210                 215                 220

Gln Lys Arg Leu Lys Glu Val Gln Thr Ala Leu Asn Gln Ala His Gly
225                 230                 235                 240

Glu Ser Ser Pro Ala His Lys Glu Leu Leu Glu Lys Val Lys Asn Leu
                245                 250                 255

Lys Thr Thr Leu Glu Arg Thr Ile Lys Ala Glu Gln Asp Leu Glu Lys
            260                 265                 270

Lys Val Glu Tyr Ser Phe Leu Leu Gly Pro Leu Leu Gly Phe Val Val
        275                 280                 285

Tyr Glu Ile Leu Glu Asn Thr Ala Val Gln His Ile Lys Asn Gln Ile
    290                 295                 300

Asp Glu Ile Lys Lys Gln Leu Asp Ser Ala Gln His Asp Leu Asp Arg
305                 310                 315                 320

Asp Val Lys Ile Ile Gly Met Leu Asn Ser Ile Asn Thr Asp Ile Asp
                325                 330                 335

Asn Leu Tyr Ser Gln Gly Gln Glu Ala Ile Lys Val Phe Gln Lys Leu
            340                 345                 350

Gln Gly Ile Trp Ala Thr Ile Gly Ala Gln Ile Glu Asn Leu Arg Thr
        355                 360                 365

Thr Ser Leu Gln Glu Val Gln Asp Ser Asp Asp Ala Asp Glu Ile Gln
    370                 375                 380

Ile Glu Leu Glu Asp Ala Ser Asp Ala Trp Leu Val Val Ala Gln Glu
385                 390                 395                 400

Ala Arg Asp Phe Thr Leu Asn Ala Tyr Ser Thr Asn Ser Arg Gln Asn
                405                 410                 415

Leu Pro Ile Asn Val Ile Ser Asp Ser Cys Asn Cys Ser Thr Thr Asn
            420                 425                 430

Met Thr Ser Asn Gln Tyr Ser Asn Pro Thr Thr Asn Met Thr Ser Asn
        435                 440                 445

Gln Tyr Met Ile Ser His Glu Tyr Thr Ser Leu Pro Asn Asn Phe Met
    450                 455                 460

Leu Ser Arg Asn Ser Asn Leu Glu Tyr Lys Cys Pro Glu Asn Asn Phe
465                 470                 475                 480

Met Ile Tyr Trp Tyr Asn Asn Ser Asp Trp Tyr Asn Asn Ser Asp Trp
                485                 490                 495

Tyr Asn Asn Asp Glu Leu Lys Ala Glu Ala Lys
            500                 505


<210> SEQ ID NO 20
<211> LENGTH: 1707
<212> TYPE: DNA
<213> ORGANISM: Artificial Sequence
<220> FEATURE:
<223> OTHER INFORMATION: synthesized maize optimized coding region

<400> SEQUENCE: 20

atggcgaaca agcacctgag cctgtccctg ttcctggtgc tgcttggcct gagcgcatcc      60

ctggcatccg gaatcattga ctccaagacc accctgccgc gtcacagcct gatccacacc     120

atcaagctga actccaacaa gaagtacgga cctggcgaca tgaccaacgg caaccagttc     180

atcatctcca agcaagagtg ggccaccatc ggagcgtaca tccagaccgg cctgggcctg     240

ccggtgaacg agcagcagct gaggactcac gtgaacctgt cccaagacat cagcatcccg     300

tccgacttct cccagctgta cgacgtgtat tgcagcgaca agacctccgc cgagtggtgg     360

aacaagaacc tgtacccgct gatcatcaag agcgccaacg acatcgcctc ctacggcttc     420
```

```
aaggtggcgg gcgacccgag catcaagaag gacggctact tcaagaagct ccaagacgag    480

ctggacaaca tcgtggacaa caactccgac gacgacgcca tcgccaaggc gatcaaggac    540

ttcaaggcga ggtgcggcat cctgatcaag gaggcgaagc agtacgagga ggcggcgaag    600

aacatcgtga cctccctgga ccagttcctg cacggcgacc agaagaagct ggagggcgtg    660

atcaacatcc agaagaggct gaaggaggtg cagaccgccc tgaatcaagc ccacggcgag    720

agcagcccgg cgcacaagga gctgctggag aaggtgaaga acctcaagac caccctggag    780

aggaccatca aggccgagca agacctggag aagaaggtgg agtactcctt cctgctgggt    840

ccgctgctgg gcttcgtggt gtacgagatc ctggagaaca ccgccgtgca gcacatcaag    900

aatcagatcg acgagatcaa gaagcagctg gactccgccc agcacgacct ggaccgcgac    960

gtgaagatca tcgggatgct gaacagcatc aacaccgaca tcgacaacct gtacagccaa   1020

ggccaagagg ccatcaaggt gttccagaag ctccaaggca tctgggcgac catcggcgcg   1080

cagatcgaga acctgaggac caccagcctc caagaggtcc aagacagcga cgacgccgac   1140

gagatccaga tcgagctgga ggacgccagc gacgcgtggc tggtggtggc ccaagaggcg   1200

agggacttca ccctgaacgc gtacagcacc aactcccgtc agaacctgcc gatcaacgtg   1260

atcagcgaca gctgcaactg ctccaccacc aacatgacca gcaaccagta ctccaacccg   1320

accaccaaca tgaccagcaa ccagtacatg atctcccacg agtacaccag cctgccgaac   1380

aacttcatgc tgtcccgcaa ctctaacctg gagtacaagt gcccggagaa caacttcatg   1440

atctactggt acaacaactc cgactggtac aacaactcag actggtacaa caactctaag   1500

accgcagtgc aagccaaggc agcgtgggct gccgtgtggg gaatcctgat cgtggtggca   1560

gtggtggctg ctggcagcta cgtggtgtac aagtataggc tgaggagcta catggactca   1620

gagatcagag cgatcatggc acagtacatg cctctggaca accaaggtga ggtgccgaac   1680

cacacccacg acgaggaccg gagctga                                       1707
```

```
<210> SEQ ID NO 21
<211> LENGTH: 568
<212> TYPE: PRT
<213> ORGANISM: Artificial Sequence
<220> FEATURE:
<223> OTHER INFORMATION: translated from synthesized maize optimized
      coding region

<400> SEQUENCE: 21

Met Ala Asn Lys His Leu Ser Leu Ser Leu Phe Leu Val Leu Leu Gly
1               5                   10                  15

Leu Ser Ala Ser Leu Ala Ser Gly Ile Ile Asp Ser Lys Thr Thr Leu
            20                  25                  30

Pro Arg His Ser Leu Ile His Thr Ile Lys Leu Asn Ser Asn Lys Lys
        35                  40                  45

Tyr Gly Pro Gly Asp Met Thr Asn Gly Asn Gln Phe Ile Ile Ser Lys
    50                  55                  60

Gln Glu Trp Ala Thr Ile Gly Ala Tyr Ile Gln Thr Gly Leu Gly Leu
65                  70                  75                  80

Pro Val Asn Glu Gln Gln Leu Arg Thr His Val Asn Leu Ser Gln Asp
                85                  90                  95

Ile Ser Ile Pro Ser Asp Phe Ser Gln Leu Tyr Asp Val Tyr Cys Ser
            100                 105                 110

Asp Lys Thr Ser Ala Glu Trp Trp Asn Lys Asn Leu Tyr Pro Leu Ile
        115                 120                 125
```

```
Ile Lys Ser Ala Asn Asp Ile Ala Ser Tyr Gly Phe Lys Val Ala Gly
    130                 135                 140

Asp Pro Ser Ile Lys Lys Asp Gly Tyr Phe Lys Lys Leu Gln Asp Glu
145                 150                 155                 160

Leu Asp Asn Ile Val Asp Asn Asn Ser Asp Asp Ala Ile Ala Lys
                165                 170                 175

Ala Ile Lys Asp Phe Lys Ala Arg Cys Gly Ile Leu Ile Lys Glu Ala
            180                 185                 190

Lys Gln Tyr Glu Glu Ala Ala Lys Asn Ile Val Thr Ser Leu Asp Gln
        195                 200                 205

Phe Leu His Gly Asp Gln Lys Lys Leu Glu Gly Val Ile Asn Ile Gln
    210                 215                 220

Lys Arg Leu Lys Glu Val Gln Thr Ala Leu Asn Gln Ala His Gly Glu
225                 230                 235                 240

Ser Ser Pro Ala His Lys Glu Leu Leu Glu Lys Val Lys Asn Leu Lys
                245                 250                 255

Thr Thr Leu Glu Arg Thr Ile Lys Ala Glu Gln Asp Leu Glu Lys Lys
            260                 265                 270

Val Glu Tyr Ser Phe Leu Leu Gly Pro Leu Leu Gly Phe Val Val Tyr
        275                 280                 285

Glu Ile Leu Glu Asn Thr Ala Val Gln His Ile Lys Asn Gln Ile Asp
    290                 295                 300

Glu Ile Lys Lys Gln Leu Asp Ser Ala Gln His Asp Leu Asp Arg Asp
305                 310                 315                 320

Val Lys Ile Ile Gly Met Leu Asn Ser Ile Asn Thr Asp Ile Asp Asn
                325                 330                 335

Leu Tyr Ser Gln Gly Gln Glu Ala Ile Lys Val Phe Gln Lys Leu Gln
            340                 345                 350

Gly Ile Trp Ala Thr Ile Gly Ala Gln Ile Glu Asn Leu Arg Thr Thr
        355                 360                 365

Ser Leu Gln Glu Val Gln Asp Ser Asp Asp Ala Asp Glu Ile Gln Ile
    370                 375                 380

Glu Leu Glu Asp Ala Ser Asp Ala Trp Leu Val Val Ala Gln Glu Ala
385                 390                 395                 400

Arg Asp Phe Thr Leu Asn Ala Tyr Ser Thr Asn Ser Arg Gln Asn Leu
                405                 410                 415

Pro Ile Asn Val Ile Ser Asp Ser Cys Asn Cys Ser Thr Thr Asn Met
            420                 425                 430

Thr Ser Asn Gln Tyr Ser Asn Pro Thr Thr Asn Met Thr Ser Asn Gln
        435                 440                 445

Tyr Met Ile Ser His Glu Tyr Thr Ser Leu Pro Asn Asn Phe Met Leu
    450                 455                 460

Ser Arg Asn Ser Asn Leu Glu Tyr Lys Cys Pro Glu Asn Asn Phe Met
465                 470                 475                 480

Ile Tyr Trp Tyr Asn Asn Ser Asp Trp Tyr Asn Asn Ser Asp Trp Tyr
                485                 490                 495

Asn Asn Ser Lys Thr Ala Val Gln Ala Lys Ala Ala Trp Ala Ala Val
            500                 505                 510

Trp Gly Ile Leu Ile Val Val Ala Val Val Ala Ala Gly Ser Tyr Val
        515                 520                 525

Val Tyr Lys Tyr Arg Leu Arg Ser Tyr Met Asp Ser Glu Ile Arg Ala
    530                 535                 540
```

```
Ile Met Ala Gln Tyr Met Pro Leu Asp Asn Gln Gly Glu Val Pro Asn
545                 550                 555                 560

His Thr His Asp Glu Asp Arg Ser
                565


<210> SEQ ID NO 22
<211> LENGTH: 1497
<212> TYPE: DNA
<213> ORGANISM: Artificial Sequence
<220> FEATURE:
<223> OTHER INFORMATION: synthesized maize optimized coding region

<400> SEQUENCE: 22

atggcgaaca agcacctgag cctgtccctg ttcctggtgc tgcttggcct gagcgcatcc      60

ctggcatccg gaatcattga ctccaagacc accctgccgc gtcacagcct gatccacacc     120

atcaagctga actccaacaa gaagtacgga cctggcgaca tgaccaacgg caaccagttc     180

atcatctcca agcaagagtg ggccaccatc ggagcgtaca tccagaccgg cctgggcctg     240

ccggtgaacg agcagcagct gaggactcac gtgaacctgt cccaagacat cagcatcccg     300

tccgacttct cccagctgta cgacgtgtat tgcagcgaca agacctccgc cgagtggtgg     360

aacaagaacc tgtacccgct gatcatcaag agcgccaacg acatcgcctc ctacggcttc     420

aaggtggcgg gcgacccgag catcaagaag gacggctact tcaagaagct ccaagacgag     480

ctggacaaca tcgtggacaa caactccgac gacgacgcca tcgccaaggc gatcaaggac     540

ttcaaggcga ggtgcggcat cctgatcaag gaggcgaagc agtacgagga ggcggcgaag     600

aacatcgtga cctccctgga ccagttcctg cacggcgacc agaagaagct ggagggcgtg     660

atcaacatcc agaagaggct gaaggaggtg cagaccgccc tgaatcaagc ccacggcgag     720

agcagcccgg cgcacaagga gctgctggag aaggtgaaga acctcaagac caccctggag     780

aggaccatca aggccgagca agacctggag aagaaggtgg agtactcctt cctgctgggt     840

ccgctgctgg gcttcgtggt gtacgagatc ctggagaaca ccgccgtgca gcacatcaag     900

aatcagatcg acgagatcaa gaagcagctg gactccgccc agcacgacct ggaccgcgac     960

gtgaagatca tcgggatgct gaacagcatc aacaccgaca tcgacaacct gtacagccaa    1020

ggccaagagg ccatcaaggt gttccagaag ctccaaggca tctgggcgac catcggcgcg    1080

cagatcgaga acctgaggac caccagcctc caagaggtcc aagacagcga cgacgccgac    1140

gagatccaga tcgagctgga ggacgccagc gacgcgtggc tggtggtggc ccaagaggcg    1200

agggacttca ccctgaacgc gtacagcacc aactcccgtc agaacctgcc gatcaacgtg    1260

atcagcgaca gctgcaactg ctccaccacc aacatgacca gcaaccagta ctccaacccg    1320

accaccaaca tgaccagcaa ccagtacatg atctcccacg agtacaccag cctgccgaac    1380

aacttcatgc tgtcccgcaa ctctaacctg gagtacaagt gcccggagaa caacttcatg    1440

atctactggt acaacaactc cgactggtac aacaactcag actggtacaa caactga       1497


<210> SEQ ID NO 23
<211> LENGTH: 498
<212> TYPE: PRT
<213> ORGANISM: Artificial Sequence
<220> FEATURE:
<223> OTHER INFORMATION: translated from synthesized maize optimized
      coding region

<400> SEQUENCE: 23

Met Ala Asn Lys His Leu Ser Leu Ser Leu Phe Leu Val Leu Leu Gly
1               5                   10                  15
```

```
Leu Ser Ala Ser Leu Ala Ser Gly Ile Ile Asp Ser Lys Thr Thr Leu
            20                  25                  30

Pro Arg His Ser Leu Ile His Thr Ile Lys Leu Asn Ser Asn Lys Lys
        35                  40                  45

Tyr Gly Pro Gly Asp Met Thr Asn Gly Asn Gln Phe Ile Ile Ser Lys
    50                  55                  60

Gln Glu Trp Ala Thr Ile Gly Ala Tyr Ile Gln Thr Gly Leu Gly Leu
65                  70                  75                  80

Pro Val Asn Glu Gln Gln Leu Arg Thr His Val Asn Leu Ser Gln Asp
                85                  90                  95

Ile Ser Ile Pro Ser Asp Phe Ser Gln Leu Tyr Asp Val Tyr Cys Ser
            100                 105                 110

Asp Lys Thr Ser Ala Glu Trp Trp Asn Lys Asn Leu Tyr Pro Leu Ile
        115                 120                 125

Ile Lys Ser Ala Asn Asp Ile Ala Ser Tyr Gly Phe Lys Val Ala Gly
    130                 135                 140

Asp Pro Ser Ile Lys Lys Asp Gly Tyr Phe Lys Lys Leu Gln Asp Glu
145                 150                 155                 160

Leu Asp Asn Ile Val Asp Asn Asn Ser Asp Asp Asp Ala Ile Ala Lys
                165                 170                 175

Ala Ile Lys Asp Phe Lys Ala Arg Cys Gly Ile Leu Ile Lys Glu Ala
            180                 185                 190

Lys Gln Tyr Glu Glu Ala Ala Lys Asn Ile Val Thr Ser Leu Asp Gln
        195                 200                 205

Phe Leu His Gly Asp Gln Lys Lys Leu Glu Gly Val Ile Asn Ile Gln
    210                 215                 220

Lys Arg Leu Lys Glu Val Gln Thr Ala Leu Asn Gln Ala His Gly Glu
225                 230                 235                 240

Ser Ser Pro Ala His Lys Glu Leu Leu Glu Lys Val Lys Asn Leu Lys
                245                 250                 255

Thr Thr Leu Glu Arg Thr Ile Lys Ala Glu Gln Asp Leu Glu Lys Lys
            260                 265                 270

Val Glu Tyr Ser Phe Leu Leu Gly Pro Leu Leu Gly Phe Val Val Tyr
        275                 280                 285

Glu Ile Leu Glu Asn Thr Ala Val Gln His Ile Lys Asn Gln Ile Asp
    290                 295                 300

Glu Ile Lys Lys Gln Leu Asp Ser Ala Gln His Asp Leu Asp Arg Asp
305                 310                 315                 320

Val Lys Ile Ile Gly Met Leu Asn Ser Ile Asn Thr Asp Ile Asp Asn
                325                 330                 335

Leu Tyr Ser Gln Gly Gln Glu Ala Ile Lys Val Phe Gln Lys Leu Gln
            340                 345                 350

Gly Ile Trp Ala Thr Ile Gly Ala Gln Ile Glu Asn Leu Arg Thr Thr
        355                 360                 365

Ser Leu Gln Glu Val Gln Asp Ser Asp Asp Ala Asp Glu Ile Gln Ile
    370                 375                 380

Glu Leu Glu Asp Ala Ser Asp Ala Trp Leu Val Val Ala Gln Glu Ala
385                 390                 395                 400

Arg Asp Phe Thr Leu Asn Ala Tyr Ser Thr Asn Ser Arg Gln Asn Leu
                405                 410                 415

Pro Ile Asn Val Ile Ser Asp Ser Cys Asn Cys Ser Thr Thr Asn Met
            420                 425                 430
```

```
Thr Ser Asn Gln Tyr Ser Asn Pro Thr Thr Asn Met Thr Ser Asn Gln
        435                 440                 445

Tyr Met Ile Ser His Glu Tyr Thr Ser Leu Pro Asn Asn Phe Met Leu
    450                 455                 460

Ser Arg Asn Ser Asn Leu Glu Tyr Lys Cys Pro Glu Asn Asn Phe Met
465                 470                 475                 480

Ile Tyr Trp Tyr Asn Asn Ser Asp Trp Tyr Asn Asn Ser Asp Trp Tyr
                485                 490                 495

Asn Asn


<210> SEQ ID NO 24
<211> LENGTH: 1515
<212> TYPE: DNA
<213> ORGANISM: Artificial Sequence
<220> FEATURE:
<223> OTHER INFORMATION: synthesized maize optimized coding region

<400> SEQUENCE: 24

atggcgaaca agcacctgag cctgtccctg ttcctggtgc tgcttggcct gagcgcatcc     60

ctggcatccg gaatcattga ctccaagacc accctgccgc gtcacagcct gatccacacc    120

atcaagctga actccaacaa gaagtacgga cctggcgaca tgaccaacgg caaccagttc    180

atcatctcca agcaagagtg ggccaccatc ggagcgtaca tccagaccgg cctgggcctg    240

ccggtgaacg agcagcagct gaggactcac gtgaacctgt cccaagacat cagcatcccg    300

tccgacttct cccagctgta cgacgtgtat tgcagcgaca agacctccgc cgagtggtgg    360

aacaagaacc tgtacccgct gatcatcaag agcgccaacg acatcgcctc ctacggcttc    420

aaggtggcgg gcgacccgag catcaagaag gacggctact tcaagaagct ccaagacgag    480

ctggacaaca tcgtggacaa caactccgac gacgacgcca tcgccaaggc gatcaaggac    540

ttcaaggcga ggtgcggcat cctgatcaag gaggcgaagc agtacgagga ggcggcgaag    600

aacatcgtga cctccctgga ccagttcctg cacggcgacc agaagaagct ggagggcgtg    660

atcaacatcc agaagaggct gaaggaggtg cagaccgccc tgaatcaagc ccacggcgag    720

agcagcccgg cgcacaagga gctgctggag aaggtgaaga acctcaagac caccctggag    780

aggaccatca aggccgagca agacctggag aagaaggtgg agtactcctt cctgctgggt    840

ccgctgctgg gcttcgtggt gtacgagatc ctggagaaca ccgccgtgca gcacatcaag    900

aatcagatcg acgagatcaa gaagcagctg gactccgccc agcacgacct ggaccgcgac    960

gtgaagatca tcgggatgct gaacagcatc aacaccgaca tcgacaacct gtacagccaa   1020

ggccaagagg ccatcaaggt gttccagaag ctccaaggca tctgggcgac catcggcgcg   1080

cagatcgaga acctgaggac caccagcctc caagaggtcc aagacagcga cgacgccgac   1140

gagatccaga tcgagctgga ggacgccagc gacgcgtggc tggtggtggc ccaagaggcg   1200

agggacttca ccctgaacgc gtacagcacc aactcccgtc agaacctgcc gatcaacgtg   1260

atcagcgaca gctgcaactg ctccaccacc aacatgacca gcaaccagta ctccaacccg   1320

accaccaaca tgaccagcaa ccagtacatg atctcccacg agtacaccag cctgccgaac   1380

aacttcatgc tgtcccgcaa ctctaacctg gagtacaagt gcccggagaa caacttcatg   1440

atctactggt acaacaactc cgactggtac aacaactcag actggtacaa caacagcgag   1500

aaggacgagc tgtga                                                    1515


<210> SEQ ID NO 25
<211> LENGTH: 504
```

```
<212> TYPE: PRT
<213> ORGANISM: Artificial Sequence
<220> FEATURE:
<223> OTHER INFORMATION: translated from synthesized maize optimized
      coding region

<400> SEQUENCE: 25

Met Ala Asn Lys His Leu Ser Leu Ser Leu Phe Leu Val Leu Leu Gly
1               5                   10                  15

Leu Ser Ala Ser Leu Ala Ser Gly Ile Ile Asp Ser Lys Thr Thr Leu
            20                  25                  30

Pro Arg His Ser Leu Ile His Thr Ile Lys Leu Asn Ser Asn Lys Lys
        35                  40                  45

Tyr Gly Pro Gly Asp Met Thr Asn Gly Asn Gln Phe Ile Ile Ser Lys
    50                  55                  60

Gln Glu Trp Ala Thr Ile Gly Ala Tyr Ile Gln Thr Gly Leu Gly Leu
65                  70                  75                  80

Pro Val Asn Glu Gln Gln Leu Arg Thr His Val Asn Leu Ser Gln Asp
                85                  90                  95

Ile Ser Ile Pro Ser Asp Phe Ser Gln Leu Tyr Asp Val Tyr Cys Ser
            100                 105                 110

Asp Lys Thr Ser Ala Glu Trp Trp Asn Lys Asn Leu Tyr Pro Leu Ile
        115                 120                 125

Ile Lys Ser Ala Asn Asp Ile Ala Ser Tyr Gly Phe Lys Val Ala Gly
    130                 135                 140

Asp Pro Ser Ile Lys Lys Asp Gly Tyr Phe Lys Lys Leu Gln Asp Glu
145                 150                 155                 160

Leu Asp Asn Ile Val Asp Asn Asn Ser Asp Asp Asp Ala Ile Ala Lys
                165                 170                 175

Ala Ile Lys Asp Phe Lys Ala Arg Cys Gly Ile Leu Ile Lys Glu Ala
            180                 185                 190

Lys Gln Tyr Glu Glu Ala Ala Lys Asn Ile Val Thr Ser Leu Asp Gln
        195                 200                 205

Phe Leu His Gly Asp Gln Lys Lys Leu Glu Gly Val Ile Asn Ile Gln
    210                 215                 220

Lys Arg Leu Lys Glu Val Gln Thr Ala Leu Asn Gln Ala His Gly Glu
225                 230                 235                 240

Ser Ser Pro Ala His Lys Glu Leu Leu Glu Lys Val Lys Asn Leu Lys
                245                 250                 255

Thr Thr Leu Glu Arg Thr Ile Lys Ala Glu Gln Asp Leu Glu Lys Lys
            260                 265                 270

Val Glu Tyr Ser Phe Leu Leu Gly Pro Leu Leu Gly Phe Val Val Tyr
        275                 280                 285

Glu Ile Leu Glu Asn Thr Ala Val Gln His Ile Lys Asn Gln Ile Asp
    290                 295                 300

Glu Ile Lys Lys Gln Leu Asp Ser Ala Gln His Asp Leu Asp Arg Asp
305                 310                 315                 320

Val Lys Ile Ile Gly Met Leu Asn Ser Ile Asn Thr Asp Ile Asp Asn
                325                 330                 335

Leu Tyr Ser Gln Gly Gln Glu Ala Ile Lys Val Phe Gln Lys Leu Gln
            340                 345                 350

Gly Ile Trp Ala Thr Ile Gly Ala Gln Ile Glu Asn Leu Arg Thr Thr
        355                 360                 365

Ser Leu Gln Glu Val Gln Asp Ser Asp Asp Ala Asp Glu Ile Gln Ile
    370                 375                 380
```

```
Glu Leu Glu Asp Ala Ser Asp Ala Trp Leu Val Val Ala Gln Glu Ala
385                 390                 395                 400

Arg Asp Phe Thr Leu Asn Ala Tyr Ser Thr Asn Ser Arg Gln Asn Leu
                405                 410                 415

Pro Ile Asn Val Ile Ser Asp Ser Cys Asn Cys Ser Thr Thr Asn Met
            420                 425                 430

Thr Ser Asn Gln Tyr Ser Asn Pro Thr Thr Asn Met Thr Ser Asn Gln
        435                 440                 445

Tyr Met Ile Ser His Glu Tyr Thr Ser Leu Pro Asn Asn Phe Met Leu
    450                 455                 460

Ser Arg Asn Ser Asn Leu Glu Tyr Lys Cys Pro Glu Asn Asn Phe Met
465                 470                 475                 480

Ile Tyr Trp Tyr Asn Asn Ser Asp Trp Tyr Asn Asn Ser Asp Trp Tyr
                485                 490                 495

Asn Asn Ser Glu Lys Asp Glu Leu
            500
```

<210> SEQ ID NO 26
<211> LENGTH: 1488
<212> TYPE: DNA
<213> ORGANISM: Artificial Sequence
<220> FEATURE:
<223> OTHER INFORMATION: synthesized maize optimized coding region

<400> SEQUENCE: 26

```
atggcaccga gaaagaggaa ggagagcaat agggagtcag cgaggaggag cagatacaga     60

aagatcattg actccaagac caccctgccg cgtcacagcc tgatccacac catcaagctg    120

aactccaaca agaagtacgg acctggcgac atgaccaacg gcaaccagtt catcatctcc    180

aagcaagagt gggccaccat cggagcgtac atccagaccg gcctgggcct gccggtgaac    240

gagcagcagc tgaggactca cgtgaacctg tcccaagaca tcagcatccc gtccgacttc    300

tcccagctgt acgacgtgta ttgcagcgac aagacctccg ccgagtggtg gaacaagaac    360

ctgtacccgc tgatcatcaa gagcgccaac gacatcgcct cctacggctt caaggtggcg    420

ggcgacccga gcatcaagaa ggacggctac ttcaagaagc tccaagacga gctggacaac    480

atcgtggaca acaactccga cgacgacgcc atcgccaagg cgatcaagga cttcaaggcg    540

aggtgcggca tcctgatcaa ggaggcgaag cagtacgagg aggcggcgaa gaacatcgtg    600

acctccctgg accagttcct gcacggcgac cagaagaagc tggagggcgt gatcaacatc    660

cagaagaggc tgaaggaggt gcagaccgcc ctgaatcaag cccacggcga gagcagcccg    720

gcgcacaagg agctgctgga gaaggtgaag aacctcaaga ccaccctgga gaggaccatc    780

aaggccgagc aagacctgga gaagaaggtg gagtactcct tcctgctggg tccgctgctg    840

ggcttcgtgg tgtacgagat cctggagaac accgccgtgc agcacatcaa gaatcagatc    900

gacgagatca agaagcagct ggactccgcc cagcacgacc tggaccgcga cgtgaagatc    960

atcgggatgc tgaacagcat caacaccgac atcgacaacc tgtacagcca aggccaagag   1020

gccatcaagg tgttccagaa gctccaaggc atctgggcga ccatcggcgc gcagatcgag   1080

aacctgagga ccaccagcct ccaagaggtc caagacagcg acgacgccga cgagatccag   1140

atcgagctgg aggacgccag cgacgcgtgg ctggtggtgg cccaagaggc gagggacttc   1200

accctgaacg cgtacagcac caactcccgt cagaacctgc cgatcaacgt gatcagcgac   1260

agctgcaact gctccaccac caacatgacc agcaaccagt actccaaccc gaccaccaac   1320
```

```
atgaccagca accagtacat gatctcccac gagtacacca gcctgccgaa caacttcatg   1380

ctgtcccgca actctaacct ggagtacaag tgcccggaga acaacttcat gatctactgg   1440

tacaacaact ccgactggta caacaactca gactggtaca acaactga                1488


<210> SEQ ID NO 27
<211> LENGTH: 495
<212> TYPE: PRT
<213> ORGANISM: Artificial Sequence
<220> FEATURE:
<223> OTHER INFORMATION: translated from synthesized maize optimized
      coding region

<400> SEQUENCE: 27

Met Ala Pro Arg Lys Arg Lys Glu Ser Asn Arg Glu Ser Ala Arg Arg
1               5                   10                  15

Ser Arg Tyr Arg Lys Ile Ile Asp Ser Lys Thr Thr Leu Pro Arg His
            20                  25                  30

Ser Leu Ile His Thr Ile Lys Leu Asn Ser Asn Lys Lys Tyr Gly Pro
        35                  40                  45

Gly Asp Met Thr Asn Gly Asn Gln Phe Ile Ile Ser Lys Gln Glu Trp
    50                  55                  60

Ala Thr Ile Gly Ala Tyr Ile Gln Thr Gly Leu Gly Leu Pro Val Asn
65                  70                  75                  80

Glu Gln Gln Leu Arg Thr His Val Asn Leu Ser Gln Asp Ile Ser Ile
                85                  90                  95

Pro Ser Asp Phe Ser Gln Leu Tyr Asp Val Tyr Cys Ser Asp Lys Thr
            100                 105                 110

Ser Ala Glu Trp Trp Asn Lys Asn Leu Tyr Pro Leu Ile Ile Lys Ser
        115                 120                 125

Ala Asn Asp Ile Ala Ser Tyr Gly Phe Lys Val Ala Gly Asp Pro Ser
    130                 135                 140

Ile Lys Lys Asp Gly Tyr Phe Lys Lys Leu Gln Asp Glu Leu Asp Asn
145                 150                 155                 160

Ile Val Asp Asn Asn Ser Asp Asp Asp Ala Ile Ala Lys Ala Ile Lys
                165                 170                 175

Asp Phe Lys Ala Arg Cys Gly Ile Leu Ile Lys Glu Ala Lys Gln Tyr
            180                 185                 190

Glu Glu Ala Ala Lys Asn Ile Val Thr Ser Leu Asp Gln Phe Leu His
        195                 200                 205

Gly Asp Gln Lys Lys Leu Glu Gly Val Ile Asn Ile Gln Lys Arg Leu
    210                 215                 220

Lys Glu Val Gln Thr Ala Leu Asn Gln Ala His Gly Glu Ser Ser Pro
225                 230                 235                 240

Ala His Lys Glu Leu Leu Glu Lys Val Lys Asn Leu Lys Thr Thr Leu
                245                 250                 255

Glu Arg Thr Ile Lys Ala Glu Gln Asp Leu Glu Lys Lys Val Glu Tyr
            260                 265                 270

Ser Phe Leu Leu Gly Pro Leu Leu Gly Phe Val Val Tyr Glu Ile Leu
        275                 280                 285

Glu Asn Thr Ala Val Gln His Ile Lys Asn Gln Ile Asp Glu Ile Lys
    290                 295                 300

Lys Gln Leu Asp Ser Ala Gln His Asp Leu Asp Arg Asp Val Lys Ile
305                 310                 315                 320

Ile Gly Met Leu Asn Ser Ile Asn Thr Asp Ile Asp Asn Leu Tyr Ser
                325                 330                 335
```

```
Gln Gly Gln Glu Ala Ile Lys Val Phe Gln Lys Leu Gln Gly Ile Trp
            340                 345                 350

Ala Thr Ile Gly Ala Gln Ile Glu Asn Leu Arg Thr Thr Ser Leu Gln
        355                 360                 365

Glu Val Gln Asp Ser Asp Asp Ala Asp Glu Ile Gln Ile Glu Leu Glu
    370                 375                 380

Asp Ala Ser Asp Ala Trp Leu Val Val Ala Gln Glu Ala Arg Asp Phe
385                 390                 395                 400

Thr Leu Asn Ala Tyr Ser Thr Asn Ser Arg Gln Asn Leu Pro Ile Asn
                405                 410                 415

Val Ile Ser Asp Ser Cys Asn Cys Ser Thr Thr Asn Met Thr Ser Asn
            420                 425                 430

Gln Tyr Ser Asn Pro Thr Thr Asn Met Thr Ser Asn Gln Tyr Met Ile
        435                 440                 445

Ser His Glu Tyr Thr Ser Leu Pro Asn Asn Phe Met Leu Ser Arg Asn
    450                 455                 460

Ser Asn Leu Glu Tyr Lys Cys Pro Glu Asn Asn Phe Met Ile Tyr Trp
465                 470                 475                 480

Tyr Asn Asn Ser Asp Trp Tyr Asn Asn Ser Asp Trp Tyr Asn Asn
                485                 490                 495
```

<210> SEQ ID NO 28
<211> LENGTH: 1482
<212> TYPE: DNA
<213> ORGANISM: Artificial Sequence
<220> FEATURE:
<223> OTHER INFORMATION: synthesized maize optimized coding region

<400> SEQUENCE: 28

```
atgatcattg actccaagac caccctgccg cgtcacagcc tgatccacac catcaagctg      60

aactccaaca agaagtacgg acctggcgac atgaccaacg gcaaccagtt catcatctcc     120

aagcaagagt gggccaccat cggagcgtac atccagaccg gcctgggcct gccggtgaac     180

gagcagcagc tgaggactca cgtgaacctg tcccaagaca tcagcatccc gtccgacttc     240

tcccagctgt acgacgtgta ttgcagcgac aagacctccg ccgagtggtg gaacaagaac     300

ctgtacccgc tgatcatcaa gagcgccaac gacatcgcct cctacggctt caaggtggcg     360

ggcgacccga gcatcaagaa ggacggctac ttcaagaagc tccaagacga gctggacaac     420

atcgtggaca acaactccga cgacgacgcc atcgccaagg cgatcaagga cttcaaggcg     480

aggtgcggca tcctgatcaa ggaggcgaag cagtacgagg aggcggcgaa gaacatcgtg     540

acctccctgg accagttcct gcacggcgac cagaagaagc tggagggcgt gatcaacatc     600

cagaagaggc tgaaggaggt gcagaccgcc ctgaatcaag cccacggcga gagcagcccg     660

gcgcacaagg agctgctgga gaaggtgaag aacctcaaga ccaccctgga gaggaccatc     720

aaggccgagc aagacctgga gaagaaggtg gagtactcct tcctgctggg tccgctgctg     780

ggcttcgtgg tgtacgagat cctggagaac accgccgtgc agcacatcaa gaatcagatc     840

gacgagatca agaagcagct ggactccgcc cagcacgacc tggaccgcga cgtgaagatc     900

atcgggatgc tgaacagcat caacaccgac atcgacaacc tgtacagcca aggccaagag     960

gccatcaagg tgttccagaa gctccaaggc atctgggcga ccatcggcgc gcagatcgag    1020

aacctgagga ccaccagcct ccaagaggtc caagacagcg acgacgccga cgagatccag    1080

atcgagctgg aggacgccag cgacgcgtgg ctggtggtgg cccaagaggc gagggacttc    1140
```

```
accctgaacg cgtacagcac caactcccgt cagaacctgc cgatcaacgt gatcagcgac   1200

agctgcaact gctccaccac caacatgacc agcaaccagt actccaaccc gaccaccaac   1260

atgaccagca accagtacat gatctcccac gagtacacca gcctgccgaa caacttcatg   1320

ctgtcccgca actctaacct ggagtacaag tgcccggaga acaacttcat gatctactgg   1380

tacaacaact ccgactggta caacaactca gactggtaca acaacagaaa gaggaaggag   1440

agcaataggg agtcagcgag gaggagcaga tacagaaagt ga                      1482
```

```
<210> SEQ ID NO 29
<211> LENGTH: 493
<212> TYPE: PRT
<213> ORGANISM: Artificial Sequence
<220> FEATURE:
<223> OTHER INFORMATION: translated from synthesized maize optimized
      coding region

<400> SEQUENCE: 29

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300
```

```
Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser Asn Gln Tyr Ser Asn
                405                 410                 415

Pro Thr Thr Asn Met Thr Ser Asn Gln Tyr Met Ile Ser His Glu Tyr
            420                 425                 430

Thr Ser Leu Pro Asn Asn Phe Met Leu Ser Arg Asn Ser Asn Leu Glu
        435                 440                 445

Tyr Lys Cys Pro Glu Asn Asn Phe Met Ile Tyr Trp Tyr Asn Asn Ser
    450                 455                 460

Asp Trp Tyr Asn Asn Ser Asp Trp Tyr Asn Asn Arg Lys Arg Lys Glu
465                 470                 475                 480

Ser Asn Arg Glu Ser Ala Arg Arg Ser Arg Tyr Arg Lys
                485                 490


<210> SEQ ID NO 30
<211> LENGTH: 1641
<212> TYPE: DNA
<213> ORGANISM: Artificial Sequence
<220> FEATURE:
<223> OTHER INFORMATION: synthesized maize optimized coding region

<400> SEQUENCE: 30

atgttggctc gccaaggagg atcactgaga gcctctcagt gtaacgctgg cctcgcgaga     60

cgcgtggagg tgggagcgtt ggttgttccg agacccataa gcgtcaacga cgtggttccc    120

catgtctatt cggctcctct gagcgtcgcg aggaggtcgt gctccaagtc atccatccgc    180

tcgactcgca gacttcagac aaccgtctgc tccatgatca ttgactccaa gaccaccctg    240

ccgcgtcaca gcctgatcca caccatcaag ctgaactcca acaagaagta cggacctggc    300

gacatgacca acggcaacca gttcatcatc tccaagcaag agtgggccac catcggagcg    360

tacatccaga ccggcctggg cctgccggtg aacgagcagc agctgaggac tcacgtgaac    420

ctgtcccaag acatcagcat cccgtccgac ttctcccagc tgtacgacgt gtattgcagc    480

gacaagacct ccgccgagtg gtggaacaag aacctgtacc cgctgatcat caagagcgcc    540

aacgacatcg cctcctacgg cttcaaggtg gcgggcgacc cgagcatcaa gaaggacggc    600

tacttcaaga agctccaaga cgagctggac aacatcgtgg acaacaactc cgacgacgac    660

gccatcgcca aggcgatcaa ggacttcaag gcgaggtgcg gcatcctgat caaggaggcg    720

aagcagtacg aggaggcggc gaagaacatc gtgacctccc tggaccagtt cctgcacggc    780

gaccagaaga agctggaggg cgtgatcaac atccagaaga ggctgaagga ggtgcagacc    840

gccctgaatc aagcccacgg cgagagcagc ccggcgcaca aggagctgct ggagaaggtg    900

aagaacctca agaccaccct ggagaggacc atcaaggccg agcaagacct ggagaagaag    960
```

```
gtggagtact ccttcctgct gggtccgctg ctgggcttcg tggtgtacga gatcctggag   1020

aacaccgccg tgcagcacat caagaatcag atcgacgaga tcaagaagca gctggactcc   1080

gcccagcacg acctggaccg cgacgtgaag atcatcggga tgctgaacag catcaacacc   1140

gacatcgaca acctgtacag ccaaggccaa gaggccatca aggtgttcca gaagctccaa   1200

ggcatctggg cgaccatcgg cgcgcagatc gagaacctga ggaccaccag cctccaagag   1260

gtccaagaca gcgacgacgc cgacgagatc cagatcgagc tggaggacgc cagcgacgcg   1320

tggctggtgg tggcccaaga ggcgagggac ttcaccctga acgcgtacag caccaactcc   1380

cgtcagaacc tgccgatcaa cgtgatcagc gacagctgca actgctccac caccaacatg   1440

accagcaacc agtactccaa cccgaccacc aacatgacca gcaaccagta catgatctcc   1500

cacgagtaca ccagcctgcc gaacaacttc atgctgtccc gcaactctaa cctggagtac   1560

aagtgcccgg agaacaactt catgatctac tggtacaaca actccgactg gtacaacaac   1620

tcagactggt acaacaactg a                                              1641
```

```
<210> SEQ ID NO 31
<211> LENGTH: 546
<212> TYPE: PRT
<213> ORGANISM: Artificial Sequence
<220> FEATURE:
<223> OTHER INFORMATION: translated from synthesized maize optimized
      coding region

<400> SEQUENCE: 31

Met Leu Ala Arg Gln Gly Gly Ser Leu Arg Ala Ser Gln Cys Asn Ala
1               5                   10                  15

Gly Leu Ala Arg Arg Val Glu Val Gly Ala Leu Val Val Pro Arg Pro
            20                  25                  30

Ile Ser Val Asn Asp Val Val Pro His Val Tyr Ser Ala Pro Leu Ser
        35                  40                  45

Val Ala Arg Arg Ser Cys Ser Lys Ser Ser Ile Arg Ser Thr Arg Arg
    50                  55                  60

Leu Gln Thr Thr Val Cys Ser Met Ile Ile Asp Ser Lys Thr Thr Leu
65                  70                  75                  80

Pro Arg His Ser Leu Ile His Thr Ile Lys Leu Asn Ser Asn Lys Lys
                85                  90                  95

Tyr Gly Pro Gly Asp Met Thr Asn Gly Asn Gln Phe Ile Ile Ser Lys
            100                 105                 110

Gln Glu Trp Ala Thr Ile Gly Ala Tyr Ile Gln Thr Gly Leu Gly Leu
        115                 120                 125

Pro Val Asn Glu Gln Gln Leu Arg Thr His Val Asn Leu Ser Gln Asp
    130                 135                 140

Ile Ser Ile Pro Ser Asp Phe Ser Gln Leu Tyr Asp Val Tyr Cys Ser
145                 150                 155                 160

Asp Lys Thr Ser Ala Glu Trp Trp Asn Lys Asn Leu Tyr Pro Leu Ile
                165                 170                 175

Ile Lys Ser Ala Asn Asp Ile Ala Ser Tyr Gly Phe Lys Val Ala Gly
            180                 185                 190

Asp Pro Ser Ile Lys Lys Asp Gly Tyr Phe Lys Lys Leu Gln Asp Glu
        195                 200                 205

Leu Asp Asn Ile Val Asp Asn Asn Ser Asp Asp Asp Ala Ile Ala Lys
    210                 215                 220

Ala Ile Lys Asp Phe Lys Ala Arg Cys Gly Ile Leu Ile Lys Glu Ala
225                 230                 235                 240
```

```
Lys Gln Tyr Glu Glu Ala Ala Lys Asn Ile Val Thr Ser Leu Asp Gln
                245                 250                 255

Phe Leu His Gly Asp Gln Lys Lys Leu Glu Gly Val Ile Asn Ile Gln
            260                 265                 270

Lys Arg Leu Lys Glu Val Gln Thr Ala Leu Asn Gln Ala His Gly Glu
        275                 280                 285

Ser Ser Pro Ala His Lys Glu Leu Leu Glu Lys Val Lys Asn Leu Lys
    290                 295                 300

Thr Thr Leu Glu Arg Thr Ile Lys Ala Glu Gln Asp Leu Glu Lys Lys
305                 310                 315                 320

Val Glu Tyr Ser Phe Leu Leu Gly Pro Leu Leu Gly Phe Val Val Tyr
                325                 330                 335

Glu Ile Leu Glu Asn Thr Ala Val Gln His Ile Lys Asn Gln Ile Asp
            340                 345                 350

Glu Ile Lys Lys Gln Leu Asp Ser Ala Gln His Asp Leu Asp Arg Asp
        355                 360                 365

Val Lys Ile Ile Gly Met Leu Asn Ser Ile Asn Thr Asp Ile Asp Asn
    370                 375                 380

Leu Tyr Ser Gln Gly Gln Glu Ala Ile Lys Val Phe Gln Lys Leu Gln
385                 390                 395                 400

Gly Ile Trp Ala Thr Ile Gly Ala Gln Ile Glu Asn Leu Arg Thr Thr
                405                 410                 415

Ser Leu Gln Glu Val Gln Asp Ser Asp Asp Ala Asp Glu Ile Gln Ile
            420                 425                 430

Glu Leu Glu Asp Ala Ser Asp Ala Trp Leu Val Val Ala Gln Glu Ala
        435                 440                 445

Arg Asp Phe Thr Leu Asn Ala Tyr Ser Thr Asn Ser Arg Gln Asn Leu
    450                 455                 460

Pro Ile Asn Val Ile Ser Asp Ser Cys Asn Cys Ser Thr Thr Asn Met
465                 470                 475                 480

Thr Ser Asn Gln Tyr Ser Asn Pro Thr Thr Asn Met Thr Ser Asn Gln
                485                 490                 495

Tyr Met Ile Ser His Glu Tyr Thr Ser Leu Pro Asn Asn Phe Met Leu
            500                 505                 510

Ser Arg Asn Ser Asn Leu Glu Tyr Lys Cys Pro Glu Asn Asn Phe Met
        515                 520                 525

Ile Tyr Trp Tyr Asn Asn Ser Asp Trp Tyr Asn Asn Ser Asp Trp Tyr
    530                 535                 540

Asn Asn
545
```

<210> SEQ ID NO 32
<211> LENGTH: 1626
<212> TYPE: DNA
<213> ORGANISM: Artificial Sequence
<220> FEATURE:
<223> OTHER INFORMATION: synthesized maize optimized coding region

<400> SEQUENCE: 32

```
atggctcaat ctagcagaat ctgccacggt gtgcagaacc catgtgtgat catttccaat      60

ctctccaaat ccaaccagaa caaatctcct ttctcagtca gcctcaagac tcaccagcag     120

cagcgtcgtg cttaccagat atctagctgg ggattgaaga agtcaaacaa cgggtccgtg     180

attcgtccgg ttaaggcaat gatcattgac tccaagacca ccctgccgcg tcacagcctg     240
```

```
atccacacca tcaagctgaa ctccaacaag aagtacggac ctggcgacat gaccaacggc    300

aaccagttca tcatctccaa gcaagagtgg gccaccatcg gagcgtacat ccagaccggc    360

ctgggcctgc cggtgaacga gcagcagctg aggactcacg tgaacctgtc ccaagacatc    420

agcatcccgt ccgacttctc ccagctgtac gacgtgtatt gcagcgacaa gacctccgcc    480

gagtggtgga acaagaacct gtacccgctg atcatcaaga gcgccaacga catcgcctcc    540

tacggcttca aggtggcggg cgacccgagc atcaagaagg acggctactt caagaagctc    600

caagacgagc tggacaacat cgtggacaac aactccgacg acgacgccat cgccaaggcg    660

atcaaggact tcaaggcgag gtgcggcatc ctgatcaagg aggcgaagca gtacgaggag    720

gcggcgaaga acatcgtgac ctccctggac cagttcctgc acggcgacca gaagaagctg    780

gagggcgtga tcaacatcca gaagaggctg aaggaggtgc agaccgccct gaatcaagcc    840

cacggcgaga gcagcccggc gcacaaggag ctgctggaga aggtgaagaa cctcaagacc    900

accctggaga ggaccatcaa ggccgagcaa gacctggaga agaaggtgga gtactccttc    960

ctgctgggtc cgctgctggg cttcgtggtg tacgagatcc tggagaacac cgccgtgcag   1020

cacatcaaga atcagatcga cgagatcaag aagcagctgg actccgccca gcacgacctg   1080

gaccgcgacg tgaagatcat cgggatgctg aacagcatca acaccgacat cgacaacctg   1140

tacagccaag gccaagaggc catcaaggtg ttccagaagc tccaaggcat ctgggcgacc   1200

atcggcgcgc agatcgagaa cctgaggacc accagcctcc aagaggtcca agacagcgac   1260

gacgccgacg agatccagat cgagctggag gacgccagcg acgcgtggct ggtggtggcc   1320

caagaggcga gggacttcac cctgaacgcg tacagcacca actcccgtca gaacctgccg   1380

atcaacgtga tcagcgacag ctgcaactgc tccaccacca acatgaccag caaccagtac   1440

tccaacccga ccaccaacat gaccagcaac cagtacatga tctcccacga gtacaccagc   1500

ctgccgaaca acttcatgct gtcccgcaac tctaacctgg agtacaagtg cccggagaac   1560

aacttcatga tctactggta caacaactcc gactggtaca acaactcaga ctggtacaac   1620

aactga                                                              1626
```

```
<210> SEQ ID NO 33
<211> LENGTH: 541
<212> TYPE: PRT
<213> ORGANISM: Artificial Sequence
<220> FEATURE:
<223> OTHER INFORMATION: translated from synthesized maize optimized
      coding region

<400> SEQUENCE: 33

Met Ala Gln Ser Ser Arg Ile Cys His Gly Val Gln Asn Pro Cys Val
1               5                   10                  15

Ile Ile Ser Asn Leu Ser Lys Ser Asn Gln Asn Lys Ser Pro Phe Ser
            20                  25                  30

Val Ser Leu Lys Thr His Gln Gln Gln Arg Arg Ala Tyr Gln Ile Ser
        35                  40                  45

Ser Trp Gly Leu Lys Lys Ser Asn Asn Gly Ser Val Ile Arg Pro Val
    50                  55                  60

Lys Ala Met Ile Ile Asp Ser Lys Thr Thr Leu Pro Arg His Ser Leu
65                  70                  75                  80

Ile His Thr Ile Lys Leu Asn Ser Asn Lys Lys Tyr Gly Pro Gly Asp
                85                  90                  95

Met Thr Asn Gly Asn Gln Phe Ile Ile Ser Lys Gln Glu Trp Ala Thr
            100                 105                 110
```

```
Ile Gly Ala Tyr Ile Gln Thr Gly Leu Gly Leu Pro Val Asn Glu Gln
        115                 120                 125

Gln Leu Arg Thr His Val Asn Leu Ser Gln Asp Ile Ser Ile Pro Ser
    130                 135                 140

Asp Phe Ser Gln Leu Tyr Asp Val Tyr Cys Ser Asp Lys Thr Ser Ala
145                 150                 155                 160

Glu Trp Trp Asn Lys Asn Leu Tyr Pro Leu Ile Ile Lys Ser Ala Asn
                165                 170                 175

Asp Ile Ala Ser Tyr Gly Phe Lys Val Ala Gly Asp Pro Ser Ile Lys
            180                 185                 190

Lys Asp Gly Tyr Phe Lys Lys Leu Gln Asp Glu Leu Asp Asn Ile Val
        195                 200                 205

Asp Asn Asn Ser Asp Asp Asp Ala Ile Ala Lys Ala Ile Lys Asp Phe
    210                 215                 220

Lys Ala Arg Cys Gly Ile Leu Ile Lys Glu Ala Lys Gln Tyr Glu Glu
225                 230                 235                 240

Ala Ala Lys Asn Ile Val Thr Ser Leu Asp Gln Phe Leu His Gly Asp
                245                 250                 255

Gln Lys Lys Leu Glu Gly Val Ile Asn Ile Gln Lys Arg Leu Lys Glu
            260                 265                 270

Val Gln Thr Ala Leu Asn Gln Ala His Gly Glu Ser Ser Pro Ala His
        275                 280                 285

Lys Glu Leu Leu Glu Lys Val Lys Asn Leu Lys Thr Thr Leu Glu Arg
    290                 295                 300

Thr Ile Lys Ala Glu Gln Asp Leu Glu Lys Lys Val Glu Tyr Ser Phe
305                 310                 315                 320

Leu Leu Gly Pro Leu Leu Gly Phe Val Val Tyr Glu Ile Leu Glu Asn
                325                 330                 335

Thr Ala Val Gln His Ile Lys Asn Gln Ile Asp Glu Ile Lys Lys Gln
            340                 345                 350

Leu Asp Ser Ala Gln His Asp Leu Asp Arg Asp Val Lys Ile Ile Gly
        355                 360                 365

Met Leu Asn Ser Ile Asn Thr Asp Ile Asp Asn Leu Tyr Ser Gln Gly
    370                 375                 380

Gln Glu Ala Ile Lys Val Phe Gln Lys Leu Gln Gly Ile Trp Ala Thr
385                 390                 395                 400

Ile Gly Ala Gln Ile Glu Asn Leu Arg Thr Thr Ser Leu Gln Glu Val
                405                 410                 415

Gln Asp Ser Asp Asp Ala Asp Glu Ile Gln Ile Glu Leu Glu Asp Ala
            420                 425                 430

Ser Asp Ala Trp Leu Val Val Ala Gln Glu Ala Arg Asp Phe Thr Leu
        435                 440                 445

Asn Ala Tyr Ser Thr Asn Ser Arg Gln Asn Leu Pro Ile Asn Val Ile
    450                 455                 460

Ser Asp Ser Cys Asn Cys Ser Thr Thr Asn Met Thr Ser Asn Gln Tyr
465                 470                 475                 480

Ser Asn Pro Thr Thr Asn Met Thr Ser Asn Gln Tyr Met Ile Ser His
                485                 490                 495

Glu Tyr Thr Ser Leu Pro Asn Asn Phe Met Leu Ser Arg Asn Ser Asn
            500                 505                 510

Leu Glu Tyr Lys Cys Pro Glu Asn Asn Phe Met Ile Tyr Trp Tyr Asn
        515                 520                 525
```

```
Asn Ser Asp Trp Tyr Asn Asn Ser Asp Trp Tyr Asn Asn
    530                 535                 540


<210> SEQ ID NO 34
<211> LENGTH: 1428
<212> TYPE: DNA
<213> ORGANISM: Artificial Sequence
<220> FEATURE:
<223> OTHER INFORMATION: synthesized coding region

<400> SEQUENCE: 34

atgattattg attctaaaac aacattacca agacattctt taattcatac tataaaatta      60

aattctaata agaaatatgg tcctggtgat atgactaatg gaaatcaatt tattatttca     120

aaacaagaat gggctactat tggagcatat attcagactg gattaggttt accagtaaat     180

gaacaacaat taagaacaca tgttaattta agtcaggata tatcaatacc tagtgatttt     240

tctcaattat atgatgttta tgcttctgat aaaacttcag cagaatggtg gaataaaaat     300

ttatatcctt taattattaa atctgctaat gatattgctt catatggttt taaagttgct     360

ggtgatcctt ctattaagaa agatggatat tttaaaaaat tgcaagatga attagataat     420

attgttgata ataattccga tgatgatgca atagctaaag ctattaaaga ttttaaagcg     480

cgatgtggta ttttaattaa agaagctaaa caatatgaag aagctgcaaa aaatattgta     540

acatctttag atcaattttt acatggtgat cagaaaaaat tagaaggtgt tatcaatatt     600

caaaaacgtt taaaagaagt tcaaacagct cttaatcaag cccatgggga aagtagtcca     660

gctcataaag agttattaga aaaagtaaaa aatttaaaaa caacattaga aaggactatt     720

aaagctgaac aagatttaga gaaaaaagta gaatatagtt ttctattagg accattgtta     780

ggatttgttg tttatgaaat tcttgaaaat actgctgttc agcatataaa aaatcaaatt     840

gatgagataa agaaacaatt agattctgct cagcatgatt tggatagaga tgttaaaatt     900

ataggaatgt taaatagtat taatacagat attgataatt tatatagtca aggacaagaa     960

gcaattaaag ttttccaaaa gttacaaggt atttgggcta ctattggagc tcaaatagaa    1020

aatcttagaa caacgtcgtt acaagaagtt caagattctg atgatgctga tgagatacaa    1080

attgaacttg aggacgcttc tgatgcttgg ttagttgtgg ctcaagaagc tcgtgatttt    1140

acactaaatg cttattcaac taatagtaga caaaatttac cgattaatgt tatatcagat    1200

tcatgtaatt gttcaacaac aaatatgaca tcaaatcaat acagtaatcc aacaacaaat    1260

atgacatcaa atcaatatat gatttcacat gaatatacaa gtttaccaaa taattttatg    1320

ttatcaagaa atagtaattt agaatataaa tgtcctgaaa ataattttat gatatattgg    1380

tataataatt cggattggta taataattcg gattggtata ataattga                1428


<210> SEQ ID NO 35
<211> LENGTH: 475
<212> TYPE: PRT
<213> ORGANISM: Artificial Sequence
<220> FEATURE:
<223> OTHER INFORMATION: synthesized coding region

<400> SEQUENCE: 35

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45
```

```
Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Ala Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser Asn Gln Tyr Ser Asn
                405                 410                 415

Pro Thr Thr Asn Met Thr Ser Asn Gln Tyr Met Ile Ser His Glu Tyr
            420                 425                 430

Thr Ser Leu Pro Asn Asn Phe Met Leu Ser Arg Asn Ser Asn Leu Glu
        435                 440                 445

Tyr Lys Cys Pro Glu Asn Asn Phe Met Ile Tyr Trp Tyr Asn Asn Ser
    450                 455                 460
```

```
Asp Trp Tyr Asn Asn Ser Asp Trp Tyr Asn Asn
465                 470                 475


<210> SEQ ID NO 36
<211> LENGTH: 1428
<212> TYPE: DNA
<213> ORGANISM: Artificial Sequence
<220> FEATURE:
<223> OTHER INFORMATION: synthesized coding region

<400> SEQUENCE: 36

atgattattg attctaaaac aacattacca agacattctt taattcatac tataaaatta      60

aattctaata agaaatatgg tcctggtgat atgactaatg gaaatcaatt tattatttca     120

aaacaagaat gggctactat tggagcatat attcagactg gattaggttt accagtaaat     180

gaacaacaat taagaacaca tgttaattta agtcaggata tatcaatacc tagtgatttt     240

tctcaattat atgatgttta ttcttctgat aaaacttcag cagaatggtg gaataaaaat     300

ttatatcctt taattattaa atctgctaat gatattgctt catatggttt taaagttgct     360

ggtgatcctt ctattaagaa agatggatat tttaaaaaat tgcaagatga attagataat     420

attgttgata ataattccga tgatgatgca atagctaaag ctattaaaga ttttaaagcg     480

cgatgtggta ttttaattaa agaagctaaa caatatgaag aagctgcaaa aaatattgta     540

acatctttag atcaattttt acatggtgat cagaaaaaat tagaaggtgt tatcaatatt     600

caaaaacgtt taaaagaagt tcaaacagct cttaatcaag cccatgggga aagtagtcca     660

gctcataaag agttattaga aaaagtaaaa aatttaaaaa caacattaga aaggactatt     720

aaagctgaac aagatttaga gaaaaaagta gaatatagtt ttctattagg accattgtta     780

ggatttgttg tttatgaaat tcttgaaaat actgctgttc agcatataaa aaatcaaatt     840

gatgagataa agaaacaatt agattctgct cagcatgatt tggatagaga tgttaaaatt     900

ataggaatgt taaatagtat taatacagat attgataatt tatatagtca aggacaagaa     960

gcaattaaag ttttccaaaa gttacaaggt atttgggcta ctattggagc tcaaatagaa    1020

aatcttagaa caacgtcgtt acaagaagtt caagattctg atgatgctga tgagatacaa    1080

attgaacttg aggacgcttc tgatgcttgg ttagttgtgg ctcaagaagc tcgtgatttt    1140

acactaaatg cttattcaac taatagtaga caaaatttac cgattaatgt tatatcagat    1200

tcatgtaatt gttcaacaac aaatatgaca tcaaatcaat acagtaatcc aacaacaaat    1260

atgacatcaa atcaatatat gatttcacat gaatatacaa gtttaccaaa taattttatg    1320

ttatcaagaa atagtaattt agaatataaa tgtcctgaaa ataattttat gatatattgg    1380

tataataatt cggattggta taataattcg gattggtata ataattga                1428


<210> SEQ ID NO 37
<211> LENGTH: 475
<212> TYPE: PRT
<213> ORGANISM: Artificial Sequence
<220> FEATURE:
<223> OTHER INFORMATION: translated from synthesized coding region

<400> SEQUENCE: 37

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45
```

```
Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Ser Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser Asn Gln Tyr Ser Asn
                405                 410                 415

Pro Thr Thr Asn Met Thr Ser Asn Gln Tyr Met Ile Ser His Glu Tyr
            420                 425                 430

Thr Ser Leu Pro Asn Asn Phe Met Leu Ser Arg Asn Ser Asn Leu Glu
        435                 440                 445

Tyr Lys Cys Pro Glu Asn Asn Phe Met Ile Tyr Trp Tyr Asn Asn Ser
    450                 455                 460
```

```
Asp Trp Tyr Asn Asn Ser Asp Trp Tyr Asn Asn
465                 470                 475


<210> SEQ ID NO 38
<211> LENGTH: 1428
<212> TYPE: DNA
<213> ORGANISM: Artificial Sequence
<220> FEATURE:
<223> OTHER INFORMATION: synthesized coding region

<400> SEQUENCE: 38

atgattattg attctaaaac aacattacca agacattctt taattcatac tataaaatta      60

aattctaata agaaatatgg tcctggtgat atgactaatg gaaatcaatt tattatttca     120

aaacaagaat gggctactat tggagcatat attcagactg gattaggttt accagtaaat     180

gaacaacaat taagaacaca tgttaattta agtcaggata tatcaatacc tagtgatttt     240

tctcaattat atgatgttta ttgttctgat aaaacttcag cagaatggtg gaataaaaat     300

ttatatcctt taattattaa atctgctaat gatattgctt catatggttt taaagttgct     360

ggtgatcctt ctattaagaa agatggatat tttaaaaaat tgcaagatga attagataat     420

attgttgata ataattccga tgatgatgca atagctaaag ctattaaaga ttttaaagcg     480

cgagctggta ttttaattaa agaagctaaa caatatgaag aagctgcaaa aaatattgta     540

acatctttag atcaattttt acatggtgat cagaaaaaat tagaaggtgt tatcaatatt     600

caaaaacgtt taaaagaagt tcaaacagct cttaatcaag cccatgggga aagtagtcca     660

gctcataaag agttattaga aaaagtaaaa aatttaaaaa caacattaga aaggactatt     720

aaagctgaac aagatttaga gaaaaaagta gaatatagtt ttctattagg accattgtta     780

ggatttgttg tttatgaaat tcttgaaaat actgctgttc agcatataaa aaatcaaatt     840

gatgagataa agaaacaatt agattctgct cagcatgatt tggatagaga tgttaaaatt     900

ataggaatgt taaatagtat taatacagat attgataatt tatatagtca aggacaagaa     960

gcaattaaag ttttccaaaa gttacaaggt atttgggcta ctattggagc tcaaatagaa    1020

aatcttagaa caacgtcgtt acaagaagtt caagattctg atgatgctga tgagatacaa    1080

attgaacttg aggacgcttc tgatgcttgg ttagttgtgg ctcaagaagc tcgtgatttt    1140

acactaaatg cttattcaac taatagtaga caaaatttac cgattaatgt tatatcagat    1200

tcatgtaatt gttcaacaac aaatatgaca tcaaatcaat acagtaatcc aacaacaaat    1260

atgacatcaa atcaatatat gatttcacat gaatatacaa gtttaccaaa taattttatg    1320

ttatcaagaa atagtaattt agaatataaa tgtcctgaaa ataattttat gatatattgg    1380

tataataatt cggattggta taataattcg gattggtata ataattga                1428


<210> SEQ ID NO 39
<211> LENGTH: 475
<212> TYPE: PRT
<213> ORGANISM: Artificial Sequence
<220> FEATURE:
<223> OTHER INFORMATION: translated from synthesized coding region

<400> SEQUENCE: 39

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45
```

```
Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Ala Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser Asn Gln Tyr Ser Asn
                405                 410                 415

Pro Thr Thr Asn Met Thr Ser Asn Gln Tyr Met Ile Ser His Glu Tyr
            420                 425                 430

Thr Ser Leu Pro Asn Asn Phe Met Leu Ser Arg Asn Ser Asn Leu Glu
        435                 440                 445

Tyr Lys Cys Pro Glu Asn Asn Phe Met Ile Tyr Trp Tyr Asn Asn Ser
    450                 455                 460
```

```
Asp Trp Tyr Asn Asn Ser Asp Trp Tyr Asn Asn
465                 470                 475


<210> SEQ ID NO 40
<211> LENGTH: 1428
<212> TYPE: DNA
<213> ORGANISM: Artificial Sequence
<220> FEATURE:
<223> OTHER INFORMATION: synthesized coding region

<400> SEQUENCE: 40

atgattattg attctaaaac aacattacca agacattctt taattcatac tataaaatta      60

aattctaata agaaatatgg tcctggtgat atgactaatg gaaatcaatt tattatttca     120

aaacaagaat gggctactat tggagcatat attcagactg gattaggttt accagtaaat     180

gaacaacaat taagaacaca tgttaattta agtcaggata tatcaatacc tagtgatttt     240

tctcaattat atgatgttta ttgttctgat aaaacttcag cagaatggtg gaataaaaat     300

ttatatcctt taattattaa atctgctaat gatattgctt catatggttt taaagttgct     360

ggtgatcctt ctattaagaa agatggatat tttaaaaaat tgcaagatga attagataat     420

attgttgata ataattccga tgatgatgca atagctaaag ctattaaaga ttttaaagcg     480

cgatctggta ttttaattaa agaagctaaa caatatgaag aagctgcaaa aaatattgta     540

acatctttag atcaattttt acatggtgat cagaaaaaat tagaaggtgt tatcaatatt     600

caaaaacgtt taaaagaagt tcaaacagct cttaatcaag cccatgggga aagtagtcca     660

gctcataaag agttattaga aaaagtaaaa aatttaaaaa caacattaga aaggactatt     720

aaagctgaac aagatttaga gaaaaaagta gaatatagtt ttctattagg accattgtta     780

ggatttgttg tttatgaaat tcttgaaaat actgctgttc agcatataaa aaatcaaatt     840

gatgagataa agaaacaatt agattctgct cagcatgatt tggatagaga tgttaaaatt     900

ataggaatgt taaatagtat taatacagat attgataatt tatatagtca aggacaagaa     960

gcaattaaag ttttccaaaa gttacaaggt atttgggcta ctattggagc tcaaatagaa    1020

aatcttagaa caacgtcgtt acaagaagtt caagattctg atgatgctga tgagatacaa    1080

attgaacttg aggacgcttc tgatgcttgg ttagttgtgg ctcaagaagc tcgtgatttt    1140

acactaaatg cttattcaac taatagtaga caaaatttac cgattaatgt tatatcagat    1200

tcatgtaatt gttcaacaac aaatatgaca tcaaatcaat acagtaatcc aacaacaaat    1260

atgacatcaa atcaatatat gatttcacat gaatatacaa gtttaccaaa taattttatg    1320

ttatcaagaa atagtaattt agaatataaa tgtcctgaaa ataattttat gatatattgg    1380

tataataatt cggattggta taataattcg gattggtata ataattga                 1428


<210> SEQ ID NO 41
<211> LENGTH: 475
<212> TYPE: PRT
<213> ORGANISM: Artificial Sequence
<220> FEATURE:
<223> OTHER INFORMATION: translated from synthesized coding region

<400> SEQUENCE: 41

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45
```

```
Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Ser Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser Asn Gln Tyr Ser Asn
                405                 410                 415

Pro Thr Thr Asn Met Thr Ser Asn Gln Tyr Met Ile Ser His Glu Tyr
            420                 425                 430

Thr Ser Leu Pro Asn Asn Phe Met Leu Ser Arg Asn Ser Asn Leu Glu
        435                 440                 445

Tyr Lys Cys Pro Glu Asn Asn Phe Met Ile Tyr Trp Tyr Asn Asn Ser
    450                 455                 460
```

```
Asp Trp Tyr Asn Asn Ser Asp Trp Tyr Asn Asn
465                 470                 475


<210> SEQ ID NO 42
<211> LENGTH: 1428
<212> TYPE: DNA
<213> ORGANISM: Artificial Sequence
<220> FEATURE:
<223> OTHER INFORMATION: synthesized coding region

<400> SEQUENCE: 42

atgattattg attctaaaac aacattacca agacattctt taattcatac tataaaatta      60

aattctaata agaaatatgg tcctggtgat atgactaatg gaaatcaatt tattatttca     120

aaacaagaat gggctactat tggagcatat attcagactg gattaggttt accagtaaat     180

gaacaacaat taagaacaca tgttaattta agtcaggata tatcaatacc tagtgatttt     240

tctcaattat atgatgttta ttgttctgat aaaacttcag cagaatggtg gaataaaaat     300

ttatatcctt taattattaa atctgctaat gatattgctt catatggttt taaagttgct     360

ggtgatcctt ctattaagaa agatggatat tttaaaaaat tgcaagatga attagataat     420

attgttgata ataattccga tgatgatgca atagctaaag ctattaaaga ttttaaagcg     480

cgatgtggta ttttaattaa agaagctaaa caatatgaag aagctgcaaa aaatattgta     540

acatctttag atcaattttt acatggtgat cagaaaaaat tagaaggtgt tatcaatatt     600

caaaaacgtt taaaagaagt tcaaacagct cttaatcaag cccatgggga aagtagtcca     660

gctcataaag agttattaga aaaagtaaaa aatttaaaaa caacattaga aaggactatt     720

aaagctgaac aagatttaga gaaaaaagta gaatatagtt ttctattagg accattgtta     780

ggatttgttg tttatgaaat tcttgaaaat actgctgttc agcatataaa aaatcaaatt     840

gatgagataa agaaacaatt agattctgct cagcatgatt tggatagaga tgttaaaatt     900

ataggaatgt taaatagtat taatacagat attgataatt tatatagtca aggacaagaa     960

gcaattaaag ttttccaaaa gttacaaggt atttgggcta ctattggagc tcaaatagaa    1020

aatcttagaa caacgtcgtt acaagaagtt caagattctg atgatgctga tgagatacaa    1080

attgaacttg aggacgcttc tgatgcttgg ttagttgtgg ctcaagaagc tcgtgatttt    1140

acactaaatg cttattcaac taatagtaga caaaatttac cgattaatgt tatatcagat    1200

tcatgtaatt gttcaacaac aaatatgaca tcaaatcaat acagtaatcc aacaacaaat    1260

atgacatcaa atcaatatat gatttcacat gaatatacaa gtttaccaaa taattttatg    1320

ttatcaagaa atagtaattt agaatataaa gctcctgaaa ataattttat gatatattgg    1380

tataataatt cggattggta taataattcg gattggtata ataattga                 1428


<210> SEQ ID NO 43
<211> LENGTH: 475
<212> TYPE: PRT
<213> ORGANISM: Artificial Sequence
<220> FEATURE:
<223> OTHER INFORMATION: translated from synthesized coding region

<400> SEQUENCE: 43

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45
```

```
Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser Asn Gln Tyr Ser Asn
                405                 410                 415

Pro Thr Thr Asn Met Thr Ser Asn Gln Tyr Met Ile Ser His Glu Tyr
            420                 425                 430

Thr Ser Leu Pro Asn Asn Phe Met Leu Ser Arg Asn Ser Asn Leu Glu
        435                 440                 445

Tyr Lys Ala Pro Glu Asn Asn Phe Met Ile Tyr Trp Tyr Asn Asn Ser
    450                 455                 460
```

```
Asp Trp Tyr Asn Asn Ser Asp Trp Tyr Asn Asn
465                 470                 475


<210> SEQ ID NO 44
<211> LENGTH: 1428
<212> TYPE: DNA
<213> ORGANISM: Artificial Sequence
<220> FEATURE:
<223> OTHER INFORMATION: synthesized coding region

<400> SEQUENCE: 44

atgattattg attctaaaac aacattacca agacattctt taattcatac tataaaatta     60

aattctaata agaaatatgg tcctggtgat atgactaatg gaaatcaatt tattatttca    120

aaacaagaat gggctactat tggagcatat attcagactg gattaggttt accagtaaat    180

gaacaacaat taagaacaca tgttaattta agtcaggata tatcaatacc tagtgatttt    240

tctcaattat atgatgttta ttgttctgat aaaacttcag cagaatggtg gaataaaaat    300

ttatatcctt taattattaa atctgctaat gatattgctt catatggttt taaagttgct    360

ggtgatcctt ctattaagaa agatggatat tttaaaaaat tgcaagatga attagataat    420

attgttgata ataattccga tgatgatgca atagctaaag ctattaaaga ttttaaagcg    480

cgatgtggta ttttaattaa agaagctaaa caatatgaag aagctgcaaa aaatattgta    540

acatctttag atcaattttt acatggtgat cagaaaaaat tagaaggtgt tatcaatatt    600

caaaaacgtt taaaagaagt tcaaacagct cttaatcaag cccatgggga aagtagtcca    660

gctcataaag agttattaga aaaagtaaaa aatttaaaaa caacattaga aaggactatt    720

aaagctgaac aagatttaga gaaaaaagta gaatatagtt ttctattagg accattgtta    780

ggatttgttg tttatgaaat tcttgaaaat actgctgttc agcatataaa aaatcaaatt    840

gatgagataa agaaacaatt agattctgct cagcatgatt tggatagaga tgttaaaatt    900

ataggaatgt taaatagtat taatacagat attgataatt tatatagtca aggacaagaa    960

gcaattaaag ttttccaaaa gttacaaggt atttgggcta ctattggagc tcaaatagaa   1020

aatcttagaa caacgtcgtt acaagaagtt caagattctg atgatgctga tgagatacaa   1080

attgaacttg aggacgcttc tgatgcttgg ttagttgtgg ctcaagaagc tcgtgatttt   1140

acactaaatg cttattcaac taatagtaga caaaatttac cgattaatgt tatatcagat   1200

tcatgtaatt gttcaacaac aaatatgaca tcaaatcaat acagtaatcc aacaacaaat   1260

atgacatcaa atcaatatat gatttcacat gaatatacaa gtttaccaaa taattttatg   1320

ttatcaagaa atagtaattt agaatataaa tctcctgaaa ataattttat gatatattgg   1380

tataataatt cggattggta taataattcg gattggtata ataattga                 1428


<210> SEQ ID NO 45
<211> LENGTH: 475
<212> TYPE: PRT
<213> ORGANISM: Artificial Sequence
<220> FEATURE:
<223> OTHER INFORMATION: translated from synthesized coding region

<400> SEQUENCE: 45

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45
```

```
Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser Asn Gln Tyr Ser Asn
                405                 410                 415

Pro Thr Thr Asn Met Thr Ser Asn Gln Tyr Met Ile Ser His Glu Tyr
            420                 425                 430

Thr Ser Leu Pro Asn Asn Phe Met Leu Ser Arg Asn Ser Asn Leu Glu
        435                 440                 445

Tyr Lys Ser Pro Glu Asn Asn Phe Met Ile Tyr Trp Tyr Asn Asn Ser
    450                 455                 460
```

```
Asp Trp Tyr Asn Asn Ser Asp Trp Tyr Asn Asn
465                 470                 475
```

<210> SEQ ID NO 46
<211> LENGTH: 1428
<212> TYPE: DNA
<213> ORGANISM: Artificial Sequence
<220> FEATURE:
<223> OTHER INFORMATION: synthesized coding region

<400> SEQUENCE: 46

```
atgattattg attctaaaac aacattacca agacattctt taattcatac tataaaatta     60

aattctaata agaaatatgg tcctggtgat atgactaatg gaaatcaatt tattatttca    120

aaacaagaat gggctactat tggagcatat attcagactg gattaggttt accagtaaat    180

gaacaacaat taagaacaca tgttaattta agtcaggata tatcaatacc tagtgatttt    240

tctcaattat atgatgttta tagttctgat aaaacttcag cagaatggtg gaataaaaat    300

ttatatcctt taattattaa atctgctaat gatattgctt catatggttt taaagttgct    360

ggtgatcctt ctattaagaa agatggatat tttaaaaaat tgcaagatga attagataat    420

attgttgata ataattccga tgatgatgca atagctaaag ctattaaaga ttttaaagcg    480

cgatgtggta ttttaattaa agaagctaaa caatatgaag aagctgcaaa aaatattgta    540

acatctttag atcaattttt acatggtgat cagaaaaaat tagaaggtgt tatcaatatt    600

caaaaacgtt taaaagaagt tcaaacagct cttaatcaag cccatgggga aagtagtcca    660

gctcataaag agttattaga aaaagtaaaa aatttaaaaa caacattaga aaggactatt    720

aaagctgaac aagatttaga gaaaaaagta gaatatagtt ttctattagg accattgtta    780

ggatttgttg tttatgaaat tcttgaaaat actgctgttc agcatataaa aaatcaaatt    840

gatgagataa agaaacaatt agattctgct cagcatgatt tggatagaga tgttaaaatt    900

ataggaatgt taaatagtat taatacagat attgataatt tatatagtca aggacaagaa    960

gcaattaaag ttttccaaaa gttacaaggt atttgggcta ctattggagc tcaaatagaa   1020

aatcttagaa caacgtcgtt acaagaagtt caagattctg atgatgctga tgagatacaa   1080

attgaacttg aggacgcttc tgatgcttgg ttagttgtgg ctcaagaagc tcgtgatttt   1140

acactaaatg cttattcaac taatagtaga caaaatttac cgattaatgt tatatcagat   1200

tcatgtaatt gttcaacaac aaatatgaca tcaaatcaat acagtaatcc aacaacaaat   1260

atgacatcaa atcaatatat gatttcacat gaatatacaa gtttaccaaa taattttatg   1320

ttatcaagaa atagtaattt agaatataaa agtcctgaaa ataattttat gatatattgg   1380

tataataatt cggattggta taataattcg gattggtata ataattga                1428
```

<210> SEQ ID NO 47
<211> LENGTH: 475
<212> TYPE: PRT
<213> ORGANISM: Artificial Sequence
<220> FEATURE:
<223> OTHER INFORMATION: translated from synthesized coding region

<400> SEQUENCE: 47

```
Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45
```

```
Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Ser Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser Asn Gln Tyr Ser Asn
                405                 410                 415

Pro Thr Thr Asn Met Thr Ser Asn Gln Tyr Met Ile Ser His Glu Tyr
            420                 425                 430

Thr Ser Leu Pro Asn Asn Phe Met Leu Ser Arg Asn Ser Asn Leu Glu
        435                 440                 445

Tyr Lys Ser Pro Glu Asn Asn Phe Met Ile Tyr Trp Tyr Asn Asn Ser
    450                 455                 460
```

```
Asp Trp Tyr Asn Asn Ser Asp Trp Tyr Asn Asn
465                 470                 475


<210> SEQ ID NO 48
<211> LENGTH: 1428
<212> TYPE: DNA
<213> ORGANISM: Artificial Sequence
<220> FEATURE:
<223> OTHER INFORMATION: synthesized coding region

<400> SEQUENCE: 48

atgattattg attctaaaac aacattacca agacattctt taattcatac tataaaatta      60

aattctaata agaaatatgg tcctggtgat atgactaatg gaaatcaatt tattatttca     120

aaacaagaat gggctactat tggagcatat attcagactg gattaggttt accagtaaat     180

gaacaacaat taagaacaca tgttaattta agtcaggata tatcaatacc tagtgatttt     240

tctcaattat atgatgttta tgcttctgat aaaacttcag cagaatggtg gaataaaaat     300

ttatatcctt taattattaa atctgctaat gatattgctt catatggttt taaagttgct     360

ggtgatcctt ctattaagaa agatggatat tttaaaaaat tgcaagatga attagataat     420

attgttgata ataattccga tgatgatgca atagctaaag ctattaaaga ttttaaagcg     480

cgatgtggta ttttaattaa agaagctaaa caatatgaag aagctgcaaa aaatattgta     540

acatctttag atcaattttt acatggtgat cagaaaaaat tagaaggtgt tatcaatatt     600

caaaaacgtt taaaagaagt tcaaacagct cttaatcaag cccatgggga aagtagtcca     660

gctcataaag agttattaga aaaagtaaaa aatttaaaaa caacattaga aaggactatt     720

aaagctgaac aagatttaga gaaaaaagta gaatatagtt ttctattagg accattgtta     780

ggatttgttg tttatgaaat tcttgaaaat actgctgttc agcatataaa aaatcaaatt     840

gatgagataa agaaacaatt agattctgct cagcatgatt tggatagaga tgttaaaatt     900

ataggaatgt taaatagtat taatacagat attgataatt tatatagtca aggacaagaa     960

gcaattaaag ttttccaaaa gttacaaggt atttgggcta ctattggagc tcaaatagaa    1020

aatcttagaa caacgtcgtt acaagaagtt caagattctg atgatgctga tgagatacaa    1080

attgaacttg aggacgcttc tgatgcttgg ttagttgtgg ctcaagaagc tcgtgatttt    1140

acactaaatg cttattcaac taatagtaga caaaatttac cgattaatgt tatatcagat    1200

tcatgtaatt gttcaacaac aaatatgaca tcaaatcaat acagtaatcc aacaacaaat    1260

atgacatcaa atcaatatat gatttcacat gaatatacaa gtttaccaaa taattttatg    1320

ttatcaagaa atagtaattt agaatataaa gctcctgaaa ataattttat gatatattgg    1380

tataataatt cggattggta taataattcg gattggtata ataattga                1428


<210> SEQ ID NO 49
<211> LENGTH: 475
<212> TYPE: PRT
<213> ORGANISM: Artificial Sequence
<220> FEATURE:
<223> OTHER INFORMATION: translated from synthesized coding region

<400> SEQUENCE: 49

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45
```

```
Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Ala Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser Asn Gln Tyr Ser Asn
                405                 410                 415

Pro Thr Thr Asn Met Thr Ser Asn Gln Tyr Met Ile Ser His Glu Tyr
            420                 425                 430

Thr Ser Leu Pro Asn Asn Phe Met Leu Ser Arg Asn Ser Asn Leu Glu
        435                 440                 445

Tyr Lys Ala Pro Glu Asn Asn Phe Met Ile Tyr Trp Tyr Asn Asn Ser
    450                 455                 460
```

```
Asp Trp Tyr Asn Asn Ser Asp Trp Tyr Asn Asn
465                 470                 475


<210> SEQ ID NO 50
<211> LENGTH: 379
<212> TYPE: PRT
<213> ORGANISM: Artificial Sequence
<220> FEATURE:
<223> OTHER INFORMATION: protease generated fragment

<400> SEQUENCE: 50

His Ser Leu Ile His Thr Ile Lys Leu Asn Ser Asn Lys Lys Tyr Gly
1               5                   10                  15

Pro Gly Asp Met Thr Asn Gly Asn Gln Phe Ile Ile Ser Lys Gln Glu
            20                  25                  30

Trp Ala Thr Ile Gly Ala Tyr Ile Gln Thr Gly Leu Gly Leu Pro Val
        35                  40                  45

Asn Glu Gln Gln Leu Arg Thr His Val Asn Leu Ser Gln Asp Ile Ser
    50                  55                  60

Ile Pro Ser Asp Phe Ser Gln Leu Tyr Asp Val Tyr Cys Ser Asp Lys
65                  70                  75                  80

Thr Ser Ala Glu Trp Trp Asn Lys Asn Leu Tyr Pro Leu Ile Ile Lys
                85                  90                  95

Ser Ala Asn Asp Ile Ala Ser Tyr Gly Phe Lys Val Ala Gly Asp Pro
            100                 105                 110

Ser Ile Lys Lys Asp Gly Tyr Phe Lys Lys Leu Gln Asp Glu Leu Asp
        115                 120                 125

Asn Ile Val Asp Asn Asn Ser Asp Asp Asp Ala Ile Ala Lys Ala Ile
    130                 135                 140

Lys Asp Phe Lys Ala Arg Cys Gly Ile Leu Ile Lys Glu Ala Lys Gln
145                 150                 155                 160

Tyr Glu Glu Ala Ala Lys Asn Ile Val Thr Ser Leu Asp Gln Phe Leu
                165                 170                 175

His Gly Asp Gln Lys Lys Leu Glu Gly Val Ile Asn Ile Gln Lys Arg
            180                 185                 190

Leu Lys Glu Val Gln Thr Ala Leu Asn Gln Ala His Gly Glu Ser Ser
        195                 200                 205

Pro Ala His Lys Glu Leu Leu Glu Lys Val Lys Asn Leu Lys Thr Thr
    210                 215                 220

Leu Glu Arg Thr Ile Lys Ala Glu Gln Asp Leu Glu Lys Lys Val Glu
225                 230                 235                 240

Tyr Ser Phe Leu Leu Gly Pro Leu Leu Gly Phe Val Val Tyr Glu Ile
                245                 250                 255

Leu Glu Asn Thr Ala Val Gln His Ile Lys Asn Gln Ile Asp Glu Ile
            260                 265                 270

Lys Lys Gln Leu Asp Ser Ala Gln His Asp Leu Asp Arg Asp Val Lys
        275                 280                 285

Ile Ile Gly Met Leu Asn Ser Ile Asn Thr Asp Ile Asp Asn Leu Tyr
    290                 295                 300

Ser Gln Gly Gln Glu Ala Ile Lys Val Phe Gln Lys Leu Gln Gly Ile
305                 310                 315                 320

Trp Ala Thr Ile Gly Ala Gln Ile Glu Asn Leu Arg Thr Thr Ser Leu
                325                 330                 335

Gln Glu Val Gln Asp Ser Asp Asp Ala Asp Glu Ile Gln Ile Glu Leu
            340                 345                 350
```

```
Glu Asp Ala Ser Asp Ala Trp Leu Val Val Ala Gln Glu Ala Arg Asp
        355                 360                 365

Phe Thr Leu Asn Ala Tyr Ser Thr Asn Ser Arg
    370                 375


<210> SEQ ID NO 51
<211> LENGTH: 32
<212> TYPE: PRT
<213> ORGANISM: Artificial Sequence
<220> FEATURE:
<223> OTHER INFORMATION: protease generated fragment

<400> SEQUENCE: 51

Asn Ser Asn Leu Glu Tyr Lys Cys Pro Glu Asn Asn Phe Met Ile Tyr
1               5                   10                  15

Trp Tyr Asn Asn Ser Asp Trp Tyr Asn Asn Ser Asp Trp Tyr Asn Asn
            20                  25                  30


<210> SEQ ID NO 52
<211> LENGTH: 25
<212> TYPE: PRT
<213> ORGANISM: Artificial Sequence
<220> FEATURE:
<223> OTHER INFORMATION: protease generated fragment

<400> SEQUENCE: 52

Cys Pro Glu Asn Asn Phe Met Ile Tyr Trp Tyr Asn Asn Ser Asp Trp
1               5                   10                  15

Tyr Asn Asn Ser Asp Trp Tyr Asn Asn
            20                  25


<210> SEQ ID NO 53
<211> LENGTH: 1332
<212> TYPE: DNA
<213> ORGANISM: Artificial Sequence
<220> FEATURE:
<223> OTHER INFORMATION: synthesized coding region

<400> SEQUENCE: 53

atgattattg atagtaaaac gactttacct agacattcac ttattcatac aattaaatta      60

aattctaata agaaatatgg tcctggtgat atgactaatg gaaatcaatt tattatttca     120

aaacaagaat gggctacgat tggagcatat attcagactg gattaggttt accagtaaat     180

gaacaacaat taagaacaca tgttaattta agtcaggata tatcaatacc tagtgatttt     240

tctcaattat atgatgttta ttgttctgat aaaacttcag cagaatggtg gaataaaaat     300

ttatatcctt taattattaa atctgctaat gatattgctt catatggttt taaagttgct     360

ggtgatcctt ctattaagaa agatggatat tttaaaaaat tgcaagatga attagataat     420

attgttgata ataattccga tgatgatgca atagctaaag ctattaaaga ttttaaagcg     480

cgatgtggta ttttaattaa agaagctaaa caatatgaag aagctgcaaa aaatattgta     540

acatctttag atcaattttt acatggtgat cagaaaaaat tagaaggtgt tatcaatatt     600

caaaaacgtt taaaagaagt tcaaacagct cttaatcaag cccatgggga aagtagtcca     660

gctcataaag agttattaga aaaagtaaaa aatttaaaaa caacattaga aaggactatt     720

aaagctgaac aagatttaga gaaaaaagta gaatatagtt ttctattagg accattgtta     780

ggatttgttg tttatgaaat tcttgaaaat actgctgttc agcatataaa aaatcaaatt     840

gatgagataa agaaacaatt agattctgct cagcatgatt tggatagaga tgttaaaatt     900

ataggaatgt taaatagtat taatacagat attgataatt tatatagtca aggacaagaa     960
```

```
gcaattaaag ttttccaaaa gttacaaggt atttgggcta ctattggagc tcaaatagaa   1020

aatcttagaa caacgtcgtt acaagaagtt caagattctg atgatgctga tgagatacaa   1080

attgaacttg aggacgcttc tgatgcttgg ttagttgtgg ctcaagaagc tcgtgatttt   1140

acactaaatg cttattcaac taatagtaga caaaatttac cgattaatgt tatatcagat   1200

tcatgtaatt gttcaacaac aaatatgaca tcaaatcaat acagtaatcc aacaacaaat   1260

atgacatcaa atcaatatat gatttcacat gaatatacaa gtttaccaaa taattttatg   1320

ttatcaagat ag                                                        1332


<210> SEQ ID NO 54
<211> LENGTH: 443
<212> TYPE: PRT
<213> ORGANISM: Artificial Sequence
<220> FEATURE:
<223> OTHER INFORMATION: translated from synthesized coding region

<400> SEQUENCE: 54

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285
```

```
Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser Asn Gln Tyr Ser Asn
                405                 410                 415

Pro Thr Thr Asn Met Thr Ser Asn Gln Tyr Met Ile Ser His Glu Tyr
            420                 425                 430

Thr Ser Leu Pro Asn Asn Phe Met Leu Ser Arg
        435                 440
```

<210> SEQ ID NO 55
<211> LENGTH: 1296
<212> TYPE: DNA
<213> ORGANISM: Artificial Sequence
<220> FEATURE:
<223> OTHER INFORMATION: synthesized coding region

<400> SEQUENCE: 55

```
atgattattg atagtaaaac gactttacct agacattcac ttattcatac aattaaatta     60

aattctaata agaaatatgg tcctggtgat atgactaatg gaaatcaatt tattatttca    120

aaacaagaat gggctacgat tggagcatat attcagactg gattaggttt accagtaaat    180

gaacaacaat taagaacaca tgttaattta agtcaggata tatcaatacc tagtgatttt    240

tctcaattat atgatgttta ttgttctgat aaaacttcag cagaatggtg gaataaaaat    300

ttatatcctt taattattaa atctgctaat gatattgctt catatggttt taaagttgct    360

ggtgatcctt ctattaagaa agatggatat tttaaaaaat tgcaagatga attagataat    420

attgttgata ataattccga tgatgatgca atagctaaag ctattaaaga ttttaaagcg    480

cgatgtggta ttttaattaa agaagctaaa caatatgaag aagctgcaaa aaatattgta    540

acatctttag atcaattttt acatggtgat cagaaaaaat tagaaggtgt tatcaatatt    600

caaaaacgtt taaaagaagt tcaaacagct cttaatcaag cccatgggga aagtagtcca    660

gctcataaag agttattaga aaaagtaaaa aatttaaaaa caacattaga aaggactatt    720

aaagctgaac aagatttaga gaaaaaagta gaatatagtt ttctattagg accattgtta    780

ggatttgttg tttatgaaat tcttgaaaat actgctgttc agcatataaa aaatcaaatt    840

gatgagataa agaaacaatt agattctgct cagcatgatt tggatagaga tgttaaaatt    900

ataggaatgt taaatagtat taatacagat attgataatt tatatagtca aggacaagaa    960

gcaattaaag ttttccaaaa gttacaaggt atttgggcta ctattggagc tcaaatagaa   1020

aatcttagaa caacgtcgtt acaagaagtt caagattctg atgatgctga tgagatacaa   1080

attgaacttg aggacgcttc tgatgcttgg ttagttgtgg ctcaagaagc tcgtgatttt   1140

acactaaatg cttattcaac taatagtaga caaaatttac cgattaatgt tatatcagat   1200
```

```
tcatgtaatt gttcaacaac aaatatgaca tcaaatcaat acagtaatcc aacaacaaat   1260

atgacatcaa atcaatatat gatttcacat gaatag                             1296


<210> SEQ ID NO 56
<211> LENGTH: 431
<212> TYPE: PRT
<213> ORGANISM: Artificial Sequence
<220> FEATURE:
<223> OTHER INFORMATION: translated from synthesized coding region

<400> SEQUENCE: 56

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
```

```
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser Asn Gln Tyr Ser Asn
                405                 410                 415

Pro Thr Thr Asn Met Thr Ser Asn Gln Tyr Met Ile Ser His Glu
            420                 425                 430
```

<210> SEQ ID NO 57
<211> LENGTH: 1236
<212> TYPE: DNA
<213> ORGANISM: Artificial Sequence
<220> FEATURE:
<223> OTHER INFORMATION: synthesized coding region

<400> SEQUENCE: 57

```
atgattattg atagtaaaac gactttacct agacattcac ttattcatac aattaaatta      60

aattctaata agaaatatgg tcctggtgat atgactaatg gaaatcaatt tattatttca     120

aaacaagaat gggctacgat tggagcatat attcagactg gattaggttt accagtaaat     180

gaacaacaat taagaacaca tgttaattta agtcaggata tatcaatacc tagtgatttt     240

tctcaattat atgatgttta ttgttctgat aaaacttcag cagaatggtg gaataaaaat     300

ttatatcctt taattattaa atctgctaat gatattgctt catatggttt taaagttgct     360

ggtgatcctt ctattaagaa agatggatat tttaaaaaat tgcaagatga attagataat     420

attgttgata ataattccga tgatgatgca atagctaaag ctattaaaga ttttaaagcg     480

cgatgtggta ttttaattaa agaagctaaa caatatgaag aagctgcaaa aaatattgta     540

acatctttag atcaattttt acatggtgat cagaaaaaat tagaaggtgt tatcaatatt     600

caaaaacgtt taaaagaagt tcaaacagct cttaatcaag cccatgggga aagtagtcca     660

gctcataaag agttattaga aaaagtaaaa aatttaaaaa caacattaga aaggactatt     720

aaagctgaac aagatttaga gaaaaaagta gaatatagtt ttctattagg accattgtta     780

ggatttgttg tttatgaaat tcttgaaaat actgctgttc agcatataaa aaatcaaatt     840

gatgagataa agaaacaatt agattctgct cagcatgatt tggatagaga tgttaaaatt     900

ataggaatgt taaatagtat taatacagat attgataatt tatatagtca aggacaagaa     960

gcaattaaag ttttccaaaa gttacaaggt atttgggcta ctattggagc tcaaatagaa    1020

aatcttagaa caacgtcgtt acaagaagtt caagattctg atgatgctga tgagatacaa    1080

attgaacttg aggacgcttc tgatgcttgg ttagttgtgg ctcaagaagc tcgtgatttt    1140

acactaaatg cttattcaac taatagtaga caaaatttac cgattaatgt tatatcagat    1200

tcatgtaatt gttcaacaac aaatatgaca tcatag                              1236
```

<210> SEQ ID NO 58
<211> LENGTH: 411
<212> TYPE: PRT
<213> ORGANISM: Artificial Sequence
<220> FEATURE:
<223> OTHER INFORMATION: translated from synthesized coding region

<400> SEQUENCE: 58

```
Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser
                405                 410
```

<210> SEQ ID NO 59
<211> LENGTH: 1203
<212> TYPE: DNA
<213> ORGANISM: Artificial Sequence
<220> FEATURE:
<223> OTHER INFORMATION: synthesized coding region

<400> SEQUENCE: 59

```
atgattattg atagtaaaac gactttacct agacattcac ttattcatac aattaaatta     60

aattctaata agaaatatgg tcctggtgat atgactaatg gaaatcaatt tattatttca    120

aaacaagaat gggctacgat tggagcatat attcagactg gattaggttt accagtaaat    180

gaacaacaat taagaacaca tgttaattta agtcaggata tatcaatacc tagtgatttt    240

tctcaattat atgatgttta ttgttctgat aaaacttcag cagaatggtg gaataaaaat    300

ttatatcctt taattattaa atctgctaat gatattgctt catatggttt taaagttgct    360

ggtgatcctt ctattaagaa agatggatat tttaaaaaat tgcaagatga attagataat    420

attgttgata ataattccga tgatgatgca atagctaaag ctattaaaga ttttaaagcg    480

cgatgtggta ttttaattaa agaagctaaa caatatgaag aagctgcaaa aaatattgta    540

acatctttag atcaattttt acatggtgat cagaaaaaat tagaaggtgt tatcaatatt    600

caaaaacgtt taaaagaagt tcaaacagct cttaatcaag cccatgggga aagtagtcca    660

gctcataaag agttattaga aaaagtaaaa aatttaaaaa caacattaga aaggactatt    720

aaagctgaac aagatttaga gaaaaaagta gaatatagtt ttctattagg accattgtta    780

ggatttgttg tttatgaaat tcttgaaaat actgctgttc agcatataaa aaatcaaatt    840

gatgagataa agaaacaatt agattctgct cagcatgatt tggatagaga tgttaaaatt    900

ataggaatgt taaatagtat taatacagat attgataatt tatatagtca aggacaagaa    960

gcaattaaag ttttccaaaa gttacaaggt atttgggcta ctattggagc tcaaatagaa   1020

aatcttagaa caacgtcgtt acaagaagtt caagattctg atgatgctga tgagatacaa   1080

attgaacttg aggacgcttc tgatgcttgg ttagttgtgg ctcaagaagc tcgtgatttt   1140

acactaaatg cttattcaac taatagtaga caaaatttac cgattaatgt tatatcagat   1200

tag                                                                 1203
```

<210> SEQ ID NO 60
<211> LENGTH: 400
<212> TYPE: PRT
<213> ORGANISM: Artificial Sequence
<220> FEATURE:
<223> OTHER INFORMATION: translated from synthesized coding region

<400> SEQUENCE: 60

```
Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95
```

```
Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400


<210> SEQ ID NO 61
<211> LENGTH: 1173
<212> TYPE: DNA
<213> ORGANISM: Artificial Sequence
<220> FEATURE:
<223> OTHER INFORMATION: synthesized coding region

<400> SEQUENCE: 61

atgattattg atagtaaaac gactttacct agacattcac ttattcatac aattaaatta      60

aattctaata agaaatatgg tcctggtgat atgactaatg gaaatcaatt tattatttca     120

aaacaagaat gggctacgat tggagcatat attcagactg gattaggttt accagtaaat     180

gaacaacaat taagaacaca tgttaattta agtcaggata tatcaatacc tagtgatttt     240

tctcaattat atgatgttta ttgttctgat aaaacttcag cagaatggtg gaataaaaat     300

ttatatcctt taattattaa atctgctaat gatattgctt catatggttt taaagttgct     360
```

```
ggtgatcctt ctattaagaa agatggatat tttaaaaaat tgcaagatga attagataat    420

attgttgata ataattccga tgatgatgca atagctaaag ctattaaaga ttttaaagcg    480

cgatgtggta ttttaattaa agaagctaaa caatatgaag aagctgcaaa aaatattgta    540

acatctttag atcaattttt acatggtgat cagaaaaaat tagaaggtgt tatcaatatt    600

caaaaacgtt taaaagaagt tcaaacagct cttaatcaag cccatgggga aagtagtcca    660

gctcataaag agttattaga aaaagtaaaa aatttaaaaa caacattaga aaggactatt    720

aaagctgaac aagatttaga gaaaaaagta gaatatagtt ttctattagg accattgtta    780

ggatttgttg tttatgaaat tcttgaaaat actgctgttc agcatataaa aaatcaaatt    840

gatgagataa agaaacaatt agattctgct cagcatgatt tggatagaga tgttaaaatt    900

ataggaatgt taaatagtat taatacagat attgataatt tatatagtca aggacaagaa    960

gcaattaaag ttttccaaaa gttacaaggt atttgggcta ctattggagc tcaaatagaa   1020

aatcttagaa caacgtcgtt acaagaagtt caagattctg atgatgctga tgagatacaa   1080

attgaacttg aggacgcttc tgatgcttgg ttagttgtgg ctcaagaagc tcgtgatttt   1140

acactaaatg cttattcaac taatagtaga tag                                1173
```

```
<210> SEQ ID NO 62
<211> LENGTH: 390
<212> TYPE: PRT
<213> ORGANISM: Artificial Sequence
<220> FEATURE:
<223> OTHER INFORMATION: translated from synthesized coding region

<400> SEQUENCE: 62

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220
```

```
Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg
385                 390
```

<210> SEQ ID NO 63
<211> LENGTH: 1413
<212> TYPE: DNA
<213> ORGANISM: Artificial Sequence
<220> FEATURE:
<223> OTHER INFORMATION: synthesized coding region

<400> SEQUENCE: 63

```
atgattattg attctaaaac aacattacca agacattctt taattcatac tataaaatta     60

aattctaata agaaatatgg tcctggtgat atgactaatg gaaatcaatt tattatttca    120

aaacaagaat gggctactat tggagcatat attcagactg gattaggttt accagtaaat    180

gaacaacaat taagaacaca tgttaattta agtcaggata tatcaatacc tagtgatttt    240

tctcaattat atgatgttta ttgttctgat aaaacttcag cagaatggtg gaataaaaat    300

ttatatcctt taattattaa atctgctaat gatattgctt catatggttt taaagttgct    360

ggtgatcctt ctattaagaa agatggatat tttaaaaaat tgcaagatga attagataat    420

attgttgata ataattccga tgatgatgca atagctaaag ctattaaaga ttttaaagcg    480

cgatgtggta ttttaattaa agaagctaaa caatatgaag aagctgcaaa aaatattgta    540

acatctttag atcaattttt acatggtgat cagaaaaaat tagaaggtgt tatcaatatt    600

caaaaacgtt taaaagaagt tcaaacagct cttaatcaag cccatgggga aagtagtcca    660

gctcataaag agttattaga aaaagtaaaa aatttaaaaa caacattaga aaggactatt    720

aaagctgaac aagatttaga gaaaaaagta gaatatagtt ttctattagg accattgtta    780

ggatttgttg tttatgaaat tcttgaaaat actgctgttc agcatataaa aaatcaaatt    840

gatgagataa agaaacaatt agattctgct cagcatgatt tggatagaga tgttaaaatt    900

ataggaatgt taaatagtat taatacagat attgataatt tatatagtca aggacaagaa    960

gcaattaaag ttttccaaaa gttacaaggt atttgggcta ctattggagc tcaaatagaa   1020

aatcttagaa caacgtcgtt acaagaagtt caagattctg atgatgctga tgagatacaa   1080
```

```
attgaacttg aggacgcttc tgatgcttgg ttagttgtgg ctcaagaagc tcgtgatttt   1140

acactaaatg cttattcaac taatagtaga aatgttatat cagattcatg taattgttca   1200

acaacaaata tgacatcaaa tcaatacagt aatccaacaa caaatatgac atcaaatcaa   1260

tatatgattt cacatgaata tacaagttta ccaaataatt ttatgttatc aagaaatagt   1320

aatttagaat ataaatgtcc tgaaaataat tttatgatat attggtataa taattcggat   1380

tggtataata attcggattg gtataataat tga                                1413


<210> SEQ ID NO 64
<211> LENGTH: 470
<212> TYPE: PRT
<213> ORGANISM: Artificial Sequence
<220> FEATURE:
<223> OTHER INFORMATION: translated from synthesized coding region

<400> SEQUENCE: 64

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300
```

```
Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Asn Val Ile Ser Asp Ser Cys Asn Cys Ser
385                 390                 395                 400

Thr Thr Asn Met Thr Ser Asn Gln Tyr Ser Asn Pro Thr Thr Asn Met
                405                 410                 415

Thr Ser Asn Gln Tyr Met Ile Ser His Glu Tyr Thr Ser Leu Pro Asn
            420                 425                 430

Asn Phe Met Leu Ser Arg Asn Ser Asn Leu Glu Tyr Lys Cys Pro Glu
        435                 440                 445

Asn Asn Phe Met Ile Tyr Trp Tyr Asn Asn Ser Asp Trp Tyr Asn Asn
    450                 455                 460

Ser Asp Trp Tyr Asn Asn
465                 470


<210> SEQ ID NO 65
<211> LENGTH: 1413
<212> TYPE: DNA
<213> ORGANISM: Artificial Sequence
<220> FEATURE:
<223> OTHER INFORMATION: synthesized coding region

<400> SEQUENCE: 65

atgattattg attctaaaac aacattacca agacattctt taattcatac tataaaatta      60

aattctaata agaaatatgg tcctggtgat atgactaatg gaaatcaatt tattatttca     120

aaacaagaat gggctactat tggagcatat attcagactg gattaggttt accagtaaat     180

gaacaacaat taagaacaca tgttaattta agtcaggata tatcaatacc tagtgatttt     240

tctcaattat atgatgttta ttgttctgat aaaacttcag cagaatggtg gaataaaaat     300

ttatatcctt taattattaa atctgctaat gatattgctt catatggttt taaagttgct     360

ggtgatcctt ctattaagaa agatggatat tttaaaaaat tgcaagatga attagataat     420

attgttgata ataattccga tgatgatgca atagctaaag ctattaaaga ttttaaagcg     480

cgatgtggta ttttaattaa agaagctaaa caatatgaag aagctgcaaa aaatattgta     540

acatctttag atcaattttt acatggtgat cagaaaaaat tagaaggtgt tatcaatatt     600

caaaaacgtt taaaagaagt tcaaacagct cttaatcaag cccatgggga aagtagtcca     660

gctcataaag agttattaga aaaagtaaaa aatttaaaaa caacattaga aaggactatt     720

aaagctgaac aagatttaga gaaaaaagta gaatatagtt ttctattagg accattgtta     780

ggatttgttg tttatgaaat tcttgaaaat actgctgttc agcatataaa aaatcaaatt     840

gatgagataa agaaacaatt agattctgct cagcatgatt tggatagaga tgttaaaatt     900

ataggaatgt taaatagtat taatacagat attgataatt tatatagtca aggacaagaa     960

gcaattaaag ttttccaaaa gttacaaggt atttgggcta ctattggagc tcaaatagaa    1020

aatcttagaa caacgtcgtt acaagaagtt caagattctg atgatgctga tgagatacaa    1080
```

```
attgaacttg aggacgcttc tgatgcttgg ttagttgtgg ctcaagaagc tcgtgatttt   1140

acactaaatg cttattcaac taatagtaga caaaatttac cgatttcatg taattgttca   1200

acaacaaata tgacatcaaa tcaatacagt aatccaacaa caaatatgac atcaaatcaa   1260

tatatgattt cacatgaata tacaagttta ccaaataatt ttatgttatc aagaaatagt   1320

aatttagaat ataaatgtcc tgaaaataat tttatgatat attggtataa taattcggat   1380

tggtataata attcggattg gtataataat tga                                1413


<210> SEQ ID NO 66
<211> LENGTH: 470
<212> TYPE: PRT
<213> ORGANISM: Artificial Sequence
<220> FEATURE:
<223> OTHER INFORMATION: translated from synthesized coding region

<400> SEQUENCE: 66

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300
```

```
Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Ser Cys Asn Cys Ser
385                 390                 395                 400

Thr Thr Asn Met Thr Ser Asn Gln Tyr Ser Asn Pro Thr Thr Asn Met
                405                 410                 415

Thr Ser Asn Gln Tyr Met Ile Ser His Glu Tyr Thr Ser Leu Pro Asn
            420                 425                 430

Asn Phe Met Leu Ser Arg Asn Ser Asn Leu Glu Tyr Lys Cys Pro Glu
        435                 440                 445

Asn Asn Phe Met Ile Tyr Trp Tyr Asn Asn Ser Asp Trp Tyr Asn Asn
    450                 455                 460

Ser Asp Trp Tyr Asn Asn
465                 470


<210> SEQ ID NO 67
<211> LENGTH: 1413
<212> TYPE: DNA
<213> ORGANISM: Artificial Sequence
<220> FEATURE:
<223> OTHER INFORMATION: synthesized coding region

<400> SEQUENCE: 67

atgattattg attctaaaac aacattacca agacattctt taattcatac tataaaatta      60

aattctaata agaaatatgg tcctggtgat atgactaatg gaaatcaatt tattatttca     120

aaacaagaat gggctactat tggagcatat attcagactg gattaggttt accagtaaat     180

gaacaacaat taagaacaca tgttaattta agtcaggata tatcaatacc tagtgatttt     240

tctcaattat atgatgttta ttgttctgat aaaacttcag cagaatggtg gaataaaaat     300

ttatatcctt taattattaa atctgctaat gatattgctt catatggttt taaagttgct     360

ggtgatcctt ctattaagaa agatggatat tttaaaaaat tgcaagatga attagataat     420

attgttgata ataattccga tgatgatgca atagctaaag ctattaaaga ttttaaagcg     480

cgatgtggta ttttaattaa agaagctaaa caatatgaag aagctgcaaa aaatattgta     540

acatctttag atcaattttt acatggtgat cagaaaaaat tagaaggtgt tatcaatatt     600

caaaaacgtt taaaagaagt tcaaacagct cttaatcaag cccatgggga aagtagtcca     660

gctcataaag agttattaga aaaagtaaaa aatttaaaaa caacattaga aaggactatt     720

aaagctgaac aagatttaga gaaaaaagta gaatatagtt ttctattagg accattgtta     780

ggatttgttg tttatgaaat tcttgaaaat actgctgttc agcatataaa aaatcaaatt     840

gatgagataa agaaacaatt agattctgct cagcatgatt tggatagaga tgttaaaatt     900

ataggaatgt taaatagtat taatacagat attgataatt tatatagtca aggacaagaa     960

gcaattaaag ttttccaaaa gttacaaggt atttgggcta ctattggagc tcaaatagaa    1020

aatcttagaa caacgtcgtt acaagaagtt caagattctg atgatgctga tgagatacaa    1080
```

```
attgaacttg aggacgcttc tgatgcttgg ttagttgtgg ctcaagaagc tcgtgatttt   1140

acactaaatg cttattcaac taatagtaga caaaatttac cgattaatgt tatatcagat   1200

acaacaaata tgacatcaaa tcaatacagt aatccaacaa caaatatgac atcaaatcaa   1260

tatatgattt cacatgaata tacaagttta ccaaataatt ttatgttatc aagaaatagt   1320

aatttagaat ataaatgtcc tgaaaataat tttatgatat attggtataa taattcggat   1380

tggtataata attcggattg gtataataat tga                                1413
```

<210> SEQ ID NO 68
<211> LENGTH: 470
<212> TYPE: PRT
<213> ORGANISM: Artificial Sequence
<220> FEATURE:
<223> OTHER INFORMATION: translated from synthesized coding region

<400> SEQUENCE: 68

```
Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300
```

```
Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Thr Thr Asn Met Thr Ser Asn Gln Tyr Ser Asn Pro Thr Thr Asn Met
                405                 410                 415

Thr Ser Asn Gln Tyr Met Ile Ser His Glu Tyr Thr Ser Leu Pro Asn
            420                 425                 430

Asn Phe Met Leu Ser Arg Asn Ser Asn Leu Glu Tyr Lys Cys Pro Glu
        435                 440                 445

Asn Asn Phe Met Ile Tyr Trp Tyr Asn Asn Ser Asp Trp Tyr Asn Asn
    450                 455                 460

Ser Asp Trp Tyr Asn Asn
465                 470


<210> SEQ ID NO 69
<211> LENGTH: 1413
<212> TYPE: DNA
<213> ORGANISM: Artificial Sequence
<220> FEATURE:
<223> OTHER INFORMATION: synthesized coding region

<400> SEQUENCE: 69

atgattattg attctaaaac aacattacca agacattctt taattcatac tataaaatta      60

aattctaata agaaatatgg tcctggtgat atgactaatg gaaatcaatt tattatttca     120

aaacaagaat gggctactat tggagcatat attcagactg gattaggttt accagtaaat     180

gaacaacaat taagaacaca tgttaattta agtcaggata tatcaatacc tagtgatttt     240

tctcaattat atgatgttta ttgttctgat aaaacttcag cagaatggtg gaataaaaat     300

ttatatcctt taattattaa atctgctaat gatattgctt catatggttt taaagttgct     360

ggtgatcctt ctattaagaa agatggatat tttaaaaaat tgcaagatga attagataat     420

attgttgata ataattccga tgatgatgca atagctaaag ctattaaaga ttttaaagcg     480

cgatgtggta ttttaattaa agaagctaaa caatatgaag aagctgcaaa aaatattgta     540

acatctttag atcaattttt acatggtgat cagaaaaaat tagaaggtgt tatcaatatt     600

caaaaacgtt taaaagaagt tcaaacagct cttaatcaag cccatgggga aagtagtcca     660

gctcataaag agttattaga aaaagtaaaa aatttaaaaa caacattaga aaggactatt     720

aaagctgaac aagatttaga gaaaaaagta gaatatagtt ttctattagg accattgtta     780

ggatttgttg tttatgaaat tcttgaaaat actgctgttc agcatataaa aaatcaaatt     840

gatgagataa agaaacaatt agattctgct cagcatgatt tggatagaga tgttaaaatt     900

ataggaatgt taaatagtat taatacagat attgataatt tatatagtca aggacaagaa     960

gcaattaaag ttttccaaaa gttacaaggt atttgggcta ctattggagc tcaaatagaa    1020

aatcttagaa caacgtcgtt acaagaagtt caagattctg atgatgctga tgagatacaa    1080
```

```
attgaacttg aggacgcttc tgatgcttgg ttagttgtgg ctcaagaagc tcgtgatttt   1140

acactaaatg cttattcaac taatagtaga caaaatttac cgattaatgt tatatcagat   1200

tcatgtaatt gttcatcaaa tcaatacagt aatccaacaa caaatatgac atcaaatcaa   1260

tatatgattt cacatgaata tacaagttta ccaaataatt ttatgttatc aagaaatagt   1320

aatttagaat ataaatgtcc tgaaaataat tttatgatat attggtataa taattcggat   1380

tggtataata attcggattg gtataataat tga                                1413
```

<210> SEQ ID NO 70
<211> LENGTH: 470
<212> TYPE: PRT
<213> ORGANISM: Artificial Sequence
<220> FEATURE:
<223> OTHER INFORMATION: translated from synthesized coding region

<400> SEQUENCE: 70

```
Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300
```

```
Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Ser Asn Gln Tyr Ser Asn Pro Thr Thr Asn Met
                405                 410                 415

Thr Ser Asn Gln Tyr Met Ile Ser His Glu Tyr Thr Ser Leu Pro Asn
            420                 425                 430

Asn Phe Met Leu Ser Arg Asn Ser Asn Leu Glu Tyr Lys Cys Pro Glu
        435                 440                 445

Asn Asn Phe Met Ile Tyr Trp Tyr Asn Asn Ser Asp Trp Tyr Asn Asn
    450                 455                 460

Ser Asp Trp Tyr Asn Asn
465                 470


<210> SEQ ID NO 71
<211> LENGTH: 1413
<212> TYPE: DNA
<213> ORGANISM: Artificial Sequence
<220> FEATURE:
<223> OTHER INFORMATION: synthesized coding region

<400> SEQUENCE: 71

atgattattg attctaaaac aacattacca agacattctt taattcatac tataaaatta      60

aattctaata agaaatatgg tcctggtgat atgactaatg gaaatcaatt tattatttca     120

aaacaagaat gggctactat tggagcatat attcagactg gattaggttt accagtaaat     180

gaacaacaat taagaacaca tgttaattta agtcaggata tatcaatacc tagtgatttt     240

tctcaattat atgatgttta ttgttctgat aaaacttcag cagaatggtg gaataaaaat     300

ttatatcctt taattattaa atctgctaat gatattgctt catatggttt taaagttgct     360

ggtgatcctt ctattaagaa agatggatat tttaaaaaat tgcaagatga attagataat     420

attgttgata ataattccga tgatgatgca atagctaaag ctattaaaga ttttaaagcg     480

cgatgtggta ttttaattaa agaagctaaa caatatgaag aagctgcaaa aaatattgta     540

acatctttag atcaattttt acatggtgat cagaaaaaat tagaaggtgt tatcaatatt     600

caaaaacgtt taaaagaagt tcaaacagct cttaatcaag cccatgggga aagtagtcca     660

gctcataaag agttattaga aaaagtaaaa aatttaaaaa caacattaga aaggactatt     720

aaagctgaac aagatttaga gaaaaaagta gaatatagtt ttctattagg accattgtta     780

ggatttgttg tttatgaaat tcttgaaaat actgctgttc agcatataaa aaatcaaatt     840

gatgagataa agaaacaatt agattctgct cagcatgatt tggatagaga tgttaaaatt     900

ataggaatgt taaatagtat taatacagat attgataatt tatatagtca aggacaagaa     960

gcaattaaag ttttccaaaa gttacaaggt atttgggcta ctattggagc tcaaatagaa    1020

aatcttagaa caacgtcgtt acaagaagtt caagattctg atgatgctga tgagatacaa    1080
```

```
attgaacttg aggacgcttc tgatgcttgg ttagttgtgg ctcaagaagc tcgtgatttt   1140

acactaaatg cttattcaac taatagtaga caaaatttac cgattaatgt tatatcagat   1200

tcatgtaatt gttcaacaac aaatatgaca aatccaacaa caaatatgac atcaaatcaa   1260

tatatgattt cacatgaata tacaagttta ccaaataatt ttatgttatc aagaaatagt   1320

aatttagaat ataaatgtcc tgaaaataat tttatgatat attggtataa taattcggat   1380

tggtataata attcggattg gtataataat tga                                1413
```

```
<210> SEQ ID NO 72
<211> LENGTH: 470
<212> TYPE: PRT
<213> ORGANISM: Artificial Sequence
<220> FEATURE:
<223> OTHER INFORMATION: translated from synthesized coding region

<400> SEQUENCE: 72

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300
```

```
Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Asn Pro Thr Thr Asn Met
                405                 410                 415

Thr Ser Asn Gln Tyr Met Ile Ser His Glu Tyr Thr Ser Leu Pro Asn
            420                 425                 430

Asn Phe Met Leu Ser Arg Asn Ser Asn Leu Glu Tyr Lys Cys Pro Glu
        435                 440                 445

Asn Asn Phe Met Ile Tyr Trp Tyr Asn Asn Ser Asp Trp Tyr Asn Asn
    450                 455                 460

Ser Asp Trp Tyr Asn Asn
465                 470


<210> SEQ ID NO 73
<211> LENGTH: 1413
<212> TYPE: DNA
<213> ORGANISM: Artificial Sequence
<220> FEATURE:
<223> OTHER INFORMATION: synthesized coding region

<400> SEQUENCE: 73

atgattattg attctaaaac aacattacca agacattctt taattcatac tataaaatta      60

aattctaata agaaatatgg tcctggtgat atgactaatg gaaatcaatt tattatttca     120

aaacaagaat gggctactat tggagcatat attcagactg gattaggttt accagtaaat     180

gaacaacaat taagaacaca tgttaattta agtcaggata tatcaatacc tagtgatttt     240

tctcaattat atgatgttta ttgttctgat aaaacttcag cagaatggtg gaataaaaat     300

ttatatcctt taattattaa atctgctaat gatattgctt catatggttt taaagttgct     360

ggtgatcctt ctattaagaa agatggatat tttaaaaaat tgcaagatga attagataat     420

attgttgata ataattccga tgatgatgca atagctaaag ctattaaaga ttttaaagcg     480

cgatgtggta ttttaattaa agaagctaaa caatatgaag aagctgcaaa aaatattgta     540

acatctttag atcaattttt acatggtgat cagaaaaaat tagaaggtgt tatcaatatt     600

caaaaacgtt taaaagaagt tcaaacagct cttaatcaag cccatgggga aagtagtcca     660

gctcataaag agttattaga aaaagtaaaa aatttaaaaa caacattaga aaggactatt     720

aaagctgaac aagatttaga gaaaaaagta gaatatagtt ttctattagg accattgtta     780

ggatttgttg tttatgaaat tcttgaaaat actgctgttc agcatataaa aaatcaaatt     840

gatgagataa agaaacaatt agattctgct cagcatgatt tggatagaga tgttaaaatt     900

ataggaatgt taaatagtat taatacagat attgataatt tatatagtca aggacaagaa     960

gcaattaaag ttttccaaaa gttacaaggt atttgggcta ctattggagc tcaaatagaa    1020

aatcttagaa caacgtcgtt acaagaagtt caagattctg atgatgctga tgagatacaa    1080
```

```
attgaacttg aggacgcttc tgatgcttgg ttagttgtgg ctcaagaagc tcgtgatttt   1140

acactaaatg cttattcaac taatagtaga caaaatttac cgattaatgt tatatcagat   1200

tcatgtaatt gttcaacaac aaatatgaca tcaaatcaat acagtatgac atcaaatcaa   1260

tatatgattt cacatgaata tacaagttta ccaaataatt ttatgttatc aagaaatagt   1320

aatttagaat ataaatgtcc tgaaaataat tttatgatat attggtataa taattcggat   1380

tggtataata attcggattg gtataataat tga                                 1413


<210> SEQ ID NO 74
<211> LENGTH: 470
<212> TYPE: PRT
<213> ORGANISM: Artificial Sequence
<220> FEATURE:
<223> OTHER INFORMATION: translated from synthesized coding region

<400> SEQUENCE: 74

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300
```

```
Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser Asn Gln Tyr Ser Met
                405                 410                 415

Thr Ser Asn Gln Tyr Met Ile Ser His Glu Tyr Thr Ser Leu Pro Asn
            420                 425                 430

Asn Phe Met Leu Ser Arg Asn Ser Asn Leu Glu Tyr Lys Cys Pro Glu
        435                 440                 445

Asn Asn Phe Met Ile Tyr Trp Tyr Asn Asn Ser Asp Trp Tyr Asn Asn
    450                 455                 460

Ser Asp Trp Tyr Asn Asn
465                 470
```

<210> SEQ ID NO 75
<211> LENGTH: 1340
<212> TYPE: DNA
<213> ORGANISM: Artificial Sequence
<220> FEATURE:
<223> OTHER INFORMATION: synthesized coding region

<400> SEQUENCE: 75

```
aatatggtcc tggtgatatg actaatggaa atcaatttat tatttcaaaa caagaatggg     60

ctactattgg agcatatatt cagactggat taggtttacc agtaaatgaa caacaattaa    120

gaacacatgt taatttaagt caggatatat caatacctag tgatttttct caattatatg    180

atgtttattg ttctgataaa acttcagcag aatggtggaa taaaaattta tatcctttaa    240

ttattaaatc tgctaatgat attgcttcat atggttttaa agttgctggt gatccttcta    300

ttaagaaaga tggatatttt aaaaaattgc aagatgaatt agataatatt gttgataata    360

attccgatga tgatgcaata gctaaagcta ttaaagattt taaagcgcga tgtggtattt    420

taattaaaga agctaaacaa tatgaagaag ctgcaaaaaa tattgtaaca tctttagatc    480

aatttttaca tggtgatcag aaaaaattag aaggtgttat caatattcaa aaacgtttaa    540

aagaagttca aacagctctt aatcaagccc atggggaaag tagtccagct cataaagagt    600

tattagaaaa agtaaaaaat ttaaaaacaa cattagaaag gactattaaa gctgaacaag    660

atttagagaa aaaagtagaa tatagttttc tattaggacc attgttagga tttgttgttt    720

atgaaattct tgaaaatact gctgttcagc atataaaaaa tcaaattgat gagataaaga    780

aacaattaga ttctgctcag catgatttgg atagagatgt taaaattata ggaatgttaa    840

atagtattaa tacagatatt gataatttat atagtcaagg acaagaagca attaaagttt    900

tccaaaagtt acaaggtatt tgggctacta ttggagctca aatagaaaat cttagaacaa    960

cgtcgttaca agaagttcaa gattctgatg atgctgatga gatacaaatt gaacttgagg   1020

acgcttctga tgcttggtta gttgtggctc aagaagctcg tgattttaca ctaaatgctt   1080
```

```
attcaactaa tagtagacaa aatttaccga ttaatgttat atcagattca tgtaattgtt   1140

caacaacaaa tatgacatca aatcaataca gtaatccaac aacaaattat atgatttcac   1200

atgaatatac aagtttacca aataatttta tgttatcaag aaatagtaat ttagaatata   1260

aatgtcctga aaataatttt atgatatatt ggtataataa ttcggattgg tataataatt   1320

cggattggta taataattga                                               1340
```

<210> SEQ ID NO 76
<211> LENGTH: 470
<212> TYPE: PRT
<213> ORGANISM: Artificial Sequence
<220> FEATURE:
<223> OTHER INFORMATION: translated from synthesized coding region

<400> SEQUENCE: 76

```
Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
```

```
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser Asn Gln Tyr Ser Asn
                405                 410                 415

Pro Thr Thr Asn Tyr Met Ile Ser His Glu Tyr Thr Ser Leu Pro Asn
            420                 425                 430

Asn Phe Met Leu Ser Arg Asn Ser Asn Leu Glu Tyr Lys Cys Pro Glu
        435                 440                 445

Asn Asn Phe Met Ile Tyr Trp Tyr Asn Asn Ser Asp Trp Tyr Asn Asn
    450                 455                 460

Ser Asp Trp Tyr Asn Asn
465                 470


<210> SEQ ID NO 77
<211> LENGTH: 1413
<212> TYPE: DNA
<213> ORGANISM: Artificial Sequence
<220> FEATURE:
<223> OTHER INFORMATION: synthesized coding region

<400> SEQUENCE: 77

atgattattg attctaaaac aacattacca agacattctt taattcatac tataaaatta     60

aattctaata agaaatatgg tcctggtgat atgactaatg gaaatcaatt tattatttca    120

aaacaagaat gggctactat tggagcatat attcagactg gattaggttt accagtaaat    180

gaacaacaat taagaacaca tgttaattta agtcaggata tatcaatacc tagtgatttt    240

tctcaattat atgatgttta ttgttctgat aaaacttcag cagaatggtg gaataaaaat    300

ttatatcctt taattattaa atctgctaat gatattgctt catatggttt taaagttgct    360

ggtgatcctt ctattaagaa agatggatat tttaaaaaat tgcaagatga attagataat    420

attgttgata ataattccga tgatgatgca atagctaaag ctattaaaga ttttaaagcg    480

cgatgtggta ttttaattaa agaagctaaa caatatgaag aagctgcaaa aaatattgta    540

acatctttag atcaattttt acatggtgat cagaaaaaat tagaaggtgt tatcaatatt    600

caaaaacgtt taaaagaagt tcaaacagct cttaatcaag cccatgggga aagtagtcca    660

gctcataaag agttattaga aaaagtaaaa aatttaaaaa caacattaga aaggactatt    720

aaagctgaac aagatttaga gaaaaaagta gaatatagtt ttctattagg accattgtta    780

ggatttgttg tttatgaaat tcttgaaaat actgctgttc agcatataaa aaatcaaatt    840

gatgagataa agaaacaatt agattctgct cagcatgatt tggatagaga tgttaaaatt    900

ataggaatgt taaatagtat taatacagat attgataatt tatatagtca aggacaagaa    960

gcaattaaag ttttccaaaa gttacaaggt atttgggcta ctattggagc tcaaatagaa   1020

aatcttagaa caacgtcgtt acaagaagtt caagattctg atgatgctga tgagatacaa   1080

attgaacttg aggacgcttc tgatgcttgg ttagttgtgg ctcaagaagc tcgtgatttt   1140
```

```
acactaaatg cttattcaac taatagtaga caaaatttac cgattaatgt tatatcagat   1200

tcatgtaatt gttcaacaac aaatatgaca tcaaatcaat acagtaatcc aacaacaaat   1260

atgacatcaa atcaatatat gatttcacat gaatatacaa gtttaccaaa taattttatg   1320

aatttagaat ataaatgtcc tgaaaataat tttatgatat attggtataa taattcggat   1380

tggtataata attcggattg gtataataat tga                                1413
```

```
<210> SEQ ID NO 78
<211> LENGTH: 470
<212> TYPE: PRT
<213> ORGANISM: Artificial Sequence
<220> FEATURE:
<223> OTHER INFORMATION: translated from synthesized coding region

<400> SEQUENCE: 78

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
```

```
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser Asn Gln Tyr Ser Asn
                405                 410                 415

Pro Thr Thr Asn Met Thr Ser Asn Gln Tyr Met Ile Ser His Glu Tyr
            420                 425                 430

Thr Ser Leu Pro Asn Asn Phe Met Asn Leu Glu Tyr Lys Cys Pro Glu
        435                 440                 445

Asn Asn Phe Met Ile Tyr Trp Tyr Asn Asn Ser Asp Trp Tyr Asn Asn
    450                 455                 460

Ser Asp Trp Tyr Asn Asn
465                 470


<210> SEQ ID NO 79
<211> LENGTH: 1398
<212> TYPE: DNA
<213> ORGANISM: Artificial Sequence
<220> FEATURE:
<223> OTHER INFORMATION: synthesized coding region

<400> SEQUENCE: 79

atgattattg attctaaaac aacattacca agacattctt taattcatac tataaaatta     60

aattctaata agaaatatgg tcctggtgat atgactaatg gaaatcaatt tattatttca    120

aaacaagaat gggctactat tggagcatat attcagactg gattaggttt accagtaaat    180

gaacaacaat taagaacaca tgttaattta agtcaggata tatcaatacc tagtgatttt    240

tctcaattat atgatgttta ttgttctgat aaaacttcag cagaatggtg gaataaaaat    300

ttatatcctt taattattaa atctgctaat gatattgctt catatggttt taaagttgct    360

ggtgatcctt ctattaagaa agatggatat tttaaaaaat tgcaagatga attagataat    420

attgttgata ataattccga tgatgatgca atagctaaag ctattaaaga ttttaaagcg    480

cgatgtggta ttttaattaa agaagctaaa caatatgaag aagctgcaaa aaatattgta    540

acatctttag atcaattttt acatggtgat cagaaaaaat tagaaggtgt tatcaatatt    600

caaaaacgtt taaaagaagt tcaaacagct cttaatcaag cccatgggga aagtagtcca    660

gctcataaag agttattaga aaaagtaaaa aatttaaaaa caacattaga aaggactatt    720

aaagctgaac aagatttaga gaaaaaagta gaatatagtt ttctattagg accattgtta    780

ggatttgttg tttatgaaat tcttgaaaat actgctgttc agcatataaa aaatcaaatt    840

gatgagataa agaaacaatt agattctgct cagcatgatt tggatagaga tgttaaaatt    900

ataggaatgt taaatagtat taatacagat attgataatt tatatagtca aggacaagaa    960

gcaattaaag ttttccaaaa gttacaaggt atttgggcta ctattggagc tcaaatagaa   1020

aatcttagaa caacgtcgtt acaagaagtt caagattctg atgatgctga tgagatacaa   1080

attgaacttg aggacgcttc tgatgcttgg ttagttgtgg ctcaagaagc tcgtgatttt   1140
```

```
acactaaatg cttattcaac taatagtaga tcatgtaatt gttcaacaac aaatatgaca   1200

tcaaatcaat acagtaatcc aacaacaaat atgacatcaa atcaatatat gatttcacat   1260

gaatatacaa gtttaccaaa taattttatg ttatcaagaa atagtaattt agaatataaa   1320

tgtcctgaaa ataattttat gatatattgg tataataatt cggattggta taataattcg   1380

gattggtata ataattga                                                 1398


<210> SEQ ID NO 80
<211> LENGTH: 465
<212> TYPE: PRT
<213> ORGANISM: Artificial Sequence
<220> FEATURE:
<223> OTHER INFORMATION: translated from synthesized coding region

<400> SEQUENCE: 80

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
```

```
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Ser Cys Asn Cys Ser Thr Thr Asn Met Thr
385                 390                 395                 400

Ser Asn Gln Tyr Ser Asn Pro Thr Thr Asn Met Thr Ser Asn Gln Tyr
                405                 410                 415

Met Ile Ser His Glu Tyr Thr Ser Leu Pro Asn Asn Phe Met Leu Ser
            420                 425                 430

Arg Asn Ser Asn Leu Glu Tyr Lys Cys Pro Glu Asn Asn Phe Met Ile
        435                 440                 445

Tyr Trp Tyr Asn Asn Ser Asp Trp Tyr Asn Asn Ser Asp Trp Tyr Asn
    450                 455                 460

Asn
465
```

<210> SEQ ID NO 81
<211> LENGTH: 1398
<212> TYPE: DNA
<213> ORGANISM: Artificial Sequence
<220> FEATURE:
<223> OTHER INFORMATION: synthesized coding region

<400> SEQUENCE: 81

```
atgattattg attctaaaac aacattacca agacattctt taattcatac tataaaatta     60

aattctaata agaaatatgg tcctggtgat atgactaatg gaaatcaatt tattatttca    120

aaacaagaat gggctactat tggagcatat attcagactg gattaggttt accagtaaat    180

gaacaacaat taagaacaca tgttaattta agtcaggata tatcaatacc tagtgatttt    240

tctcaattat atgatgttta ttgttctgat aaaacttcag cagaatggtg gaataaaaat    300

ttatatcctt taattattaa atctgctaat gatattgctt catatggttt taaagttgct    360

ggtgatcctt ctattaagaa agatggatat tttaaaaaat tgcaagatga attagataat    420

attgttgata ataattccga tgatgatgca atagctaaag ctattaaaga ttttaaagcg    480

cgatgtggta ttttaattaa agaagctaaa caatatgaag aagctgcaaa aaatattgta    540

acatctttag atcaattttt acatggtgat cagaaaaaat tagaaggtgt tatcaatatt    600

caaaaacgtt taaaagaagt tcaaacagct cttaatcaag cccatgggga aagtagtcca    660

gctcataaag agttattaga aaaagtaaaa aatttaaaaa caacattaga aaggactatt    720

aaagctgaac aagatttaga gaaaaaagta gaatatagtt ttctattagg accattgtta    780

ggatttgttg tttatgaaat tcttgaaaat actgctgttc agcatataaa aaatcaaatt    840

gatgagataa agaaacaatt agattctgct cagcatgatt tggatagaga tgttaaaatt    900

ataggaatgt taaatagtat taatacagat attgataatt tatatagtca aggacaagaa    960

gcaattaaag ttttccaaaa gttacaaggt atttgggcta ctattggagc tcaaatagaa   1020

aatcttagaa caacgtcgtt acaagaagtt caagattctg atgatgctga tgagatacaa   1080

attgaacttg aggacgcttc tgatgcttgg ttagttgtgg ctcaagaagc tcgtgatttt   1140
```

```
acactaaatg cttattcaac taatagtaga caaaatttac cgattaatgt tatatcagat   1200

tcaaatcaat acagtaatcc aacaacaaat atgacatcaa atcaatatat gatttcacat   1260

gaatatacaa gtttaccaaa taattttatg ttatcaagaa atagtaattt agaatataaa   1320

tgtcctgaaa ataattttat gatatattgg tataataatt cggattggta taataattcg   1380

gattggtata ataattga                                                  1398


<210> SEQ ID NO 82
<211> LENGTH: 465
<212> TYPE: PRT
<213> ORGANISM: Artificial Sequence
<220> FEATURE:
<223> OTHER INFORMATION: translated from synthesized coding region

<400> SEQUENCE: 82

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
```

```
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Asn Gln Tyr Ser Asn Pro Thr Thr Asn Met Thr Ser Asn Gln Tyr
                405                 410                 415

Met Ile Ser His Glu Tyr Thr Ser Leu Pro Asn Asn Phe Met Leu Ser
            420                 425                 430

Arg Asn Ser Asn Leu Glu Tyr Lys Cys Pro Glu Asn Asn Phe Met Ile
        435                 440                 445

Tyr Trp Tyr Asn Asn Ser Asp Trp Tyr Asn Asn Ser Asp Trp Tyr Asn
    450                 455                 460

Asn
465
```

<210> SEQ ID NO 83
<211> LENGTH: 1398
<212> TYPE: DNA
<213> ORGANISM: Artificial Sequence
<220> FEATURE:
<223> OTHER INFORMATION: synthesized coding region

<400> SEQUENCE: 83

```
atgattattg attctaaaac aacattacca agacattctt taattcatac tataaaatta     60

aattctaata agaaatatgg tcctggtgat atgactaatg gaaatcaatt tattatttca    120

aaacaagaat gggctactat tggagcatat attcagactg gattaggttt accagtaaat    180

gaacaacaat taagaacaca tgttaattta agtcaggata tatcaatacc tagtgatttt    240

tctcaattat atgatgttta ttgttctgat aaaacttcag cagaatggtg gaataaaaat    300

ttatatcctt taattattaa atctgctaat gatattgctt catatggttt taaagttgct    360

ggtgatcctt ctattaagaa agatggatat tttaaaaaat tgcaagatga attagataat    420

attgttgata ataattccga tgatgatgca atagctaaag ctattaaaga ttttaaagcg    480

cgatgtggta ttttaattaa agaagctaaa caatatgaag aagctgcaaa aaatattgta    540

acatctttag atcaattttt acatggtgat cagaaaaaat tagaaggtgt tatcaatatt    600

caaaaacgtt taaaagaagt tcaaacagct cttaatcaag cccatgggga aagtagtcca    660

gctcataaag agttattaga aaaagtaaaa aatttaaaaa caacattaga aaggactatt    720

aaagctgaac aagatttaga gaaaaaagta gaatatagtt ttctattagg accattgtta    780

ggatttgttg tttatgaaat tcttgaaaat actgctgttc agcatataaa aaatcaaatt    840

gatgagataa agaaacaatt agattctgct cagcatgatt tggatagaga tgttaaaatt    900

ataggaatgt taaatagtat taatacagat attgataatt tatatagtca aggacaagaa    960

gcaattaaag ttttccaaaa gttacaaggt atttgggcta ctattggagc tcaaatagaa   1020

aatcttagaa caacgtcgtt acaagaagtt caagattctg atgatgctga tgagatacaa   1080

attgaacttg aggacgcttc tgatgcttgg ttagttgtgg ctcaagaagc tcgtgatttt   1140
```

```
acactaaatg cttattcaac taatagtaga caaaatttac cgattaatgt tatatcagat   1200

tcatgtaatt gttcaacaac aaatatgaca atgacatcaa atcaatatat gatttcacat   1260

gaatatacaa gtttaccaaa taattttatg ttatcaagaa atagtaattt agaatataaa   1320

tgtcctgaaa ataattttat gatatattgg tataataatt cggattggta taataattcg   1380

gattggtata ataattga                                                  1398


<210> SEQ ID NO 84
<211> LENGTH: 465
<212> TYPE: PRT
<213> ORGANISM: Artificial Sequence
<220> FEATURE:
<223> OTHER INFORMATION: translated from synthesized coding region

<400> SEQUENCE: 84

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
```

```
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Met Thr Ser Asn Gln Tyr
                405                 410                 415

Met Ile Ser His Glu Tyr Thr Ser Leu Pro Asn Asn Phe Met Leu Ser
            420                 425                 430

Arg Asn Ser Asn Leu Glu Tyr Lys Cys Pro Glu Asn Asn Phe Met Ile
        435                 440                 445

Tyr Trp Tyr Asn Asn Ser Asp Trp Tyr Asn Asn Ser Asp Trp Tyr Asn
    450                 455                 460

Asn
465
```

<210> SEQ ID NO 85
<211> LENGTH: 1398
<212> TYPE: DNA
<213> ORGANISM: Artificial Sequence
<220> FEATURE:
<223> OTHER INFORMATION: synthesized coding region

<400> SEQUENCE: 85

```
atgattattg attctaaaac aacattacca agacattctt taattcatac tataaaatta      60

aattctaata agaaatatgg tcctggtgat atgactaatg gaaatcaatt tattatttca     120

aaacaagaat gggctactat tggagcatat attcagactg gattaggttt accagtaaat     180

gaacaacaat taagaacaca tgttaattta agtcaggata tatcaatacc tagtgatttt     240

tctcaattat atgatgttta ttgttctgat aaaacttcag cagaatggtg gaataaaaat     300

ttatatcctt taattattaa atctgctaat gatattgctt catatggttt taaagttgct     360

ggtgatcctt ctattaagaa agatggatat tttaaaaaat tgcaagatga attagataat     420

attgttgata ataattccga tgatgatgca atagctaaag ctattaaaga ttttaaagcg     480

cgatgtggta ttttaattaa agaagctaaa caatatgaag aagctgcaaa aaatattgta     540

acatctttag atcaattttt acatggtgat cagaaaaaat tagaaggtgt tatcaatatt     600

caaaaacgtt taaaagaagt tcaaacagct cttaatcaag cccatgggga aagtagtcca     660

gctcataaag agttattaga aaaagtaaaa aatttaaaaa caacattaga aaggactatt     720

aaagctgaac aagatttaga gaaaaaagta gaatatagtt ttctattagg accattgtta     780

ggatttgttg tttatgaaat tcttgaaaat actgctgttc agcatataaa aaatcaaatt     840

gatgagataa agaaacaatt agattctgct cagcatgatt tggatagaga tgttaaaatt     900

ataggaatgt taaatagtat taatacagat attgataatt tatatagtca aggacaagaa     960

gcaattaaag ttttccaaaa gttacaaggt atttgggcta ctattggagc tcaaatagaa    1020

aatcttagaa caacgtcgtt acaagaagtt caagattctg atgatgctga tgagatacaa    1080

attgaacttg aggacgcttc tgatgcttgg ttagttgtgg ctcaagaagc tcgtgatttt    1140
```

```
acactaaatg cttattcaac taatagtaga caaaatttac cgattaatgt tatatcagat   1200

tcatgtaatt gttcaacaac aaatatgaca tcaaatcaat acagtaatcc aacaacaaat   1260

gaatatacaa gtttaccaaa taattttatg ttatcaagaa atagtaattt agaatataaa   1320

tgtcctgaaa ataattttat gatatattgg tataataatt cggattggta taataattcg   1380

gattggtata ataattga                                                 1398


<210> SEQ ID NO 86
<211> LENGTH: 465
<212> TYPE: PRT
<213> ORGANISM: Artificial Sequence
<220> FEATURE:
<223> OTHER INFORMATION: translated from synthesized coding region

<400> SEQUENCE: 86

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
```

```
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser Asn Gln Tyr Ser Asn
                405                 410                 415

Pro Thr Thr Asn Glu Tyr Thr Ser Leu Pro Asn Asn Phe Met Leu Ser
            420                 425                 430

Arg Asn Ser Asn Leu Glu Tyr Lys Cys Pro Glu Asn Asn Phe Met Ile
        435                 440                 445

Tyr Trp Tyr Asn Asn Ser Asp Trp Tyr Asn Asn Ser Asp Trp Tyr Asn
    450                 455                 460

Asn
465
```

<210> SEQ ID NO 87
<211> LENGTH: 1398
<212> TYPE: DNA
<213> ORGANISM: Artificial Sequence
<220> FEATURE:
<223> OTHER INFORMATION: synthesized coding region

<400> SEQUENCE: 87

```
atgattattg attctaaaac aacattacca agacattctt taattcatac tataaaatta     60

aattctaata agaaatatgg tcctggtgat atgactaatg gaaatcaatt tattatttca    120

aaacaagaat gggctactat tggagcatat attcagactg gattaggttt accagtaaat    180

gaacaacaat taagaacaca tgttaattta agtcaggata tatcaatacc tagtgatttt    240

tctcaattat atgatgttta ttgttctgat aaaacttcag cagaatggtg gaataaaaat    300

ttatatcctt taattattaa atctgctaat gatattgctt catatggttt taaagttgct    360

ggtgatcctt ctattaagaa agatggatat tttaaaaaat tgcaagatga attagataat    420

attgttgata ataattccga tgatgatgca atagctaaag ctattaaaga ttttaaagcg    480

cgatgtggta ttttaattaa agaagctaaa caatatgaag aagctgcaaa aaatattgta    540

acatctttag atcaattttt acatggtgat cagaaaaaat tagaaggtgt tatcaatatt    600

caaaaacgtt taaaagaagt tcaaacagct cttaatcaag cccatgggga aagtagtcca    660

gctcataaag agttattaga aaaagtaaaa aatttaaaaa caacattaga aaggactatt    720

aaagctgaac aagatttaga gaaaaaagta gaatatagtt ttctattagg accattgtta    780

ggatttgttg tttatgaaat tcttgaaaat actgctgttc agcatataaa aaatcaaatt    840

gatgagataa agaaacaatt agattctgct cagcatgatt tggatagaga tgttaaaatt    900

ataggaatgt taaatagtat taatacagat attgataatt tatatagtca aggacaagaa    960

gcaattaaag ttttccaaaa gttacaaggt atttgggcta ctattggagc tcaaatagaa   1020

aatcttagaa caacgtcgtt acaagaagtt caagattctg atgatgctga tgagatacaa   1080

attgaacttg aggacgcttc tgatgcttgg ttagttgtgg ctcaagaagc tcgtgatttt   1140
```

```
acactaaatg cttattcaac taatagtaga caaaatttac cgattaatgt tatatcagat   1200

tcatgtaatt gttcaacaac aaatatgaca tcaaatcaat acagtaatcc aacaacaaat   1260

atgacatcaa atcaatatat gatttcacat ttatcaagaa atagtaattt agaatataaa   1320

tgtcctgaaa ataattttat gatatattgg tataataatt cggattggta taataattcg   1380

gattggtata ataattga                                                 1398


<210> SEQ ID NO 88
<211> LENGTH: 465
<212> TYPE: PRT
<213> ORGANISM: Artificial Sequence
<220> FEATURE:
<223> OTHER INFORMATION: translated from synthesized coding region

<400> SEQUENCE: 88

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
```

```
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser Asn Gln Tyr Ser Asn
                405                 410                 415

Pro Thr Thr Asn Met Thr Ser Asn Gln Tyr Met Ile Ser His Leu Ser
            420                 425                 430

Arg Asn Ser Asn Leu Glu Tyr Lys Cys Pro Glu Asn Asn Phe Met Ile
        435                 440                 445

Tyr Trp Tyr Asn Asn Ser Asp Trp Tyr Asn Asn Ser Asp Trp Tyr Asn
    450                 455                 460

Asn
465
```

<210> SEQ ID NO 89
<211> LENGTH: 1383
<212> TYPE: DNA
<213> ORGANISM: Artificial Sequence
<220> FEATURE:
<223> OTHER INFORMATION: synthesized coding region

<400> SEQUENCE: 89

```
atgattattg attctaaaac aacattacca agacattctt taattcatac tataaaatta     60

aattctaata agaaatatgg tcctggtgat atgactaatg gaaatcaatt tattatttca    120

aaacaagaat gggctactat tggagcatat attcagactg gattaggttt accagtaaat    180

gaacaacaat taagaacaca tgttaattta agtcaggata tatcaatacc tagtgatttt    240

tctcaattat atgatgttta ttgttctgat aaaacttcag cagaatggtg gaataaaaat    300

ttatatcctt taattattaa atctgctaat gatattgctt catatggttt taaagttgct    360

ggtgatcctt ctattaagaa agatggatat tttaaaaaat tgcaagatga attagataat    420

attgttgata ataattccga tgatgatgca atagctaaag ctattaaaga ttttaaagcg    480

cgatgtggta ttttaattaa agaagctaaa caatatgaag aagctgcaaa aaatattgta    540

acatctttag atcaattttt acatggtgat cagaaaaaat tagaaggtgt tatcaatatt    600

caaaaacgtt taaaagaagt tcaaacagct cttaatcaag cccatgggga aagtagtcca    660

gctcataaag agttattaga aaaagtaaaa aatttaaaaa caacattaga aaggactatt    720

aaagctgaac aagatttaga gaaaaaagta gaatatagtt ttctattagg accattgtta    780

ggatttgttg tttatgaaat tcttgaaaat actgctgttc agcatataaa aaatcaaatt    840

gatgagataa agaaacaatt agattctgct cagcatgatt tggatagaga tgttaaaatt    900

ataggaatgt taaatagtat taatacagat attgataatt tatatagtca aggacaagaa    960

gcaattaaag ttttccaaaa gttacaaggt atttgggcta ctattggagc tcaaatagaa   1020

aatcttagaa caacgtcgtt acaagaagtt caagattctg atgatgctga tgagatacaa   1080

attgaacttg aggacgcttc tgatgcttgg ttagttgtgg ctcaagaagc tcgtgatttt   1140
```

```
acactaaatg cttattcaac taatagtaga acaacaaata tgacatcaaa tcaatacagt   1200

aatccaacaa caaatatgac atcaaatcaa tatatgattt cacatgaata tacaagttta   1260

ccaaataatt ttatgttatc aagaaatagt aatttagaat ataaatgtcc tgaaaataat   1320

tttatgatat attggtataa taattcggat tggtataata attcggattg gtataataat   1380

tga                                                                 1383
```

<210> SEQ ID NO 90
<211> LENGTH: 460
<212> TYPE: PRT
<213> ORGANISM: Artificial Sequence
<220> FEATURE:
<223> OTHER INFORMATION: translated from synthesized coding region

<400> SEQUENCE: 90

```
Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
```

```
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Thr Thr Asn Met Thr Ser Asn Gln Tyr Ser
385                 390                 395                 400

Asn Pro Thr Thr Asn Met Thr Ser Asn Gln Tyr Met Ile Ser His Glu
                405                 410                 415

Tyr Thr Ser Leu Pro Asn Asn Phe Met Leu Ser Arg Asn Ser Asn Leu
            420                 425                 430

Glu Tyr Lys Cys Pro Glu Asn Asn Phe Met Ile Tyr Trp Tyr Asn Asn
        435                 440                 445

Ser Asp Trp Tyr Asn Asn Ser Asp Trp Tyr Asn Asn
    450                 455                 460
```

```
<210> SEQ ID NO 91
<211> LENGTH: 1383
<212> TYPE: DNA
<213> ORGANISM: Artificial Sequence
<220> FEATURE:
<223> OTHER INFORMATION: synthesized coding region

<400> SEQUENCE: 91

atgattattg attctaaaac aacattacca agacattctt taattcatac tataaaatta      60

aattctaata agaaatatgg tcctggtgat atgactaatg gaaatcaatt tattatttca     120

aaacaagaat gggctactat tggagcatat attcagactg gattaggttt accagtaaat     180

gaacaacaat taagaacaca tgttaattta agtcaggata tatcaatacc tagtgatttt     240

tctcaattat atgatgttta ttgttctgat aaaacttcag cagaatggtg gaataaaaat     300

ttatatcctt taattattaa atctgctaat gatattgctt catatggttt taaagttgct     360

ggtgatcctt ctattaagaa agatggatat tttaaaaaat tgcaagatga attagataat     420

attgttgata ataattccga tgatgatgca atagctaaag ctattaaaga ttttaaagcg     480

cgatgtggta ttttaattaa agaagctaaa caatatgaag aagctgcaaa aaatattgta     540

acatctttag atcaattttt acatggtgat cagaaaaaat tagaaggtgt tatcaatatt     600

caaaaacgtt taaaagaagt tcaaacagct cttaatcaag cccatgggga aagtagtcca     660

gctcataaag agttattaga aaaagtaaaa aatttaaaaa caacattaga aaggactatt     720

aaagctgaac aagatttaga gaaaaaagta gaatatagtt ttctattagg accattgtta     780

ggatttgttg tttatgaaat tcttgaaaat actgctgttc agcatataaa aaatcaaatt     840

gatgagataa agaaacaatt agattctgct cagcatgatt tggatagaga tgttaaaatt     900

ataggaatgt taaatagtat taatacagat attgataatt tatatagtca aggacaagaa     960

gcaattaaag ttttccaaaa gttacaaggt atttgggcta ctattggagc tcaaatagaa    1020

aatcttagaa caacgtcgtt acaagaagtt caagattctg atgatgctga tgagatacaa    1080

attgaacttg aggacgcttc tgatgcttgg ttagttgtgg ctcaagaagc tcgtgatttt    1140

acactaaatg cttattcaac taatagtaga caaaatttac cgattaatgt tatatcagat    1200
```

```
tcatgtaatt gttcaatgac atcaaatcaa tatatgattt cacatgaata tacaagttta   1260

ccaaataatt ttatgttatc aagaaatagt aatttagaat ataaatgtcc tgaaaataat   1320

tttatgatat attggtataa taattcggat tggtataata attcggattg gtataataat   1380

tga                                                                 1383
```

<210> SEQ ID NO 92
<211> LENGTH: 460
<212> TYPE: PRT
<213> ORGANISM: Artificial Sequence
<220> FEATURE:
<223> OTHER INFORMATION: translated from synthesized coding region

<400> SEQUENCE: 92

```
Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
```

```
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Met Thr Ser Asn Gln Tyr Met Ile Ser His Glu
                405                 410                 415

Tyr Thr Ser Leu Pro Asn Asn Phe Met Leu Ser Arg Asn Ser Asn Leu
            420                 425                 430

Glu Tyr Lys Cys Pro Glu Asn Asn Phe Met Ile Tyr Trp Tyr Asn Asn
        435                 440                 445

Ser Asp Trp Tyr Asn Asn Ser Asp Trp Tyr Asn Asn
    450                 455                 460


<210> SEQ ID NO 93
<211> LENGTH: 1383
<212> TYPE: DNA
<213> ORGANISM: Artificial Sequence
<220> FEATURE:
<223> OTHER INFORMATION: synthesized coding region

<400> SEQUENCE: 93

atgattattg attctaaaac aacattacca agacattctt taattcatac tataaaatta     60

aattctaata agaaatatgg tcctggtgat atgactaatg gaaatcaatt tattatttca    120

aaacaagaat gggctactat tggagcatat attcagactg gattaggttt accagtaaat    180

gaacaacaat taagaacaca tgttaattta agtcaggata tatcaatacc tagtgatttt    240

tctcaattat atgatgttta ttgttctgat aaaacttcag cagaatggtg gaataaaaat    300

ttatatcctt taattattaa atctgctaat gatattgctt catatggttt taaagttgct    360

ggtgatcctt ctattaagaa agatggatat tttaaaaaat tgcaagatga attagataat    420

attgttgata ataattccga tgatgatgca atagctaaag ctattaaaga ttttaaagcg    480

cgatgtggta ttttaattaa agaagctaaa caatatgaag aagctgcaaa aaatattgta    540

acatctttag atcaattttt acatggtgat cagaaaaaat tagaaggtgt tatcaatatt    600

caaaaacgtt taaaagaagt tcaaacagct cttaatcaag cccatgggga aagtagtcca    660

gctcataaag agttattaga aaaagtaaaa aatttaaaaa caacattaga aaggactatt    720

aaagctgaac aagatttaga gaaaaaagta gaatatagtt ttctattagg accattgtta    780

ggatttgttg tttatgaaat tcttgaaaat actgctgttc agcatataaa aaatcaaatt    840

gatgagataa agaaacaatt agattctgct cagcatgatt tggatagaga tgttaaaatt    900

ataggaatgt taaatagtat taatacagat attgataatt tatatagtca aggacaagaa    960

gcaattaaag ttttccaaaa gttacaaggt atttgggcta ctattggagc tcaaatagaa   1020

aatcttagaa caacgtcgtt acaagaagtt caagattctg atgatgctga tgagatacaa   1080

attgaacttg aggacgcttc tgatgcttgg ttagttgtgg ctcaagaagc tcgtgatttt   1140

acactaaatg cttattcaac taatagtaga caaaatttac cgattaatgt tatatcagat   1200

tcatgtaatt gttcaacaac aaatatgaca tcaaatcaat acagtaatcc aacaacaaat   1260

ccaaataatt ttatgttatc aagaaatagt aatttagaat ataaatgtcc tgaaaataat   1320
```

```
tttatgatat attggtataa taattcggat tggtataata attcggattg gtataataat   1380

tga                                                                  1383


<210> SEQ ID NO 94
<211> LENGTH: 460
<212> TYPE: PRT
<213> ORGANISM: Artificial Sequence
<220> FEATURE:
<223> OTHER INFORMATION: translated from synthesized coding region

<400> SEQUENCE: 94

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
```

```
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser Asn Gln Tyr Ser Asn
                405                 410                 415

Pro Thr Thr Asn Pro Asn Asn Phe Met Leu Ser Arg Asn Ser Asn Leu
            420                 425                 430

Glu Tyr Lys Cys Pro Glu Asn Asn Phe Met Ile Tyr Trp Tyr Asn Asn
        435                 440                 445

Ser Asp Trp Tyr Asn Asn Ser Asp Trp Tyr Asn Asn
    450                 455                 460


<210> SEQ ID NO 95
<211> LENGTH: 1383
<212> TYPE: DNA
<213> ORGANISM: Artificial Sequence
<220> FEATURE:
<223> OTHER INFORMATION: synthesized coding region

<400> SEQUENCE: 95

atgattattg attctaaaac aacattacca agacattctt taattcatac tataaaatta      60

aattctaata agaaatatgg tcctggtgat atgactaatg gaaatcaatt tattatttca     120

aaacaagaat gggctactat tggagcatat attcagactg gattaggttt accagtaaat     180

gaacaacaat taagaacaca tgttaattta agtcaggata tatcaatacc tagtgatttt     240

tctcaattat atgatgttta ttgttctgat aaaacttcag cagaatggtg gaataaaaat     300

ttatatcctt taattattaa atctgctaat gatattgctt catatggttt taaagttgct     360

ggtgatcctt ctattaagaa agatggatat tttaaaaaat tgcaagatga attagataat     420

attgttgata ataattccga tgatgatgca atagctaaag ctattaaaga ttttaaagcg     480

cgatgtggta ttttaattaa agaagctaaa caatatgaag aagctgcaaa aaatattgta     540

acatctttag atcaattttt acatggtgat cagaaaaaat tagaaggtgt tatcaatatt     600

caaaaacgtt taaaagaagt tcaaacagct cttaatcaag cccatgggga aagtagtcca     660

gctcataaag agttattaga aaaagtaaaa aatttaaaaa caacattaga aaggactatt     720

aaagctgaac aagatttaga gaaaaaagta gaatatagtt ttctattagg accattgtta     780

ggatttgttg tttatgaaat tcttgaaaat actgctgttc agcatataaa aaatcaaatt     840

gatgagataa agaaacaatt agattctgct cagcatgatt tggatagaga tgttaaaatt     900

ataggaatgt taaatagtat taatacagat attgataatt tatatagtca aggacaagaa     960

gcaattaaag ttttccaaaa gttacaaggt atttgggcta ctattggagc tcaaatagaa    1020

aatcttagaa caacgtcgtt acaagaagtt caagattctg atgatgctga tgagatacaa    1080

attgaacttg aggacgcttc tgatgcttgg ttagttgtgg ctcaagaagc tcgtgatttt    1140

acactaaatg cttattcaac taatagtaga caaaatttac cgattaatgt tatatcagat    1200

tcatgtaatt gttcaacaac aaatatgaca tcaaatcaat acagtaatcc aacaacaaat    1260

atgacatcaa atcaatatat gattaatagt aatttagaat ataaatgtcc tgaaaataat    1320

tttatgatat attggtataa taattcggat tggtataata attcggattg gtataataat    1380
```

tga 1383

<210> SEQ ID NO 96
<211> LENGTH: 460
<212> TYPE: PRT
<213> ORGANISM: Artificial Sequence
<220> FEATURE:
<223> OTHER INFORMATION: translated from synthesized coding region

<400> SEQUENCE: 96

```
Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
```

```
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser Asn Gln Tyr Ser Asn
                405                 410                 415

Pro Thr Thr Asn Met Thr Ser Asn Gln Tyr Met Ile Asn Ser Asn Leu
            420                 425                 430

Glu Tyr Lys Cys Pro Glu Asn Asn Phe Met Ile Tyr Trp Tyr Asn Asn
        435                 440                 445

Ser Asp Trp Tyr Asn Asn Ser Asp Trp Tyr Asn Asn
    450                 455                 460


<210> SEQ ID NO 97
<211> LENGTH: 1368
<212> TYPE: DNA
<213> ORGANISM: Artificial Sequence
<220> FEATURE:
<223> OTHER INFORMATION: synthesized coding region

<400> SEQUENCE: 97

atgattattg attctaaaac aacattacca agacattctt taattcatac tataaaatta      60

aattctaata agaaatatgg tcctggtgat atgactaatg gaaatcaatt tattatttca     120

aaacaagaat gggctactat tggagcatat attcagactg gattaggttt accagtaaat     180

gaacaacaat taagaacaca tgttaattta agtcaggata tatcaatacc tagtgatttt     240

tctcaattat atgatgttta ttgttctgat aaaacttcag cagaatggtg gaataaaaat     300

ttatatcctt taattattaa atctgctaat gatattgctt catatggttt taaagttgct     360

ggtgatcctt ctattaagaa agatggatat tttaaaaaat tgcaagatga attagataat     420

attgttgata ataattccga tgatgatgca atagctaaag ctattaaaga ttttaaagcg     480

cgatgtggta ttttaattaa agaagctaaa caatatgaag aagctgcaaa aaatattgta     540

acatctttag atcaattttt acatggtgat cagaaaaaat tagaaggtgt tatcaatatt     600

caaaaacgtt taaaagaagt tcaaacagct cttaatcaag cccatgggga aagtagtcca     660

gctcataaag agttattaga aaaagtaaaa aatttaaaaa caacattaga aaggactatt     720

aaagctgaac aagatttaga gaaaaaagta gaatatagtt ttctattagg accattgtta     780

ggatttgttg tttatgaaat tcttgaaaat actgctgttc agcatataaa aaatcaaatt     840

gatgagataa agaaacaatt agattctgct cagcatgatt tggatagaga tgttaaaatt     900

ataggaatgt taaatagtat taatacagat attgataatt tatatagtca aggacaagaa     960

gcaattaaag ttttccaaaa gttacaaggt atttgggcta ctattggagc tcaaatagaa    1020

aatcttagaa caacgtcgtt acaagaagtt caagattctg atgatgctga tgagatacaa    1080

attgaacttg aggacgcttc tgatgcttgg ttagttgtgg ctcaagaagc tcgtgatttt    1140

acactaaatg cttattcaac taatagtaga tcaaatcaat acagtaatcc aacaacaaat    1200

atgacatcaa atcaatatat gatttcacat gaatatacaa gtttaccaaa taattttatg    1260

ttatcaagaa atagtaattt agaatataaa tgtcctgaaa ataattttat gatatattgg    1320

tataataatt cggattggta taataattcg gattggtata ataattga                 1368


<210> SEQ ID NO 98
<211> LENGTH: 455
```

```
<212> TYPE: PRT
<213> ORGANISM: Artificial Sequence
<220> FEATURE:
<223> OTHER INFORMATION: translated from synthesized coding region

<400> SEQUENCE: 98

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380
```

```
Tyr Ser Thr Asn Ser Arg Ser Asn Gln Tyr Ser Asn Pro Thr Thr Asn
385                 390                 395                 400

Met Thr Ser Asn Gln Tyr Met Ile Ser His Glu Tyr Thr Ser Leu Pro
                405                 410                 415

Asn Asn Phe Met Leu Ser Arg Asn Ser Asn Leu Glu Tyr Lys Cys Pro
            420                 425                 430

Glu Asn Asn Phe Met Ile Tyr Trp Tyr Asn Asn Ser Asp Trp Tyr Asn
        435                 440                 445

Asn Ser Asp Trp Tyr Asn Asn
    450                 455
```

```
<210> SEQ ID NO 99
<211> LENGTH: 1368
<212> TYPE: DNA
<213> ORGANISM: Artificial Sequence
<220> FEATURE:
<223> OTHER INFORMATION: synthesized coding region

<400> SEQUENCE: 99

atgattattg attctaaaac aacattacca agacattctt taattcatac tataaaatta     60

aattctaata agaaatatgg tcctggtgat atgactaatg gaaatcaatt tattatttca    120

aaacaagaat gggctactat tggagcatat attcagactg gattaggttt accagtaaat    180

gaacaacaat taagaacaca tgttaattta agtcaggata tatcaatacc tagtgatttt    240

tctcaattat atgatgttta ttgttctgat aaaacttcag cagaatggtg gaataaaaat    300

ttatatcctt taattattaa atctgctaat gatattgctt catatggttt taaagttgct    360

ggtgatcctt ctattaagaa agatggatat tttaaaaaat tgcaagatga attagataat    420

attgttgata ataattccga tgatgatgca atagctaaag ctattaaaga ttttaaagcg    480

cgatgtggta ttttaattaa agaagctaaa caatatgaag aagctgcaaa aaatattgta    540

acatctttag atcaattttt acatggtgat cagaaaaaat tagaaggtgt tatcaatatt    600

caaaaacgtt taaaagaagt tcaaacagct cttaatcaag cccatgggga aagtagtcca    660

gctcataaag agttattaga aaaagtaaaa aatttaaaaa caacattaga aaggactatt    720

aaagctgaac aagatttaga gaaaaaagta gaatatagtt ttctattagg accattgtta    780

ggatttgttg tttatgaaat tcttgaaaat actgctgttc agcatataaa aaatcaaatt    840

gatgagataa agaaacaatt agattctgct cagcatgatt tggatagaga tgttaaaatt    900

ataggaatgt taaatagtat taatacagat attgataatt tatatagtca aggacaagaa    960

gcaattaaag ttttccaaaa gttacaaggt atttgggcta ctattggagc tcaaatagaa   1020

aatcttagaa caacgtcgtt acaagaagtt caagattctg atgatgctga tgagatacaa   1080

attgaacttg aggacgcttc tgatgcttgg ttagttgtgg ctcaagaagc tcgtgatttt   1140

acactaaatg cttattcaac taatagtaga caaaatttac cgattaatgt tatatcagat   1200

tcatgtaatt gttcaacaac aaatatgaca gaatatacaa gtttaccaaa taattttatg   1260

ttatcaagaa atagtaattt agaatataaa tgtcctgaaa ataattttat gatatattgg   1320

tataataatt cggattggta taataattcg gattggtata ataattga                1368
```

```
<210> SEQ ID NO 100
<211> LENGTH: 455
<212> TYPE: PRT
<213> ORGANISM: Artificial Sequence
<220> FEATURE:
<223> OTHER INFORMATION: translated from synthesized coding region
```

```
<400> SEQUENCE: 100

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Glu Tyr Thr Ser Leu Pro
                405                 410                 415
```

```
Asn Asn Phe Met Leu Ser Arg Asn Ser Asn Leu Glu Tyr Lys Cys Pro
            420                 425                 430

Glu Asn Asn Phe Met Ile Tyr Trp Tyr Asn Asn Ser Asp Trp Tyr Asn
        435                 440                 445

Asn Ser Asp Trp Tyr Asn Asn
    450                 455


<210> SEQ ID NO 101
<211> LENGTH: 1368
<212> TYPE: DNA
<213> ORGANISM: Artificial Sequence
<220> FEATURE:
<223> OTHER INFORMATION: synthesized coding region

<400> SEQUENCE: 101

atgattattg attctaaaac aacattacca agacattctt taattcatac tataaaatta     60

aattctaata agaaatatgg tcctggtgat atgactaatg gaaatcaatt tattatttca    120

aaacaagaat gggctactat tggagcatat attcagactg gattaggttt accagtaaat    180

gaacaacaat taagaacaca tgttaattta agtcaggata tatcaatacc tagtgatttt    240

tctcaattat atgatgttta ttgttctgat aaaacttcag cagaatggtg gaataaaaat    300

ttatatcctt taattattaa atctgctaat gatattgctt catatggttt taaagttgct    360

ggtgatcctt ctattaagaa agatggatat tttaaaaaat tgcaagatga attagataat    420

attgttgata ataattccga tgatgatgca atagctaaag ctattaaaga ttttaaagcg    480

cgatgtggta ttttaattaa agaagctaaa caatatgaag aagctgcaaa aaatattgta    540

acatctttag atcaattttt acatggtgat cagaaaaaat tagaaggtgt tatcaatatt    600

caaaaacgtt taaaagaagt tcaaacagct cttaatcaag cccatgggga aagtagtcca    660

gctcataaag agttattaga aaaagtaaaa aatttaaaaa caacattaga aaggactatt    720

aaagctgaac aagatttaga gaaaaaagta gaatatagtt ttctattagg accattgtta    780

ggatttgttg tttatgaaat tcttgaaaat actgctgttc agcatataaa aaatcaaatt    840

gatgagataa agaaacaatt agattctgct cagcatgatt tggatagaga tgttaaaatt    900

ataggaatgt taaatagtat taatacagat attgataatt tatatagtca aggacaagaa    960

gcaattaaag ttttccaaaa gttacaaggt atttgggcta ctattggagc tcaaatagaa   1020

aatcttagaa caacgtcgtt acaagaagtt caagattctg atgatgctga tgagatacaa   1080

attgaacttg aggacgcttc tgatgcttgg ttagttgtgg ctcaagaagc tcgtgatttt   1140

acactaaatg cttattcaac taatagtaga caaaatttac cgattaatgt tatatcagat   1200

tcatgtaatt gttcaacaac aaatatgaca tcaaatcaat acagtaatcc aacaacaaat   1260

atgacatcaa atagtaattt agaatataaa tgtcctgaaa ataattttat gatatattgg   1320

tataataatt cggattggta taataattcg gattggtata ataattga                1368


<210> SEQ ID NO 102
<211> LENGTH: 455
<212> TYPE: PRT
<213> ORGANISM: Artificial Sequence
<220> FEATURE:
<223> OTHER INFORMATION: translated from synthesized coding region

<400> SEQUENCE: 102

Met Ile Ile Asp Ser Lys Thr Thr Leu Pro Arg His Ser Leu Ile His
1               5                   10                  15
```

```
Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser Asn Gln Tyr Ser Asn
                405                 410                 415

Pro Thr Thr Asn Met Thr Ser Asn Ser Asn Leu Glu Tyr Lys Cys Pro
            420                 425                 430

Glu Asn Asn Phe Met Ile Tyr Trp Tyr Asn Asn Ser Asp Trp Tyr Asn
```

```
        435                 440                 445

Asn Ser Asp Trp Tyr Asn Asn
    450                 455


<210> SEQ ID NO 103
<211> LENGTH: 1353
<212> TYPE: DNA
<213> ORGANISM: Artificial Sequence
<220> FEATURE:
<223> OTHER INFORMATION: synthesized coding region

<400> SEQUENCE: 103

atgattattg attctaaaac aacattacca agacattctt taattcatac tataaaatta     60

aattctaata agaaatatgg tcctggtgat atgactaatg gaaatcaatt tattatttca    120

aaacaagaat gggctactat tggagcatat attcagactg gattaggttt accagtaaat    180

gaacaacaat taagaacaca tgttaattta agtcaggata tatcaatacc tagtgatttt    240

tctcaattat atgatgttta ttgttctgat aaaacttcag cagaatggtg gaataaaaat    300

ttatatcctt taattattaa atctgctaat gatattgctt catatggttt taaagttgct    360

ggtgatcctt ctattaagaa agatggatat tttaaaaaat tgcaagatga attagataat    420

attgttgata ataattccga tgatgatgca atagctaaag ctattaaaga ttttaaagcg    480

cgatgtggta ttttaattaa agaagctaaa caatatgaag aagctgcaaa aaatattgta    540

acatctttag atcaattttt acatggtgat cagaaaaaat tagaaggtgt tatcaatatt    600

caaaaacgtt taaaagaagt tcaaacagct cttaatcaag cccatgggga aagtagtcca    660

gctcataaag agttattaga aaaagtaaaa aatttaaaaa caacattaga aaggactatt    720

aaagctgaac aagatttaga gaaaaaagta gaatatagtt ttctattagg accattgtta    780

ggatttgttg tttatgaaat tcttgaaaat actgctgttc agcatataaa aaatcaaatt    840

gatgagataa agaaacaatt agattctgct cagcatgatt tggatagaga tgttaaaatt    900

ataggaatgt taaatagtat taatacagat attgataatt tatatagtca aggacaagaa    960

gcaattaaag ttttccaaaa gttacaaggt atttgggcta ctattggagc tcaaatagaa   1020

aatcttagaa caacgtcgtt acaagaagtt caagattctg atgatgctga tgagatacaa   1080

attgaacttg aggacgcttc tgatgcttgg ttagttgtgg ctcaagaagc tcgtgatttt   1140

acactaaatg cttattcaac taatagtaga aatccaacaa caaatatgac atcaaatcaa   1200

tatatgattt cacatgaata tacaagttta ccaaataatt ttatgttatc aagaaatagt   1260

aatttagaat ataaatgtcc tgaaaataat tttatgatat attggtataa taattcggat   1320

tggtataata attcggattg gtataataat tga                                 1353


<210> SEQ ID NO 104
<211> LENGTH: 450
<212> TYPE: PRT
<213> ORGANISM: Artificial Sequence
<220> FEATURE:
<223> OTHER INFORMATION: translated from synthesized coding region

<400> SEQUENCE: 104

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45
```

```
Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Asn Pro Thr Thr Asn Met Thr Ser Asn Gln
385                 390                 395                 400

Tyr Met Ile Ser His Glu Tyr Thr Ser Leu Pro Asn Asn Phe Met Leu
                405                 410                 415

Ser Arg Asn Ser Asn Leu Glu Tyr Lys Cys Pro Glu Asn Asn Phe Met
            420                 425                 430

Ile Tyr Trp Tyr Asn Asn Ser Asp Trp Tyr Asn Asn Ser Asp Trp Tyr
        435                 440                 445

Asn Asn
    450
```

<210> SEQ ID NO 105
<211> LENGTH: 1353
<212> TYPE: DNA
<213> ORGANISM: Artificial Sequence
<220> FEATURE:
<223> OTHER INFORMATION: synthesized coding region

<400> SEQUENCE: 105

```
atgattattg attctaaaac aacattacca agacattctt taattcatac tataaaatta     60

aattctaata agaaatatgg tcctggtgat atgactaatg gaaatcaatt tattatttca    120

aaacaagaat gggctactat tggagcatat attcagactg gattaggttt accagtaaat    180

gaacaacaat taagaacaca tgttaattta agtcaggata tatcaatacc tagtgatttt    240

tctcaattat atgatgttta ttgttctgat aaaacttcag cagaatggtg gaataaaaat    300

ttatatcctt taattattaa atctgctaat gatattgctt catatggttt taaagttgct    360

ggtgatcctt ctattaagaa agatggatat tttaaaaaat tgcaagatga attagataat    420

attgttgata ataattccga tgatgatgca atagctaaag ctattaaaga ttttaaagcg    480

cgatgtggta ttttaattaa agaagctaaa caatatgaag aagctgcaaa aaatattgta    540

acatctttag atcaattttt acatggtgat cagaaaaaat tagaaggtgt tatcaatatt    600

caaaaacgtt taaaagaagt tcaaacagct cttaatcaag cccatgggga aagtagtcca    660

gctcataaag agttattaga aaaagtaaaa aatttaaaaa caacattaga aaggactatt    720

aaagctgaac aagatttaga gaaaaaagta gaatatagtt ttctattagg accattgtta    780

ggatttgttg tttatgaaat tcttgaaaat actgctgttc agcatataaa aaatcaaatt    840

gatgagataa agaaacaatt agattctgct cagcatgatt tggatagaga tgttaaaatt    900

ataggaatgt taaatagtat taatacagat attgataatt tatatagtca aggacaagaa    960

gcaattaaag ttttccaaaa gttacaaggt atttgggcta ctattggagc tcaaatagaa   1020

aatcttagaa caacgtcgtt acaagaagtt caagattctg atgatgctga tgagatacaa   1080

attgaacttg aggacgcttc tgatgcttgg ttagttgtgg ctcaagaagc tcgtgatttt   1140

acactaaatg cttattcaac taatagtaga caaaatttac cgattaatgt tatatcagat   1200

tcatgtaatt gttcaacaac aaatatgaca tcaaatcaat acagtttatc aagaaatagt   1260

aatttagaat ataaatgtcc tgaaaataat tttatgatat attggtataa taattcggat   1320

tggtataata attcggattg gtataataat tga                                1353
```

<210> SEQ ID NO 106
<211> LENGTH: 450
<212> TYPE: PRT
<213> ORGANISM: Artificial Sequence
<220> FEATURE:
<223> OTHER INFORMATION: translated from synthesized coding region

<400> SEQUENCE: 106

```
Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
```

```
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser Asn Gln Tyr Ser Leu
                405                 410                 415

Ser Arg Asn Ser Asn Leu Glu Tyr Lys Cys Pro Glu Asn Asn Phe Met
            420                 425                 430

Ile Tyr Trp Tyr Asn Asn Ser Asp Trp Tyr Asn Asn Ser Asp Trp Tyr
        435                 440                 445

Asn Asn
    450
```

<210> SEQ ID NO 107
<211> LENGTH: 1353
<212> TYPE: DNA
<213> ORGANISM: Artificial Sequence
<220> FEATURE:
<223> OTHER INFORMATION: synthesized coding region

<400> SEQUENCE: 107

```
atgattattg attctaaaac aacattacca agacattctt taattcatac tataaaatta     60

aattctaata agaaatatgg tcctggtgat atgactaatg gaaatcaatt tattatttca    120

aaacaagaat gggctactat tggagcatat attcagactg gattaggttt accagtaaat    180

gaacaacaat taagaacaca tgttaattta agtcaggata tatcaatacc tagtgatttt    240

tctcaattat atgatgttta ttgttctgat aaaacttcag cagaatggtg gaataaaaat    300

ttatatcctt taattattaa atctgctaat gatattgctt catatggttt taaagttgct    360

ggtgatcctt ctattaagaa agatggatat tttaaaaaat tgcaagatga attagataat    420

attgttgata ataattccga tgatgatgca atagctaaag ctattaaaga ttttaaagcg    480

cgatgtggta ttttaattaa agaagctaaa caatatgaag aagctgcaaa aaatattgta    540

acatctttag atcaattttt acatggtgat cagaaaaaat tagaaggtgt tatcaatatt    600

caaaaacgtt taaaagaagt tcaaacagct cttaatcaag cccatgggga aagtagtcca    660

gctcataaag agttattaga aaaagtaaaa aatttaaaaa caacattaga aaggactatt    720

aaagctgaac aagatttaga gaaaaaagta gaatatagtt ttctattagg accattgtta    780

ggatttgttg tttatgaaat tcttgaaaat actgctgttc agcatataaa aaatcaaatt    840

gatgagataa agaaacaatt agattctgct cagcatgatt tggatagaga tgttaaaatt    900

ataggaatgt taaatagtat taatacagat attgataatt tatatagtca aggacaagaa    960

gcaattaaag ttttccaaaa gttacaaggt atttgggcta ctattggagc tcaaatagaa   1020

aatcttagaa caacgtcgtt acaagaagtt caagattctg atgatgctga tgagatacaa   1080

attgaacttg aggacgcttc tgatgcttgg ttagttgtgg ctcaagaagc tcgtgatttt   1140

acactaaatg cttattcaac taatagtaga caaaatttac cgattaatgt tatatcagat   1200

tcatgtaatt gttcaacaac aaatatgaca tcaaatcaat acagtaatcc aacaaatagt   1260

aatttagaat ataaatgtcc tgaaaataat tttatgatat attggtataa taattcggat   1320

tggtataata attcggattg gtataataat tga                                1353
```

<210> SEQ ID NO 108
<211> LENGTH: 450
<212> TYPE: PRT
<213> ORGANISM: Artificial Sequence
<220> FEATURE:
<223> OTHER INFORMATION: translated from synthesized coding region

<400> SEQUENCE: 108

```
Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95
```

```
Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser Asn Gln Tyr Ser Asn
                405                 410                 415

Pro Thr Asn Ser Asn Leu Glu Tyr Lys Cys Pro Glu Asn Asn Phe Met
            420                 425                 430

Ile Tyr Trp Tyr Asn Asn Ser Asp Trp Tyr Asn Asn Ser Asp Trp Tyr
        435                 440                 445

Asn Asn
    450
```

<210> SEQ ID NO 109
<211> LENGTH: 1299
<212> TYPE: DNA
<213> ORGANISM: Artificial Sequence
<220> FEATURE:
<223> OTHER INFORMATION: synthesized coding region

<400> SEQUENCE: 109

```
atgattattg attctaaaac aacattacca agacattctt taattcatac tataaaatta      60

aattctaata agaaatatgg tcctggtgat atgactaatg gaaatcaatt tattatttca     120

aaacaagaat gggctactat tggagcatat attcagactg gattaggttt accagtaaat     180

gaacaacaat taagaacaca tgttaattta agtcaggata tatcaatacc tagtgatttt     240

tctcaattat atgatgttta ttgttctgat aaaacttcag cagaatggtg gaataaaaat     300

ttatatcctt taattattaa atctgctaat gatattgctt catatggttt taaagttgct     360

ggtgatcctt ctattaagaa agatggatat tttaaaaaat tgcaagatga attagataat     420

attgttgata ataattccga tgatgatgca atagctaaag ctattaaaga ttttaaagcg     480

cgatgtggta ttttaattaa agaagctaaa caatatgaag aagctgcaaa aaatattgta     540

acatctttag atcaattttt acatggtgat cagaaaaaat tagaaggtgt tatcaatatt     600

caaaaacgtt taaaagaagt tcaaacagct cttaatcaag cccatgggga aagtagtcca     660

gctcataaag agttattaga aaaagtaaaa aatttaaaaa caacattaga aaggactatt     720

aaagctgaac aagatttaga gaaaaaagta gaatatagtt ttctattagg accattgtta     780

ggatttgttg tttatgaaat tcttgaaaat actgctgttc agcatataaa aaatcaaatt     840

gatgagataa agaaacaatt agattctgct cagcatgatt tggatagaga tgttaaaatt     900

ataggaatgt taaatagtat taatacagat attgataatt tatatagtca aggacaagaa     960

gcaattaaag ttttccaaaa gttacaaggt atttgggcta ctattggagc tcaaatagaa    1020

aatcttagaa caacgtcgtt acaagaagtt caagattctg atgatgctga tgagatacaa    1080

attgaacttg aggacgcttc tgatgcttgg ttagttgtgg ctcaagaagc tcgtgatttt    1140

acactaaatg cttattcaac taatagtaga caaaatttac cgattaatgt tatatcagat    1200

aatagtaatt tagaatataa atgtcctgaa aataatttta tgatatattg gtataataat    1260

tcggattggt ataataattc ggattggtat aataattga                           1299
```

```
<210> SEQ ID NO 110
<211> LENGTH: 432
<212> TYPE: PRT
<213> ORGANISM: Artificial Sequence
<220> FEATURE:
<223> OTHER INFORMATION: translated from synthesized coding region

<400> SEQUENCE: 110

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
```

```
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Asn Ser Asn Leu Glu Tyr Lys Cys Pro Glu Asn Asn Phe Met Ile Tyr
                405                 410                 415

Trp Tyr Asn Asn Ser Asp Trp Tyr Asn Asn Ser Asp Trp Tyr Asn Asn
            420                 425                 430


<210> SEQ ID NO 111
<211> LENGTH: 1299
<212> TYPE: DNA
<213> ORGANISM: Artificial Sequence
<220> FEATURE:
<223> OTHER INFORMATION: synthesized coding region

<400> SEQUENCE: 111

atgattattg attctaaaac aacattacca agacattctt taattcatac tataaaatta      60

aattctaata agaaatatgg tcctggtgat atgactaatg gaaatcaatt tattatttca     120

aaacaagaat gggctactat tggagcatat attcagactg gattaggttt accagtaaat     180

gaacaacaat taagaacaca tgttaattta agtcaggata tatcaatacc tagtgatttt     240

tctcaattat atgatgttta ttgttctgat aaaacttcag cagaatggtg gaataaaaat     300

ttatatcctt taattattaa atctgctaat gatattgctt catatggttt taaagttgct     360

ggtgatcctt ctattaagaa agatggatat tttaaaaaat tgcaagatga attagataat     420
```

```
attgttgata ataattccga tgatgatgca atagctaaag ctattaaaga ttttaaagcg    480

cgatgtggta ttttaattaa agaagctaaa caatatgaag aagctgcaaa aaatattgta    540

acatctttag atcaattttt acatggtgat cagaaaaaat tagaaggtgt tatcaatatt    600

caaaaacgtt taaaagaagt tcaaacagct cttaatcaag cccatgggga aagtagtcca    660

gctcataaag agttattaga aaaagtaaaa aatttaaaaa caacattaga aaggactatt    720

aaagctgaac aagatttaga gaaaaaagta gaatatagtt ttctattagg accattgtta    780

ggatttgttg tttatgaaat tcttgaaaat actgctgttc agcatataaa aaatcaaatt    840

gatgagataa agaaacaatt agattctgct cagcatgatt tggatagaga tgttaaaatt    900

ataggaatgt taaatagtat taatacagat attgataatt tatatagtca aggacaagaa    960

gcaattaaag ttttccaaaa gttacaaggt atttgggcta ctattggagc tcaaatagaa   1020

aatcttagaa caacgtcgtt acaagaagtt caagattctg atgatgctga tgagatacaa   1080

attgaacttg aggacgcttc tgatgcttgg ttagttgtgg ctcaagaagc tcgtgatttt   1140

acactaaatg cttattcaac taatagtaga agtttaccaa ataattttat gttatcaaga   1200

aatagtaatt tagaatataa atgtcctgaa aataatttta tgatatattg gtataataat   1260

tcggattggt ataataattc ggattggtat aataattga                          1299
```

```
<210> SEQ ID NO 112
<211> LENGTH: 432
<212> TYPE: PRT
<213> ORGANISM: Artificial Sequence
<220> FEATURE:
<223> OTHER INFORMATION: translated from synthesized coding region

<400> SEQUENCE: 112

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205
```

```
Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Ser Leu Pro Asn Asn Phe Met Leu Ser Arg
385                 390                 395                 400

Asn Ser Asn Leu Glu Tyr Lys Cys Pro Glu Asn Asn Phe Met Ile Tyr
                405                 410                 415

Trp Tyr Asn Asn Ser Asp Trp Tyr Asn Asn Ser Asp Trp Tyr Asn Asn
            420                 425                 430
```

<210> SEQ ID NO 113
<211> LENGTH: 1299
<212> TYPE: DNA
<213> ORGANISM: Artificial Sequence
<220> FEATURE:
<223> OTHER INFORMATION: synthesized coding region

<400> SEQUENCE: 113

```
atgattattg attctaaaac aacattacca agacattctt taattcatac tataaaatta     60

aattctaata agaaatatgg tcctggtgat atgactaatg gaaatcaatt tattatttca    120

aaacaagaat gggctactat tggagcatat attcagactg gattaggttt accagtaaat    180

gaacaacaat taagaacaca tgttaattta agtcaggata tatcaatacc tagtgatttt    240

tctcaattat atgatgttta ttgttctgat aaaacttcag cagaatggtg gaataaaaat    300

ttatatcctt taattattaa atctgctaat gatattgctt catatggttt taaagttgct    360

ggtgatcctt ctattaagaa agatggatat tttaaaaaat tgcaagatga attagataat    420

attgttgata ataattccga tgatgatgca atagctaaag ctattaaaga ttttaaagcg    480

cgatgtggta ttttaattaa agaagctaaa caatatgaag aagctgcaaa aaatattgta    540

acatctttag atcaattttt acatggtgat cagaaaaaat tagaaggtgt tatcaatatt    600

caaaaacgtt taaaagaagt tcaaacagct cttaatcaag cccatgggga aagtagtcca    660

gctcataaag agttattaga aaaagtaaaa aatttaaaaa caacattaga aaggactatt    720

aaagctgaac aagatttaga gaaaaaagta gaatatagtt ttctattagg accattgtta    780
```

```
ggatttgttg tttatgaaat tcttgaaaat actgctgttc agcatataaa aaatcaaatt    840

gatgagataa agaaacaatt agattctgct cagcatgatt tggatagaga tgttaaaatt    900

ataggaatgt taaatagtat taatacagat attgataatt tatatagtca aggacaagaa    960

gcaattaaag ttttccaaaa gttacaaggt atttgggcta ctattggagc tcaaatagaa   1020

aatcttagaa caacgtcgtt acaagaagtt caagattctg atgatgctga tgagatacaa   1080

attgaacttg aggacgcttc tgatgcttgg ttagttgtgg ctcaagaagc tcgtgatttt   1140

acactaaatg cttattcaac taatagtaga agtaatccaa caacaaatat gacatcaaat   1200

aatagtaatt tagaatataa atgtcctgaa aataatttta tgatatattg gtataataat   1260

tcggattggt ataataattc ggattggtat aataattga                          1299
```

<210> SEQ ID NO 114
<211> LENGTH: 432
<212> TYPE: PRT
<213> ORGANISM: Artificial Sequence
<220> FEATURE:
<223> OTHER INFORMATION: translated from synthesized coding region

<400> SEQUENCE: 114

```
Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270
```

```
Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Ser Asn Pro Thr Thr Asn Met Thr Ser Asn
385                 390                 395                 400

Asn Ser Asn Leu Glu Tyr Lys Cys Pro Glu Asn Asn Phe Met Ile Tyr
                405                 410                 415

Trp Tyr Asn Asn Ser Asp Trp Tyr Asn Asn Ser Asp Trp Tyr Asn Asn
            420                 425                 430
```

<210> SEQ ID NO 115
<211> LENGTH: 1251
<212> TYPE: DNA
<213> ORGANISM: Artificial Sequence
<220> FEATURE:
<223> OTHER INFORMATION: synthesized coding region

<400> SEQUENCE: 115

```
atgattattg attctaaaac aacattacca agacattctt taattcatac tataaaatta     60

aattctaata agaaatatgg tcctggtgat atgactaatg gaaatcaatt tattatttca    120

aaacaagaat gggctactat tggagcatat attcagactg gattaggttt accagtaaat    180

gaacaacaat taagaacaca tgttaattta agtcaggata tatcaatacc tagtgatttt    240

tctcaattat atgatgttta ttgttctgat aaaacttcag cagaatggtg gaataaaaat    300

ttatatcctt taattattaa atctgctaat gatattgctt catatggttt taaagttgct    360

ggtgatcctt ctattaagaa agatggatat tttaaaaaat tgcaagatga attagataat    420

attgttgata ataattccga tgatgatgca atagctaaag ctattaaaga ttttaaagcg    480

cgatgtggta ttttaattaa agaagctaaa caatatgaag aagctgcaaa aaatattgta    540

acatctttag atcaattttt acatggtgat cagaaaaaat tagaaggtgt tatcaatatt    600

caaaaacgtt taaaagaagt tcaaacagct cttaatcaag cccatgggga aagtagtcca    660

gctcataaag agttattaga aaaagtaaaa aatttaaaaa caacattaga aaggactatt    720

aaagctgaac aagatttaga gaaaaaagta gaatatagtt ttctattagg accattgtta    780

ggatttgttg tttatgaaat tcttgaaaat actgctgttc agcatataaa aaatcaaatt    840

gatgagataa agaaacaatt agattctgct cagcatgatt tggatagaga tgttaaaatt    900

ataggaatgt taaatagtat taatacagat attgataatt tatatagtca aggacaagaa    960

gcaattaaag ttttccaaaa gttacaaggt atttgggcta ctattggagc tcaaatagaa   1020

aatcttagaa caacgtcgtt acaagaagtt caagattctg atgatgctga tgagatacaa   1080

attgaacttg aggacgcttc tgatgcttgg ttagttgtgg ctcaagaagc tcgtgatttt   1140

acactaaatg cttattcagt tgctacaatt acatctggtg aaaataattt tatgatatat   1200
```

```
tggtataata attcggattg gtataataat tcggattggt ataataattg a          1251


<210> SEQ ID NO 116
<211> LENGTH: 416
<212> TYPE: PRT
<213> ORGANISM: Artificial Sequence
<220> FEATURE:
<223> OTHER INFORMATION: translated from synthesized coding region

<400> SEQUENCE: 116

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350
```

```
Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Val Ala Thr Ile Thr Ser Gly Glu Asn Asn Phe Met Ile Tyr
385                 390                 395                 400

Trp Tyr Asn Asn Ser Asp Trp Tyr Asn Asn Ser Asp Trp Tyr Asn Asn
                405                 410                 415


<210> SEQ ID NO 117
<211> LENGTH: 1245
<212> TYPE: DNA
<213> ORGANISM: Artificial Sequence
<220> FEATURE:
<223> OTHER INFORMATION: synthesized coding region

<400> SEQUENCE: 117

atgattattg attctaaaac aacattacca agacattctt taattcatac tataaaatta      60

aattctaata agaaatatgg tcctggtgat atgactaatg gaaatcaatt tattatttca     120

aaacaagaat gggctactat tggagcatat attcagactg gattaggttt accagtaaat     180

gaacaacaat taagaacaca tgttaattta agtcaggata tatcaatacc tagtgatttt     240

tctcaattat atgatgttta ttgttctgat aaaacttcag cagaatggtg gaataaaaat     300

ttatatcctt taattattaa atctgctaat gatattgctt catatggttt taaagttgct     360

ggtgatcctt ctattaagaa agatggatat tttaaaaaat tgcaagatga attagataat     420

attgttgata ataattccga tgatgatgca atagctaaag ctattaaaga ttttaaagcg     480

cgatgtggta ttttaattaa agaagctaaa caatatgaag aagctgcaaa aaatattgta     540

acatctttag atcaattttt acatggtgat cagaaaaaat tagaaggtgt tatcaatatt     600

caaaaacgtt taaaagaagt tcaaacagct cttaatcaag cccatgggga aagtagtcca     660

gctcataaag agttattaga aaaagtaaaa aatttaaaaa caacattaga aaggactatt     720

aaagctgaac aagatttaga gaaaaaagta gaatatagtt ttctattagg accattgtta     780

ggatttgttg tttatgaaat tcttgaaaat actgctgttc agcatataaa aaatcaaatt     840

gatgagataa agaaacaatt agattctgct cagcatgatt tggatagaga tgttaaaatt     900

ataggaatgt taaatagtat taatacagat attgataatt tatatagtca aggacaagaa     960

gcaattaaag ttttccaaaa gttacaaggt atttgggcta ctattggagc tcaaatagaa    1020

aatcttagaa caacgtcgtt acaagaagtt caagattctg atgatgctga tgagatacaa    1080

attgaacttg aggacgcttc tgatgcttgg ttagttgtgg ctcaagaagc tcgtgatttt    1140

acactaaatg cttattcagt tgctacaatt acatctggtg aatttatgat atattggtat    1200

aataattcgg attggtataa taattcggat tggtataata attga                    1245


<210> SEQ ID NO 118
<211> LENGTH: 414
<212> TYPE: PRT
<213> ORGANISM: Artificial Sequence
<220> FEATURE:
<223> OTHER INFORMATION: translated from synthesized coding region

<400> SEQUENCE: 118

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30
```

```
Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Val Ala Thr Ile Thr Ser Gly Glu Phe Met Ile Tyr Trp Tyr
385                 390                 395                 400

Asn Asn Ser Asp Trp Tyr Asn Asn Ser Asp Trp Tyr Asn Asn
                405                 410
```

<210> SEQ ID NO 119
<211> LENGTH: 1245
<212> TYPE: DNA
<213> ORGANISM: Artificial Sequence
<220> FEATURE:

<223> OTHER INFORMATION: synthesized coding region

<400> SEQUENCE: 119

```
atgattattg attctaaaac aacattacca agacattctt taattcatac tataaaatta      60
aattctaata agaaatatgg tcctggtgat atgactaatg gaaatcaatt tattatttca     120
aaacaagaat gggctactat tggagcatat attcagactg gattaggttt accagtaaat     180
gaacaacaat taagaacaca tgttaattta agtcaggata tatcaatacc tagtgatttt     240
tctcaattat atgatgttta ttgttctgat aaaacttcag cagaatggtg gaataaaaat     300
ttatatcctt taattattaa atctgctaat gatattgctt catatggttt taaagttgct     360
ggtgatcctt ctattaagaa agatggatat tttaaaaaat tgcaagatga attagataat     420
attgttgata ataattccga tgatgatgca atagctaaag ctattaaaga ttttaaagcg     480
cgatgtggta ttttaattaa agaagctaaa caatatgaag aagctgcaaa aaatattgta     540
acatctttag atcaattttt acatggtgat cagaaaaaat tagaaggtgt tatcaatatt     600
caaaaacgtt taaaagaagt tcaaacagct cttaatcaag cccatgggga aagtagtcca     660
gctcataaag agttattaga aaaagtaaaa aatttaaaaa caacattaga aaggactatt     720
aaagctgaac aagatttaga gaaaaaagta gaatatagtt ttctattagg accattgtta     780
ggatttgttg tttatgaaat tcttgaaaat actgctgttc agcatataaa aaatcaaatt     840
gatgagataa agaaacaatt agattctgct cagcatgatt tggatagaga tgttaaaatt     900
ataggaatgt taaatagtat taatacagat attgataatt tatatagtca aggacaagaa     960
gcaattaaag ttttccaaaa gttacaaggt atttgggcta ctattggagc tcaaatagaa    1020
aatcttagaa caacgtcgtt acaagaagtt caagattctg atgatgctga tgagatacaa    1080
attgaacttg aggacgcttc tgatgcttgg ttagttgtgg ctcaagaagc tcgtgatttt    1140
acactaaatg cttatgctac aattacatct ggtgaaaata attttatgat atattggtat    1200
aataattcgg attggtataa taattcggat tggtataata attga                   1245
```

<210> SEQ ID NO 120
<211> LENGTH: 414
<212> TYPE: PRT
<213> ORGANISM: Artificial Sequence
<220> FEATURE:
<223> OTHER INFORMATION: translated from synthesized coding region

<400> SEQUENCE: 120

```
Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125
```

```
Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ala Thr Ile Thr Ser Gly Glu Asn Asn Phe Met Ile Tyr Trp Tyr
385                 390                 395                 400

Asn Asn Ser Asp Trp Tyr Asn Asn Ser Asp Trp Tyr Asn Asn
                405                 410


<210> SEQ ID NO 121
<211> LENGTH: 1233
<212> TYPE: DNA
<213> ORGANISM: Artificial Sequence
<220> FEATURE:
<223> OTHER INFORMATION: synthesized coding region

<400> SEQUENCE: 121

atgattattg attctaaaac aacattacca agacattctt taattcatac tataaaatta     60

aattctaata agaaatatgg tcctggtgat atgactaatg gaaatcaatt tattatttca    120

aaacaagaat gggctactat tggagcatat attcagactg gattaggttt accagtaaat    180

gaacaacaat taagaacaca tgttaattta agtcaggata tatcaatacc tagtgatttt    240

tctcaattat atgatgttta ttgttctgat aaaacttcag cagaatggtg gaataaaaat    300

ttatatcctt taattattaa atctgctaat gatattgctt catatggttt taaagttgct    360

ggtgatcctt ctattaagaa agatggatat tttaaaaaat tgcaagatga attagataat    420
```

```
attgttgata ataattccga tgatgatgca atagctaaag ctattaaaga ttttaaagcg    480

cgatgtggta ttttaattaa agaagctaaa caatatgaag aagctgcaaa aaatattgta    540

acatctttag atcaattttt acatggtgat cagaaaaaat tagaaggtgt tatcaatatt    600

caaaaacgtt taaaagaagt tcaaacagct cttaatcaag cccatgggga aagtagtcca    660

gctcataaag agttattaga aaaagtaaaa aatttaaaaa caacattaga aaggactatt    720

aaagctgaac aagatttaga gaaaaaagta gaatatagtt ttctattagg accattgtta    780

ggatttgttg tttatgaaat tcttgaaaat actgctgttc agcatataaa aaatcaaatt    840

gatgagataa agaaacaatt agattctgct cagcatgatt tggatagaga tgttaaaatt    900

ataggaatgt taaatagtat taatacagat attgataatt tatatagtca aggacaagaa    960

gcaattaaag ttttccaaaa gttacaaggt atttgggcta ctattggagc tcaaatagaa   1020

aatcttagaa caacgtcgtt acaagaagtt caagattctg atgatgctga tgagatacaa   1080

attgaacttg aggacgcttc tgatgcttgg ttagttgtgg ctcaagaagc tcgtgatttt   1140

acactaaatt gggttatata taatgaattt gttatgatat attggtataa taattcggat   1200

tggtataata attcggattg gtataataat tga                                 1233
```

```
<210> SEQ ID NO 122
<211> LENGTH: 410
<212> TYPE: PRT
<213> ORGANISM: Artificial Sequence
<220> FEATURE:
<223> OTHER INFORMATION: translated from synthesized coding region

<400> SEQUENCE: 122

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220
```

```
Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Trp
    370                 375                 380

Val Ile Tyr Asn Glu Phe Val Met Ile Tyr Trp Tyr Asn Asn Ser Asp
385                 390                 395                 400

Trp Tyr Asn Asn Ser Asp Trp Tyr Asn Asn
                405                 410
```

<210> SEQ ID NO 123
<211> LENGTH: 1251
<212> TYPE: DNA
<213> ORGANISM: Artificial Sequence
<220> FEATURE:
<223> OTHER INFORMATION: synthesized coding region

<400> SEQUENCE: 123

```
atgattattg attctaaaac aacattacca agacattctt taattcatac tataaaatta     60

aattctaata agaaatatgg tcctggtgat atgactaatg gaaatcaatt tattatttca    120

aaacaagaat gggctactat tggagcatat attcagactg gattaggttt accagtaaat    180

gaacaacaat taagaacaca tgttaattta agtcaggata tatcaatacc tagtgatttt    240

tctcaattat atgatgttta ttgttctgat aaaacttcag cagaatggtg gaataaaaat    300

ttatatcctt taattattaa atctgctaat gatattgctt catatggttt taaagttgct    360

ggtgatcctt ctattaagaa agatggatat tttaaaaaat tgcaagatga attagataat    420

attgttgata ataattccga tgatgatgca atagctaaag ctattaaaga ttttaaagcg    480

cgatgtggta ttttaattaa agaagctaaa caatatgaag aagctgcaaa aaatattgta    540

acatctttag atcaattttt acatggtgat cagaaaaaat tagaaggtgt tatcaatatt    600

caaaaacgtt taaaagaagt tcaaacagct cttaatcaag cccatgggga aagtagtcca    660

gctcataaag agttattaga aaaagtaaaa aatttaaaaa caacattaga aaggactatt    720

aaagctgaac aagatttaga gaaaaaagta gaatatagtt ttctattagg accattgtta    780

ggatttgttg tttatgaaat tcttgaaaat actgctgttc agcatataaa aaatcaaatt    840

gatgagataa agaaacaatt agattctgct cagcatgatt tggatagaga tgttaaaatt    900

ataggaatgt taaatagtat taatacagat attgataatt tatatagtca aggacaagaa    960
```

```
gcaattaaag ttttccaaaa gttacaaggt atttgggcta ctattggagc tcaaatagaa   1020

aatcttagaa caacgtcgtt acaagaagtt caagattctg atgatgctga tgagatacaa   1080

attgaacttg aggacgcttc tgatgcttgg ttagttgtgg ctcaagaagc tcgtgatttt   1140

acactaaatg cttattcatg ggttatatat aatgaatttg ttaataattt tatgatatat   1200

tggtataata attcggattg gtataataat tcggattggt ataataattg a            1251


<210> SEQ ID NO 124
<211> LENGTH: 416
<212> TYPE: PRT
<213> ORGANISM: Artificial Sequence
<220> FEATURE:
<223> OTHER INFORMATION: translated from synthesized coding region

<400> SEQUENCE: 124

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320
```

```
Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Trp Val Ile Tyr Asn Glu Phe Val Asn Asn Phe Met Ile Tyr
385                 390                 395                 400

Trp Tyr Asn Asn Ser Asp Trp Tyr Asn Asn Ser Asp Trp Tyr Asn Asn
                405                 410                 415


<210> SEQ ID NO 125
<211> LENGTH: 1239
<212> TYPE: DNA
<213> ORGANISM: Artificial Sequence
<220> FEATURE:
<223> OTHER INFORMATION: synthesized coding region

<400> SEQUENCE: 125

atgattattg attctaaaac aacattacca agacattctt taattcatac tataaaatta      60

aattctaata agaaatatgg tcctggtgat atgactaatg gaaatcaatt tattatttca     120

aaacaagaat gggctactat tggagcatat attcagactg gattaggttt accagtaaat     180

gaacaacaat taagaacaca tgttaattta agtcaggata tatcaatacc tagtgatttt     240

tctcaattat atgatgttta ttgttctgat aaaacttcag cagaatggtg gaataaaaat     300

ttatatcctt taattattaa atctgctaat gatattgctt catatggttt taaagttgct     360

ggtgatcctt ctattaagaa agatggatat tttaaaaaat tgcaagatga attagataat     420

attgttgata ataattccga tgatgatgca atagctaaag ctattaaaga ttttaaagcg     480

cgatgtggta ttttaattaa agaagctaaa caatatgaag aagctgcaaa aaatattgta     540

acatctttag atcaattttt acatggtgat cagaaaaaat tagaaggtgt tatcaatatt     600

caaaaacgtt taaaagaagt tcaaacagct cttaatcaag cccatgggga aagtagtcca     660

gctcataaag agttattaga aaaagtaaaa aatttaaaaa caacattaga aaggactatt     720

aaagctgaac aagatttaga gaaaaaagta gaatatagtt ttctattagg accattgtta     780

ggatttgttg tttatgaaat tcttgaaaat actgctgttc agcatataaa aaatcaaatt     840

gatgagataa agaaacaatt agattctgct cagcatgatt tggatagaga tgttaaaatt     900

ataggaatgt taaatagtat taatacagat attgataatt tatatagtca aggacaagaa     960

gcaattaaag ttttccaaaa gttacaaggt atttgggcta ctattggagc tcaaatagaa    1020

aatcttagaa caacgtcgtt acaagaagtt caagattctg atgatgctga tgagatacaa    1080

attgaacttg aggacgcttc tgatgcttgg ttagttgtgg ctcaagaagc tcgtgatttt    1140

acactaaatg gatgggttat atataatgaa tttgttggta tgatatattg gtataataat    1200

tcggattggt ataataattc ggattggtat aataattga                           1239


<210> SEQ ID NO 126
<211> LENGTH: 412
<212> TYPE: PRT
<213> ORGANISM: Artificial Sequence
<220> FEATURE:
<223> OTHER INFORMATION: translated from synthesized coding region
```

<400> SEQUENCE: 126

```
Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Gly
    370                 375                 380

Trp Val Ile Tyr Asn Glu Phe Val Gly Met Ile Tyr Trp Tyr Asn Asn
385                 390                 395                 400

Ser Asp Trp Tyr Asn Asn Ser Asp Trp Tyr Asn Asn
                405                 410
```

<210> SEQ ID NO 127
<211> LENGTH: 1251
<212> TYPE: DNA
<213> ORGANISM: Artificial Sequence
<220> FEATURE:
<223> OTHER INFORMATION: synthesized coding region

<400> SEQUENCE: 127

```
atgattattg attctaaaac aacattacca agacattctt taattcatac tataaaatta     60

aattctaata agaaatatgg tcctggtgat atgactaatg gaaatcaatt tattatttca    120

aaacaagaat gggctactat tggagcatat attcagactg gattaggttt accagtaaat    180

gaacaacaat taagaacaca tgttaattta agtcaggata tatcaatacc tagtgatttt    240

tctcaattat atgatgttta ttgttctgat aaaacttcag cagaatggtg gaataaaaat    300

ttatatcctt taattattaa atctgctaat gatattgctt catatggttt taaagttgct    360

ggtgatcctt ctattaagaa agatggatat tttaaaaaat tgcaagatga attagataat    420

attgttgata ataattccga tgatgatgca atagctaaag ctattaaaga ttttaaagcg    480

cgatgtggta ttttaattaa agaagctaaa caatatgaag aagctgcaaa aaatattgta    540

acatctttag atcaattttt acatggtgat cagaaaaaat tagaaggtgt tatcaatatt    600

caaaaacgtt taaaagaagt tcaaacagct cttaatcaag cccatgggga aagtagtcca    660

gctcataaag agttattaga aaaagtaaaa aatttaaaaa caacattaga aaggactatt    720

aaagctgaac aagatttaga gaaaaaagta gaatatagtt ttctattagg accattgtta    780

ggatttgttg tttatgaaat tcttgaaaat actgctgttc agcatataaa aaatcaaatt    840

gatgagataa agaaacaatt agattctgct cagcatgatt tggatagaga tgttaaaatt    900

ataggaatgt taaatagtat taatacagat attgataatt tatatagtca aggacaagaa    960

gcaattaaag ttttccaaaa gttacaaggt atttgggcta ctattggagc tcaaatagaa   1020

aatcttagaa caacgtcgtt acaagaagtt caagattctg atgatgctga tgagatacaa   1080

attgaacttg aggacgcttc tgatgcttgg ttagttgtgg ctcaagaagc tcgtgatttt   1140

acactaaatg cttatggatg ggttatatat aatgaatttg ttggtaattt tatgatatat   1200

tggtataata attcggattg gtataataat tcggattggt ataataattg a            1251
```

<210> SEQ ID NO 128
<211> LENGTH: 416
<212> TYPE: PRT
<213> ORGANISM: Artificial Sequence
<220> FEATURE:
<223> OTHER INFORMATION: translated from synthesized coding region

<400> SEQUENCE: 128

```
Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
```

```
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Gly Trp Val Ile Tyr Asn Glu Phe Val Gly Asn Phe Met Ile Tyr
385                 390                 395                 400

Trp Tyr Asn Asn Ser Asp Trp Tyr Asn Asn Ser Asp Trp Tyr Asn Asn
                405                 410                 415


<210> SEQ ID NO 129
<211> LENGTH: 1239
<212> TYPE: DNA
<213> ORGANISM: Artificial Sequence
<220> FEATURE:
<223> OTHER INFORMATION: synthesized coding region

<400> SEQUENCE: 129

atgattattg attctaaaac aacattacca agacattctt taattcatac tataaaatta      60

aattctaata agaaatatgg tcctggtgat atgactaatg gaaatcaatt tattatttca     120

aaacaagaat gggctactat tggagcatat attcagactg gattaggttt accagtaaat     180

gaacaacaat taagaacaca tgttaattta agtcaggata tatcaatacc tagtgatttt     240
```

```
tctcaattat atgatgttta ttgttctgat aaaacttcag cagaatggtg gaataaaaat    300

ttatatcctt taattattaa atctgctaat gatattgctt catatggttt taaagttgct    360

ggtgatcctt ctattaagaa agatggatat tttaaaaaat tgcaagatga attagataat    420

attgttgata ataattccga tgatgatgca atagctaaag ctattaaaga ttttaaagcg    480

cgatgtggta ttttaattaa agaagctaaa caatatgaag aagctgcaaa aaatattgta    540

acatctttag atcaattttt acatggtgat cagaaaaaat tagaaggtgt tatcaatatt    600

caaaaacgtt taaaagaagt tcaaacagct cttaatcaag cccatgggga aagtagtcca    660

gctcataaag agttattaga aaaagtaaaa aatttaaaaa caacattaga aaggactatt    720

aaagctgaac aagatttaga gaaaaaagta gaatatagtt ttctattagg accattgtta    780

ggatttgttg tttatgaaat tcttgaaaat actgctgttc agcatataaa aaatcaaatt    840

gatgagataa agaaacaatt agattctgct cagcatgatt tggatagaga tgttaaaatt    900

ataggaatgt taaatagtat taatacagat attgataatt tatatagtca aggacaagaa    960

gcaattaaag ttttccaaaa gttacaaggt atttgggcta ctattggagc tcaaatagaa   1020

aatcttagaa caacgtcgtt acaagaagtt caagattctg atgatgctga tgagatacaa   1080

attgaacttg aggacgcttc tgatgcttgg ttagttgtgg ctcaagaagc tcgtgatttt   1140

acactaaatg gagattctag tattaaaaaa gatggtttta tgatatattg gtataataat   1200

tcggattggt ataataattc ggattggtat aataattga                          1239
```

<210> SEQ ID NO 130
<211> LENGTH: 412
<212> TYPE: PRT
<213> ORGANISM: Artificial Sequence
<220> FEATURE:
<223> OTHER INFORMATION: translated from synthesized coding region

<400> SEQUENCE: 130

```
Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
```

```
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Gly
    370                 375                 380

Asp Ser Ser Ile Lys Lys Asp Gly Phe Met Ile Tyr Trp Tyr Asn Asn
385                 390                 395                 400

Ser Asp Trp Tyr Asn Asn Ser Asp Trp Tyr Asn Asn
                405                 410
```

<210> SEQ ID NO 131
<211> LENGTH: 1251
<212> TYPE: DNA
<213> ORGANISM: Artificial Sequence
<220> FEATURE:
<223> OTHER INFORMATION: synthesized coding region

<400> SEQUENCE: 131

```
atgattattg attctaaaac aacattacca agacattctt taattcatac tataaaatta     60

aattctaata agaaatatgg tcctggtgat atgactaatg gaaatcaatt tattatttca    120

aaacaagaat gggctactat tggagcatat attcagactg gattaggttt accagtaaat    180

gaacaacaat taagaacaca tgttaattta agtcaggata tatcaatacc tagtgatttt    240

tctcaattat atgatgttta ttgttctgat aaaacttcag cagaatggtg gaataaaaat    300

ttatatcctt taattattaa atctgctaat gatattgctt catatggttt taaagttgct    360

ggtgatcctt ctattaagaa agatggatat tttaaaaaat tgcaagatga attagataat    420

attgttgata ataattccga tgatgatgca atagctaaag ctattaaaga ttttaaagcg    480

cgatgtggta ttttaattaa agaagctaaa caatatgaag aagctgcaaa aaatattgta    540

acatctttag atcaattttt acatggtgat cagaaaaaat tagaaggtgt tatcaatatt    600

caaaaacgtt taaaagaagt tcaaacagct cttaatcaag cccatgggga aagtagtcca    660

gctcataaag agttattaga aaaagtaaaa aatttaaaaa caacattaga aaggactatt    720

aaagctgaac aagatttaga gaaaaaagta gaatatagtt ttctattagg accattgtta    780
```

```
ggatttgttg tttatgaaat tcttgaaaat actgctgttc agcatataaa aaatcaaatt    840

gatgagataa agaaacaatt agattctgct cagcatgatt tggatagaga tgttaaaatt    900

ataggaatgt taaatagtat taatacagat attgataatt tatatagtca aggacaagaa    960

gcaattaaag ttttccaaaa gttacaaggt atttgggcta ctattggagc tcaaatagaa   1020

aatcttagaa caacgtcgtt acaagaagtt caagattctg atgatgctga tgagatacaa   1080

attgaacttg aggacgcttc tgatgcttgg ttagttgtgg ctcaagaagc tcgtgatttt   1140

acactaaatg cttatggaga ttctagtatt aaaaaagatg gtaataattt tatgatatat   1200

tggtataata attcggattg gtataataat tcggattggt ataataattg a            1251
```

```
<210> SEQ ID NO 132
<211> LENGTH: 416
<212> TYPE: PRT
<213> ORGANISM: Artificial Sequence
<220> FEATURE:
<223> OTHER INFORMATION: translated from synthesized coding region

<400> SEQUENCE: 132

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
```

```
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Gly Asp Ser Ser Ile Lys Lys Asp Gly Asn Asn Phe Met Ile Tyr
385                 390                 395                 400

Trp Tyr Asn Asn Ser Asp Trp Tyr Asn Asn Ser Asp Trp Tyr Asn Asn
                405                 410                 415


<210> SEQ ID NO 133
<211> LENGTH: 1239
<212> TYPE: DNA
<213> ORGANISM: Artificial Sequence
<220> FEATURE:
<223> OTHER INFORMATION: synthesized coding region

<400> SEQUENCE: 133

atgattattg attctaaaac aacattacca agacattctt taattcatac tataaaatta      60

aattctaata agaaatatgg tcctggtgat atgactaatg gaaatcaatt tattatttca     120

aaacaagaat gggctactat tggagcatat attcagactg gattaggttt accagtaaat     180

gaacaacaat taagaacaca tgttaattta agtcaggata tatcaatacc tagtgatttt     240

tctcaattat atgatgttta ttgttctgat aaaacttcag cagaatggtg gaataaaaat     300

ttatatcctt taattattaa atctgctaat gatattgctt catatggttt taaagttgct     360

ggtgatcctt ctattaagaa agatggatat tttaaaaaat tgcaagatga attagataat     420

attgttgata ataattccga tgatgatgca atagctaaag ctattaaaga ttttaaagcg     480

cgatgtggta ttttaattaa agaagctaaa caatatgaag aagctgcaaa aaatattgta     540

acatctttag atcaattttt acatggtgat cagaaaaaat tagaaggtgt tatcaatatt     600

caaaaacgtt taaaagaagt tcaaacagct cttaatcaag cccatgggga aagtagtcca     660

gctcataaag agttattaga aaaagtaaaa aatttaaaaa caacattaga aaggactatt     720

aaagctgaac aagatttaga gaaaaaagta gaatatagtt ttctattagg accattgtta     780

ggatttgttg tttatgaaat tcttgaaaat actgctgttc agcatataaa aaatcaaatt     840

gatgagataa agaaacaatt agattctgct cagcatgatt tggatagaga tgttaaaatt     900

ataggaatgt taaatagtat taatacagat attgataatt tatatagtca aggacaagaa     960

gcaattaaag ttttccaaaa gttacaaggt atttgggcta ctattggagc tcaaatagaa    1020

aatcttagaa caacgtcgtt acaagaagtt caagattctg atgatgctga tgagatacaa    1080

attgaacttg aggacgcttc tgatgcttgg ttagttgtgg ctcaagaagc tcgtgatttt    1140

acactaaatg gagatcctag tattaaaaaa gatggtttta tgatatattg gtataataat    1200

tcggattggt ataataattc ggattggtat aataattga                            1239
```

```
<210> SEQ ID NO 134
<211> LENGTH: 412
<212> TYPE: PRT
<213> ORGANISM: Artificial Sequence
<220> FEATURE:
<223> OTHER INFORMATION: translated from synthesized coding region

<400> SEQUENCE: 134

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Gly
```

```
    370                 375                 380

Asp Pro Ser Ile Lys Lys Asp Gly Phe Met Ile Tyr Trp Tyr Asn Asn
385                 390                 395                 400

Ser Asp Trp Tyr Asn Asn Ser Asp Trp Tyr Asn Asn
                405                 410
```

<210> SEQ ID NO 135
<211> LENGTH: 1251
<212> TYPE: DNA
<213> ORGANISM: Artificial Sequence
<220> FEATURE:
<223> OTHER INFORMATION: synthesized coding region

<400> SEQUENCE: 135

```
atgattattg attctaaaac aacattacca agacattctt taattcatac tataaaatta      60

aattctaata agaaatatgg tcctggtgat atgactaatg gaaatcaatt tattatttca     120

aaacaagaat gggctactat tggagcatat attcagactg gattaggttt accagtaaat     180

gaacaacaat taagaacaca tgttaattta agtcaggata tatcaatacc tagtgatttt     240

tctcaattat atgatgttta ttgttctgat aaaacttcag cagaatggtg gaataaaaat     300

ttatatcctt taattattaa atctgctaat gatattgctt catatggttt taaagttgct     360

ggtgatcctt ctattaagaa agatggatat tttaaaaaat tgcaagatga attagataat     420

attgttgata ataattccga tgatgatgca atagctaaag ctattaaaga ttttaaagcg     480

cgatgtggta ttttaattaa agaagctaaa caatatgaag aagctgcaaa aaatattgta     540

acatctttag atcaattttt acatggtgat cagaaaaaat tagaaggtgt tatcaatatt     600

caaaaacgtt taaaagaagt tcaaacagct cttaatcaag cccatgggga aagtagtcca     660

gctcataaag agttattaga aaaagtaaaa aatttaaaaa caacattaga aaggactatt     720

aaagctgaac aagatttaga gaaaaaagta gaatatagtt ttctattagg accattgtta     780

ggatttgttg tttatgaaat tcttgaaaat actgctgttc agcatataaa aaatcaaatt     840

gatgagataa agaaacaatt agattctgct cagcatgatt tggatagaga tgttaaaatt     900

ataggaatgt taaatagtat taatacagat attgataatt tatatagtca aggacaagaa     960

gcaattaaag ttttccaaaa gttacaaggt atttgggcta ctattggagc tcaaatagaa    1020

aatcttagaa caacgtcgtt acaagaagtt caagattctg atgatgctga tgagatacaa    1080

attgaacttg aggacgcttc tgatgcttgg ttagttgtgg ctcaagaagc tcgtgatttt    1140

acactaaatg cttatggaga tcctagtatt aaaaaagatg gtaataattt tatgatatat    1200

tggtataata attcggattg gtataataat tcggattggt ataataattg a             1251
```

<210> SEQ ID NO 136
<211> LENGTH: 416
<212> TYPE: PRT
<213> ORGANISM: Artificial Sequence
<220> FEATURE:
<223> OTHER INFORMATION: translated from synthesized coding region

<400> SEQUENCE: 136

```
Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45
```

```
Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Gly Asp Pro Ser Ile Lys Lys Asp Gly Asn Asn Phe Met Ile Tyr
385                 390                 395                 400

Trp Tyr Asn Asn Ser Asp Trp Tyr Asn Asn Ser Asp Trp Tyr Asn Asn
                405                 410                 415
```

<210> SEQ ID NO 137
<211> LENGTH: 1251
<212> TYPE: DNA
<213> ORGANISM: Artificial Sequence
<220> FEATURE:
<223> OTHER INFORMATION: synthesized maize optimized coding region

<400> SEQUENCE: 137

```
atgatcattg actccaagac caccctgccg cgtcacagcc tgatccacac catcaagctg      60
aactccaaca agaagtacgg acctggcgac atgaccaacg gcaaccagtt catcatctcc     120
aagcaagagt gggccaccat cggagcgtac atccagaccg gcctgggcct gccggtgaac     180
gagcagcagc tgaggactca cgtgaacctg tcccaagaca tcagcatccc gtccgacttc     240
tcccagctgt acgacgtgta ttgcagcgac aagacctccg ccgagtggtg gaacaagaac     300
ctgtacccgc tgatcatcaa gagcgccaac gacatcgcct cctacggctt caaggtggcg     360
ggcgacccga gcatcaagaa ggacggctac ttcaagaagc tccaagacga gctggacaac     420
atcgtggaca acaactccga cgacgacgcc atcgccaagg cgatcaagga cttcaaggcg     480
aggtgcggca tcctgatcaa ggaggcgaag cagtacgagg aggcggcgaa gaacatcgtg     540
acctccctgg accagttcct gcacggcgac cagaagaagc tggagggcgt gatcaacatc     600
cagaagaggc tgaaggaggt gcagaccgcc ctgaatcaag cccacggcga gagcagcccg     660
gcgcacaagg agctgctgga gaaggtgaag aacctcaaga ccaccctgga gaggaccatc     720
aaggccgagc aagacctgga gaagaaggtg gagtactcct tcctgctggg tccgctgctg     780
ggcttcgtgg tgtacgagat cctggagaac accgccgtgc agcacatcaa gaatcagatc     840
gacgagatca agaagcagct ggactccgcc cagcacgacc tggaccgcga cgtgaagatc     900
atcgggatgc tgaacagcat caacaccgac atcgacaacc tgtacagcca aggccaagag     960
gccatcaagg tgttccagaa gctccaaggc atctgggcga ccatcggcgc gcagatcgag    1020
aacctgagga ccaccagcct ccaagaggtc caagacagcg acgacgccga cgagatccag    1080
atcgagctgg aggacgccag cgacgcgtgg ctggtggtgg ctcaagaggc gagggacttc    1140
accctgaacg cgtacagcgt ggccaccatc accagcggcg agaacaactt catgatctac    1200
tggtacaaca actccgactg gtacaacaac tcagactggt acaacaactg a             1251
```

```
<210> SEQ ID NO 138
<211> LENGTH: 416
<212> TYPE: PRT
<213> ORGANISM: Artificial Sequence
<220> FEATURE:
<223> OTHER INFORMATION: translated from synthesized maize optimized
      coding region

<400> SEQUENCE: 138

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140
```

```
Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Val Ala Thr Ile Thr Ser Gly Glu Asn Asn Phe Met Ile Tyr
385                 390                 395                 400

Trp Tyr Asn Asn Ser Asp Trp Tyr Asn Asn Ser Asp Trp Tyr Asn Asn
                405                 410                 415
```

<210> SEQ ID NO 139
<211> LENGTH: 1449
<212> TYPE: DNA
<213> ORGANISM: Artificial Sequence
<220> FEATURE:
<223> OTHER INFORMATION: synthesized maize optimized coding region

<400> SEQUENCE: 139

```
atggctcaat ctagcagaat ctgccacggt gtgcagaacc catgtgtgat catttccaat     60

ctctccaaat ccaaccagaa caaatctcct ttctcagtca gcctcaagac tcaccagcag    120

cagcgtcgtg cttaccagat atctagctgg ggattgaaga agtcaaacaa cgggtccgtg    180

attcgtccgg ttaaggcaat gatcattgac tccaagacca ccctgccgcg tcacagcctg    240

atccacacca tcaagctgaa ctccaacaag aagtacggac ctggcgacat gaccaacggc    300

aaccagttca tcatctccaa gcaagagtgg gccaccatcg gagcgtacat ccagaccggc    360

ctgggcctgc cggtgaacga gcagcagctg aggactcacg tgaacctgtc ccaagacatc    420

agcatcccgt ccgacttctc ccagctgtac gacgtgtatt gcagcgacaa gacctccgcc    480

gagtggtgga acaagaacct gtacccgctg atcatcaaga gcgccaacga catcgcctcc    540
```

```
tacggcttca aggtggcggg cgacccgagc atcaagaagg acggctactt caagaagctc    600

caagacgagc tggacaacat cgtggacaac aactccgacg acgacgccat cgccaaggcg    660

atcaaggact tcaaggcgag gtgcggcatc ctgatcaagg aggcgaagca gtacgaggag    720

gcggcgaaga acatcgtgac ctccctggac cagttcctgc acggcgacca gaagaagctg    780

gagggcgtga tcaacatcca gaagaggctg aaggaggtgc agaccgccct gaatcaagcc    840

cacggcgaga gcagcccggc gcacaaggag ctgctggaga aggtgaagaa cctcaagacc    900

accctggaga ggaccatcaa ggccgagcaa gacctggaga agaaggtgga gtactccttc    960

ctgctgggtc cgctgctggg cttcgtggtg tacgagatcc tggagaacac cgccgtgcag   1020

cacatcaaga atcagatcga cgagatcaag aagcagctgg actccgccca gcacgacctg   1080

gaccgcgacg tgaagatcat cgggatgctg aacagcatca acaccgacat cgacaacctg   1140

tacagccaag gccaagaggc catcaaggtg ttccagaagc tccaaggcat ctgggcgacc   1200

atcggcgcgc agatcgagaa cctgaggacc accagcctcc aagaggtcca agacagcgac   1260

gacgccgacg agatccagat cgagctggag gacgccagcg acgcgtggct ggtggtggct   1320

caagaggcga gggacttcac cctgaacgcg tacagcgtgg ccaccatcac cagcggcgag   1380

aacaacttca tgatctactg gtacaacaac tccgactggt acaacaactc agactggtac   1440

aacaactga                                                           1449
```

<210> SEQ ID NO 140
<211> LENGTH: 482
<212> TYPE: PRT
<213> ORGANISM: Artificial Sequence
<220> FEATURE:
<223> OTHER INFORMATION: translated from synthesized maize optimized coding region

<400> SEQUENCE: 140

```
Met Ala Gln Ser Ser Arg Ile Cys His Gly Val Gln Asn Pro Cys Val
1               5                   10                  15

Ile Ile Ser Asn Leu Ser Lys Ser Asn Gln Asn Lys Ser Pro Phe Ser
            20                  25                  30

Val Ser Leu Lys Thr His Gln Gln Gln Arg Arg Ala Tyr Gln Ile Ser
        35                  40                  45

Ser Trp Gly Leu Lys Lys Ser Asn Asn Gly Ser Val Ile Arg Pro Val
    50                  55                  60

Lys Ala Met Ile Ile Asp Ser Lys Thr Thr Leu Pro Arg His Ser Leu
65                  70                  75                  80

Ile His Thr Ile Lys Leu Asn Ser Asn Lys Lys Tyr Gly Pro Gly Asp
                85                  90                  95

Met Thr Asn Gly Asn Gln Phe Ile Ile Ser Lys Gln Glu Trp Ala Thr
            100                 105                 110

Ile Gly Ala Tyr Ile Gln Thr Gly Leu Gly Leu Pro Val Asn Glu Gln
        115                 120                 125

Gln Leu Arg Thr His Val Asn Leu Ser Gln Asp Ile Ser Ile Pro Ser
    130                 135                 140

Asp Phe Ser Gln Leu Tyr Asp Val Tyr Cys Ser Asp Lys Thr Ser Ala
145                 150                 155                 160

Glu Trp Trp Asn Lys Asn Leu Tyr Pro Leu Ile Ile Lys Ser Ala Asn
                165                 170                 175

Asp Ile Ala Ser Tyr Gly Phe Lys Val Ala Gly Asp Pro Ser Ile Lys
            180                 185                 190
```

```
Lys Asp Gly Tyr Phe Lys Lys Leu Gln Asp Glu Leu Asp Asn Ile Val
        195                 200                 205

Asp Asn Asn Ser Asp Asp Asp Ala Ile Ala Lys Ala Ile Lys Asp Phe
    210                 215                 220

Lys Ala Arg Cys Gly Ile Leu Ile Lys Glu Ala Lys Gln Tyr Glu Glu
225                 230                 235                 240

Ala Ala Lys Asn Ile Val Thr Ser Leu Asp Gln Phe Leu His Gly Asp
                245                 250                 255

Gln Lys Lys Leu Glu Gly Val Ile Asn Ile Gln Lys Arg Leu Lys Glu
            260                 265                 270

Val Gln Thr Ala Leu Asn Gln Ala His Gly Glu Ser Ser Pro Ala His
        275                 280                 285

Lys Glu Leu Leu Glu Lys Val Lys Asn Leu Lys Thr Thr Leu Glu Arg
    290                 295                 300

Thr Ile Lys Ala Glu Gln Asp Leu Glu Lys Lys Val Glu Tyr Ser Phe
305                 310                 315                 320

Leu Leu Gly Pro Leu Leu Gly Phe Val Val Tyr Glu Ile Leu Glu Asn
                325                 330                 335

Thr Ala Val Gln His Ile Lys Asn Gln Ile Asp Glu Ile Lys Lys Gln
            340                 345                 350

Leu Asp Ser Ala Gln His Asp Leu Asp Arg Asp Val Lys Ile Ile Gly
        355                 360                 365

Met Leu Asn Ser Ile Asn Thr Asp Ile Asp Asn Leu Tyr Ser Gln Gly
    370                 375                 380

Gln Glu Ala Ile Lys Val Phe Gln Lys Leu Gln Gly Ile Trp Ala Thr
385                 390                 395                 400

Ile Gly Ala Gln Ile Glu Asn Leu Arg Thr Thr Ser Leu Gln Glu Val
                405                 410                 415

Gln Asp Ser Asp Asp Ala Asp Glu Ile Gln Ile Glu Leu Glu Asp Ala
            420                 425                 430

Ser Asp Ala Trp Leu Val Val Ala Gln Glu Ala Arg Asp Phe Thr Leu
        435                 440                 445

Asn Ala Tyr Ser Val Ala Thr Ile Thr Ser Gly Glu Asn Asn Phe Met
    450                 455                 460

Ile Tyr Trp Tyr Asn Asn Ser Asp Trp Tyr Asn Asn Ser Asp Trp Tyr
465                 470                 475                 480

Asn Asn
```

```
<210> SEQ ID NO 141
<211> LENGTH: 1251
<212> TYPE: DNA
<213> ORGANISM: Artificial Sequence
<220> FEATURE:
<223> OTHER INFORMATION: Maize codon bias version DIG-1036

<400> SEQUENCE: 141

atgatcattg actccaagac caccctgccg cgtcacagcc tgatccacac catcaagctg      60

aactccaaca agaagtacgg acctggcgac atgaccaacg gcaaccagtt catcatctcc     120

aagcaagagt gggccaccat cggagcgtac atccagaccg gcctgggcct gccggtgaac     180

gagcagcagc tgaggactca cgtgcagctg tcccaagaca tcagcatccc gtccgacttc     240

tcccagctgt acgacgtgta ttgcagcgac aagacctccg ccgagtggtg gaacaagaac     300

ctgtacccgc tgatcatcaa gagcgccaac gacatcgcct cctacggctt caaggtggcg     360
```

```
ggcgacccga gcatcaagaa ggacggctac ttcaagaagc tccaagacga gctggacaac    420

atcgtggacc agaactccga cgacgacgcc atcgccaagg cgatcaagga cttcaaggcg    480

aggtgcggca tcctgatcaa ggaggcgaag cagtacgagg aggcggcgaa gaacatcgtg    540

acctccctgg accagttcct gcacggcgac cagaagaagc tggagggcgt gatcaacatc    600

cagaagaggc tgaaggaggt gcagaccgcc ctgaatcaag cccacggcga gagcagcccg    660

gcgcacaagg agctgctgga gaaggtgaag aacctcaaga ccaccctgga gaggaccatc    720

aaggccgagc aagacctgga gaagaaggtg gagtactcct tcctgctggg tccgctgctg    780

ggcttcgtgg tgtacgagat cctggagaac accgccgtgc agcacatcaa gaatcagatc    840

gacgagatca agaagcagct ggactccgcc cagcacgacc tggaccgcga cgtgaagatc    900

atcgggatgc tgaacagcat caacaccgac atcgacaacc tgtacagcca aggccaagag    960

gccatcaagg tgttccagaa gctccaaggc atctgggcga ccatcggcgc gcagatcgag   1020

aacctgagga ccaccagcct ccaagaggtc caagacagcg acgacgccga cgagatccag   1080

atcgagctgg aggacgccag cgacgcgtgg ctggtggtgg cccaagaggc gagggacttc   1140

accctgaacg cctacagcgt ggccaccatc accagcggcg agaacaactt catgatctac   1200

tggtatcaga actccgactg gtatcagaac tcagactggt acaacaactg a            1251
```

<210> SEQ ID NO 142
<211> LENGTH: 1338
<212> TYPE: DNA
<213> ORGANISM: Artificial Sequence
<220> FEATURE:
<223> OTHER INFORMATION: Highest GC+ERLS maize highest GC version of DIG-1036 with ER Localization Sequence

<400> SEQUENCE: 142

```
atggcgaaca agcacctgag cctgtccctg ttcctggtgc tgcttggcct gagcgcatcc     60

ctggcatccg gaatcattga ctccaagacc accctgccgc gtcacagcct gatccacacc    120

atcaagctga actccaacaa gaagtacgga cctggcgaca tgaccaacgg caaccagttc    180

atcatctcca agcaagagtg ggccaccatc ggagcgtaca tccagaccgg cctgggcctg    240

ccggtgaacg agcagcagct gaggactcac gtgcagctgt cccaagacat cagcatcccg    300

tccgacttct cccagctgta cgacgtgtat tgcagcgaca agacctccgc cgagtggtgg    360

aacaagaacc tgtacccgct gatcatcaag agcgccaacg acatcgcctc ctacggcttc    420

aaggtggcgg gcgacccgag catcaagaag gacggctact tcaagaagct ccaagacgag    480

ctggacaaca tcgtggacca gaactccgac gacgacgcca tcgccaaggc gatcaaggac    540

ttcaaggcga ggtgcggcat cctgatcaag gaggcgaagc agtacgagga ggcggcgaag    600

aacatcgtga cctccctgga ccagttcctg cacggcgacc agaagaagct ggagggcgtg    660

atcaacatcc agaagaggct gaaggaggtg cagaccgccc tgaatcaagc ccacggcgag    720

agcagcccgg cgcacaagga gctgctggag aaggtgaaga acctcaagac caccctggag    780

aggaccatca aggccgagca agacctggag aagaaggtgg agtactcctt cctgctgggt    840

ccgctgctgg gcttcgtggt gtacgagatc ctggagaaca ccgccgtgca gcacatcaag    900

aatcagatcg acgagatcaa gaagcagctg gactccgccc agcacgacct ggaccgcgac    960

gtgaagatca tcgggatgct gaacagcatc aacaccgaca tcgacaacct gtacagccaa   1020

ggccaagagg ccatcaaggt gttccagaag ctccaaggca tctgggcgac catcggcgcg   1080

cagatcgaga acctgaggac caccagcctc caagaggtcc aagacagcga cgacgccgac   1140
```

```
gagatccaga tcgagctgga ggacgccagc gacgcgtggc tggtggtggc ccaagaggcg   1200

agggacttca ccctgaacgc ctacagcgtg gccaccatca ccagcggcga gaacaacttc   1260

atgatctact ggtatcagaa ctccgactgg tatcagaact cagactggta caacaacagc   1320

gagaaggacg agctgtga                                                 1338


<210> SEQ ID NO 143
<211> LENGTH: 1347
<212> TYPE: DNA
<213> ORGANISM: Artificial Sequence
<220> FEATURE:
<223> OTHER INFORMATION: Highest GC+VLS maize highest GC version of
      DIG-1036 with Vacuole Localization Sequence

<400> SEQUENCE: 143

atgagtagct caccgtcctt tggcctgctg gcggttgcgg ccctgcttct ggcgcttagc     60

ctggcgcaac acggcatcat tgactccaag accaccctgc cgcgtcacag cctgatccac    120

accatcaagc tgaactccaa caagaagtac ggacctggcg acatgaccaa cggcaaccag    180

ttcatcatct ccaagcaaga gtgggccacc atcggagcgt acatccagac cggcctgggc    240

ctgccggtga acgagcagca gctgaggact cacgtgcagc tgtcccaaga catcagcatc    300

ccgtccgact tctcccagct gtacgacgtg tattgcagcg acaagacctc cgccgagtgg    360

tggaacaaga acctgtaccc gctgatcatc aagagcgcca acgacatcgc ctcctacggc    420

ttcaaggtgg cgggcgaccc gagcatcaag aaggacggct acttcaagaa gctccaagac    480

gagctggaca acatcgtgga ccagaactcc gacgacgacg ccatcgccaa ggcgatcaag    540

gacttcaagg cgaggtgcgg catcctgatc aaggaggcga agcagtacga ggaggcggcg    600

aagaacatcg tgacctccct ggaccagttc ctgcacggcg accagaagaa gctggagggc    660

gtgatcaaca tccagaagag gctgaaggag gtgcagaccg ccctgaatca agcccacggc    720

gagagcagcc cggcgcacaa ggagctgctg gagaaggtga agaacctcaa gaccaccctg    780

gagaggacca tcaaggccga gcaagacctg gagaagaagg tggagtactc cttcctgctg    840

ggtccgctgc tgggcttcgt ggtgtacgag atcctggaga acaccgccgt gcagcacatc    900

aagaatcaga tcgacgagat caagaagcag ctggactccg cccagcacga cctggaccgc    960

gacgtgaaga tcatcgggat gctgaacagc atcaacaccg acatcgacaa cctgtacagc   1020

caaggccaag aggccatcaa ggtgttccag aagctccaag gcatctgggc gaccatcggc   1080

gcgcagatcg agaacctgag gaccaccagc ctccaagagg tccaagacag cgacgacgcc   1140

gacgagatcc agatcgagct ggaggacgcc agcgacgcgt ggctggtggt ggcccaagag   1200

gcgagggact tcaccctgaa cgcctacagc gtggccacca tcaccagcgg cgagaacaac   1260

ttcatgatct actggtatca gaactccgac tggtatcaga actcagactg gtacaacaac   1320

gacgagctga aggctgaggc caagtga                                       1347


<210> SEQ ID NO 144
<211> LENGTH: 416
<212> TYPE: PRT
<213> ORGANISM: Artificial Sequence
<220> FEATURE:
<223> OTHER INFORMATION: The polypeptide encoded by DIG-1036 (DIG-1000
      minus glycosylation sites: N69>Q; N144>Q; N403>Q; N409>Q)

<400> SEQUENCE: 144

Met Ile Ile Asp Ser Lys Thr Thr Leu Pro Arg His Ser Leu Ile His
1               5                   10                  15
```

-continued

```
Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Gln Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Gln
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Val Ala Thr Ile Thr Ser Gly Glu Asn Asn Phe Met Ile Tyr
385                 390                 395                 400

Trp Tyr Gln Asn Ser Asp Trp Tyr Gln Asn Ser Asp Trp Tyr Asn Asn
                405                 410                 415
```